(12) United States Patent
Reed

(10) Patent No.: US 7,998,435 B2
(45) Date of Patent: Aug. 16, 2011

(54) HIGH DENSITY PLATE FILLER

(75) Inventor: Mark T. Reed, Menlo Park, CA (US)

(73) Assignee: Life Technologies Corporation, Carlsbad, CA (US)

( * ) Notice: Subject to any disclaimer, the term of this patent is extended or adjusted under 35 U.S.C. 154(b) by 1164 days.

(21) Appl. No.: 11/393,061

(22) Filed: Mar. 30, 2006

(65) Prior Publication Data

US 2006/0233672 A1 Oct. 19, 2006

Related U.S. Application Data

(63) Continuation-in-part of application No. 11/086,800, filed on Mar. 22, 2005, now abandoned, which is a continuation-in-part of application No. 10/944,673, filed on Sep. 17, 2004, now abandoned, and a continuation-in-part of application No. 10/944,691, filed on Sep. 17, 2004, now abandoned, said application No. 10/944,691 is a continuation-in-part of application No. 10/913,601, filed on Aug. 5, 2004, now Pat. No. 7,233,393.

(60) Provisional application No. 60/504,052, filed on Sep. 19, 2003, provisional application No. 60/589,224, filed on Jul. 19, 2004, provisional application No. 60/589,225, filed on Jul. 19, 2004, provisional application No. 60/601,716, filed on Aug. 13, 2004.

(51) Int. Cl.
*B01L 3/00* (2006.01)

(52) U.S. Cl. ........ 422/507; 422/501; 422/502; 422/503; 422/504; 436/180

(58) Field of Classification Search .......... 422/100–104, 422/501, 502, 503, 504, 507; 436/180
See application file for complete search history.

(56) References Cited

U.S. PATENT DOCUMENTS

| | | | |
|---|---|---|---|
| 4,459,267 A | 7/1984 | Bunce et al. |
| 4,491,156 A | 1/1985 | Lee, II |
| 4,492,360 A | 1/1985 | Lee, II et al. |
| 4,565,100 A | 1/1986 | Malinoff |
| 4,586,546 A | 5/1986 | Mezei et al. |
| 4,592,089 A | 5/1986 | Hartman |
| 4,699,715 A | 10/1987 | Lee, II |
| 4,706,705 A | 11/1987 | Lee, II |
| 4,715,231 A | 12/1987 | Lee, II et al. |

(Continued)

FOREIGN PATENT DOCUMENTS

WO    WO 94/27719    12/1994

(Continued)

*Primary Examiner* — Jill Warden
*Assistant Examiner* — Dwayne K Handy

(57) ABSTRACT

A filling apparatus for filling a microplate. The microplate having a plurality of wells each sized to receive an assay. The filling apparatus can comprise an output layer having a plurality of capillaries, wherein a first grouping of the capillaries is separated from a second grouping by a hydrophobic feature. Each of the plurality of capillaries can comprise an inlet and an outlet. A funnel assembly can comprise a funnel member sized to receive the assay. The funnel member can comprise an outlet for delivering a fluid bead of the assay along a top surface of the output layer and in fluid communication with each of the plurality of capillaries such that a portion of the fluid bead can be drawn within at least some of the plurality of capillaries in response to capillary force. The funnel assembly and the output layer can be moveable relative to each other between a first position and a second position to draw the fluid bead across the top surface.

28 Claims, 87 Drawing Sheets

U.S. PATENT DOCUMENTS

| | | |
|---|---|---|
| 4,753,727 A | 6/1988 | Lee, II et al. |
| 4,766,924 A | 8/1988 | Lee, III et al. |
| 4,804,468 A | 2/1989 | Lee, II et al. |
| 4,819,009 A | 4/1989 | Kniepkamp |
| 4,867,333 A | 9/1989 | Kolp, Jr. et al. |
| 4,930,553 A | 6/1990 | Grillo |
| 4,944,487 A | 7/1990 | Holtermann |
| 4,958,661 A | 9/1990 | Holtermann et al. |
| 4,966,667 A | 10/1990 | Rising et al. |
| 5,007,454 A | 4/1991 | Lee, II |
| 5,023,990 A | 6/1991 | Lee, II et al. |
| 5,085,402 A | 2/1992 | O'Dell |
| 5,121,947 A | 6/1992 | Lee, III et al. |
| 5,126,276 A | 6/1992 | Fish et al. |
| 5,160,226 A | 11/1992 | Lee, II |
| 5,274,240 A | 12/1993 | Mathies et al. |
| 5,284,425 A | 2/1994 | Holtermann et al. |
| 5,422,780 A | 6/1995 | Lignar |
| 5,505,229 A | 4/1996 | Lee, II |
| 5,511,585 A | 4/1996 | Lee, II |
| 5,545,531 A | 8/1996 | Rava et al. |
| 5,618,701 A | 4/1997 | Landegren |
| 5,676,309 A | 10/1997 | Lee, II et al. |
| 5,759,779 A | 6/1998 | Dehlinger |
| 5,763,278 A | 6/1998 | Sickinger et al. |
| 5,819,799 A | 10/1998 | O'Dell |
| 5,843,767 A | 12/1998 | Beattie |
| 5,874,219 A | 2/1999 | Rava et al. |
| 5,875,967 A | 3/1999 | Ruth, III |
| 5,888,830 A | 3/1999 | Mohan et al. |
| 5,916,524 A | 6/1999 | Tisone |
| 5,927,547 A | 7/1999 | Papen et al. |
| 6,003,557 A | 12/1999 | Brelig et al. |
| 6,033,911 A | 3/2000 | Schultz et al. |
| 6,043,880 A | 3/2000 | Andrews et al. |
| 6,063,339 A | 5/2000 | Tisone et al. |
| 6,079,283 A | 6/2000 | Papen et al. |
| 6,083,761 A | 7/2000 | Kedar et al. |
| 6,086,825 A | 7/2000 | Sundberg et al. |
| 6,090,251 A | 7/2000 | Sundberg et al. |
| 6,094,966 A | 8/2000 | Papen et al. |
| 6,112,605 A | 9/2000 | Papen et al. |
| 6,124,138 A | 9/2000 | Woudenberg et al. |
| 6,126,899 A | 10/2000 | Woudenberg et al. |
| 6,140,044 A | 10/2000 | Besemer et al. |
| 6,203,759 B1 | 3/2001 | Pelc et al. |
| 6,220,075 B1 | 4/2001 | Papen et al. |
| 6,235,520 B1 | 5/2001 | Malin et al. |
| 6,238,910 B1 | 5/2001 | Custance et al. |
| 6,254,826 B1 | 7/2001 | Acosta et al. |
| 6,258,103 B1 | 7/2001 | Saracione |
| 6,274,091 B1 | 8/2001 | Mohan et al. |
| 6,302,159 B1 | 10/2001 | Ryan et al. |
| 6,309,608 B1 | 10/2001 | Zhou et al. |
| 6,323,043 B1 | 11/2001 | Caren et al. |
| 6,360,792 B1 | 3/2002 | Ganz et al. |
| 6,374,683 B1 | 4/2002 | Hunicke-Smith et al. |
| 6,379,897 B1 | 4/2002 | Weidenhammer et al. |
| 6,387,031 B1 | 5/2002 | Hunicke-Smith et al. |
| 6,395,559 B1 | 5/2002 | Swenson |
| 6,408,878 B2 | 6/2002 | Unger et al. |
| 6,422,431 B2 | 7/2002 | Pelc et al. |
| 6,429,027 B1 | 8/2002 | Chee et al. |
| 6,432,696 B2 | 8/2002 | Custance et al. |
| 6,447,489 B1 | 9/2002 | Peterson |
| 6,451,188 B1 | 9/2002 | Sundberg et al. |
| 6,461,812 B2 | 10/2002 | Barth et al. |
| 6,464,942 B2 | 10/2002 | Coffman et al. |
| 6,472,218 B1 | 10/2002 | Stylli et al. |
| 6,475,809 B1 | 11/2002 | Wagner et al. |
| 6,485,690 B1* | 11/2002 | Pfost et al. .................. 422/102 |
| 6,496,309 B1 | 12/2002 | Bliton et al. |
| 6,498,010 B1 | 12/2002 | Fitzgerald et al. |
| 6,521,187 B1 | 2/2003 | Papen |
| 6,537,817 B1 | 3/2003 | Papen |
| 6,551,557 B1 | 4/2003 | Rose et al. |
| 6,558,960 B1 | 5/2003 | Parce et al. |
| 6,576,295 B2 | 6/2003 | Tisone |
| 6,585,296 B1 | 7/2003 | Picha et al. |
| 6,589,791 B1 | 7/2003 | La Budde et al. |
| 6,592,825 B2 | 7/2003 | Pelc et al. |
| 6,596,237 B1 | 7/2003 | Borrelli et al. |
| RE38,281 E | 10/2003 | Tisone |
| 6,642,046 B1 | 11/2003 | McGarry et al. |
| 6,660,232 B1 | 12/2003 | Krueger et al. |
| 6,669,909 B2 | 12/2003 | Shvets et al. |
| 6,677,162 B1 | 1/2004 | Wendelbo et al. |
| 6,680,202 B2 | 1/2004 | Young |
| 6,682,702 B2 | 1/2004 | Barth et al. |
| 6,703,247 B1 | 3/2004 | Chu |
| 6,708,978 B2 | 3/2004 | Kägi |
| 6,709,559 B2 | 3/2004 | Sundberg et al. |
| 6,709,872 B1 | 3/2004 | Downs et al. |
| 6,713,021 B1 | 3/2004 | Shvets et al. |
| 6,716,629 B2 | 4/2004 | Hess et al. |
| 6,720,149 B1 | 4/2004 | Rava et al. |
| 6,723,569 B1 | 4/2004 | Moore et al. |
| 6,730,883 B2 | 5/2004 | Brown et al. |
| 6,743,633 B1 | 6/2004 | Hunter |
| 6,756,019 B1 | 6/2004 | Dubrow et al. |
| 6,776,965 B2 | 8/2004 | Wyzgol et al. |
| 6,781,121 B1 | 8/2004 | Davis et al. |
| 6,800,250 B1 | 10/2004 | Hunicke-Smith et al. |
| 6,812,030 B2 | 11/2004 | Ozbal et al. |
| 6,816,259 B1 | 11/2004 | Auton et al. |
| 6,824,024 B2 | 11/2004 | Ingenhoven et al. |
| 6,852,291 B1 | 2/2005 | Johnson et al. |
| 6,869,571 B2 | 3/2005 | Ingenhoven et al. |
| 6,874,699 B2 | 4/2005 | Larson et al. |
| 7,329,393 B2* | 2/2008 | Backes et al. .................. 422/102 |
| 2001/0032675 A1 | 10/2001 | Russell |
| 2002/0001544 A1 | 1/2002 | Hess et al. |
| 2002/0012611 A1 | 1/2002 | Stylli et al. |
| 2002/0064482 A1 | 5/2002 | Tisone et al. |
| 2002/0064880 A1 | 5/2002 | Merten et al. |
| 2002/0086329 A1 | 7/2002 | Shvets et al. |
| 2002/0098593 A1 | 7/2002 | Nelson et al. |
| 2002/0104389 A1 | 8/2002 | Hovey |
| 2002/0106812 A1 | 8/2002 | Fisher |
| 2002/0119077 A1 | 8/2002 | Shumate et al. |
| 2002/0159919 A1 | 10/2002 | Churchill et al. |
| 2002/0168297 A1 | 11/2002 | Shvets et al. |
| 2002/0173048 A1 | 11/2002 | Nakazawa et al. |
| 2002/0176803 A1 | 11/2002 | Hamel et al. |
| 2002/0179849 A1 | 12/2002 | Maher et al. |
| 2002/0182113 A1 | 12/2002 | Shvets et al. |
| 2002/0182117 A1 | 12/2002 | Coassin et al. |
| 2002/0192119 A1 | 12/2002 | DeSilets et al. |
| 2003/0008412 A1 | 1/2003 | Coffman et al. |
| 2003/0010386 A1 | 1/2003 | Doyen |
| 2003/0017085 A1 | 1/2003 | Kercso et al. |
| 2003/0032198 A1 | 2/2003 | Lugmair et al. |
| 2003/0038248 A1 | 2/2003 | Maher et al. |
| 2003/0067118 A1 | 4/2003 | Kagi |
| 2003/0086828 A1 | 5/2003 | Chiou et al. |
| 2003/0087446 A1 | 5/2003 | Eggers |
| 2003/0087455 A1 | 5/2003 | Eggers et al. |
| 2003/0092034 A1 | 5/2003 | Cooper et al. |
| 2003/0108868 A1 | 6/2003 | Richards |
| 2003/0109060 A1 | 6/2003 | Cook et al. |
| 2003/0125753 A1 | 7/2003 | Saracione |
| 2003/0175163 A1 | 9/2003 | Shvets et al. |
| 2003/0207464 A1 | 11/2003 | Lemmo et al. |
| 2003/0215956 A1 | 11/2003 | Reed |
| 2003/0215957 A1 | 11/2003 | Lemmo et al. |
| 2004/0014238 A1 | 1/2004 | Krug et al. |
| 2004/0037748 A1 | 2/2004 | Hasan et al. |
| 2004/0082076 A1 | 4/2004 | Zengerle et al. |
| 2004/0096358 A1 | 5/2004 | Blankenstein et al. |
| 2004/0101445 A1 | 5/2004 | Shvets et al. |
| 2004/0115831 A1 | 6/2004 | Meathrel et al. |
| 2004/0126283 A1 | 7/2004 | Backes et al. |
| 2004/0131505 A1 | 7/2004 | Koeda |
| 2004/0132128 A1 | 7/2004 | Shvets et al. |
| 2004/0203047 A1 | 10/2004 | Caren et al. |
| 2004/0203173 A1 | 10/2004 | Peck et al. |
| 2004/0206179 A1 | 10/2004 | Kamiyama |

| | | |
|---|---|---|
| 2004/0206408 A1 | 10/2004 | Peters et al. |
| 2004/0209381 A1 | 10/2004 | Peters et al. |
| 2004/0219689 A1 | 11/2004 | Soma |
| 2004/0246549 A1 | 12/2004 | Buchholz |
| 2004/0250878 A1 | 12/2004 | Watanabe et al. |
| 2005/0032242 A1 | 2/2005 | Sasaki |

FOREIGN PATENT DOCUMENTS

| | | |
|---|---|---|
| WO | WO 95/11262 | 4/1995 |
| WO | WO 02/064812 | 8/2002 |
| WO | WO 03/057369 | 7/2003 |

* cited by examiner

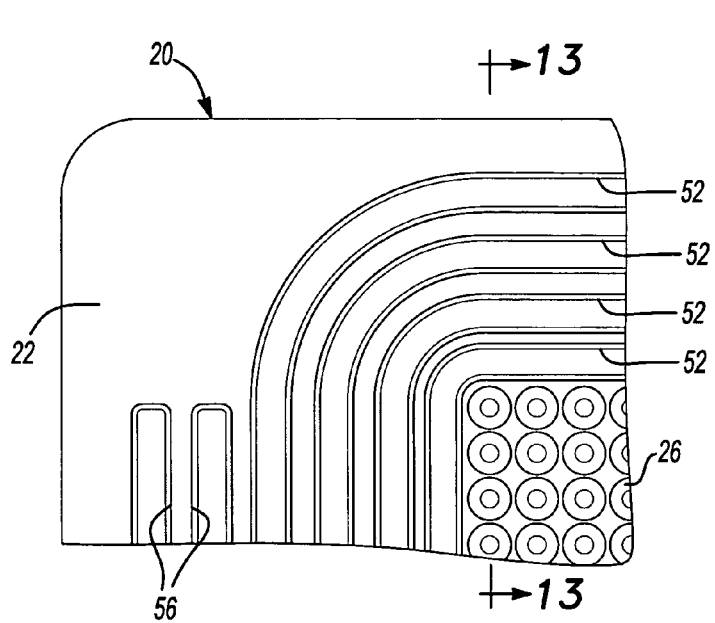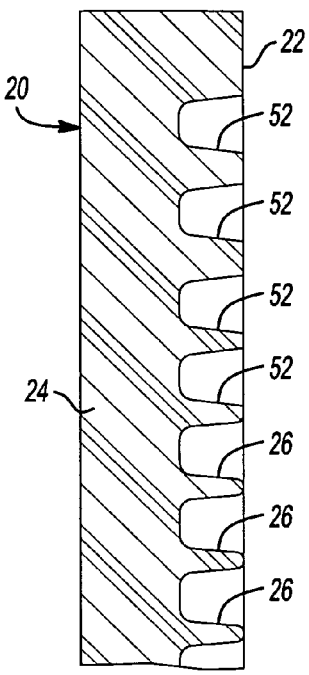
Fig-12  Fig-13
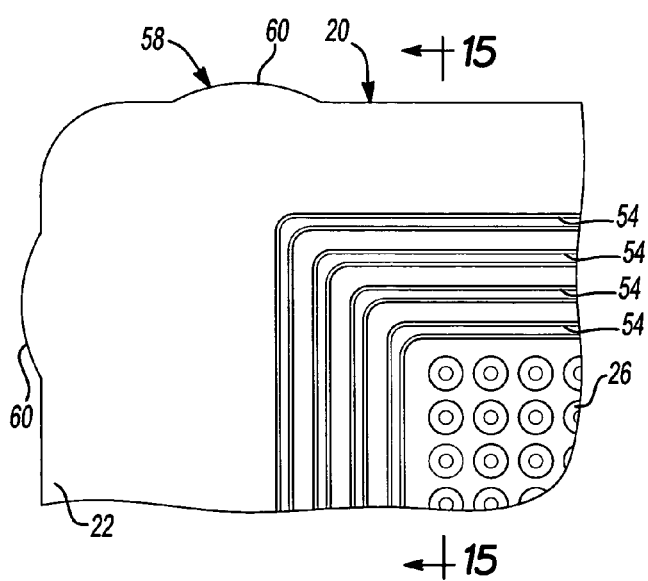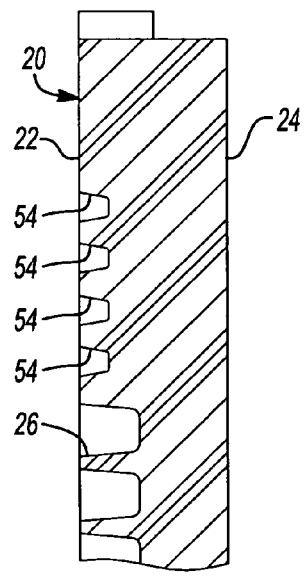
Fig-14  Fig-15

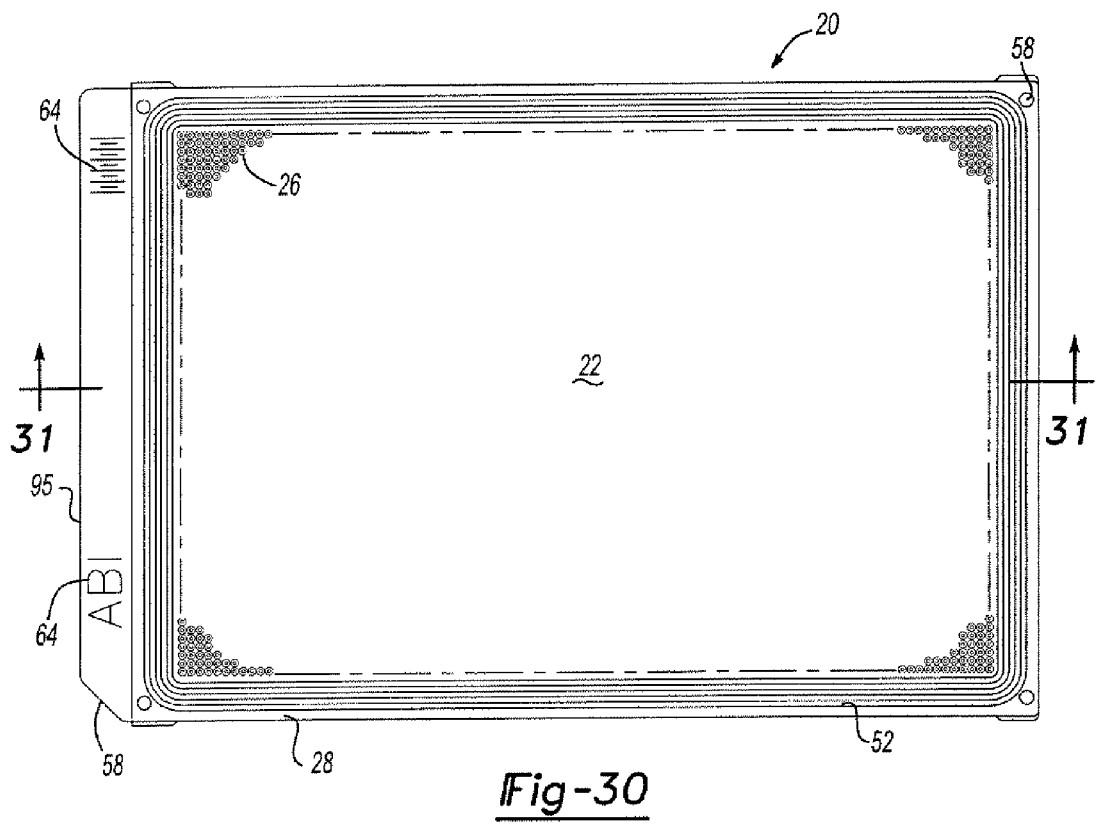
Fig-30
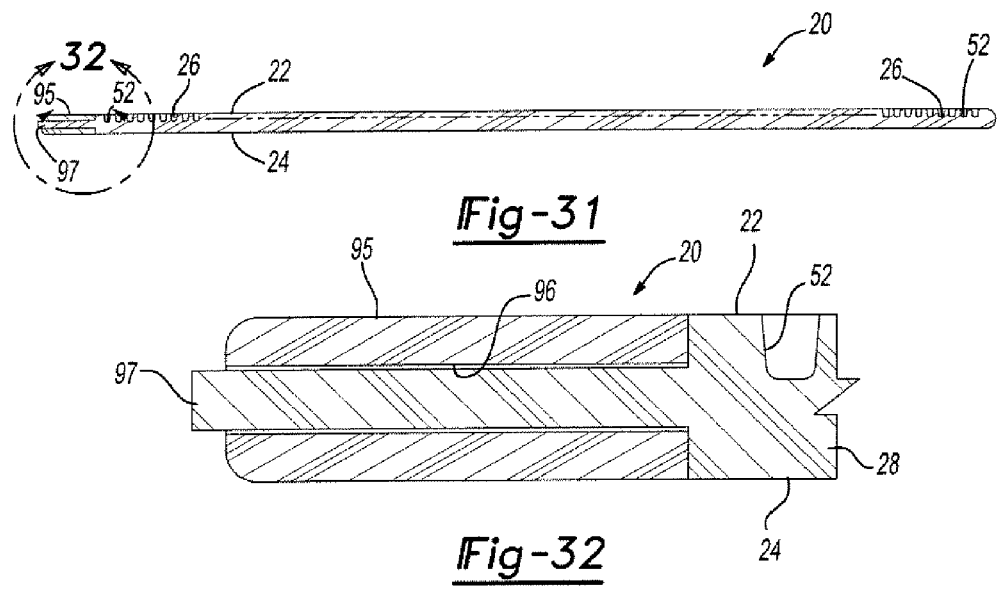
Fig-31
Fig-32

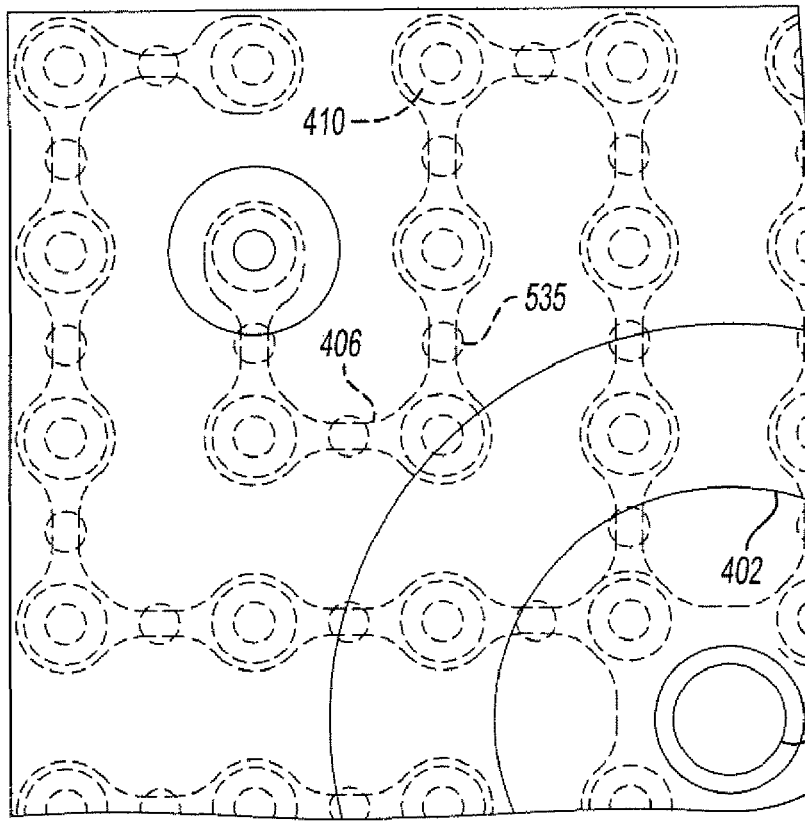
_Fig-44_
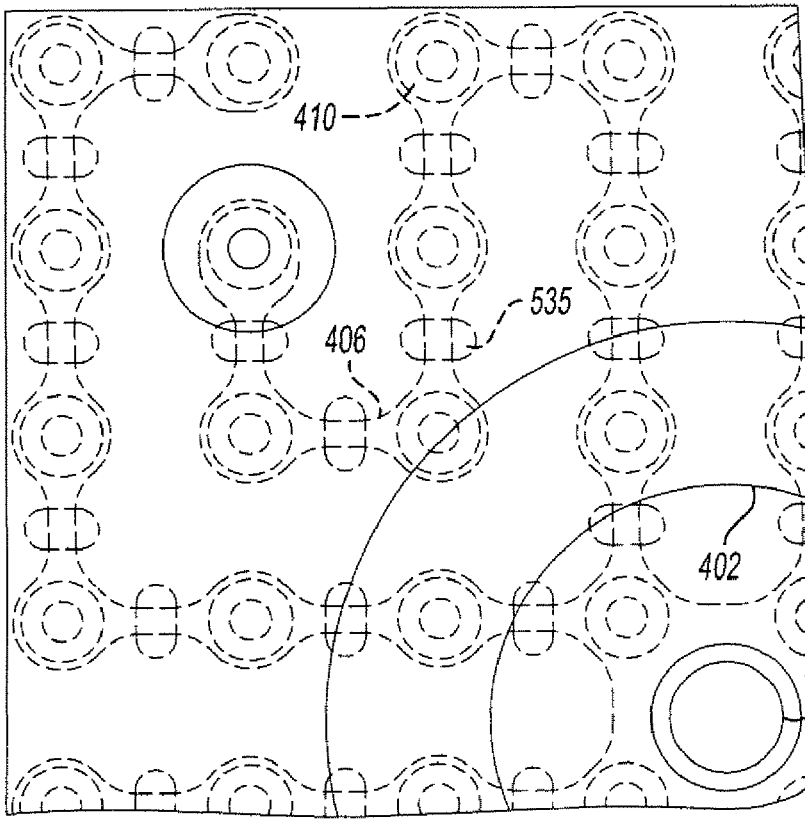
_Fig-45_

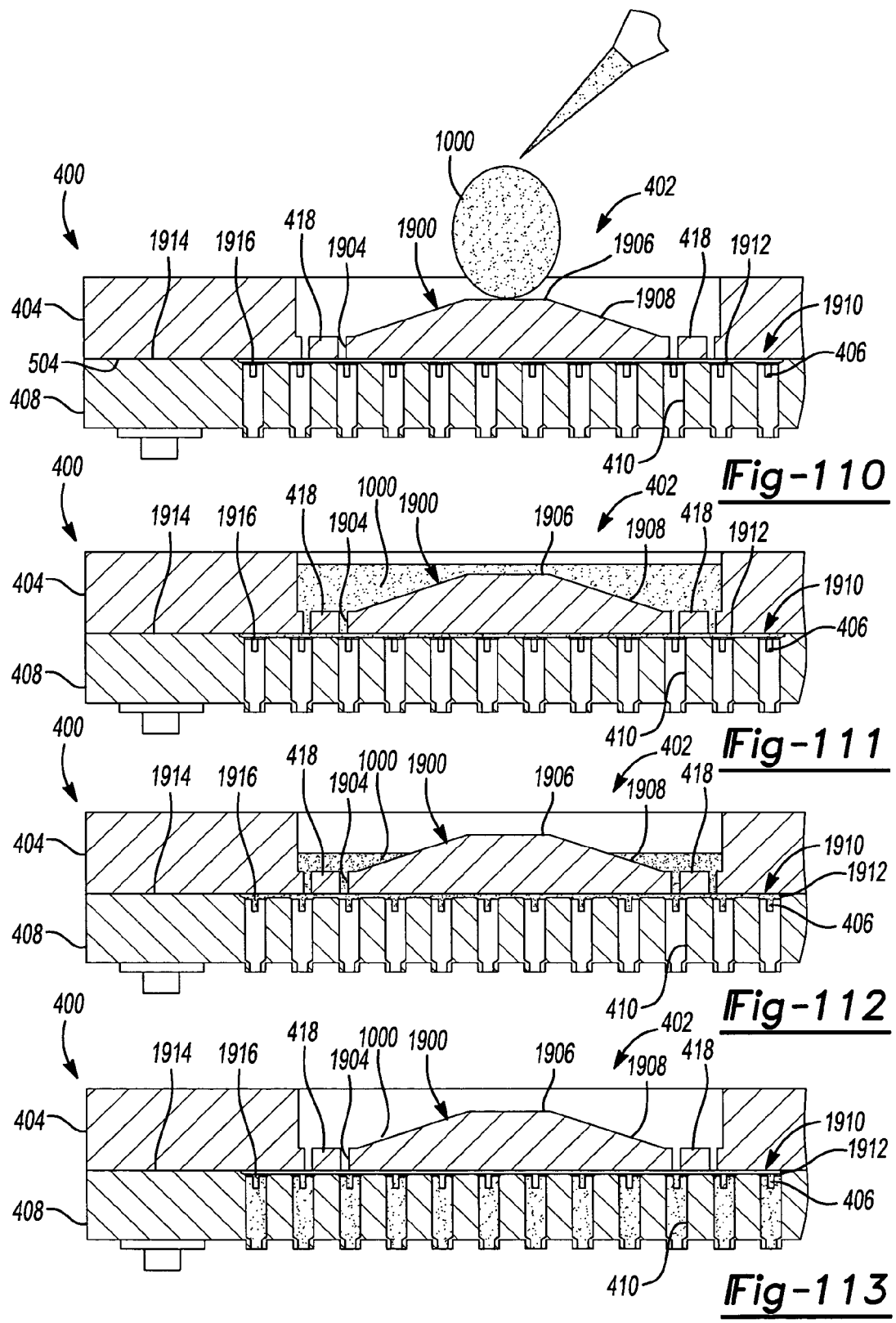

HIGH DENSITY PLATE FILLER

CROSS-REFERENCE TO RELATED APPLICATIONS

This application is a continuation-in-part of U.S. patent application Ser. No. 11/086,800 filed on Mar. 22, 2005 now abandoned. U.S. patent application Ser. No. 11/086,800 is a continuation-in-part of U.S. patent application Ser. No. 10/944,673 filed on Sep. 17, 2004, now abandoned and U.S. patent application Ser. No. 10/944,691 filed on Sep. 17, 2004 now abandoned.

U.S. patent application Ser. No. 10/944,673 claims a benefit to U.S. Provisional Application No. 60/504,500 filed on Sep. 19, 2003; U.S. Provisional Application No. 60/504,052 filed on Sep. 19, 2003; U.S. Provisional Application No. 60/589,224 filed Jul. 19, 2004; U.S. Provisional Application No. 60/589,225 filed on Jul. 19, 2004; and U.S. Provisional Application No. 60/601,716 filed on Aug. 13, 2004.

U.S. patent application Ser. No. 10/944,691 is a continuation-in-part of U.S. patent application Ser. No. 10/913,601 filed on Aug. 5, 2004 now U.S. Pat. No. 7,233,393 and claims the benefit of U.S. Provisional Application No. 60/504,052 filed on Sep. 19, 2003; U.S. Provisional Application No. 60/504,500 filed on Sep. 19, 2003; U.S. Provisional Application No. 60/589,224 filed Jul. 19, 2004; U.S. Provisional Application No. 60/589,225 filed on Jul. 19, 2004; and U.S. Provisional Application No. 60/601,716 filed on Aug. 13, 2004.

All literature and similar materials cited in this application, including but not limited to, patents, patent applications, articles, books, treatises, and internet web pages, regardless of the format of such literature and similar materials, are expressly incorporated by reference in their entirety for any purpose. In the event that one or more of the incorporated literature and similar materials differs from or contradicts this application, including but not limited to defined terms, term usage, described techniques, or the like, this application controls.

INTRODUCTION

Currently, genomic analysis, including that of the estimated 30,000 human genes is a major focus of basic and applied biochemical and pharmaceutical research. Such analysis may aid in developing diagnostics, medicines, and therapies for a wide variety of disorders. However, the complexity of the human genome and the interrelated functions of genes often make this task difficult. There is a continuing need for methods and apparatus to aid in such analysis.

DRAWINGS

The skilled artisan will understand that the drawings, described herein, are for illustration purposes only. The drawings are not intended to limit the scope of the present teachings in any way.

FIG. 12 is an enlarged top view illustrating a corner of the microplate illustrated in FIG. 11;

FIG. 13 is a cross-sectional view of the microplate of FIG. 12 taken along Line 13-13;

FIG. 14 is an enlarged top view illustrating a corner of a microplate according to some embodiments;

FIG. 15 is a cross-sectional view of the microplate of FIG. 14 taken along Line 15-15;

Figure 26:
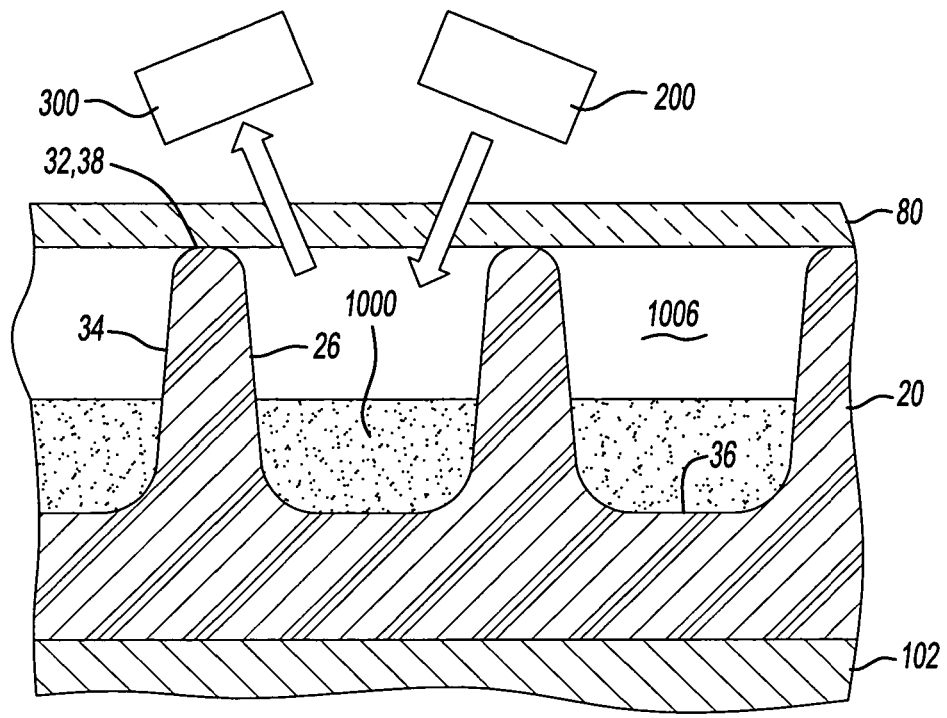
Figure 27:
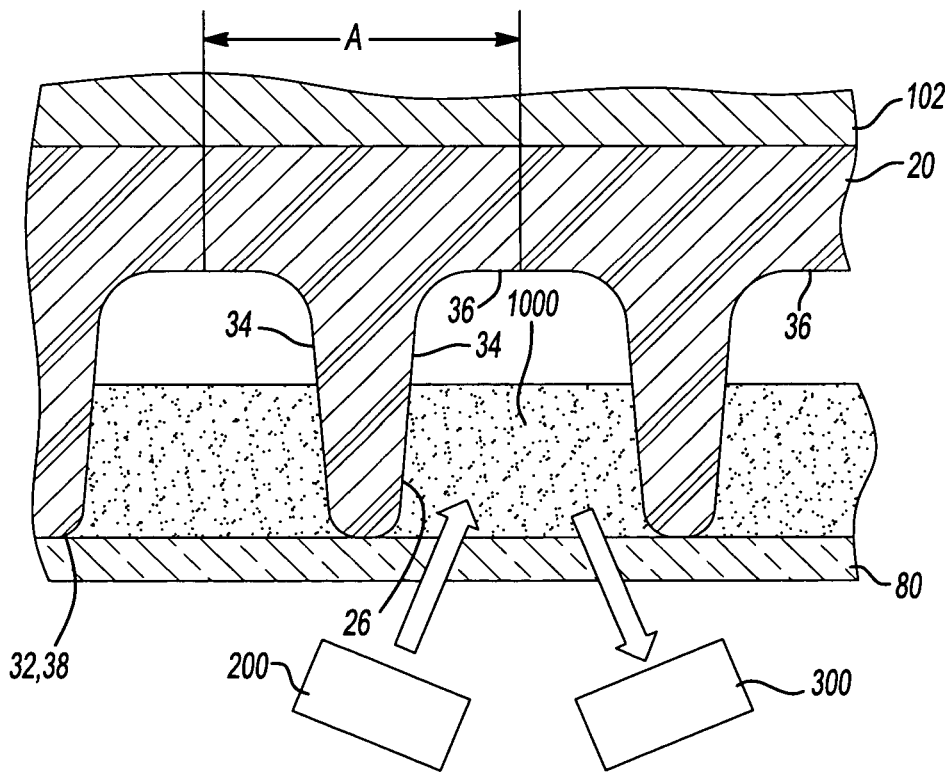
Figure 28:
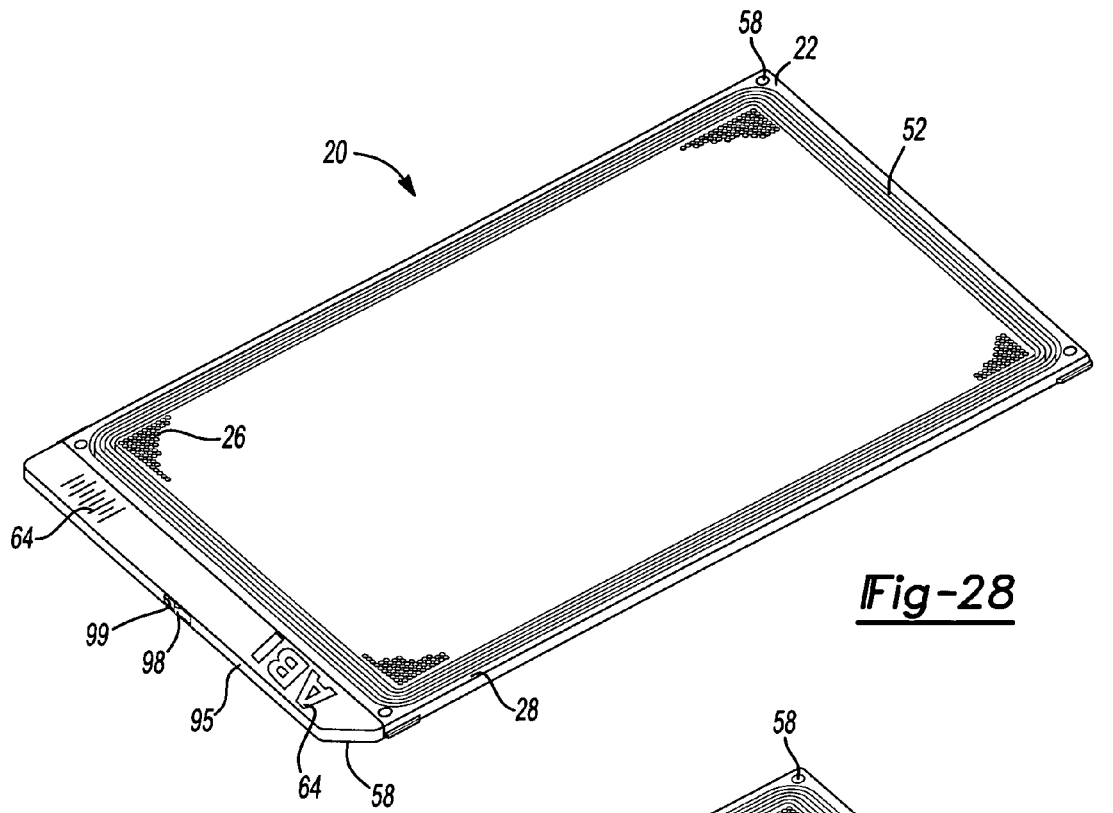
Figure 29:
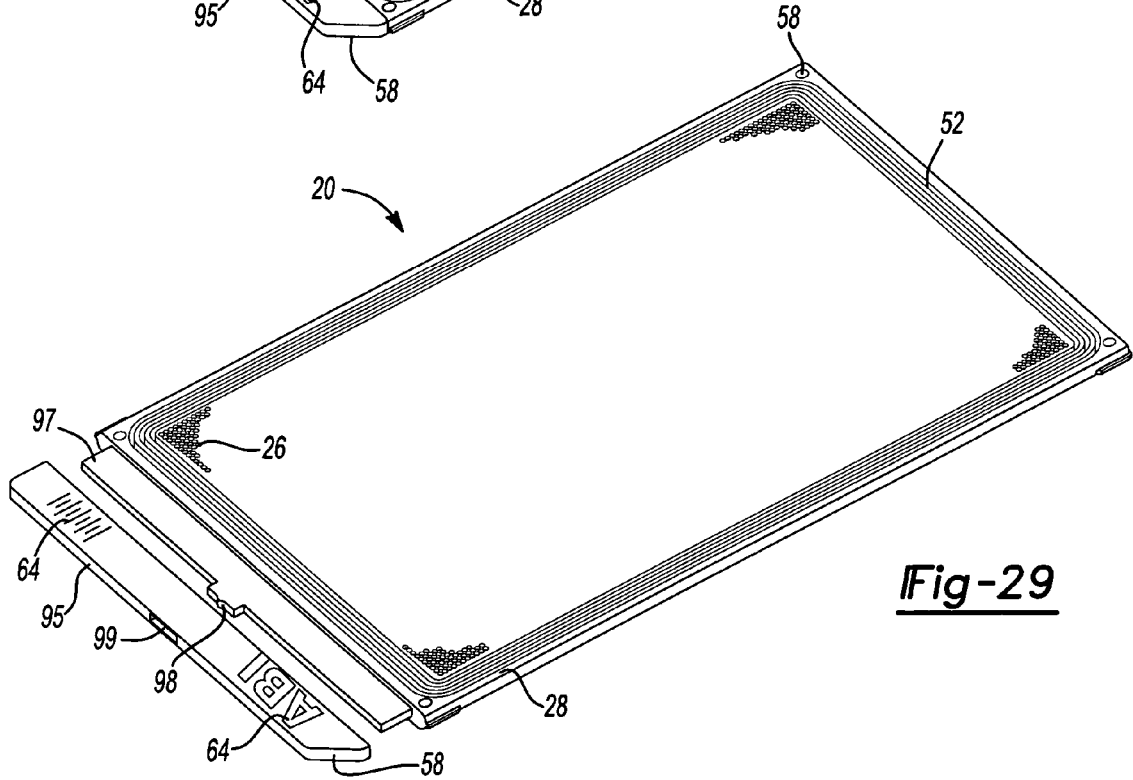
Figure 33:
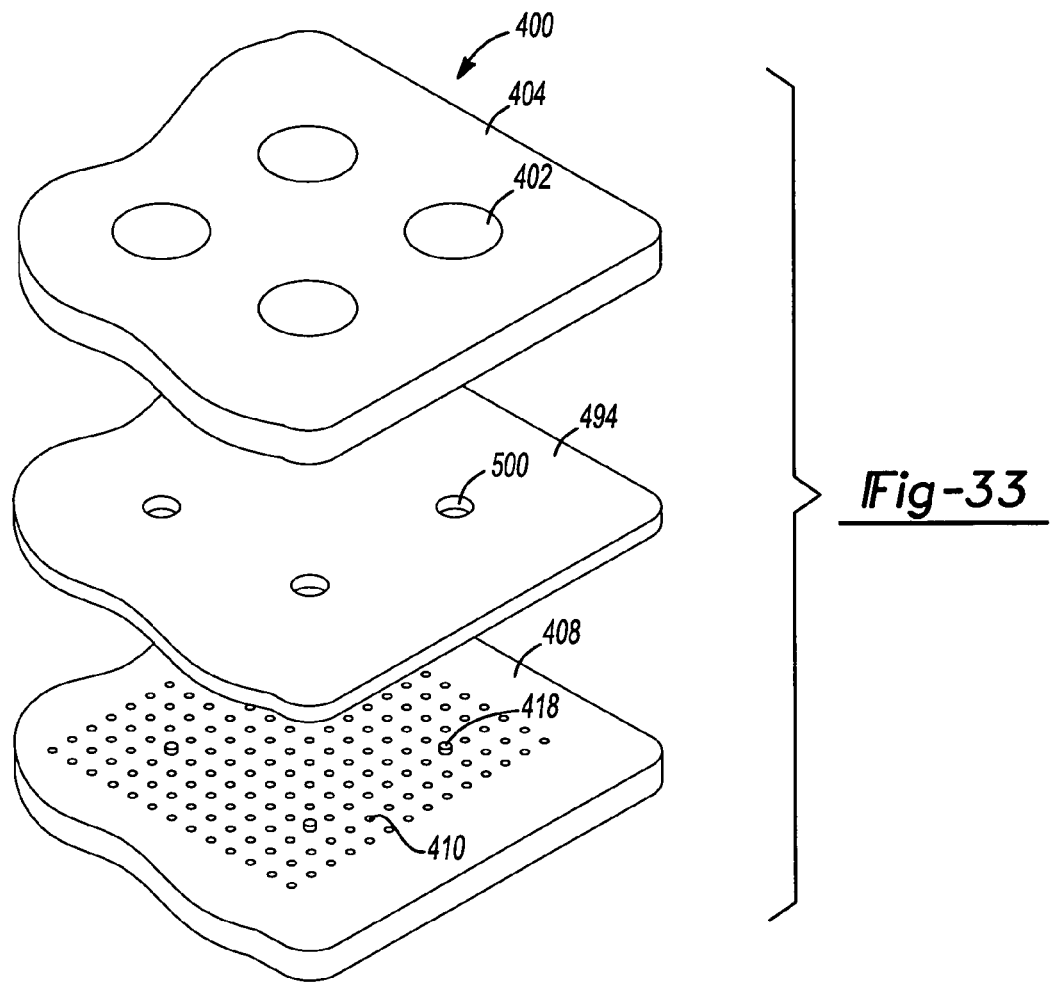
Figure 34:
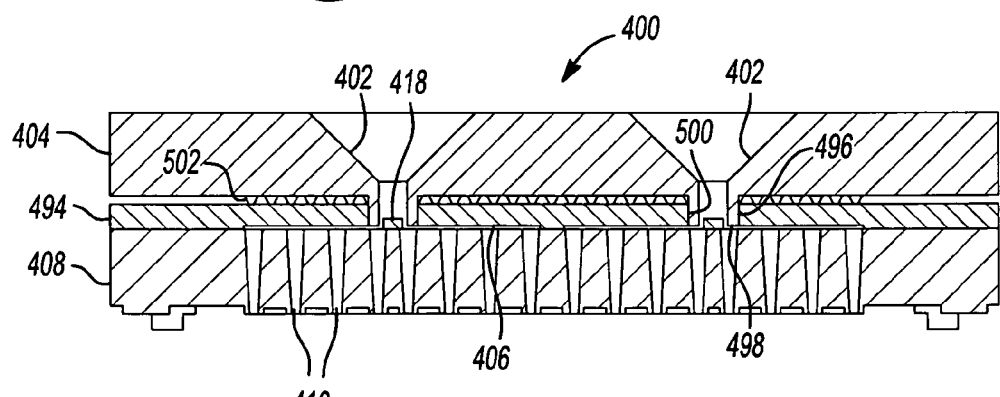
Figure 35:
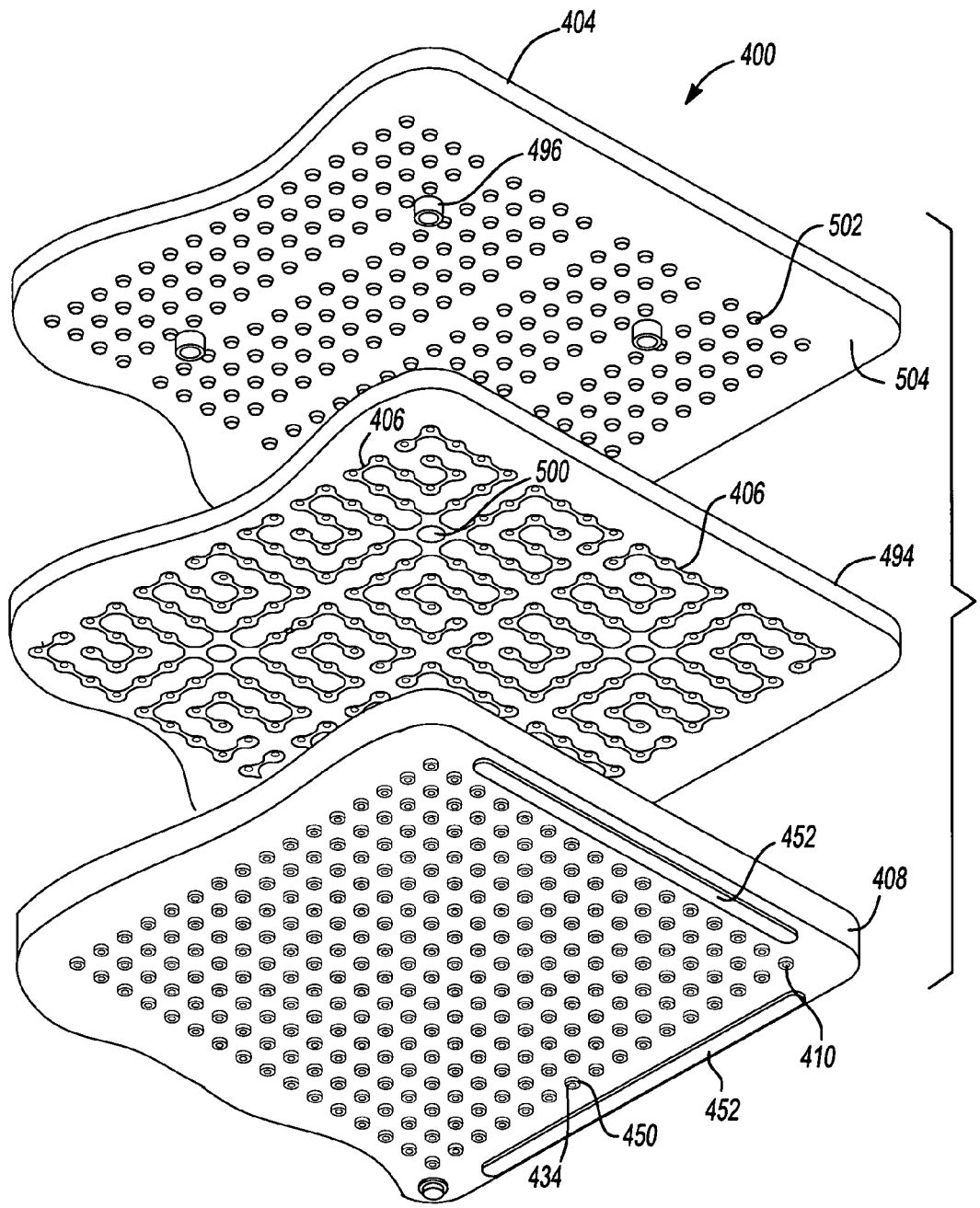
Figure 36:
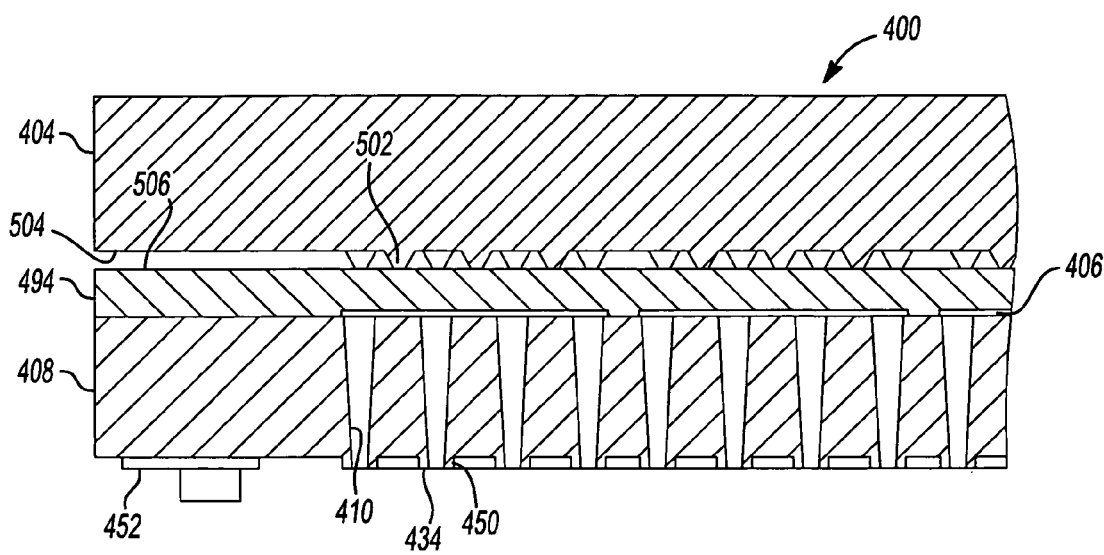
Figure 37:
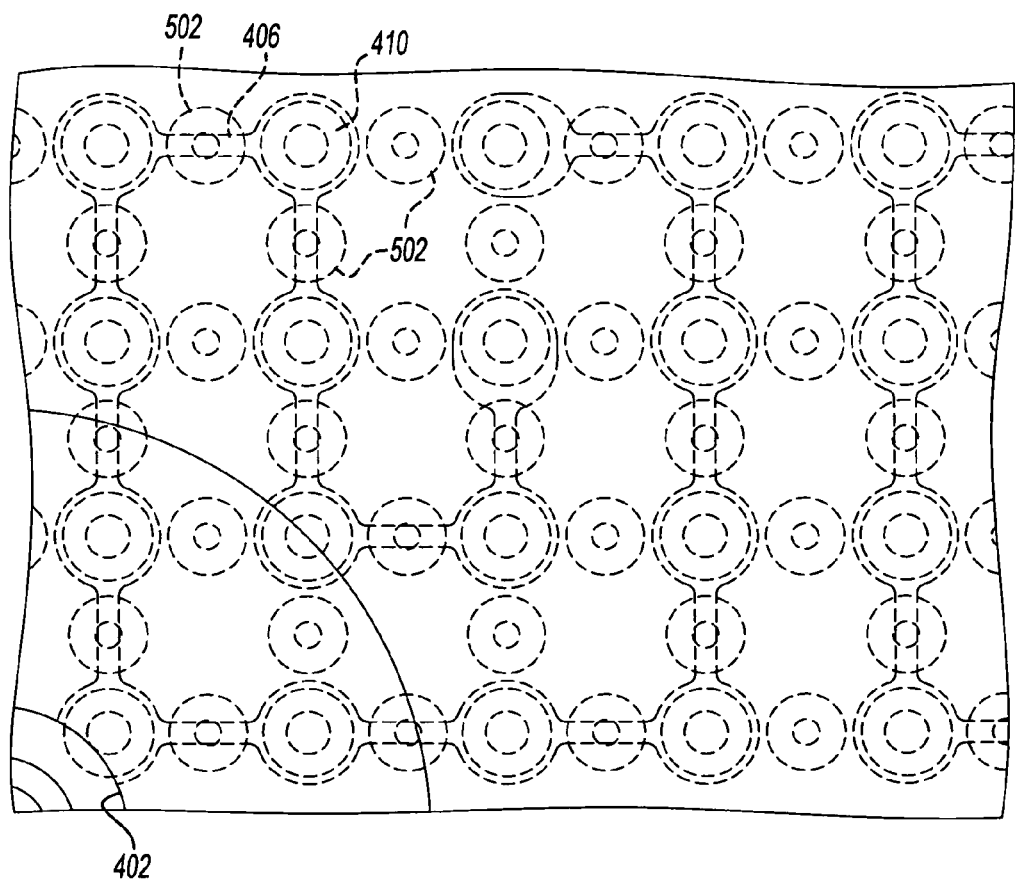
Figure 38:
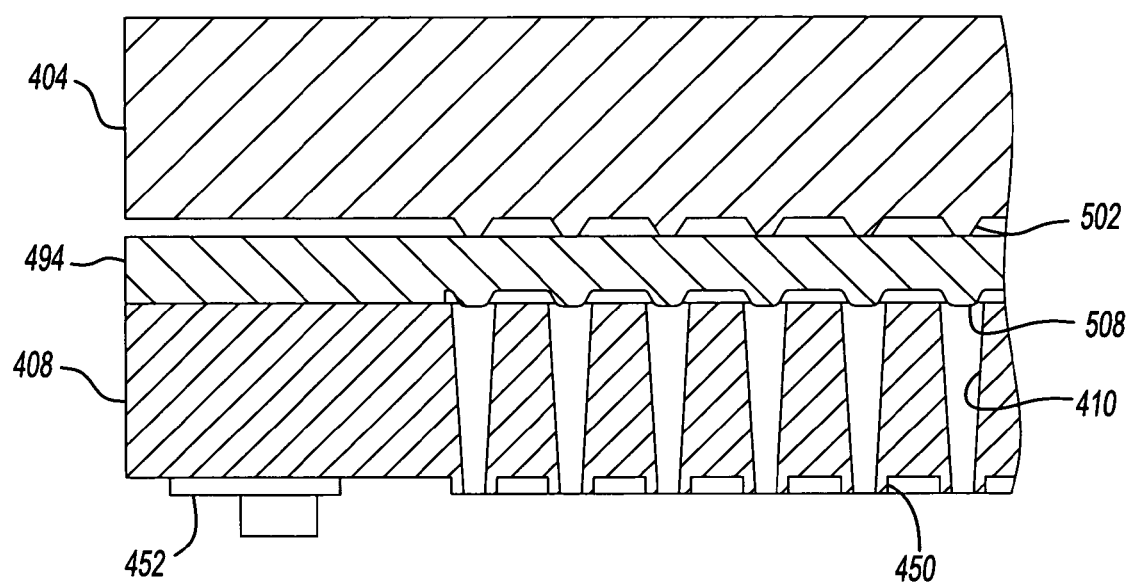
Figure 39:
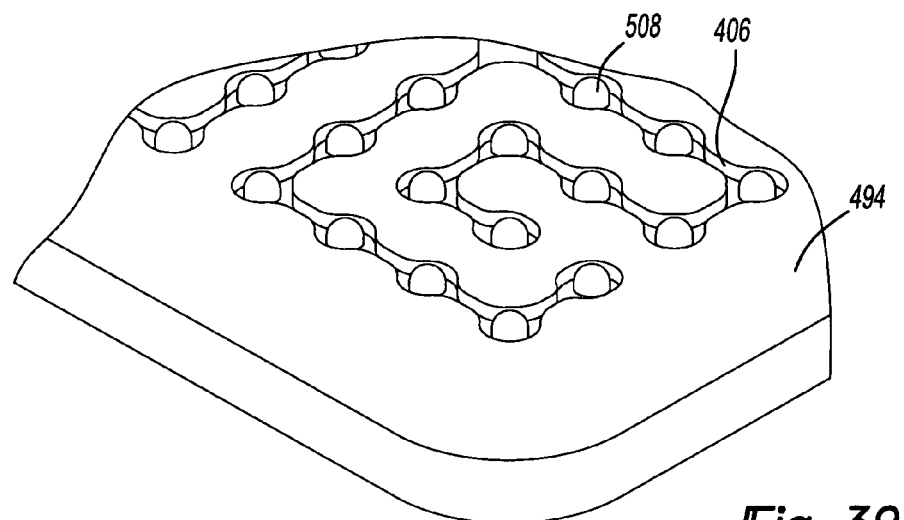
Figure 40:
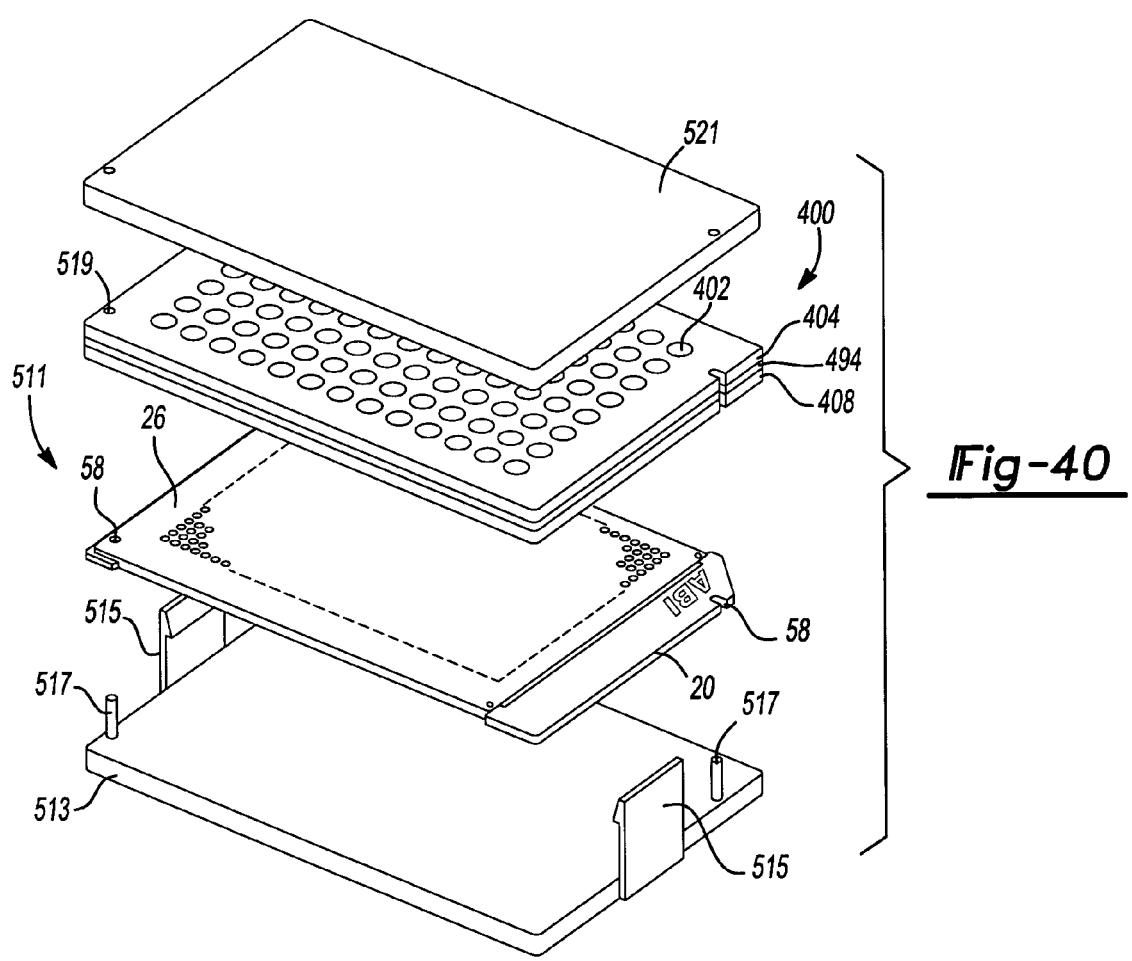
Figure 41:
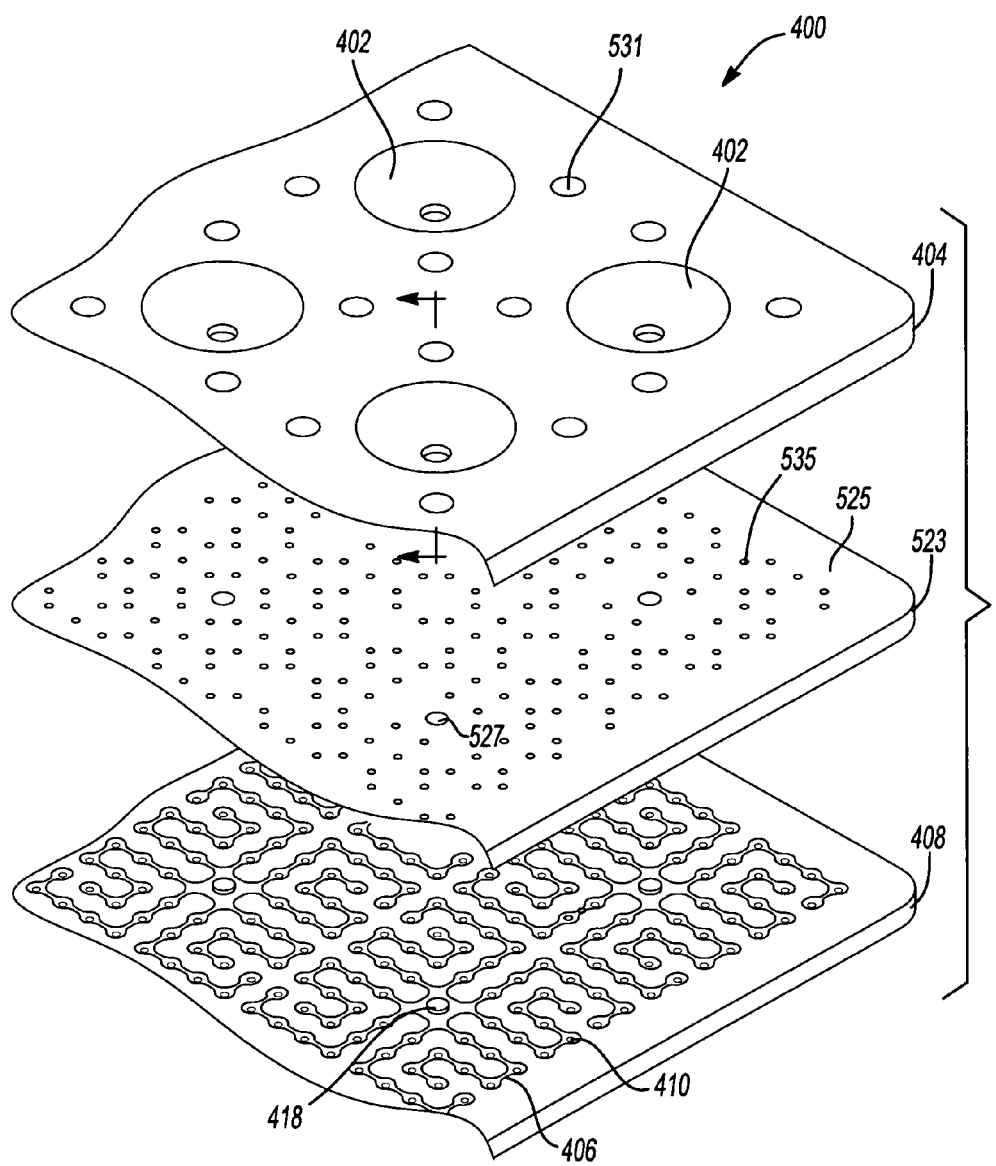
Figure 42:
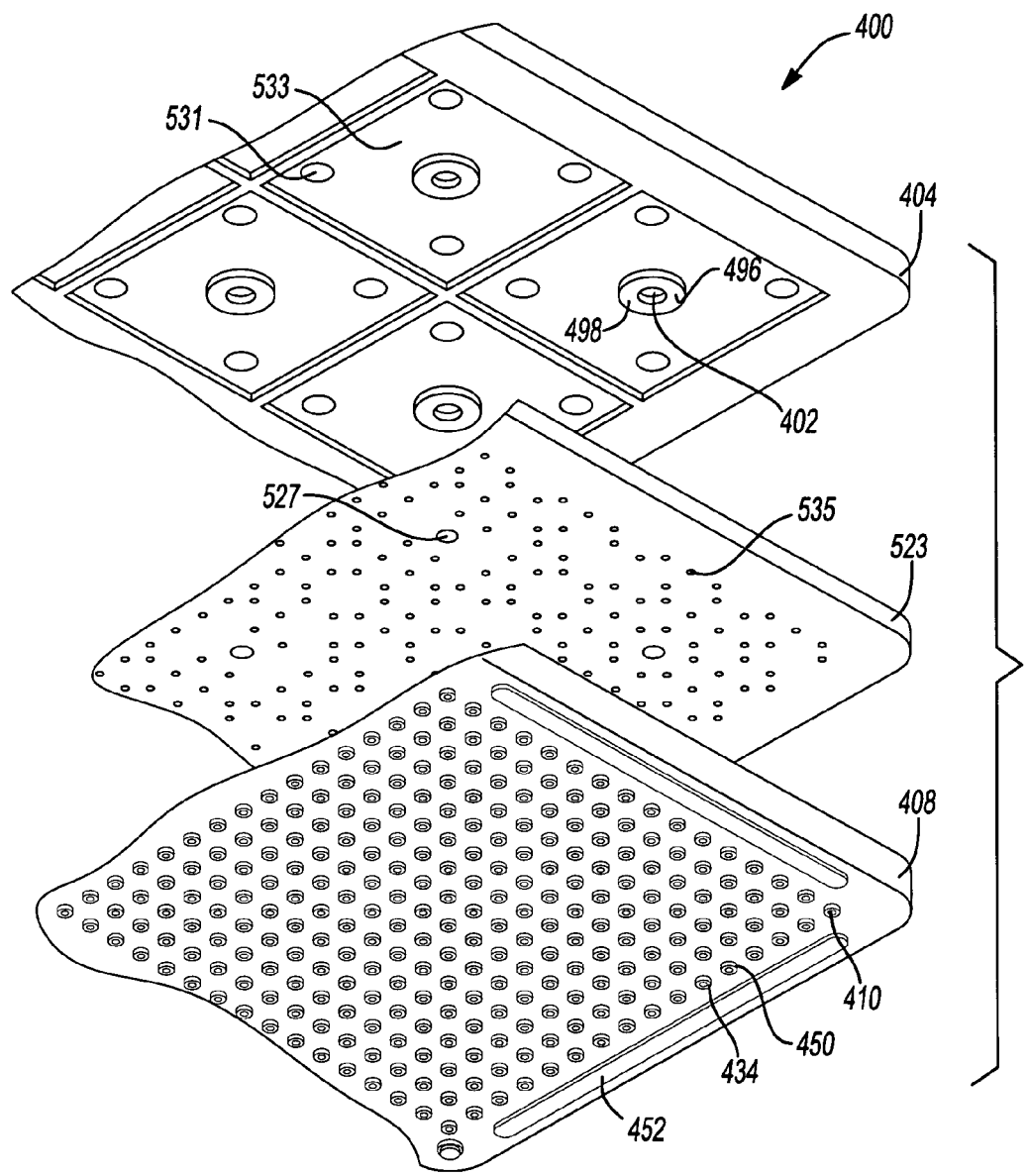
Figure 43:
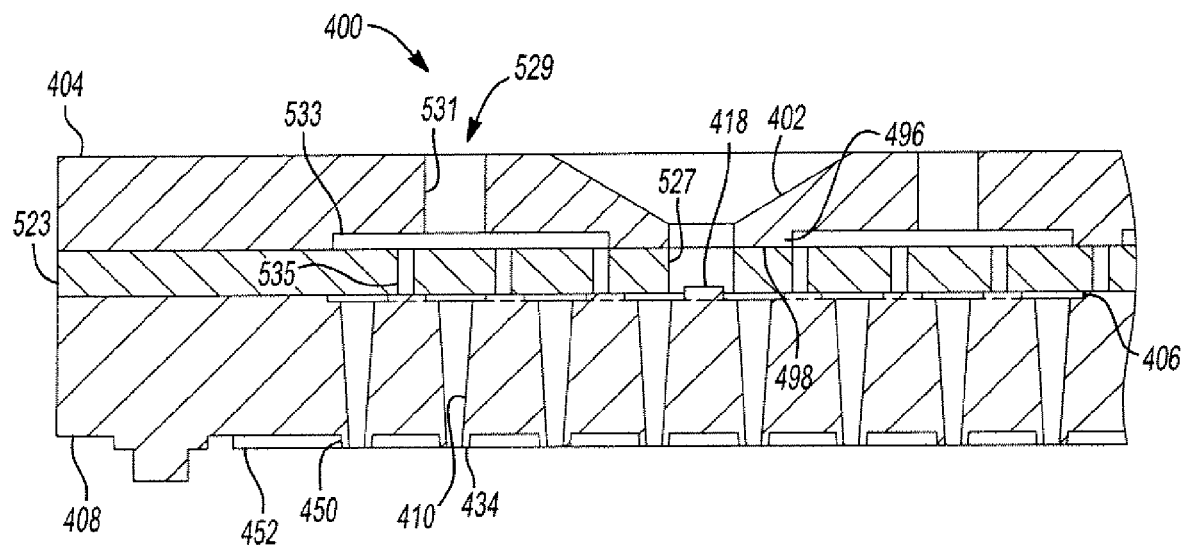
Figure 46:
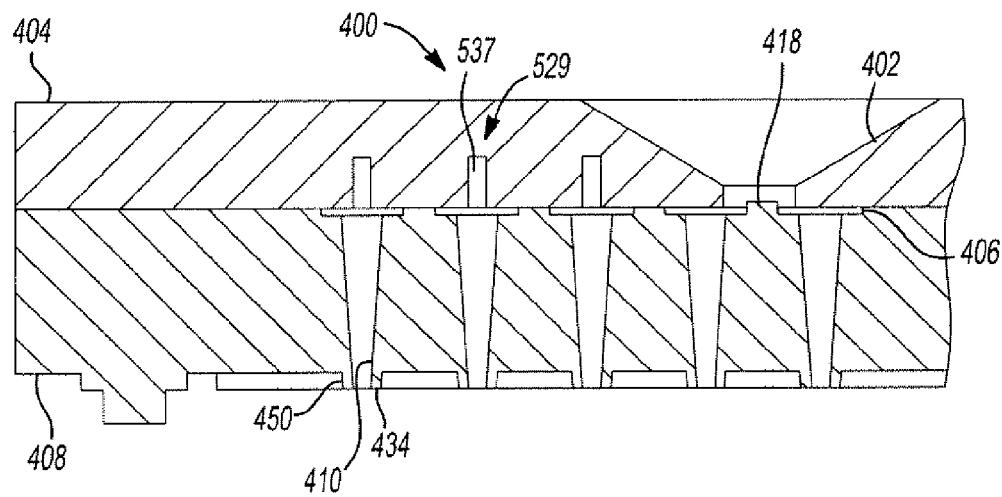
Figure 47:
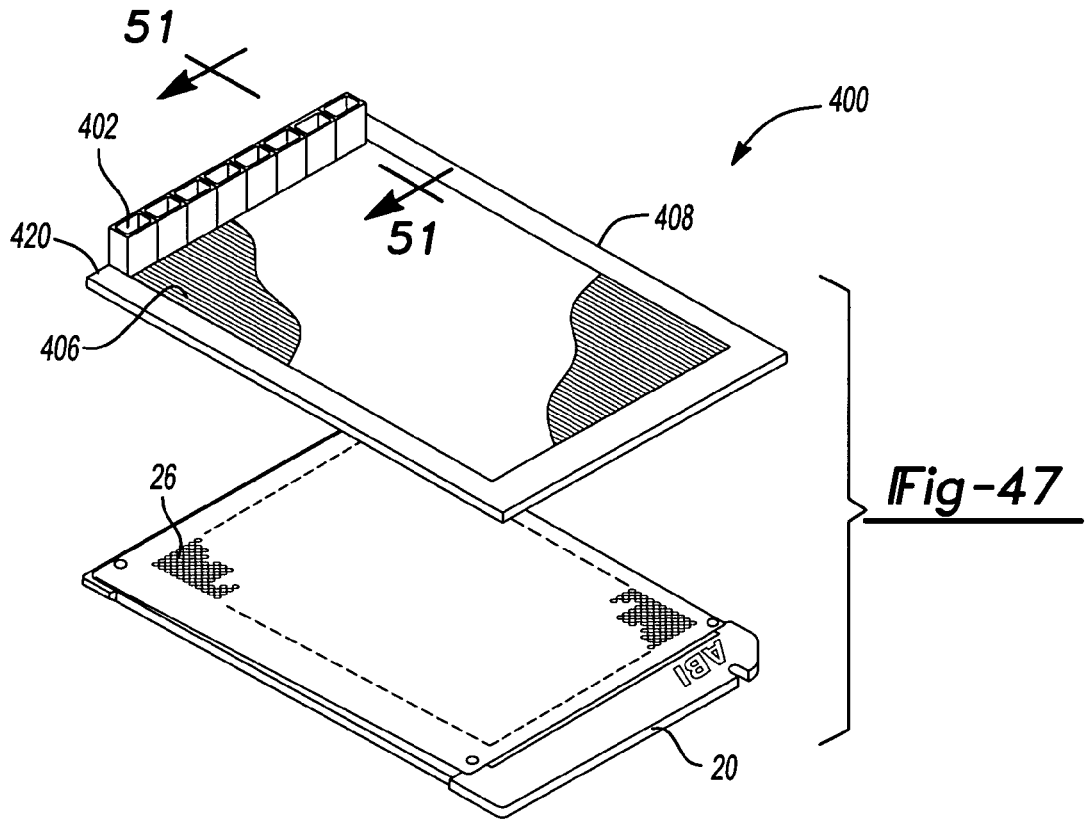
Figure 48:
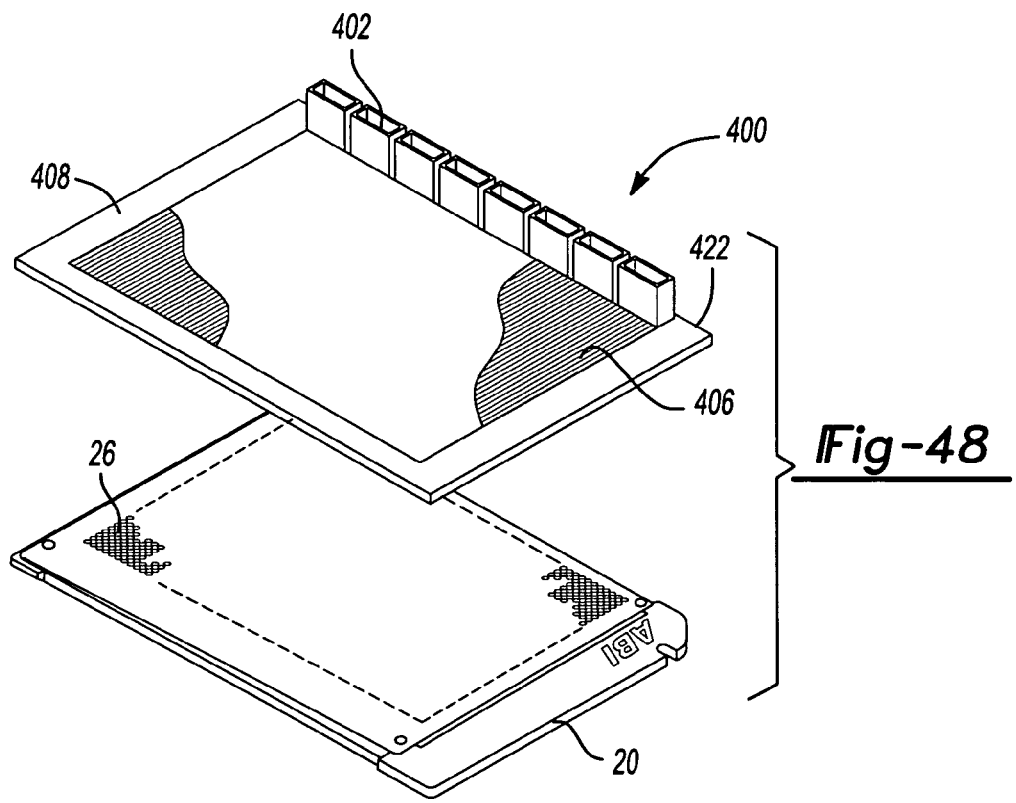
Figure 49:
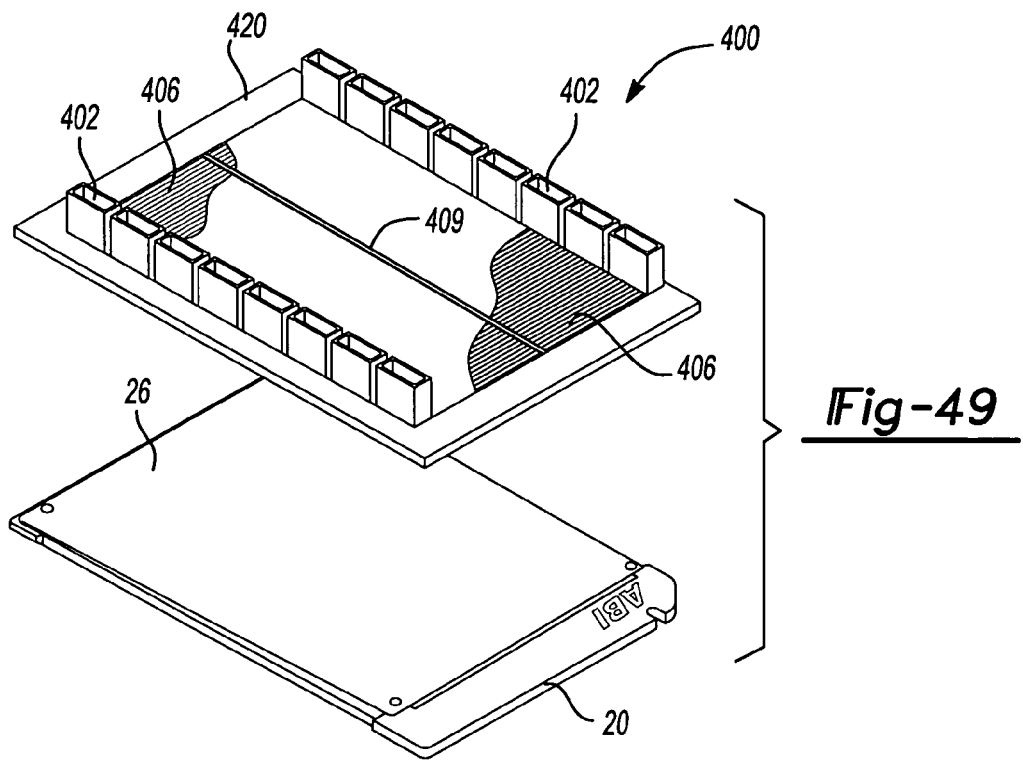
Figure 50:
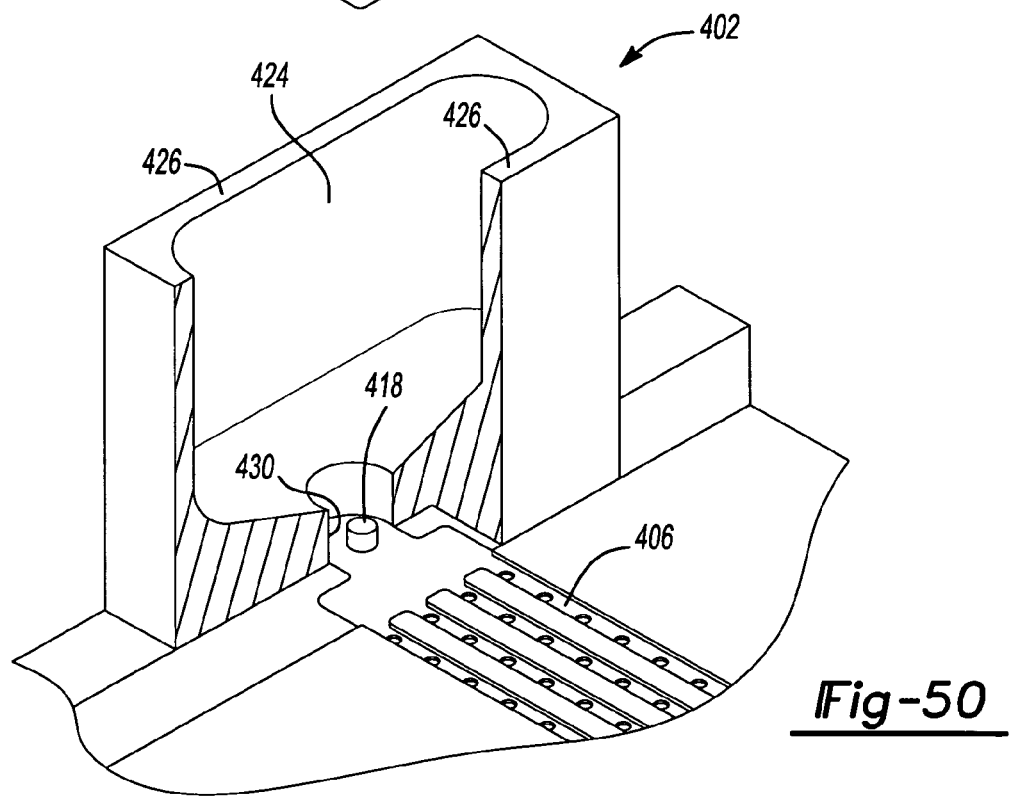
Figure 51:
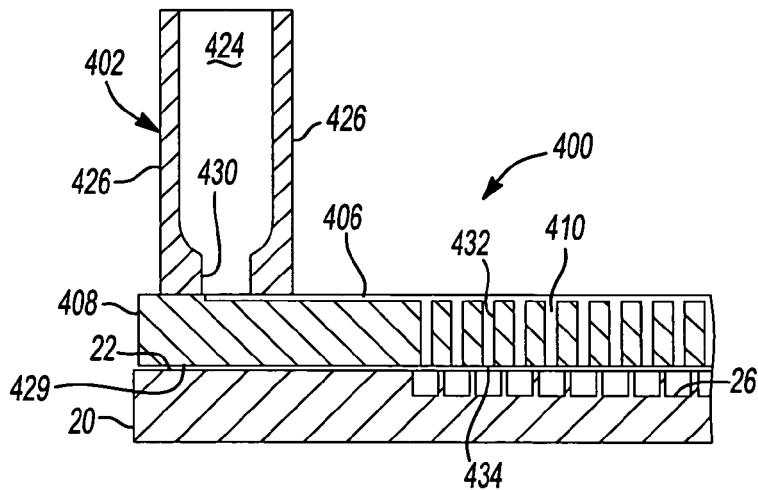
Figure 59:
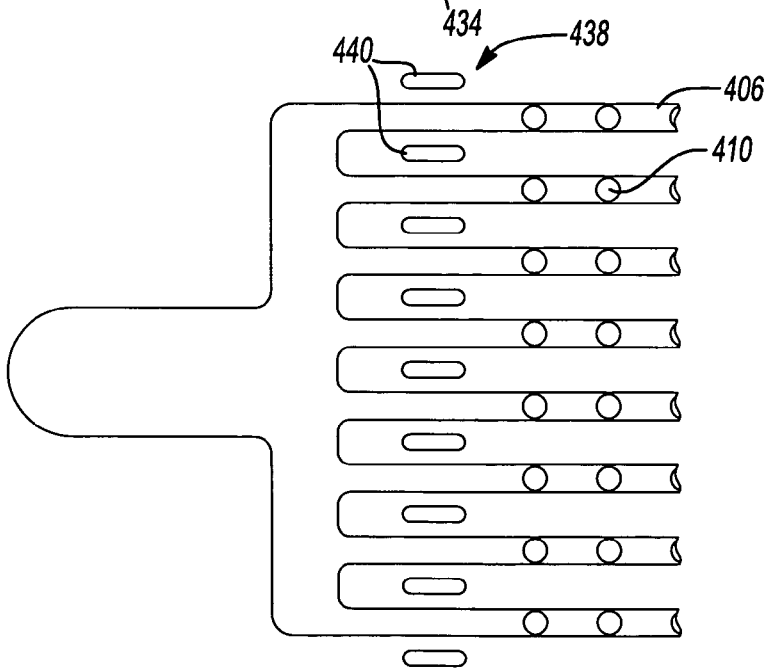
Figure 67:
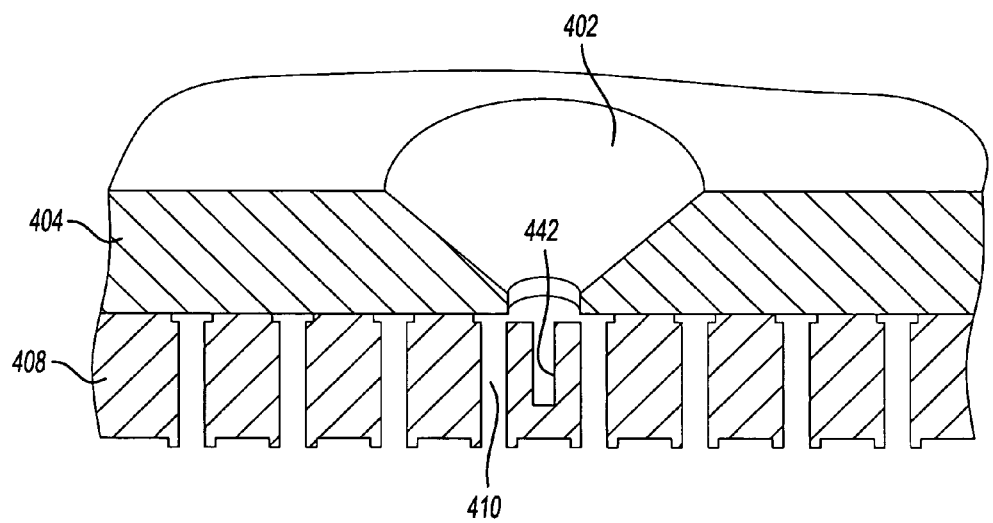
Figure 70:
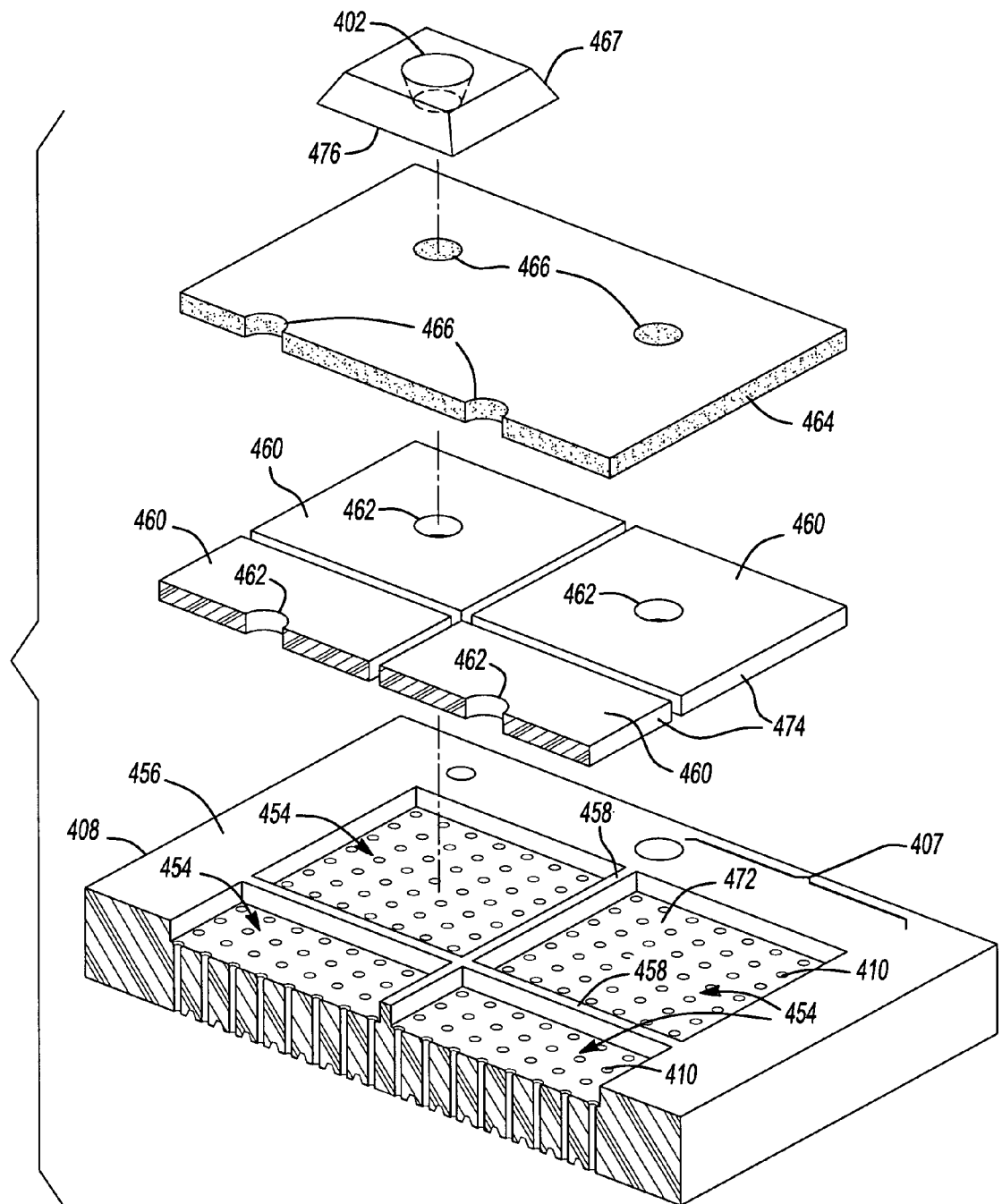
Figure 71:
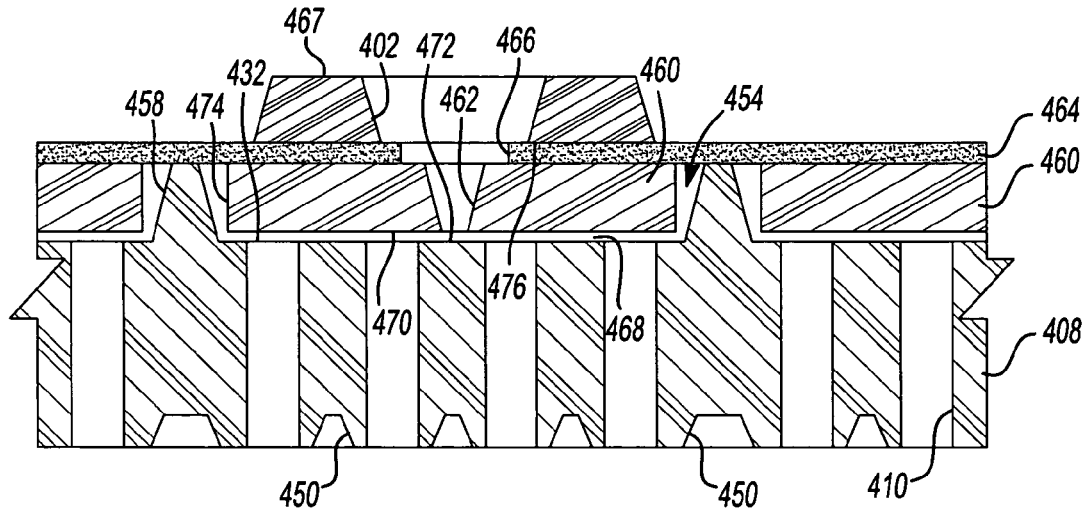
Figure 72:
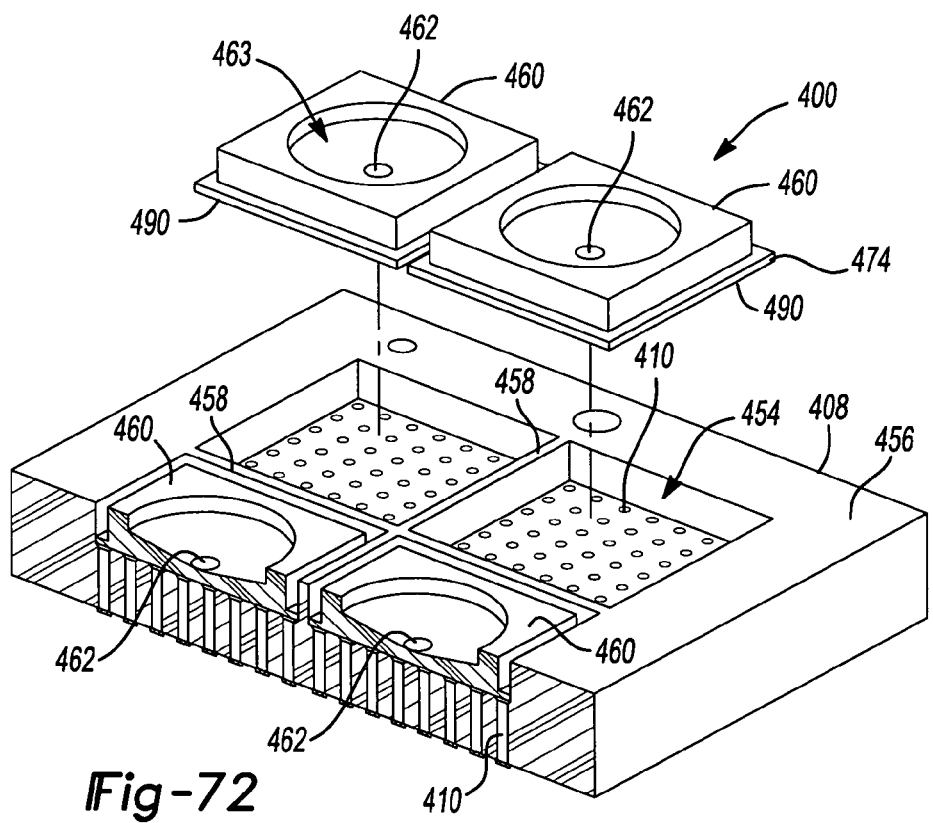
Figure 73:
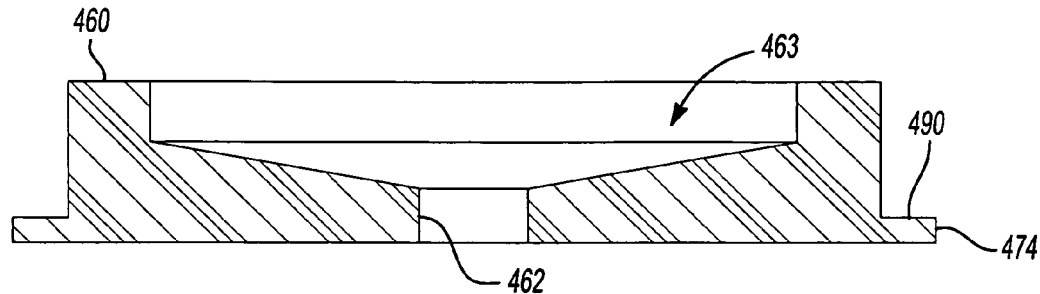
Figure 74:
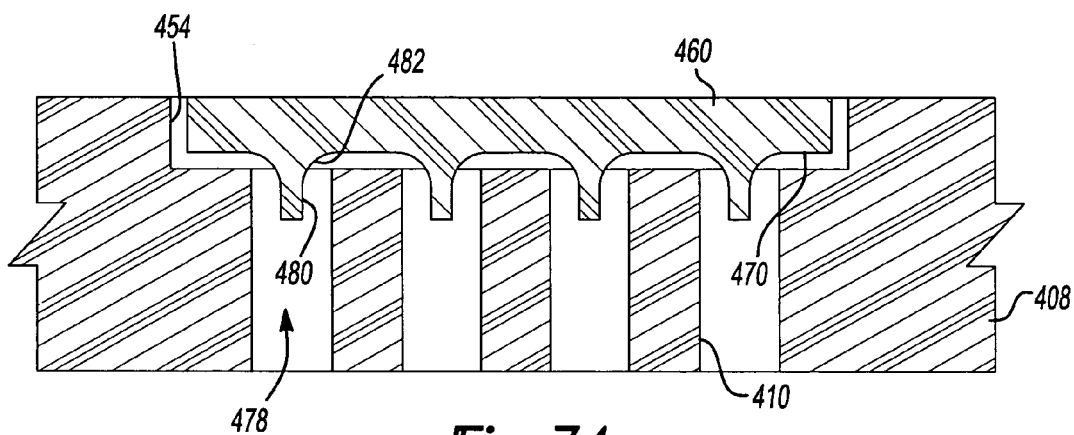
Figure 75:
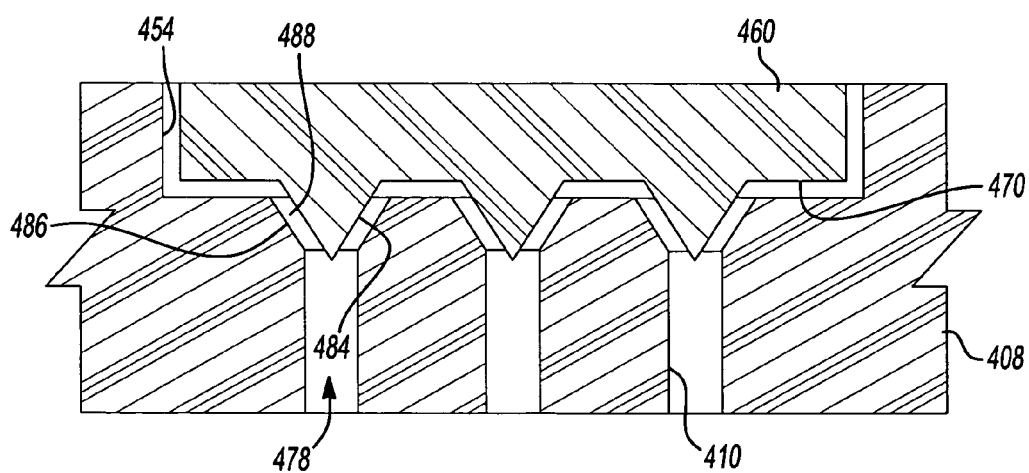
Figure 76:
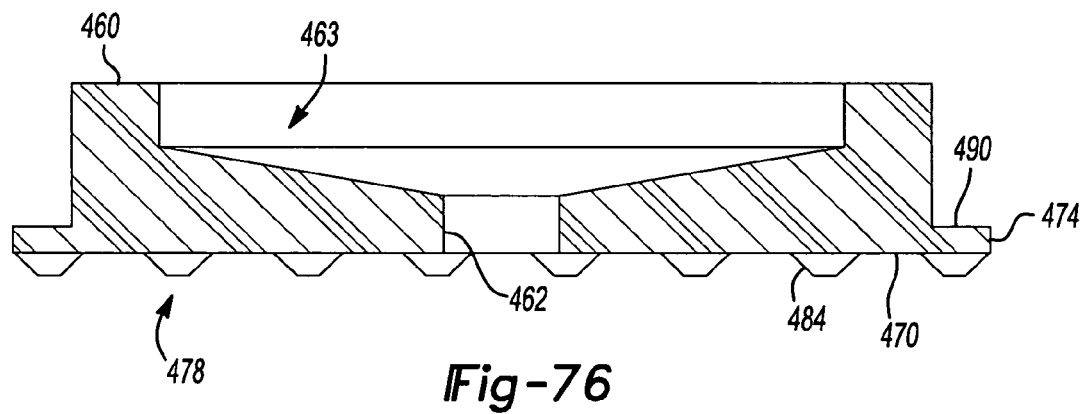
Figure 77:
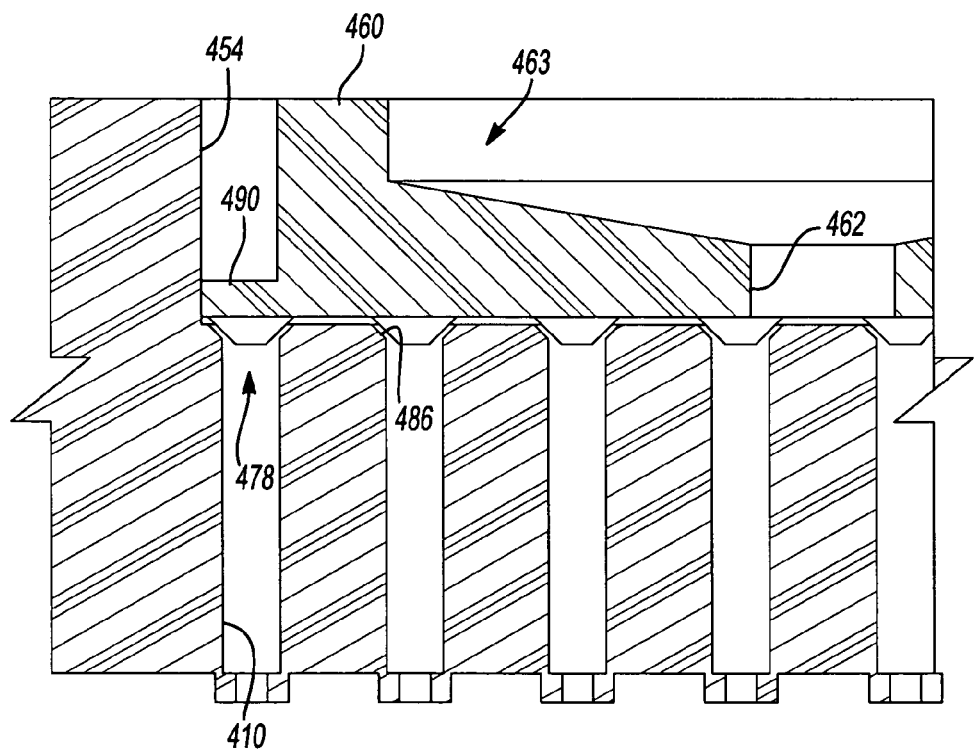
Figure 78:
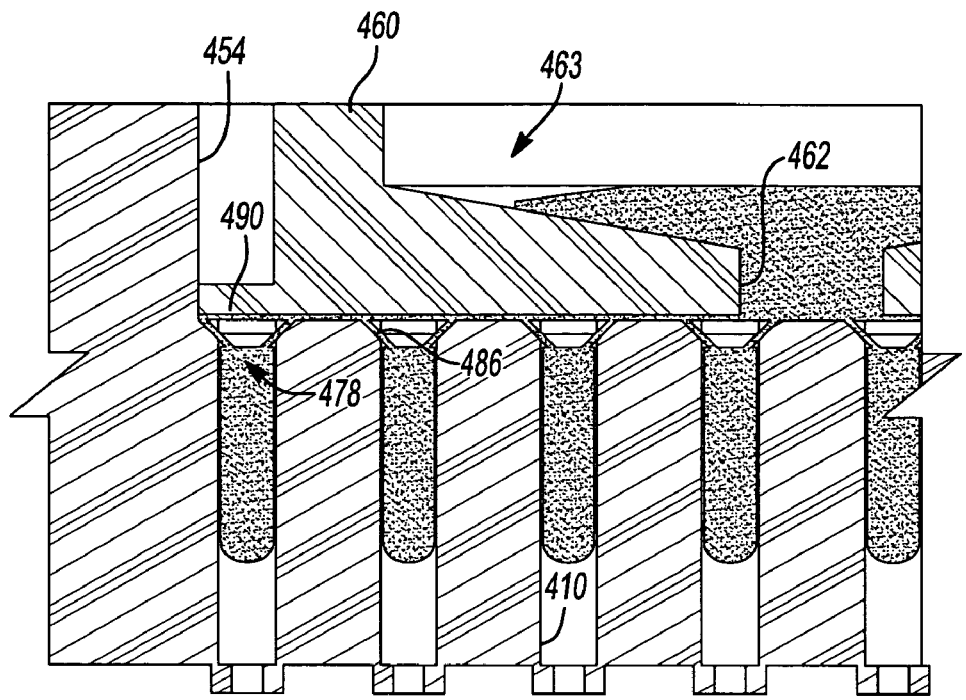
Figure 79:
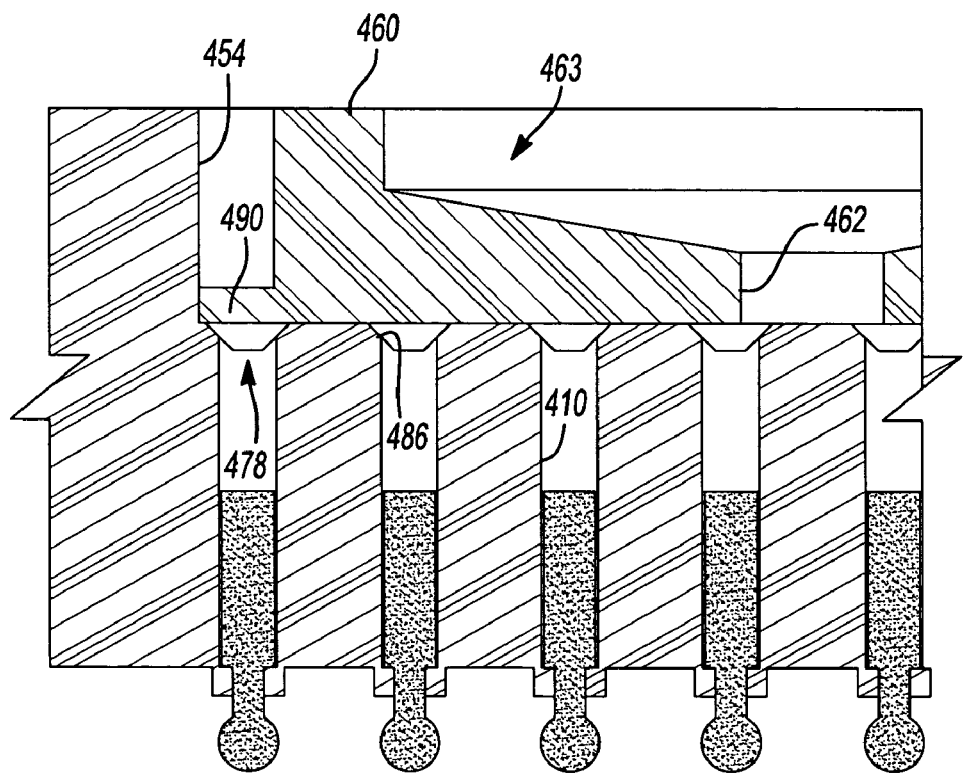
Figure 80:
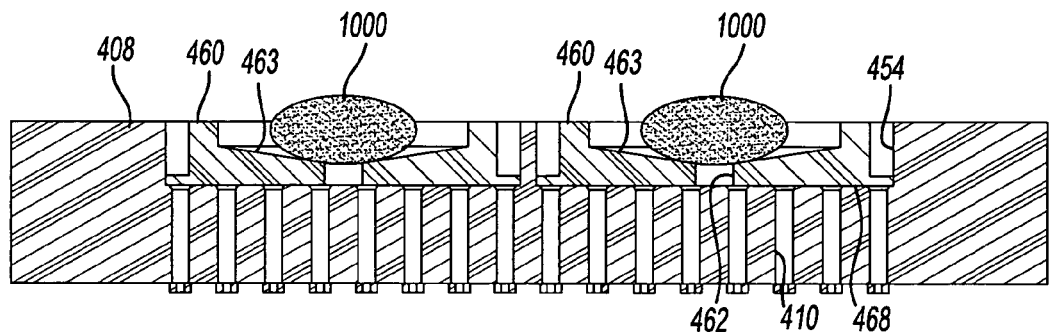
Figure 81:
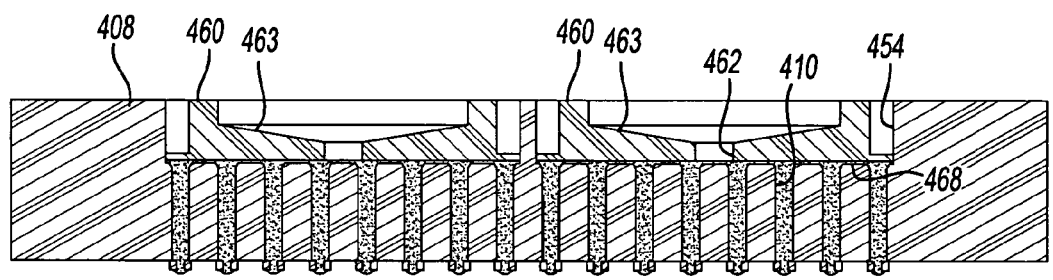
Figure 82:
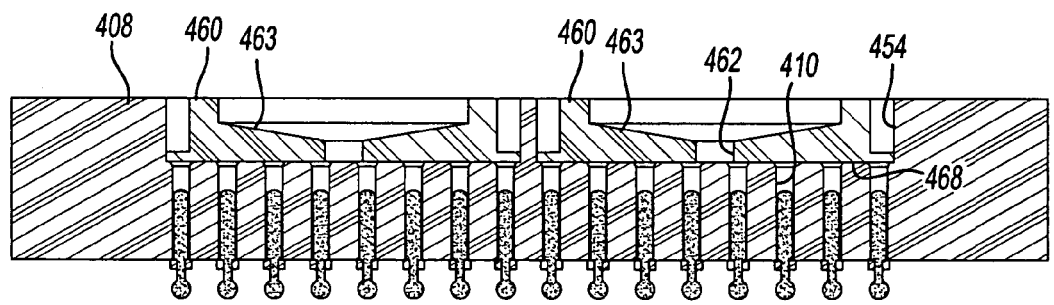
Figure 83:
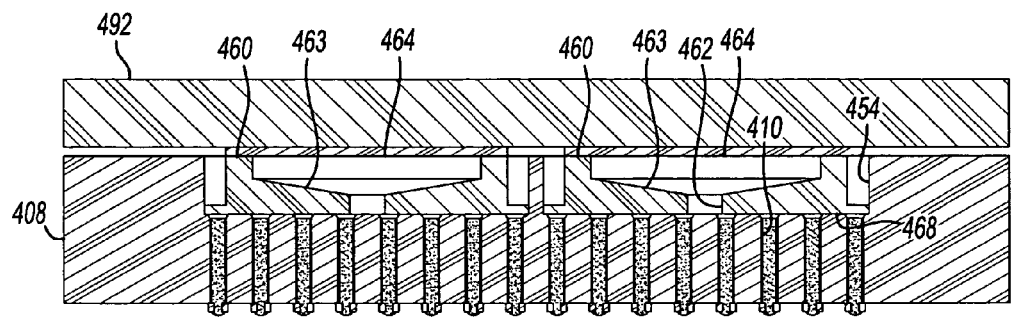
Figure 84:
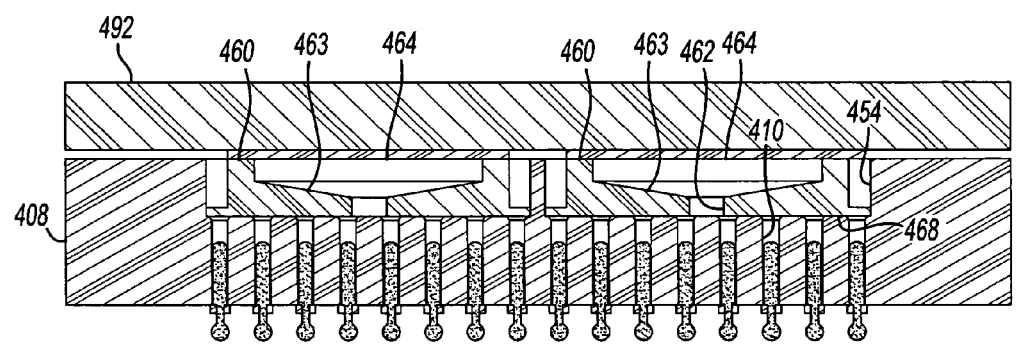
Figure 85:
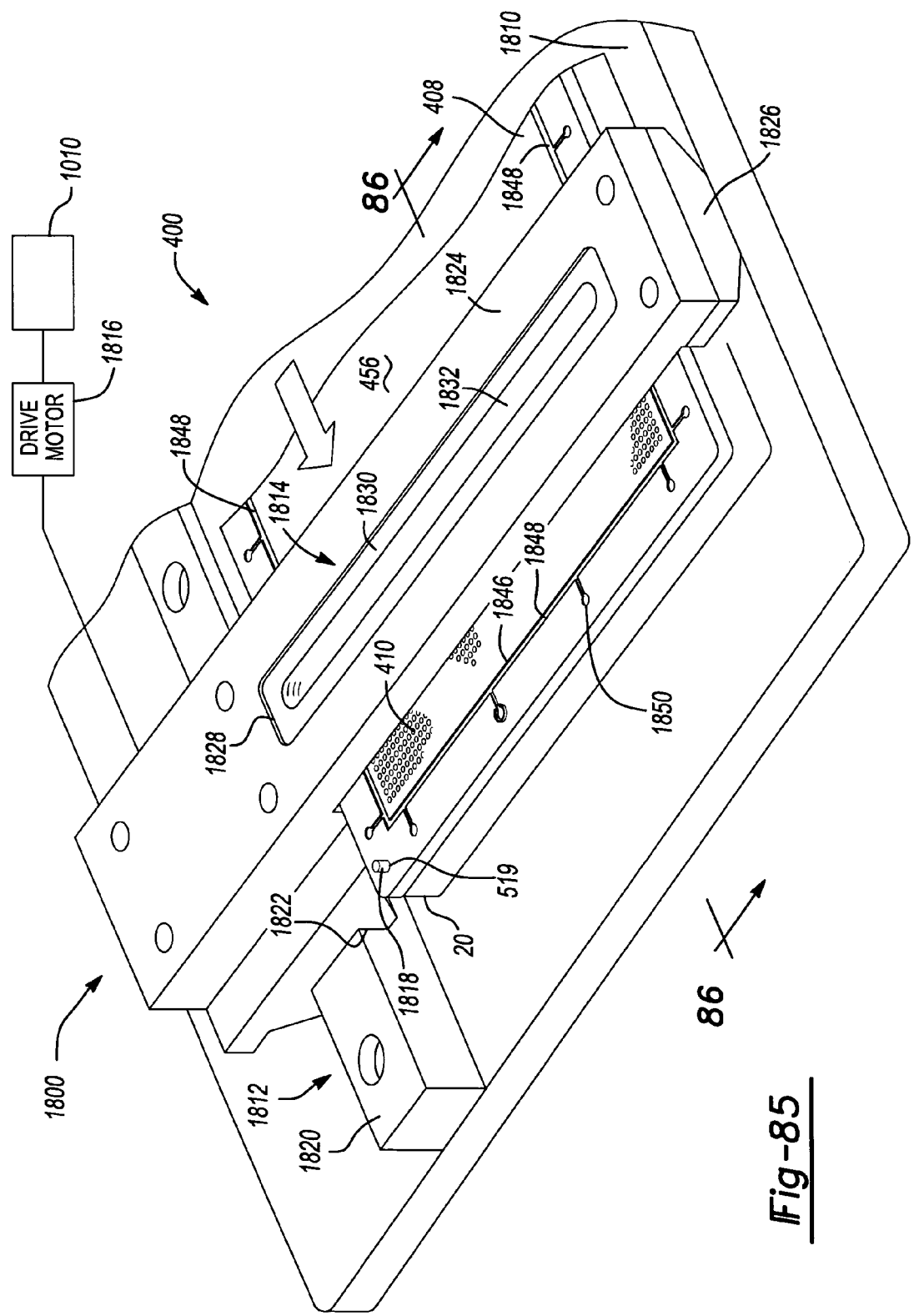
Figure 86:
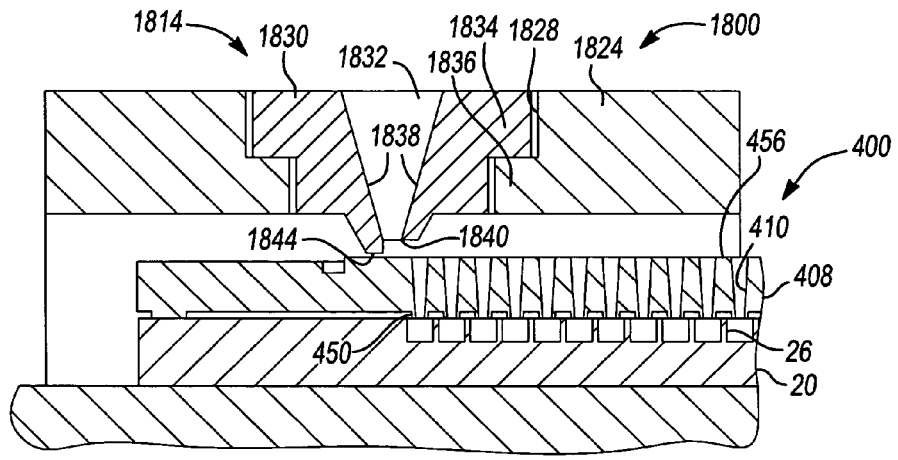
Figure 87:
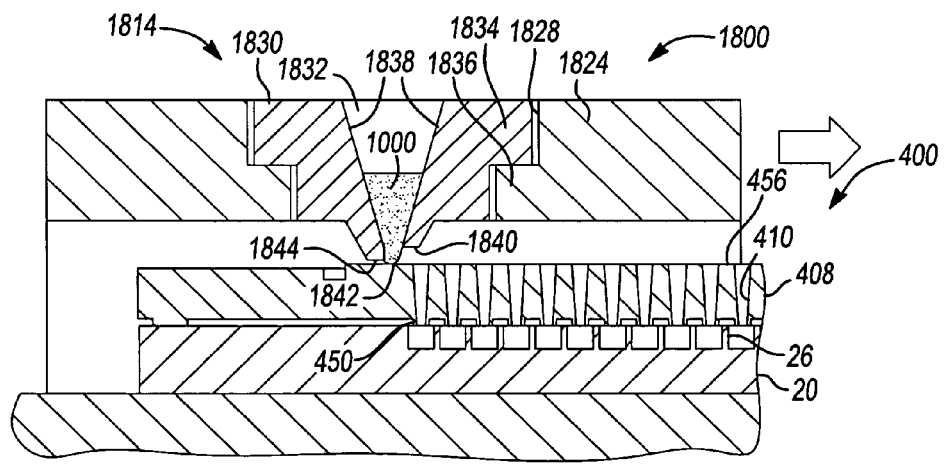
Figure 88:
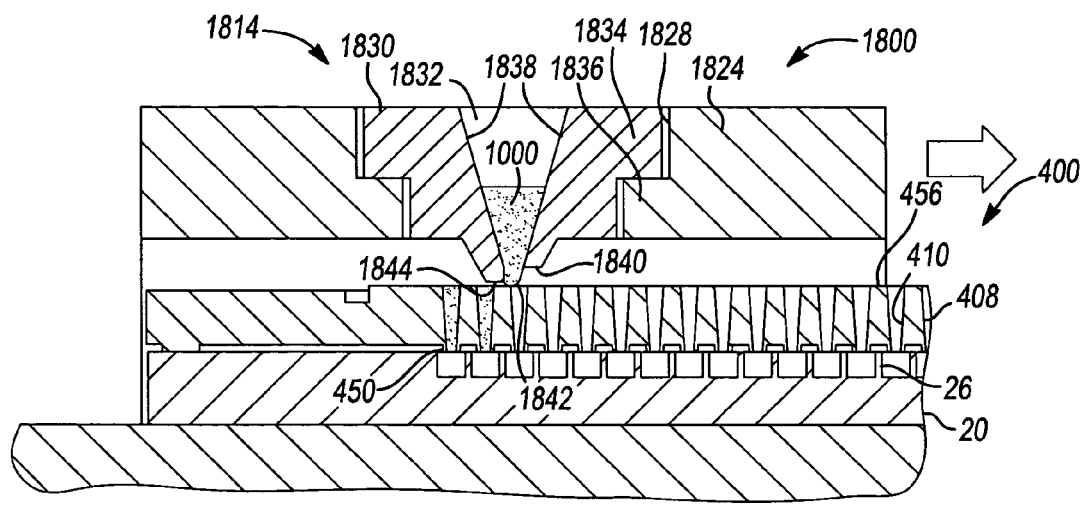
Figure 89:
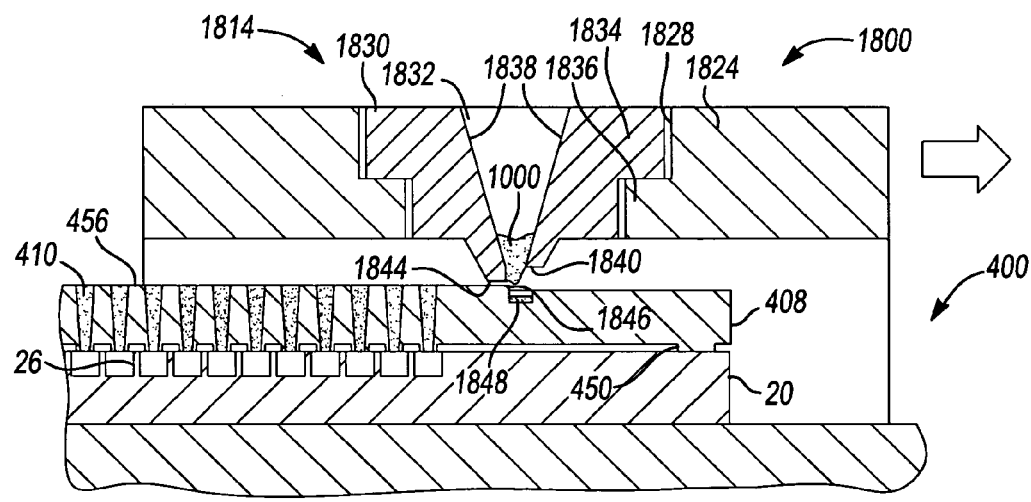
Figure 90:
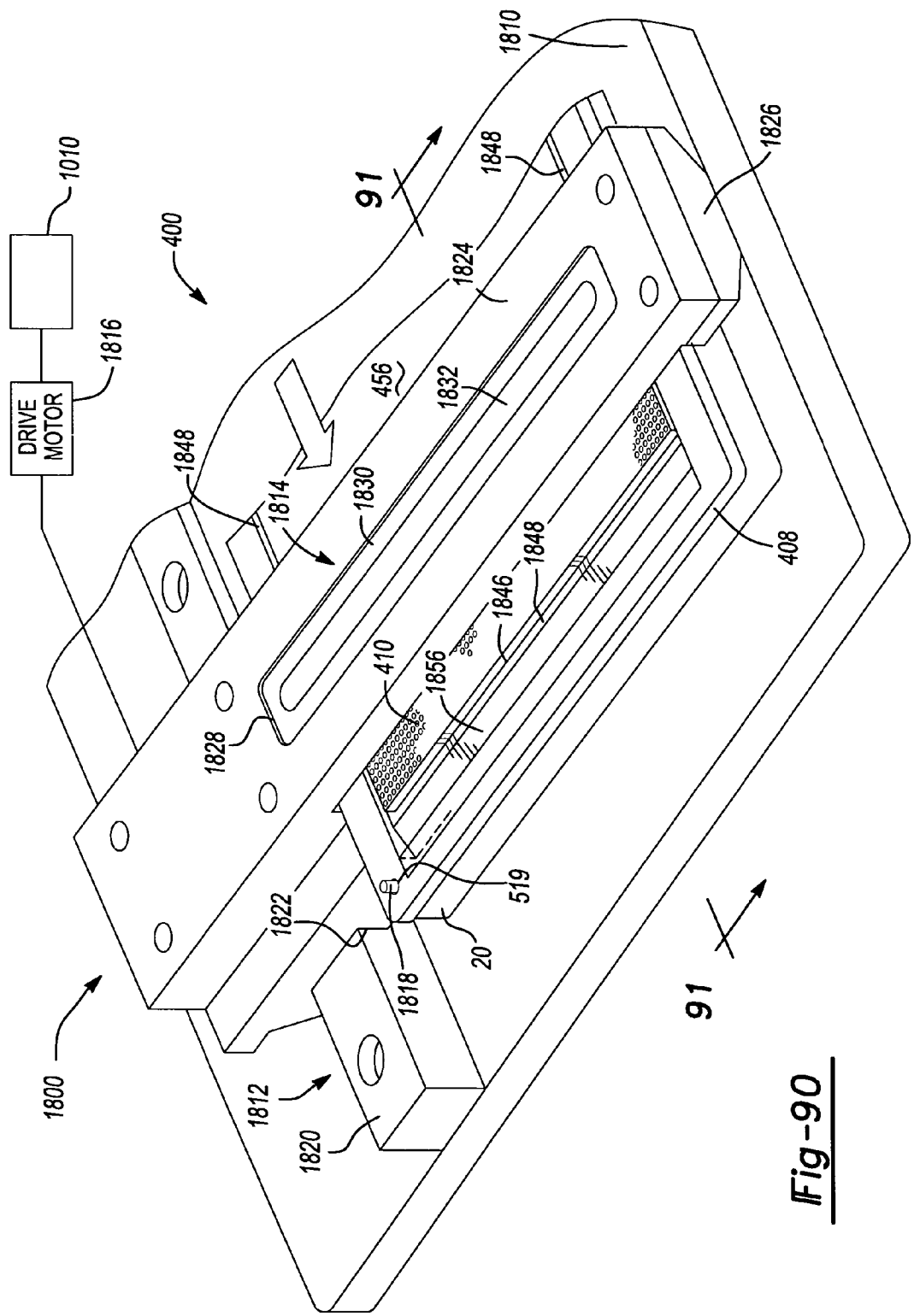
Figure 91:
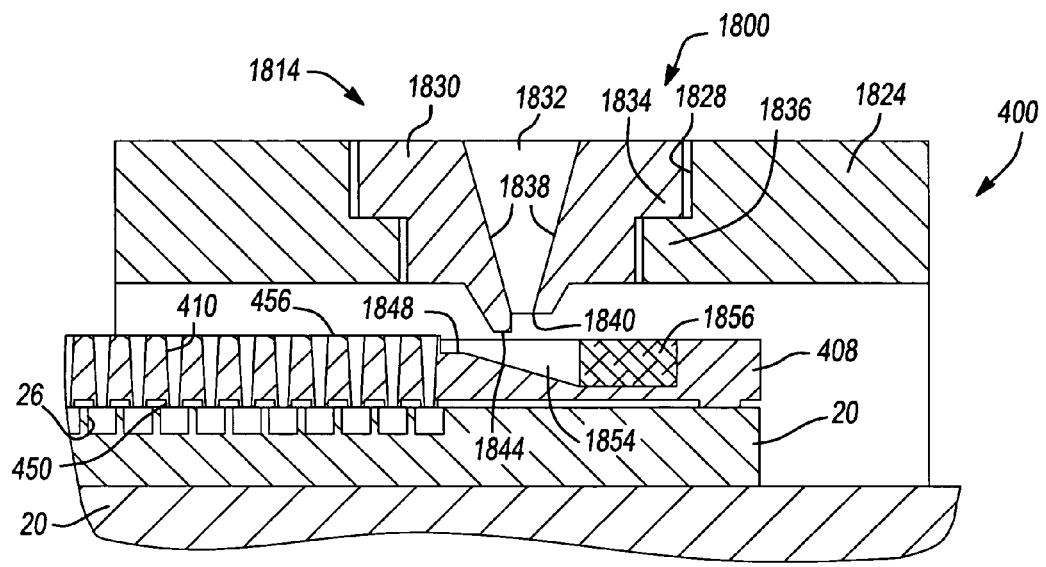
Figure 92:
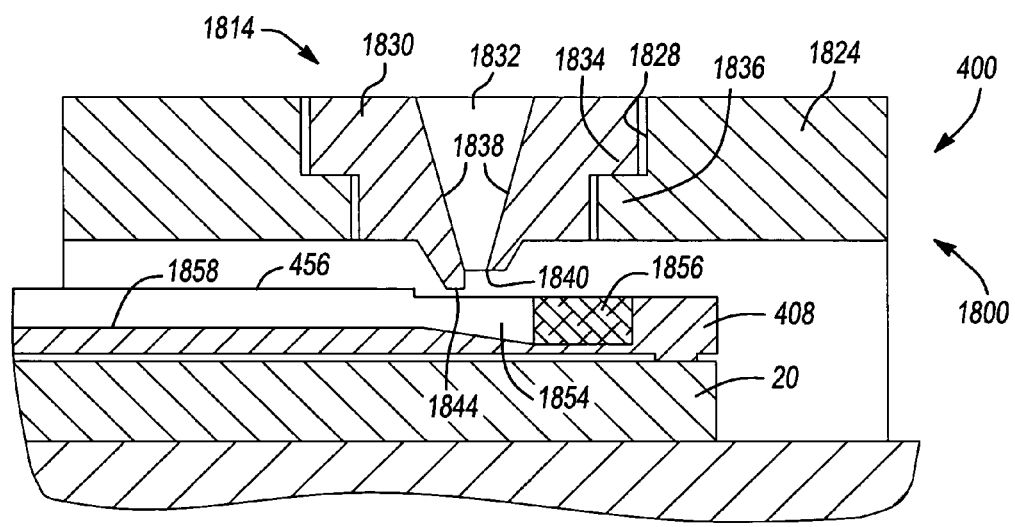
Figure 93:
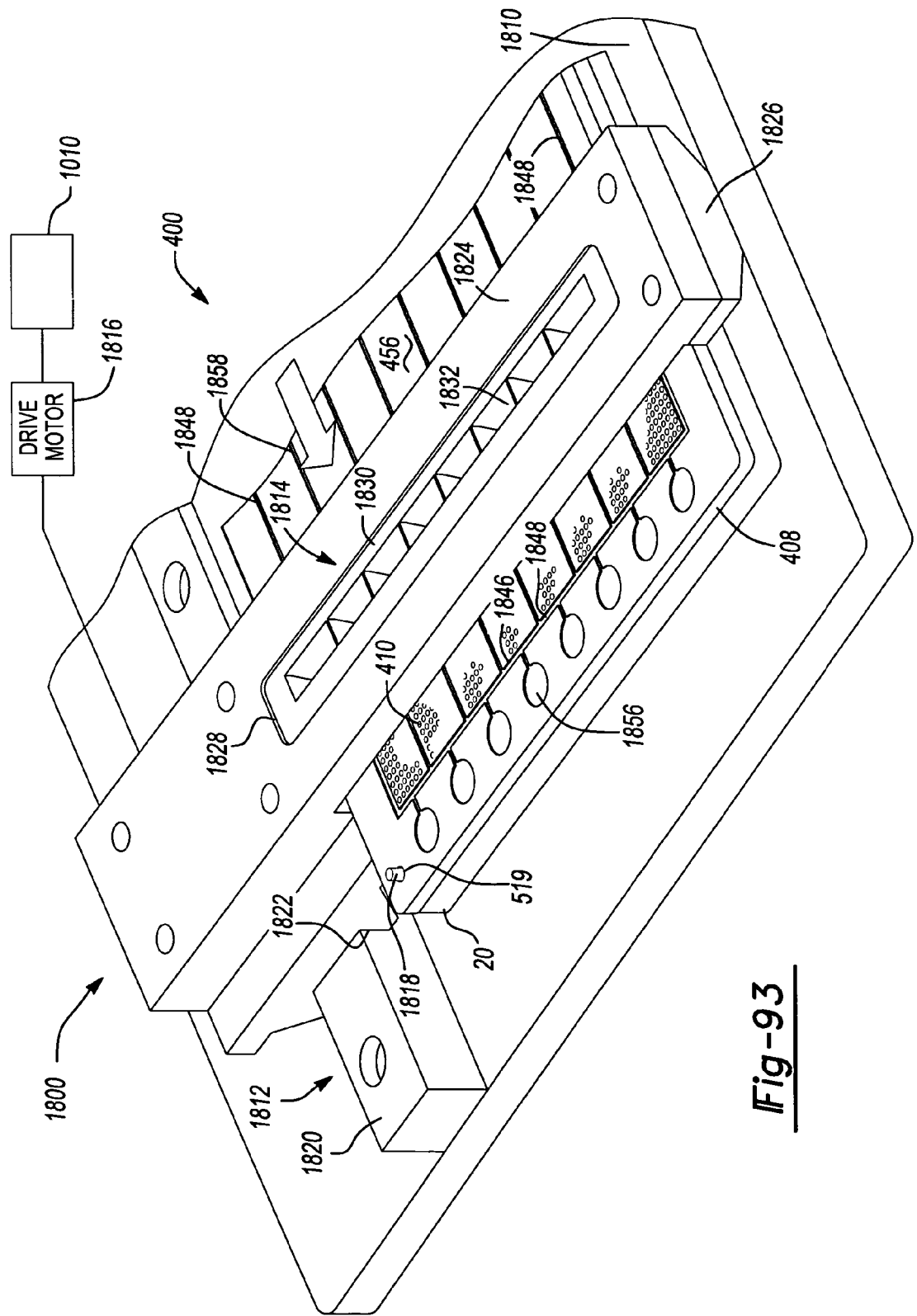
Figure 94:
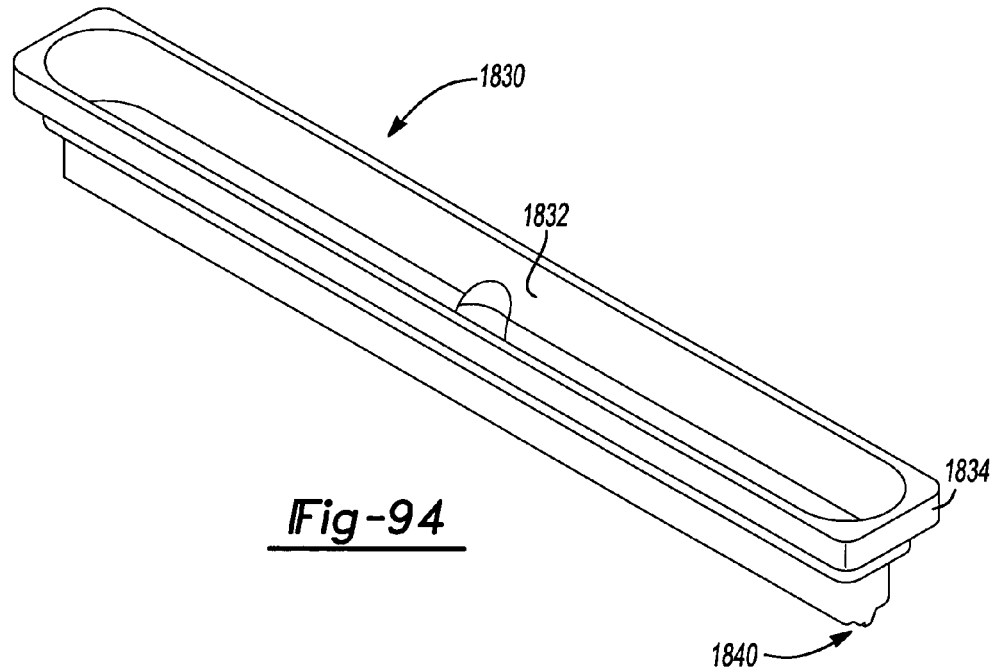
Figure 95:
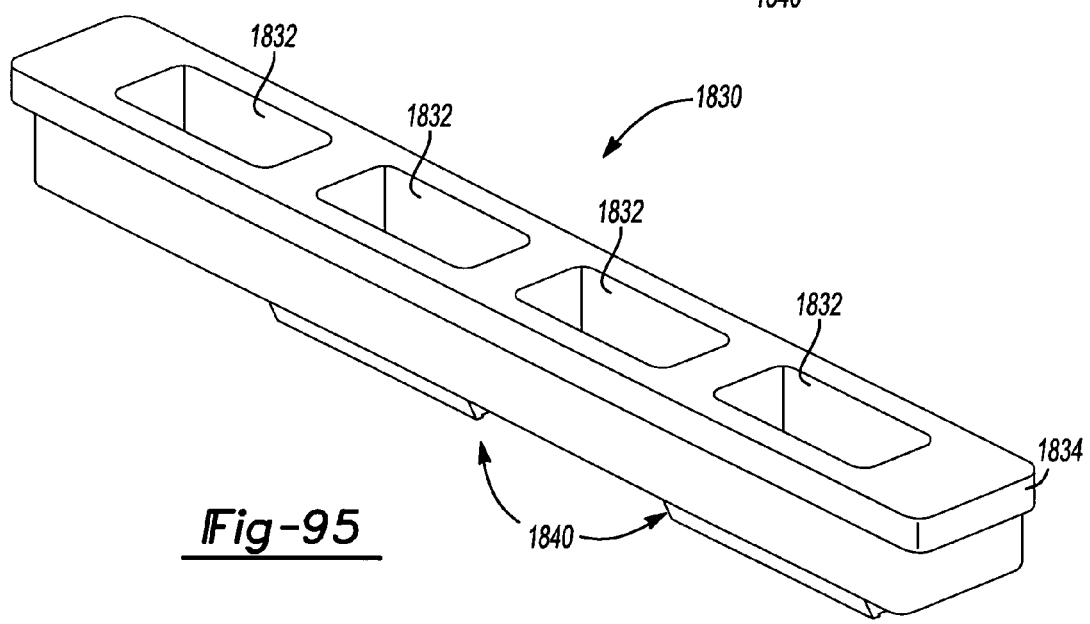
Figure 96:
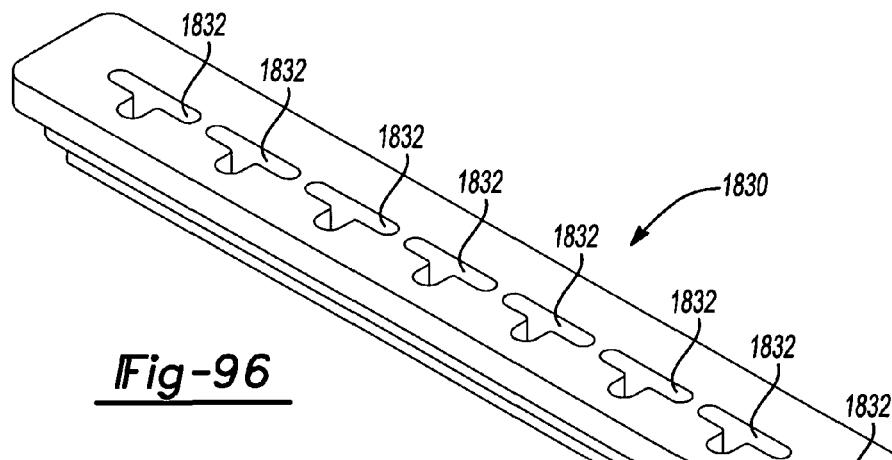
Figure 97:
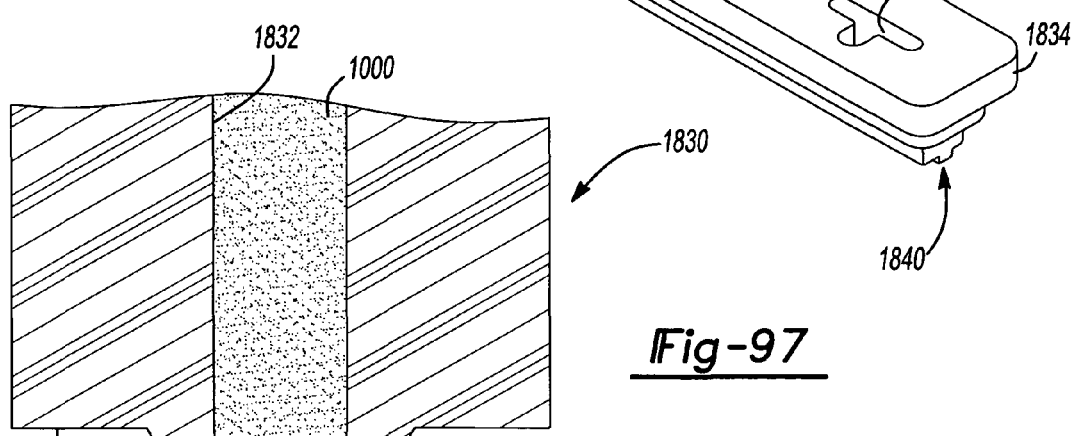
Figure 98:
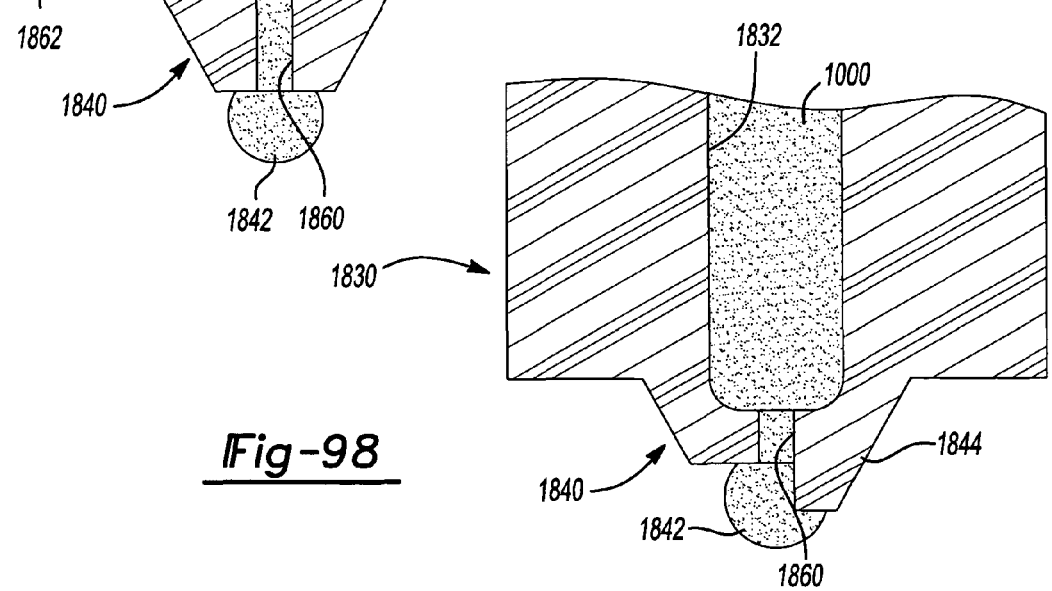
Figure 99:
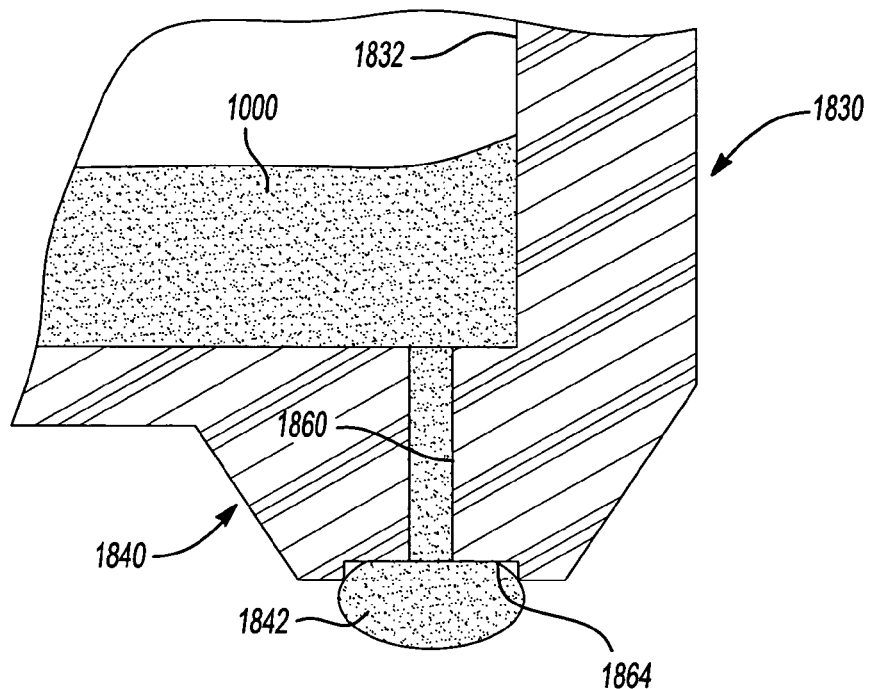
Figure 100:
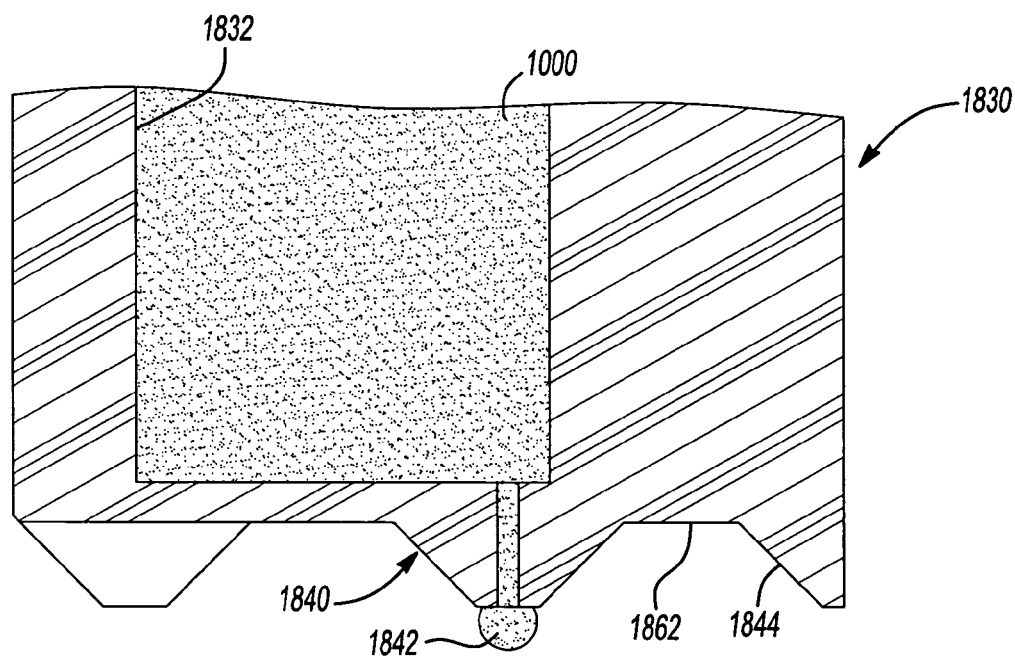
Figure 101:
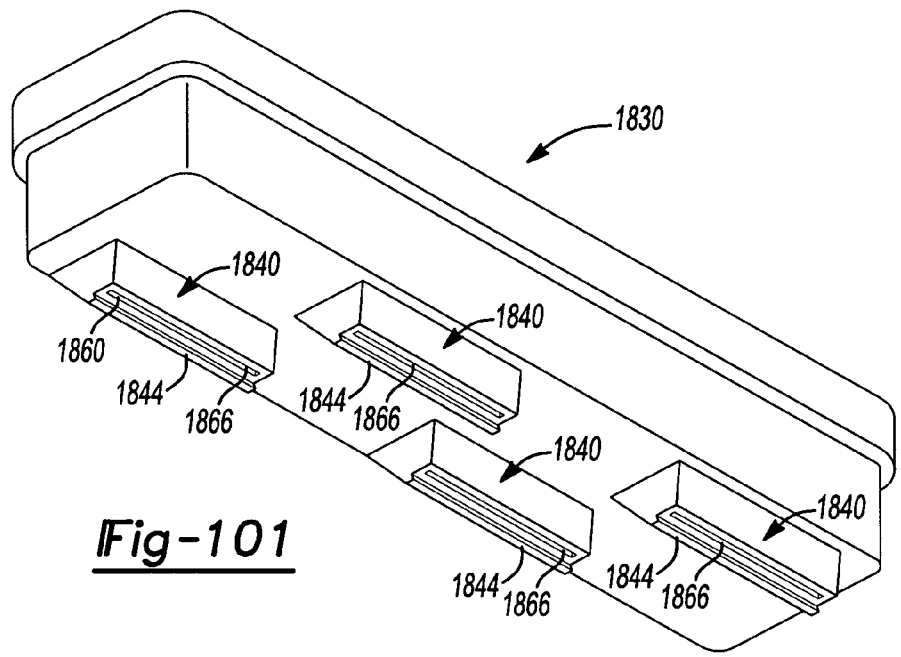
Figure 102:
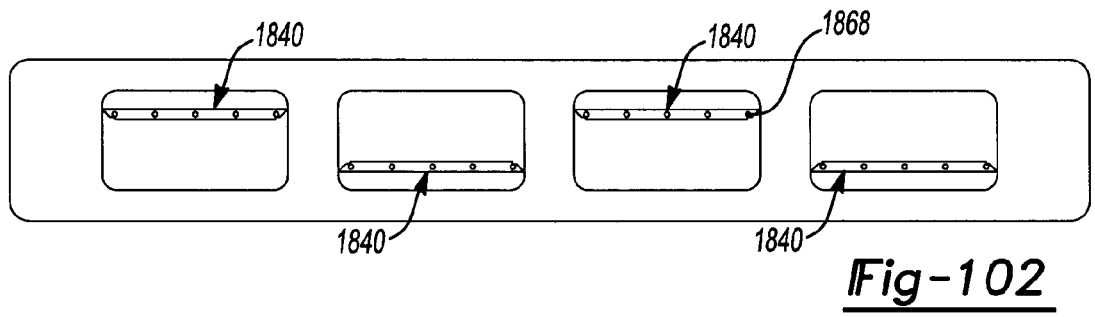
Figure 103:
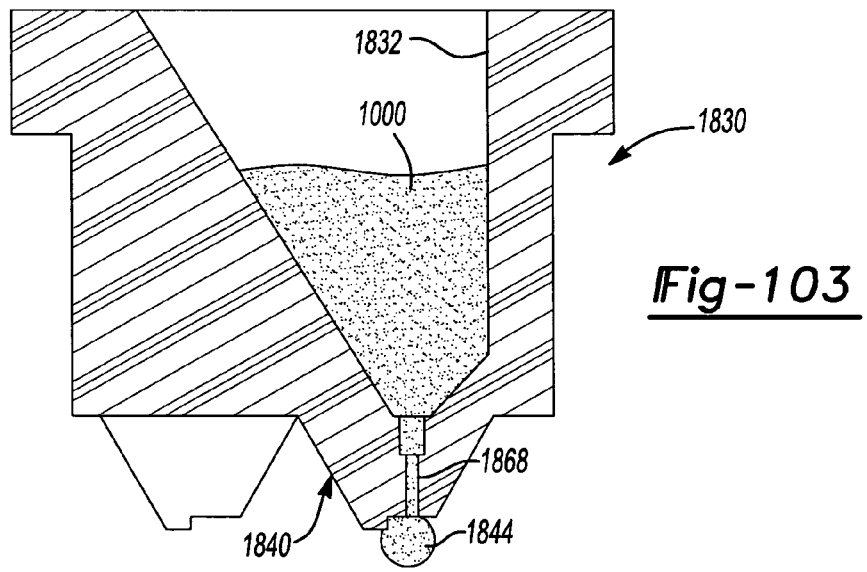
Figure 104:
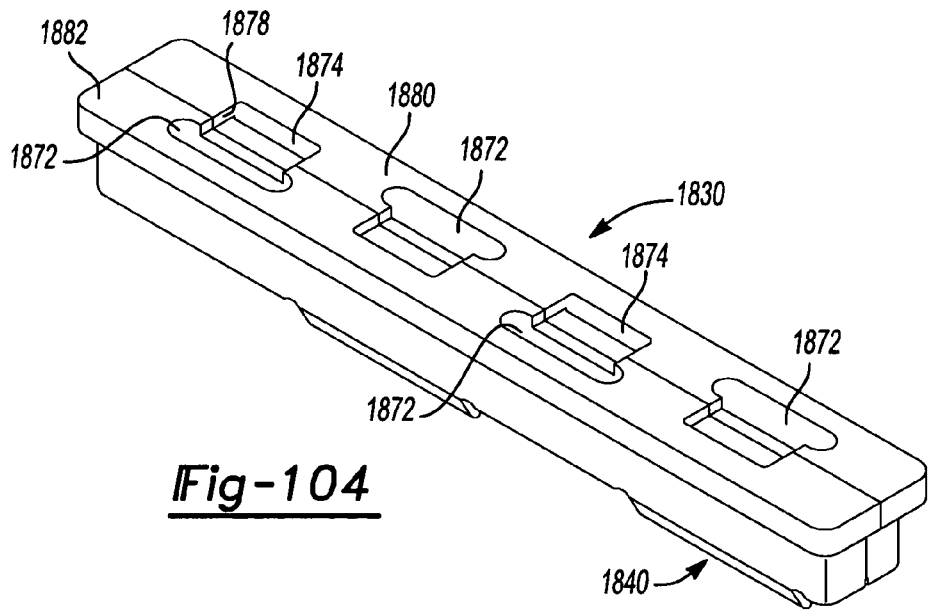
Figure 105:
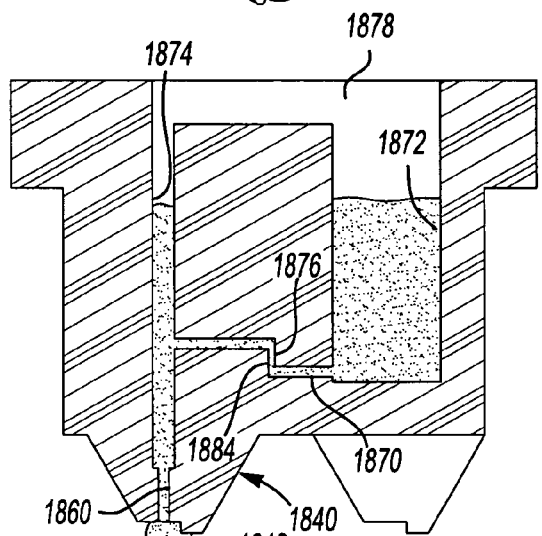
Figure 106:
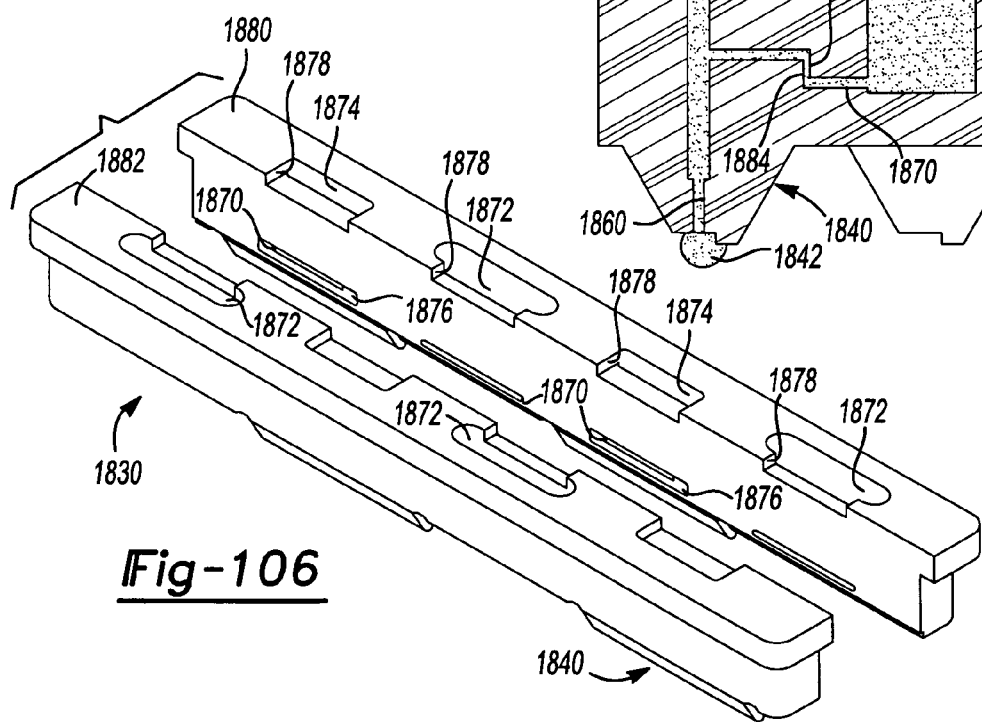
Figure 107:
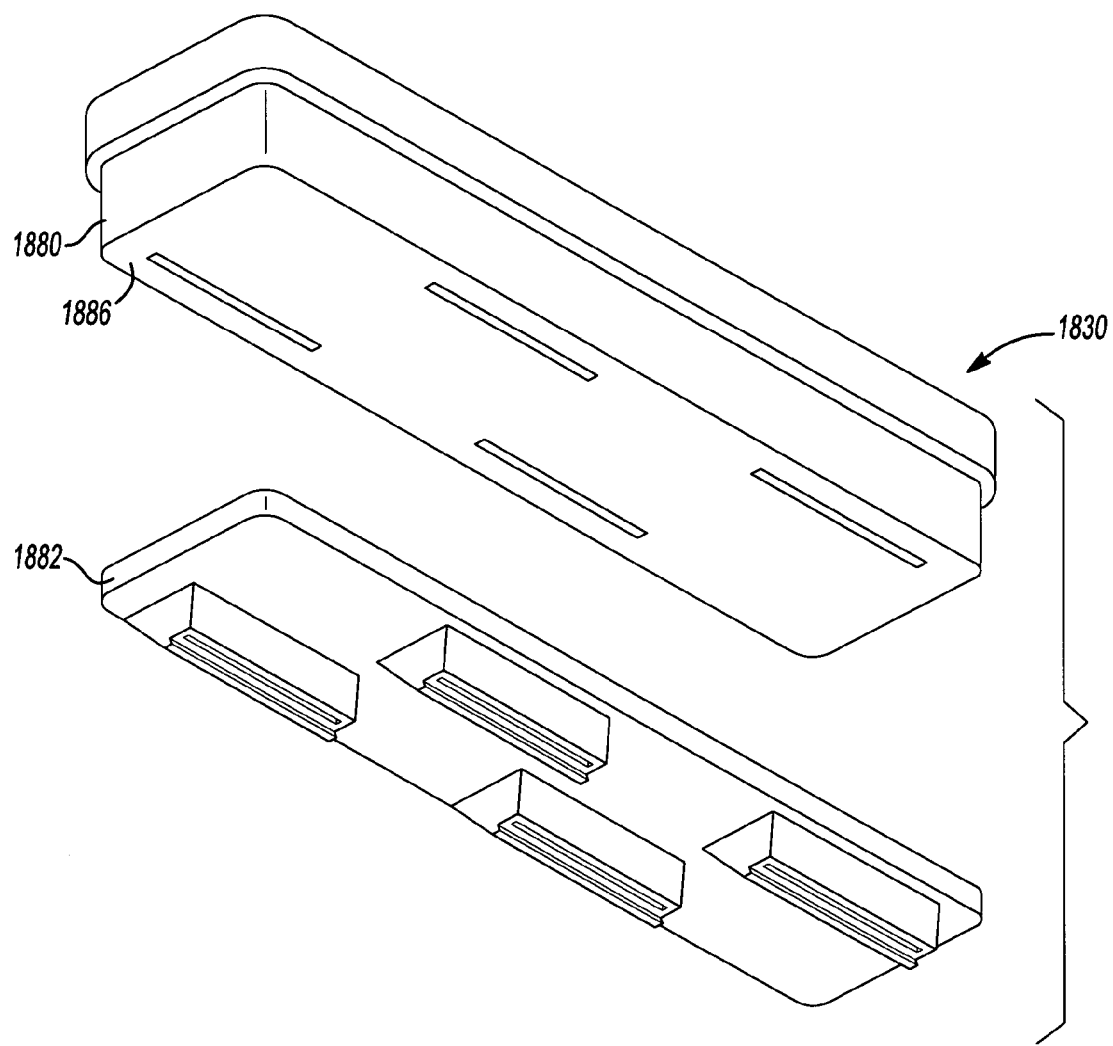
Figure 108:
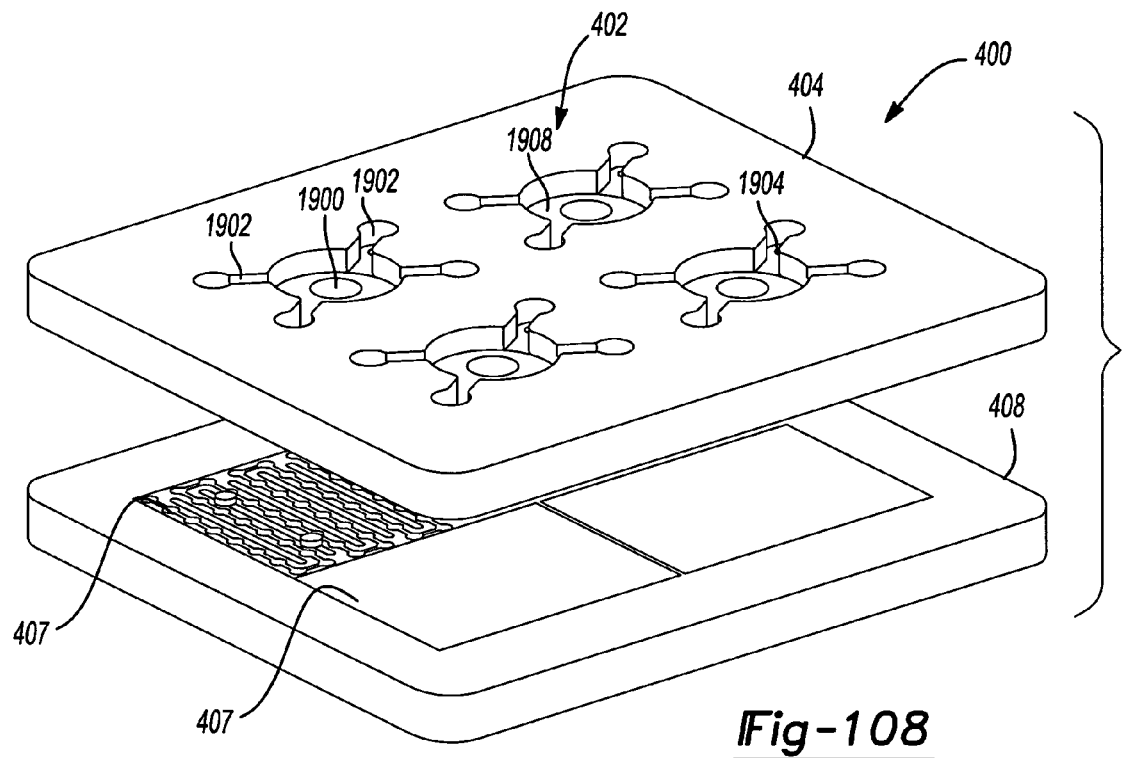
Figure 109:
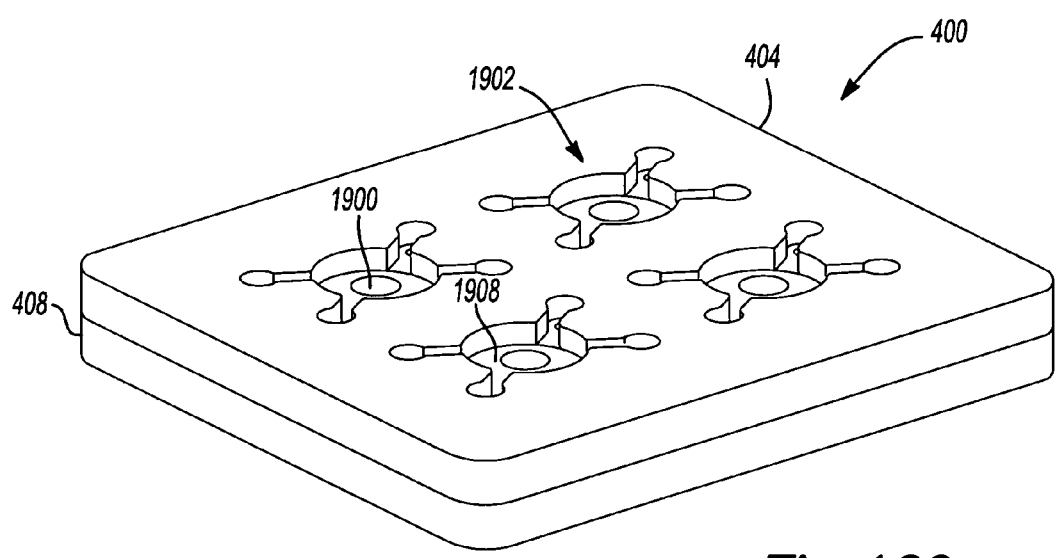
Figure 120:
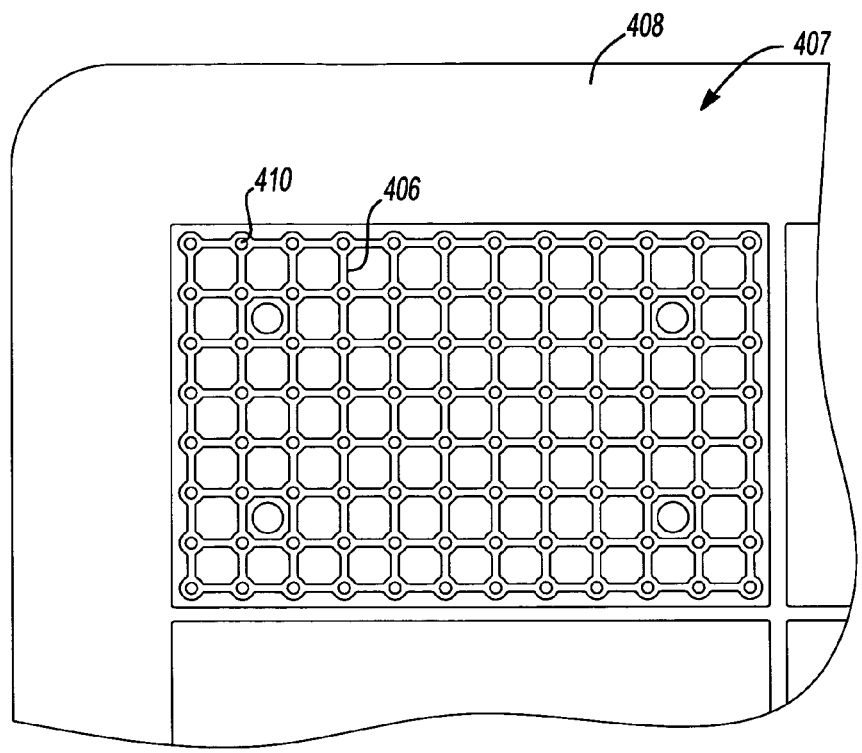
Figure 121:
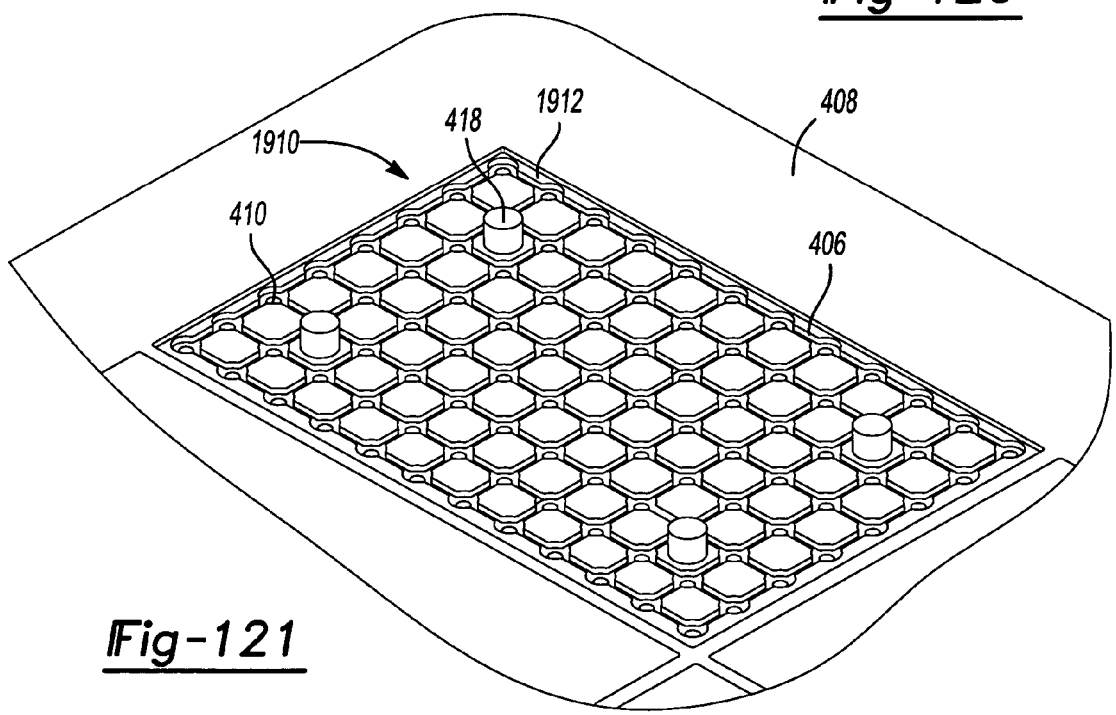
Figure 122:
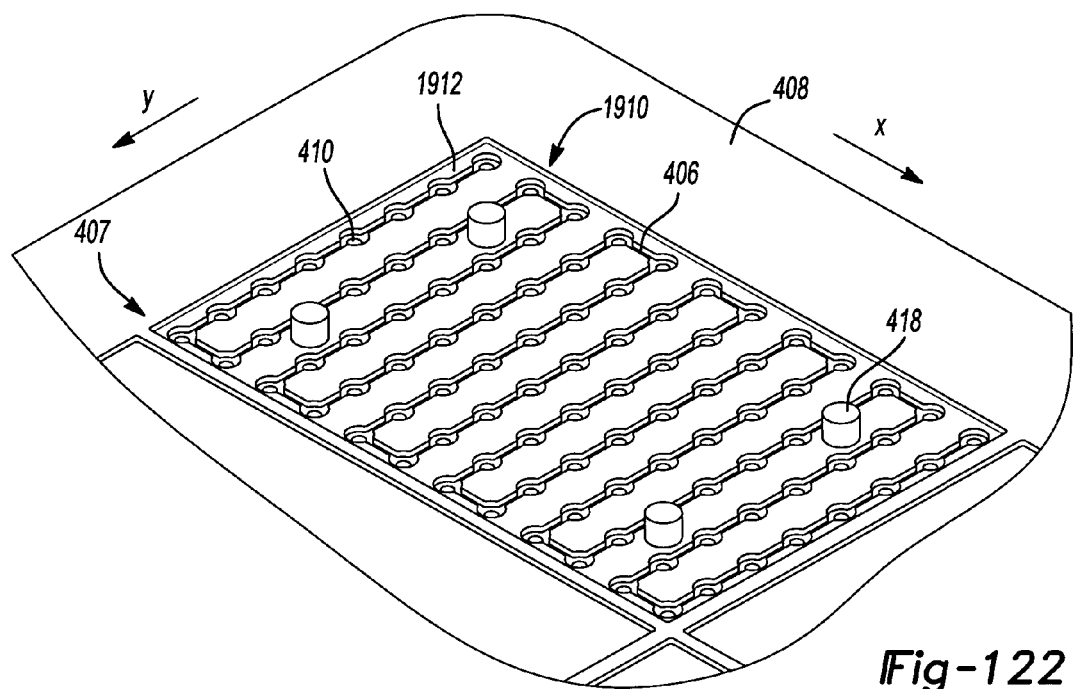
Figure 123:
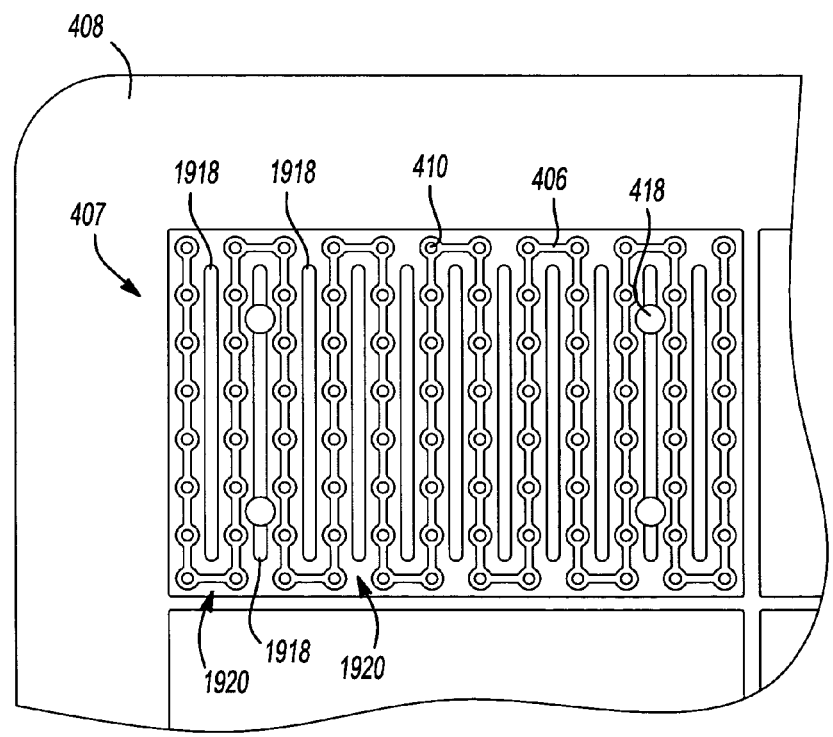
Figure 124:
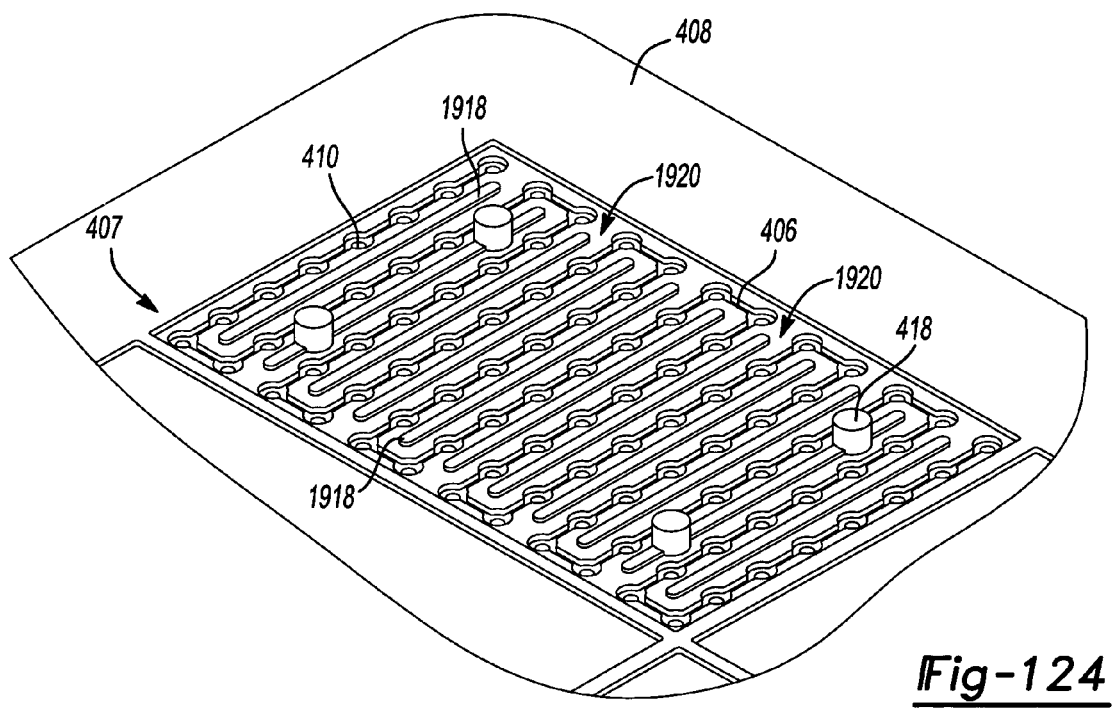
Figure 125:
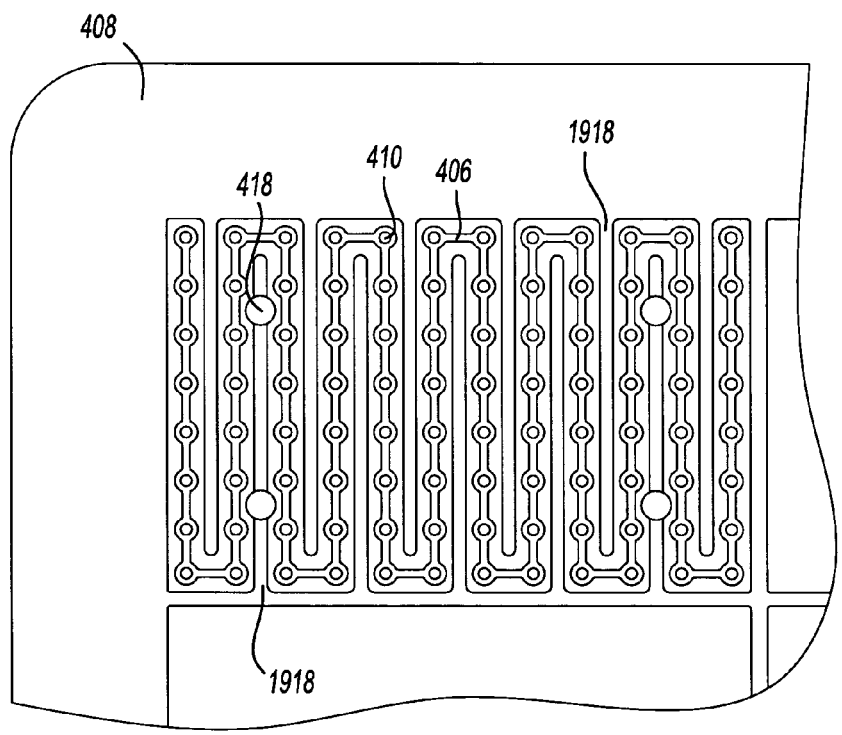
Figure 126:
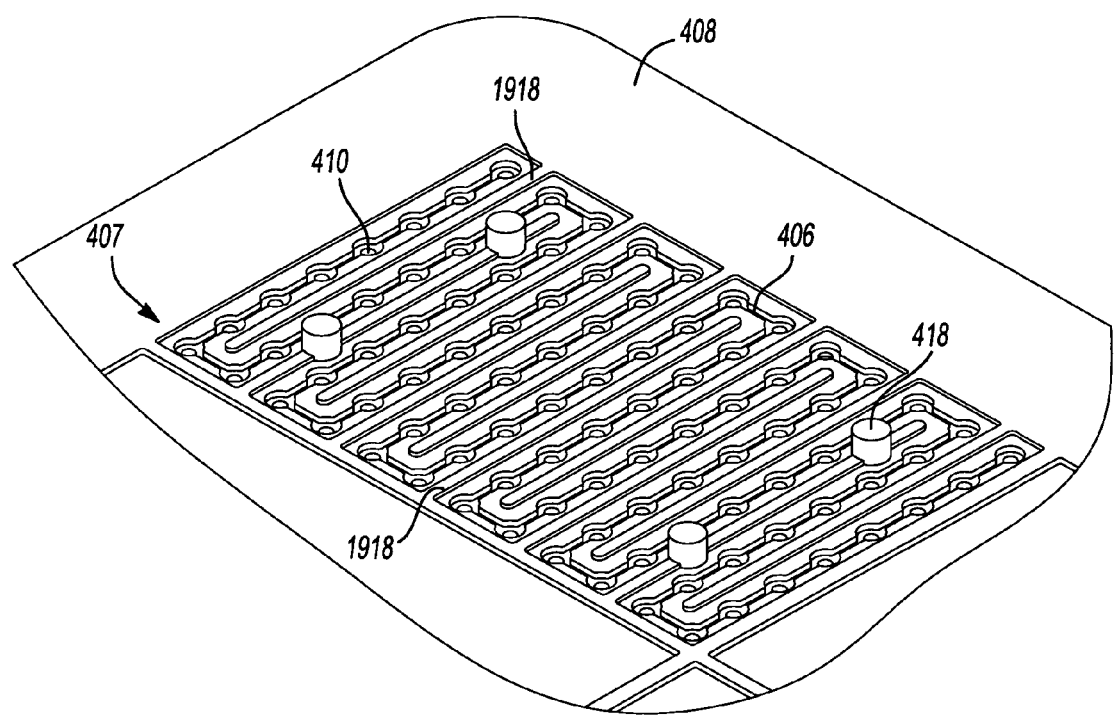
Figure 127:
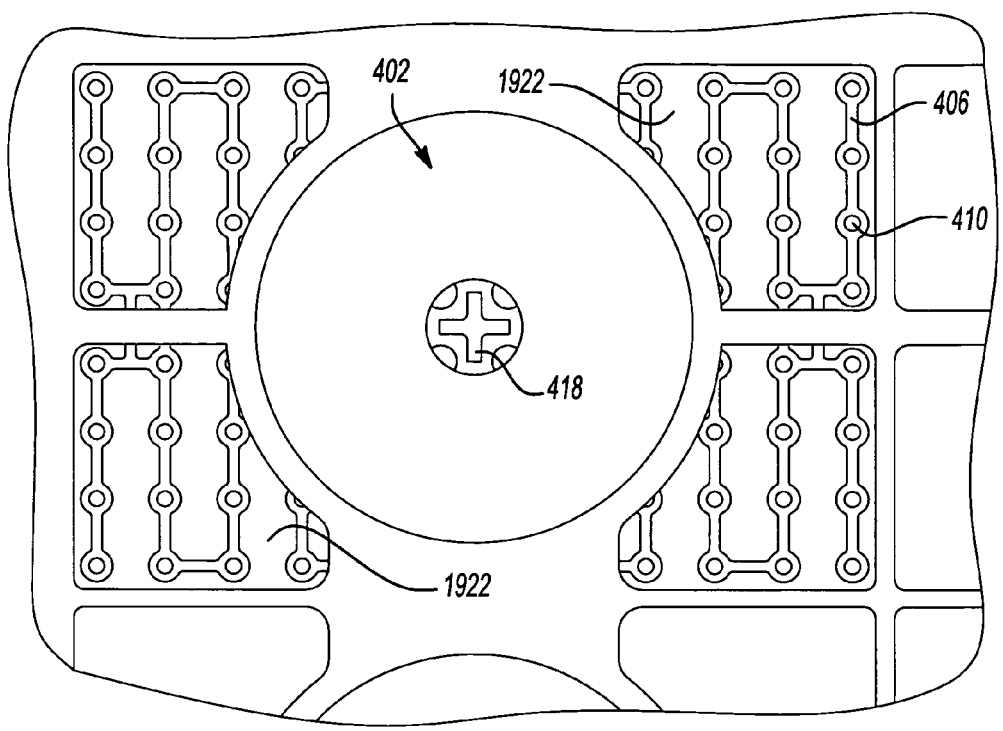
Figure 128:
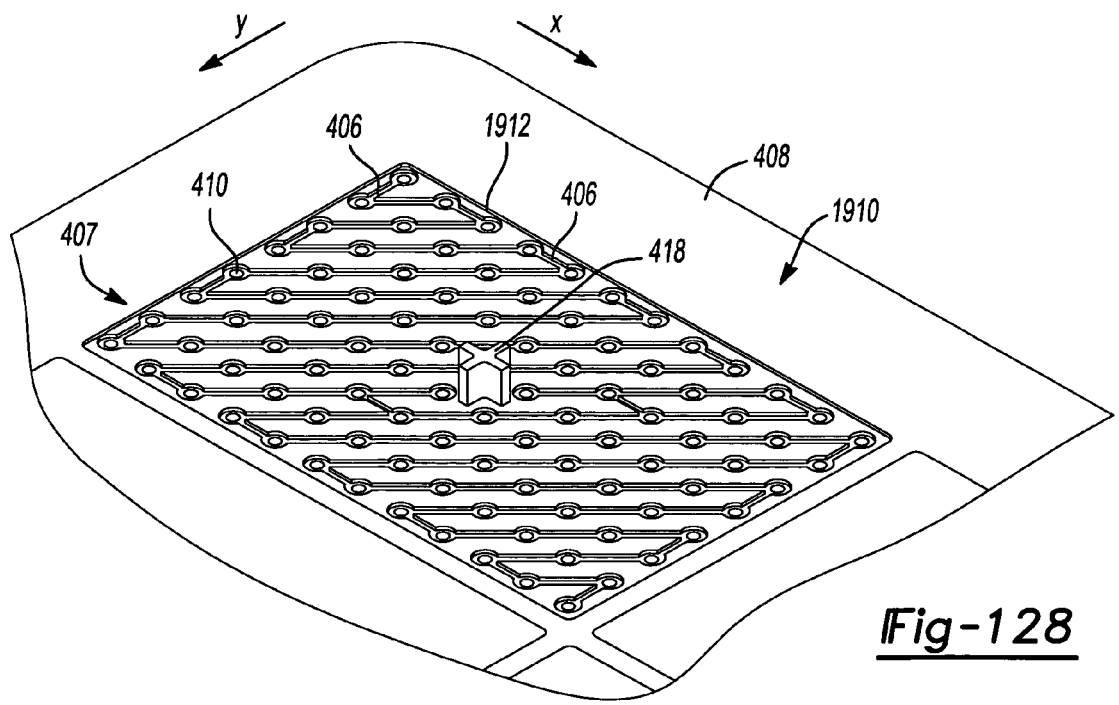
Figure 129:
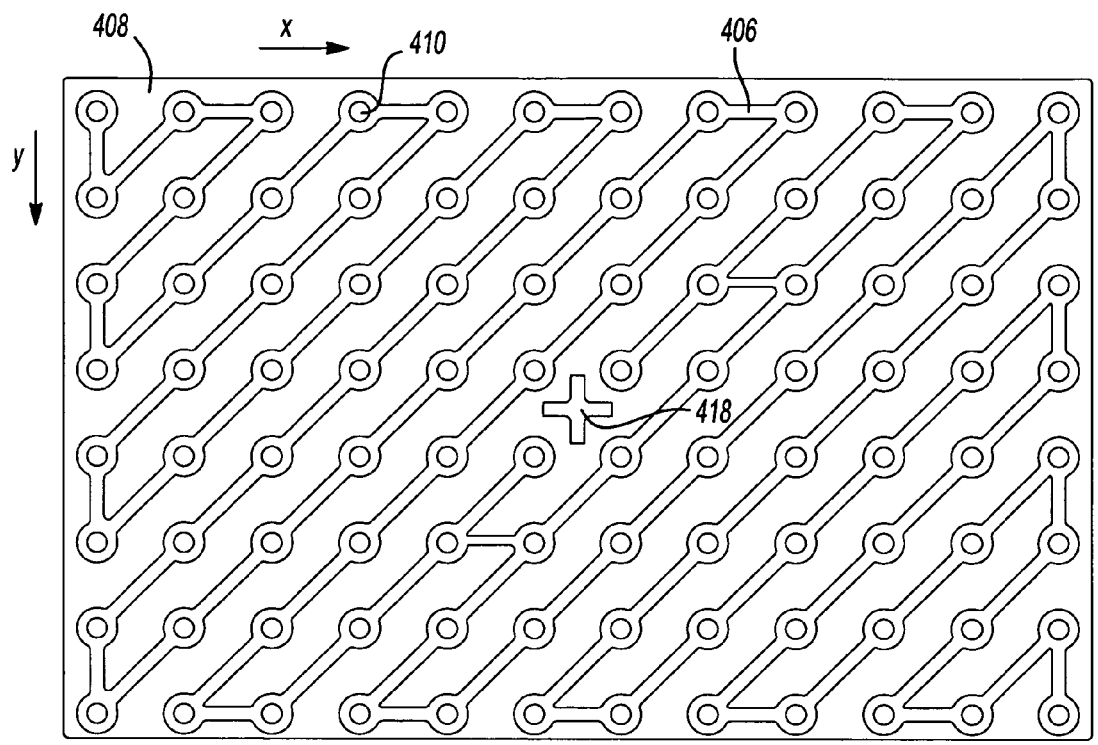
Figure 130:
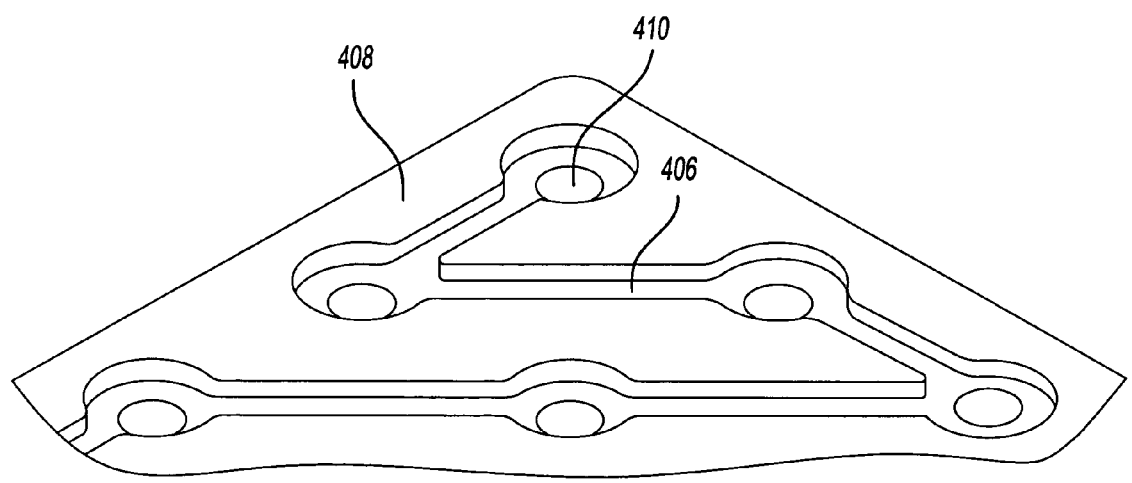
Figure 131:
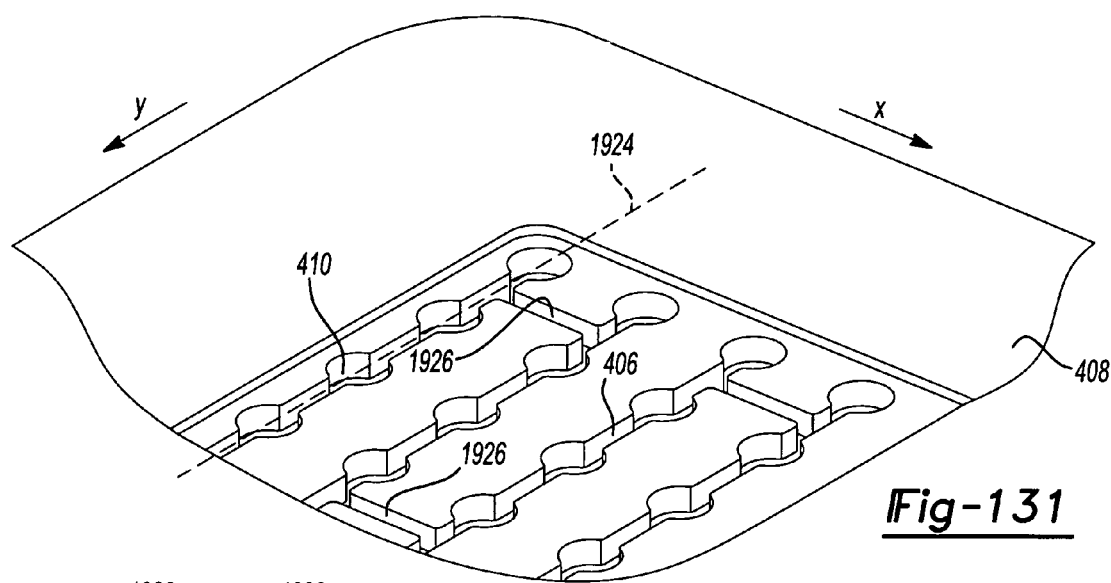
Figure 132:
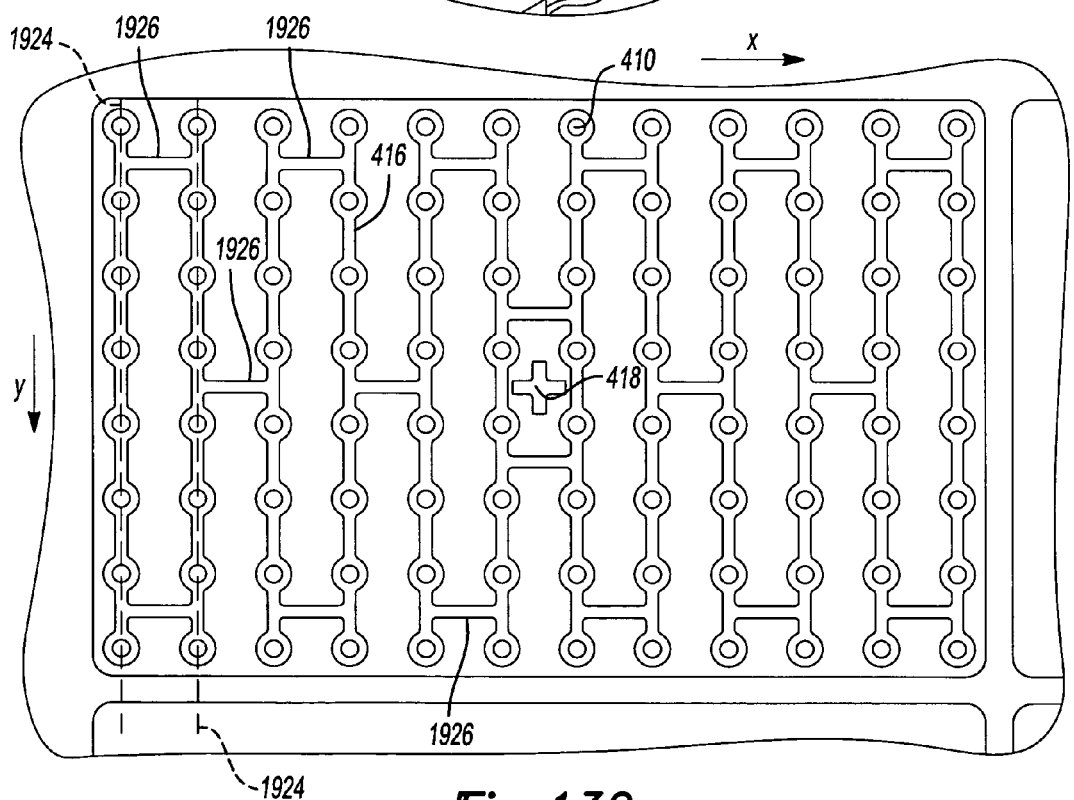
Figure 133:
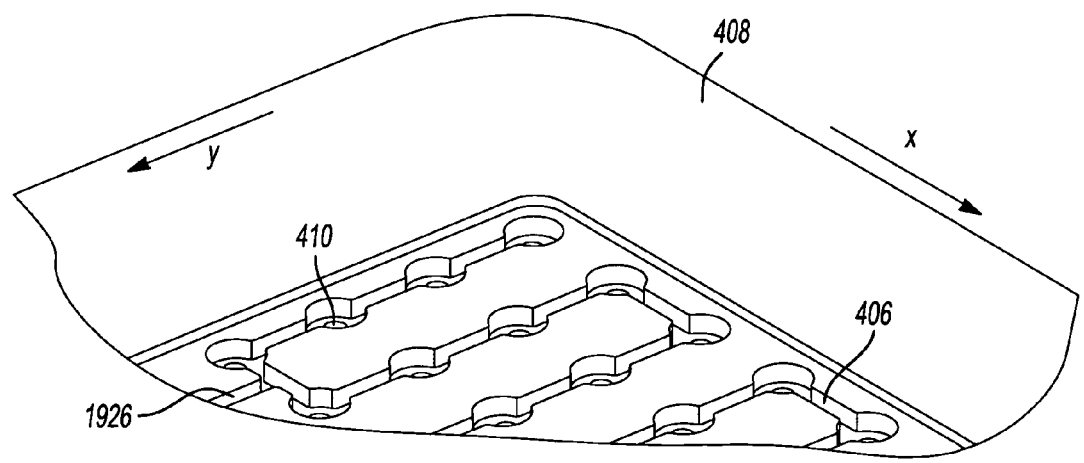
Figure 134:
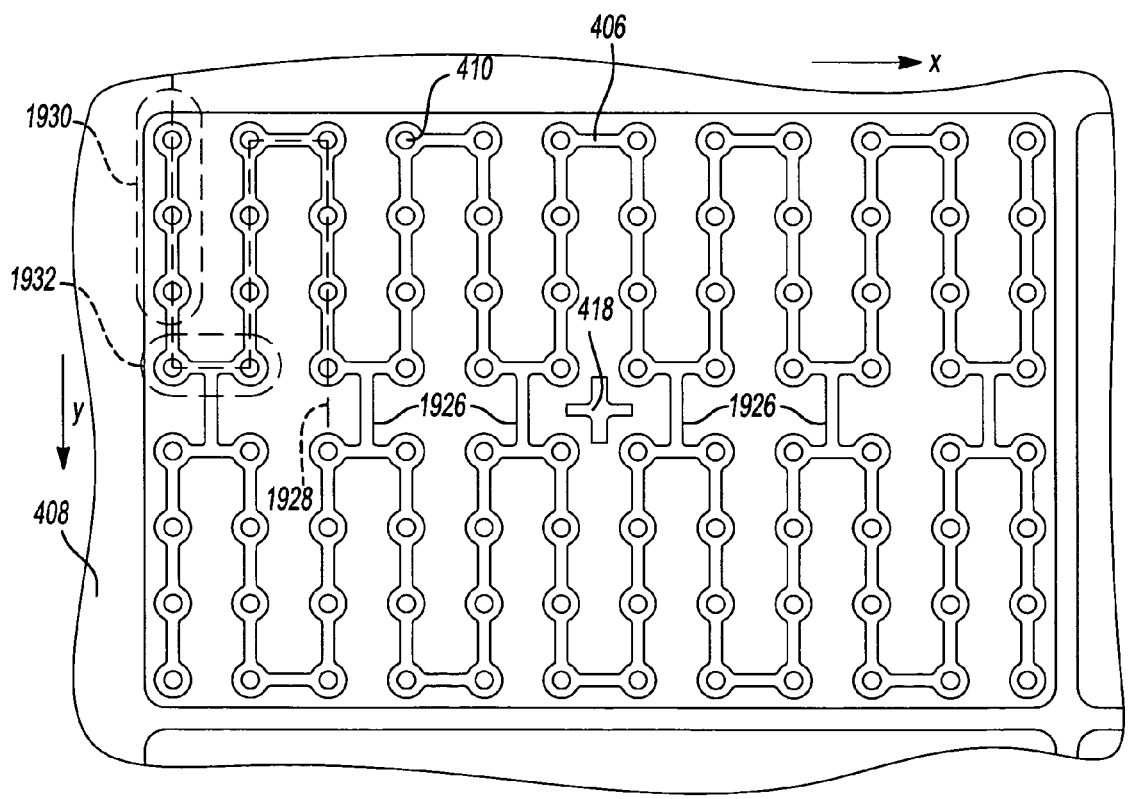
Figure 135:
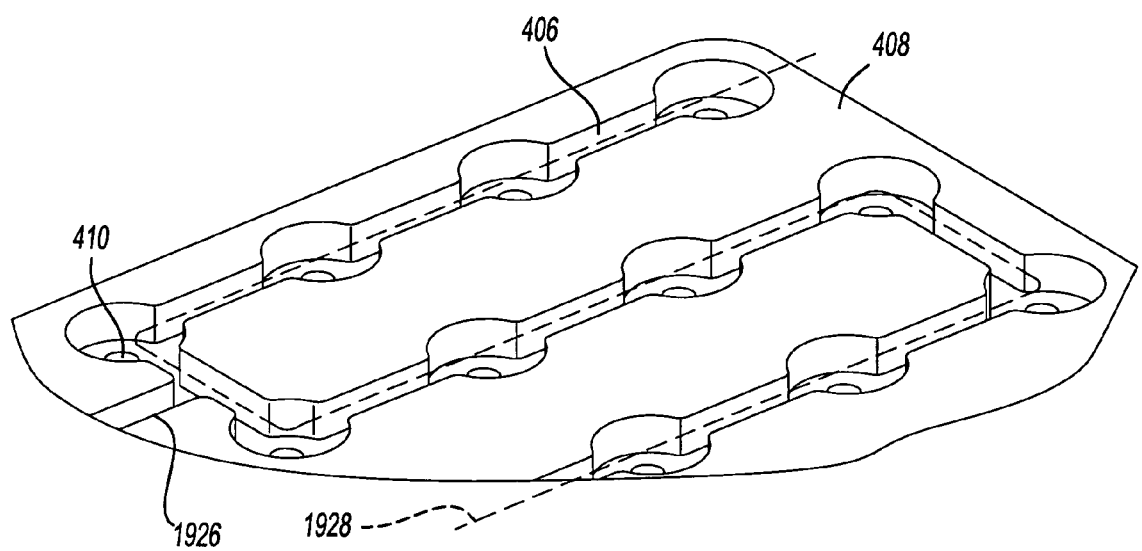
Figure 136:
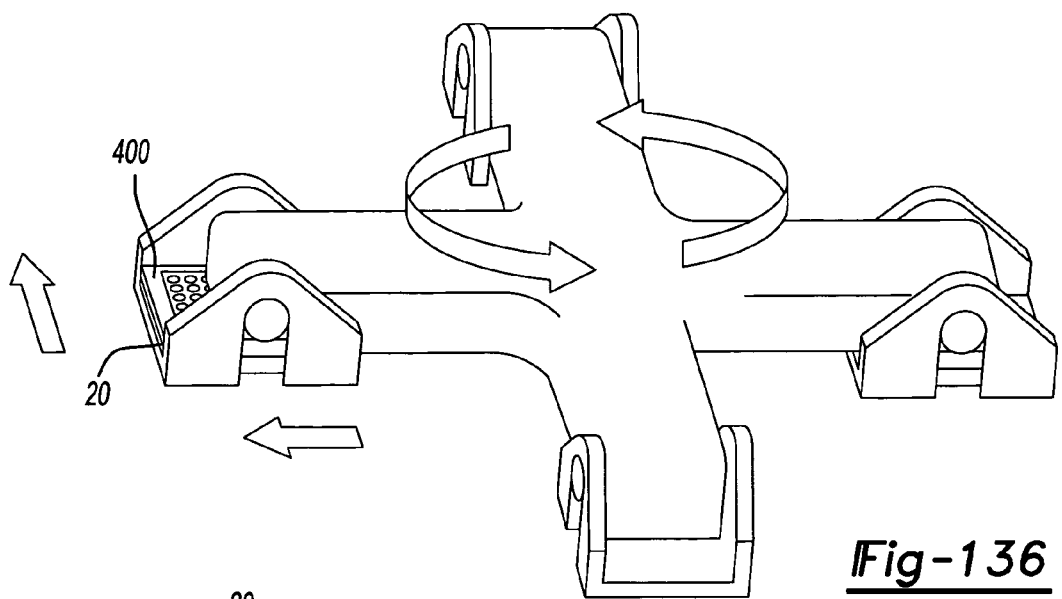
Figure 137:
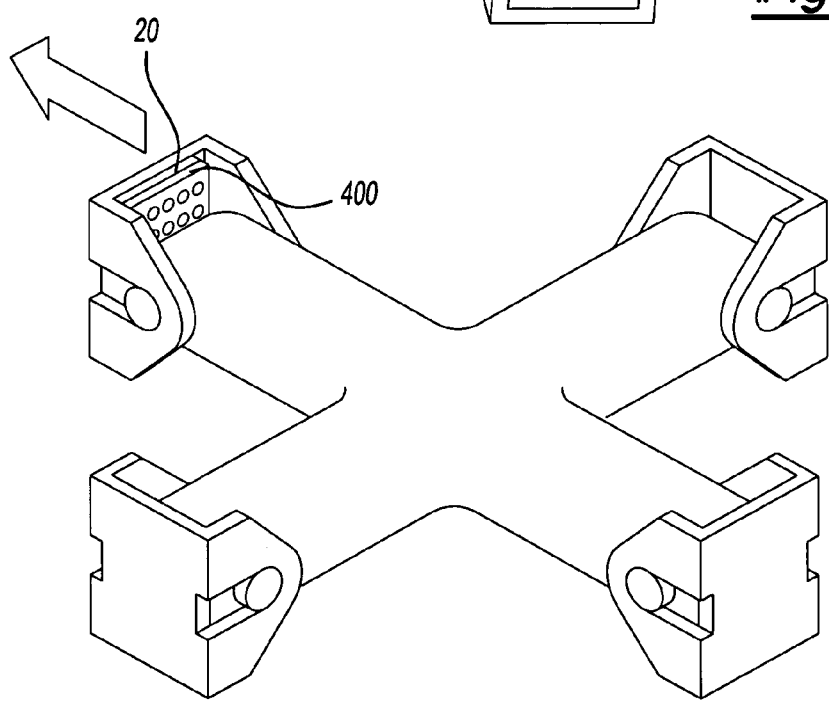
Figure 138:
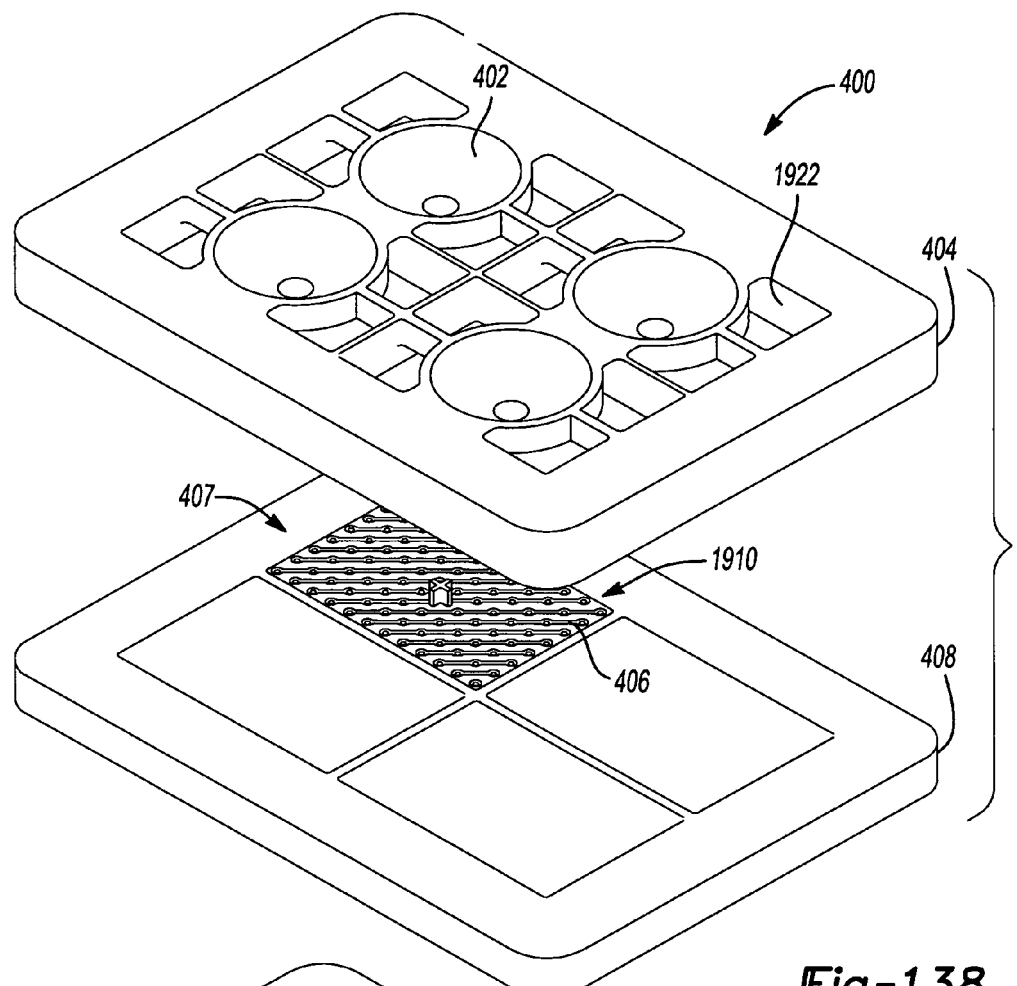
Figure 139:
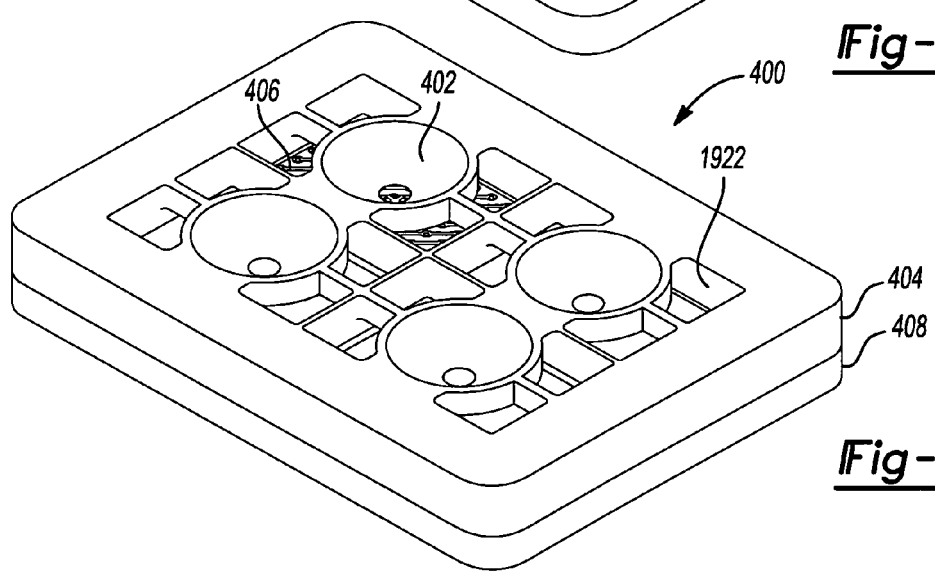
Figure 140:
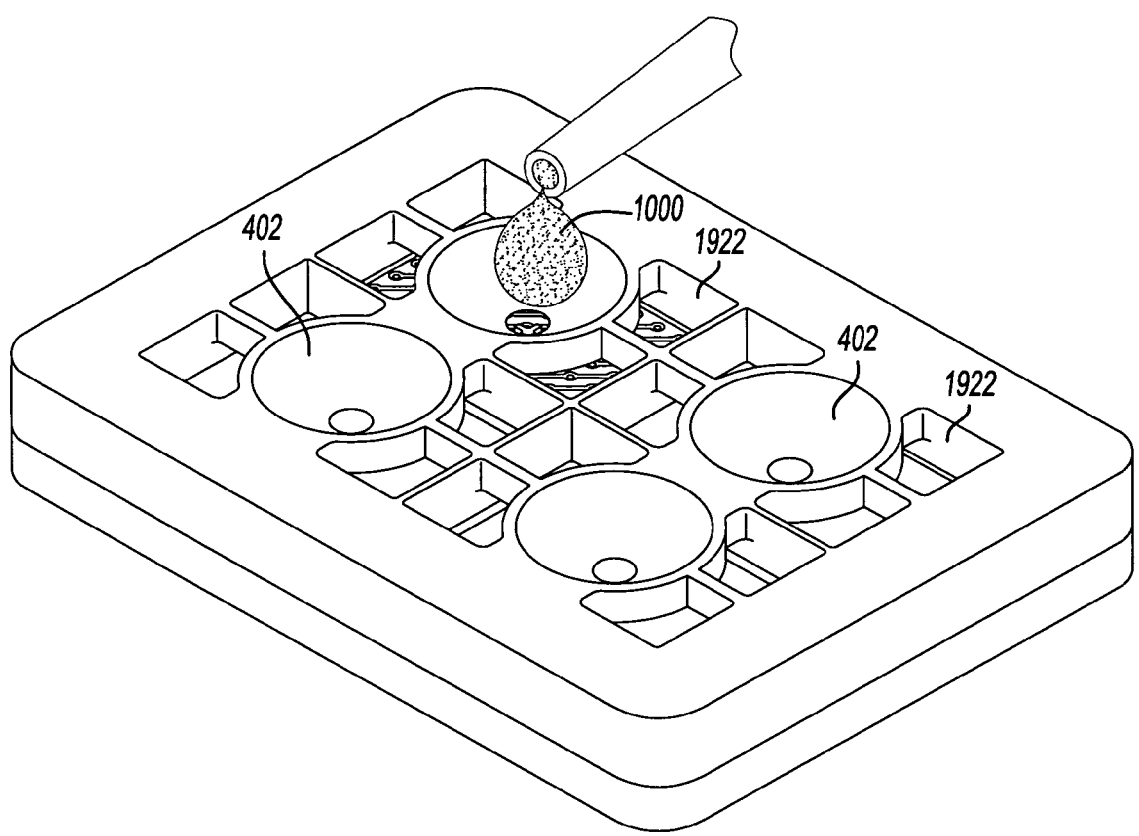
Figure 141:
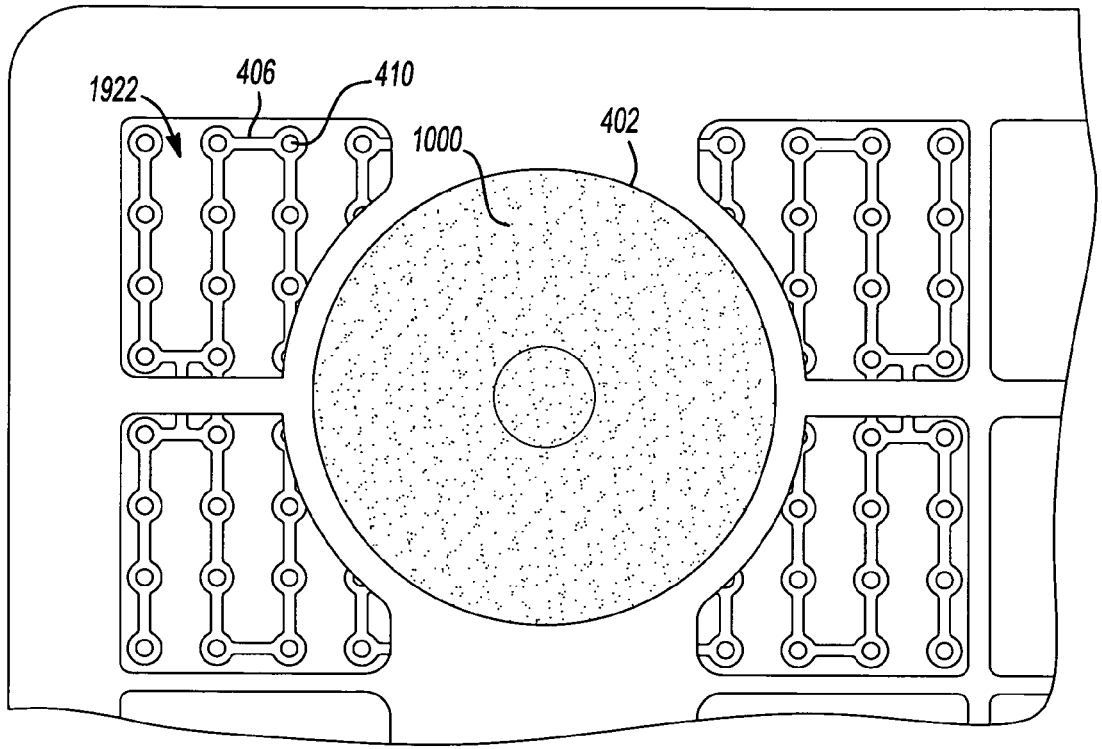
Figure 142:
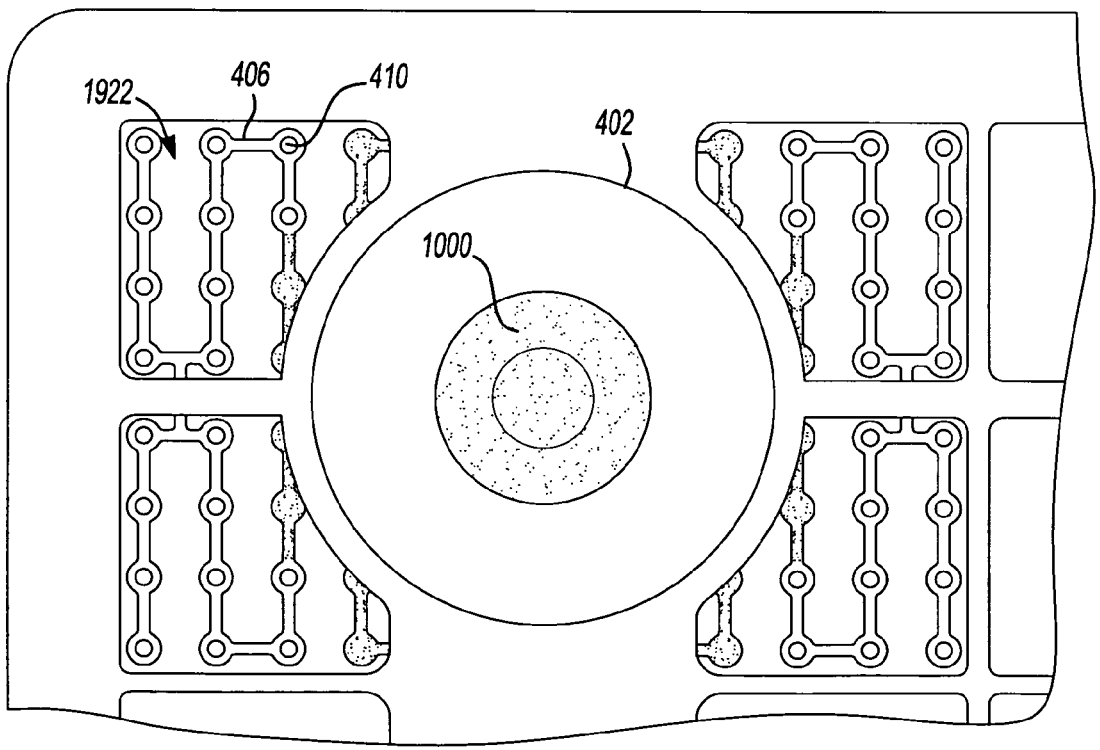
Figure 143:
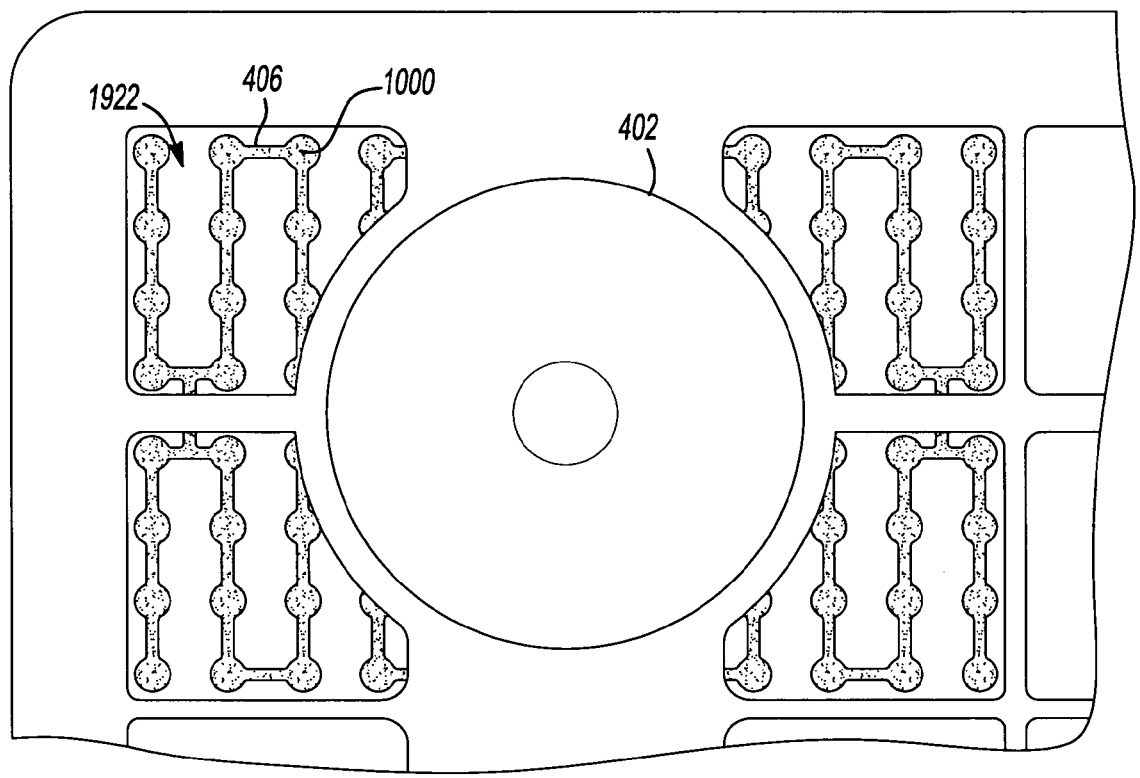
Figure 144:
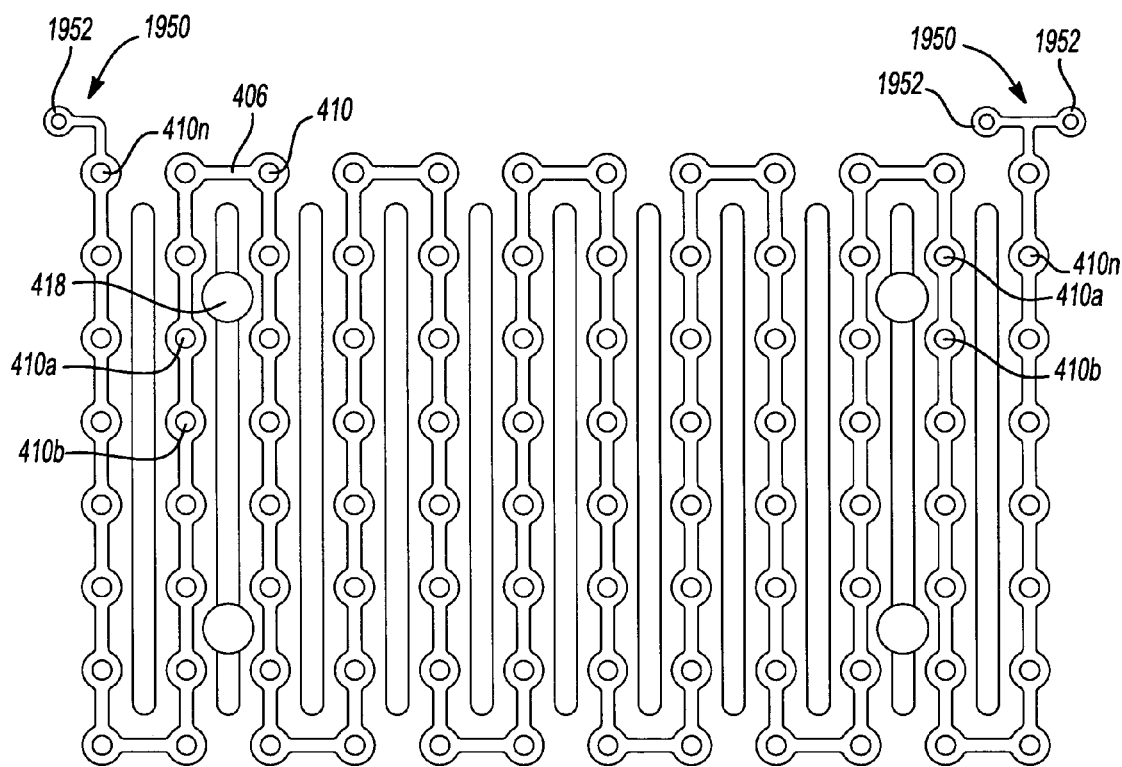
Figure 149:
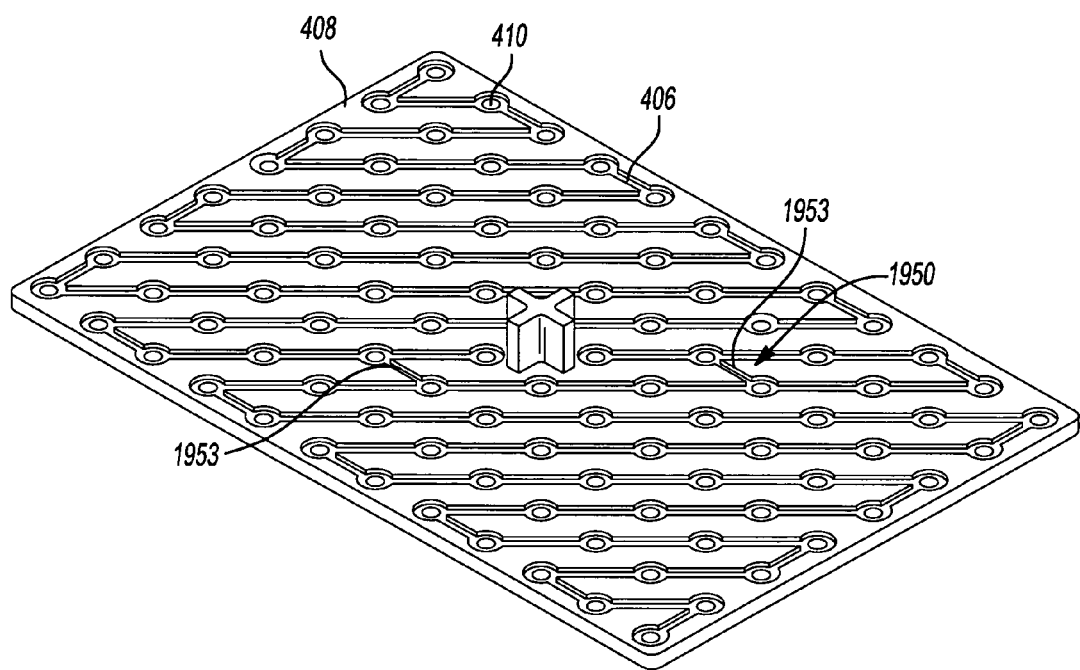
Figure 150:
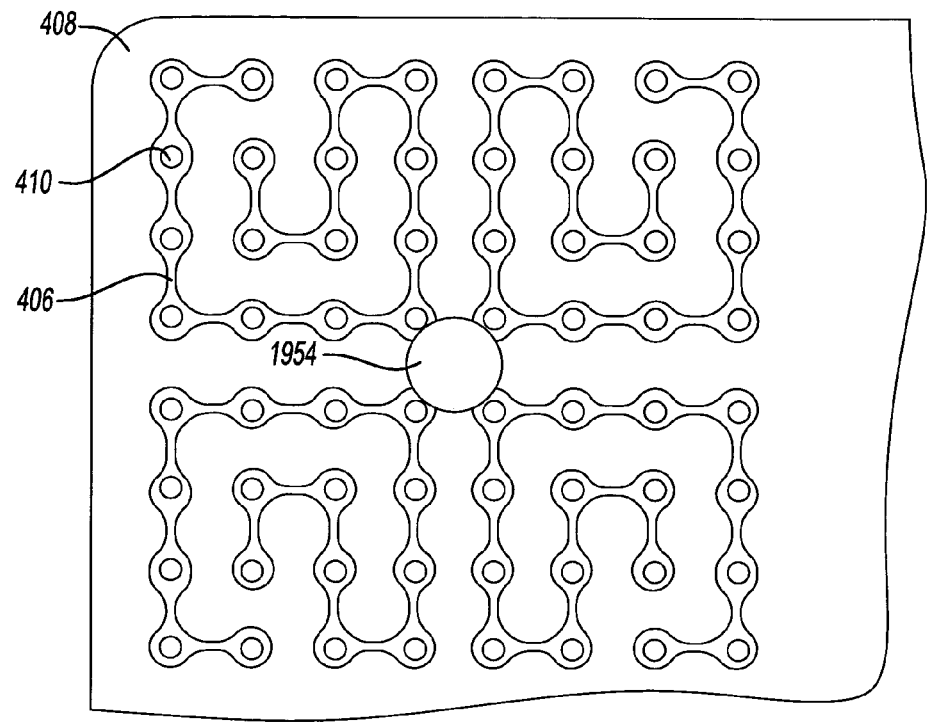
Figure 151:
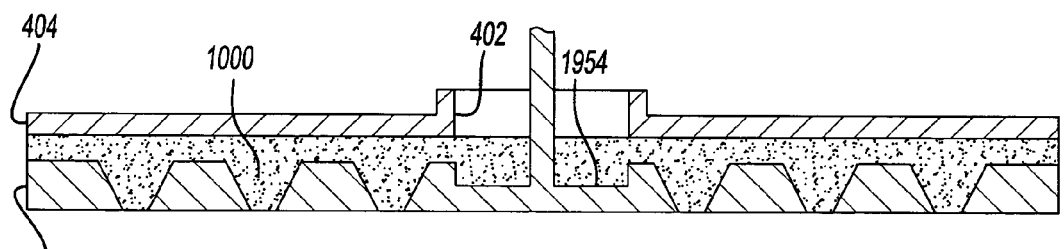
Figure 152:
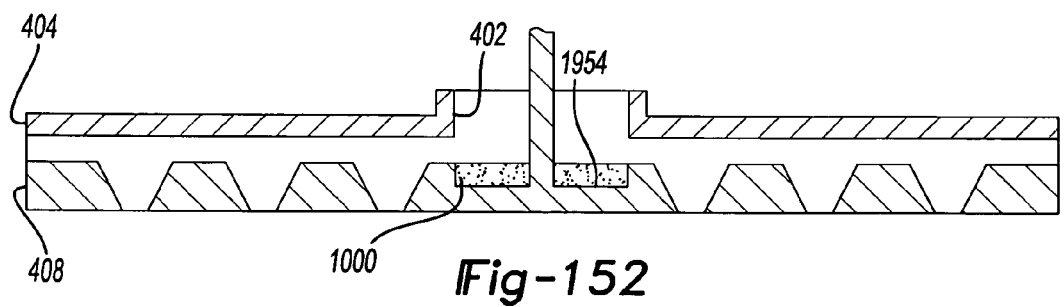
Figure 153:
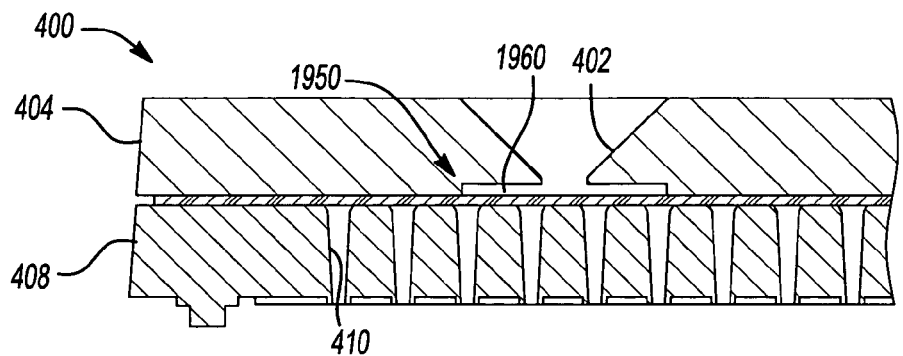
Figure 154:
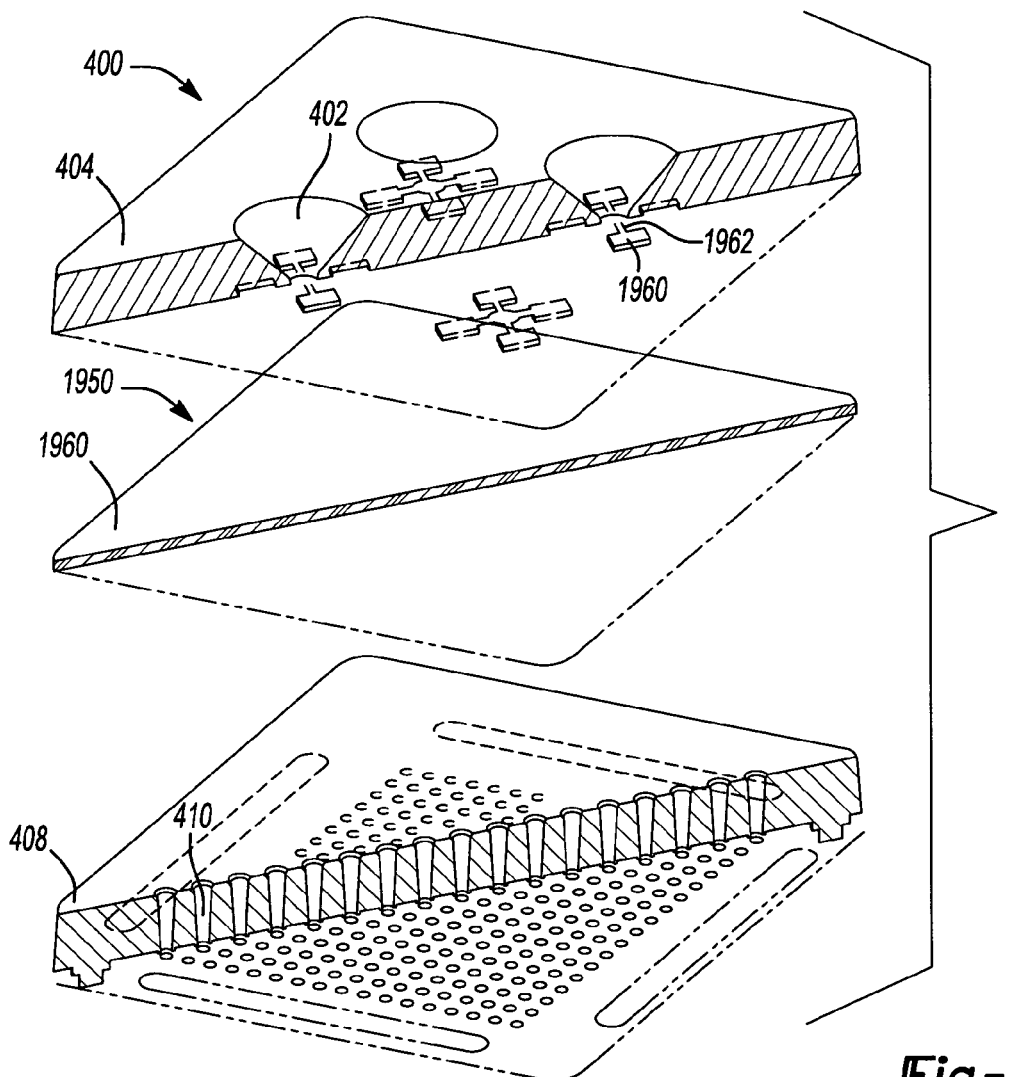
Figure 157:
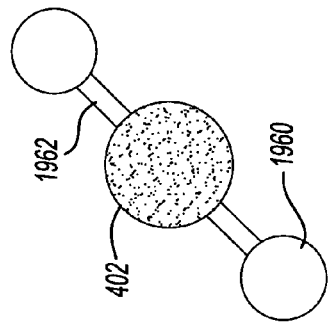
Figure 160:
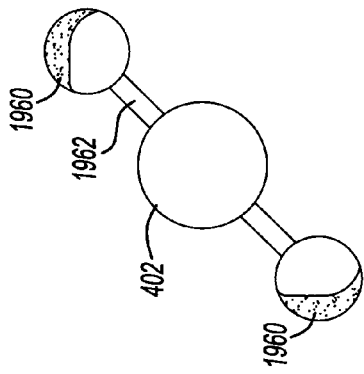
Figure 156:
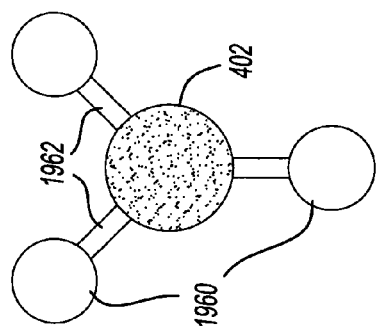
Figure 159:
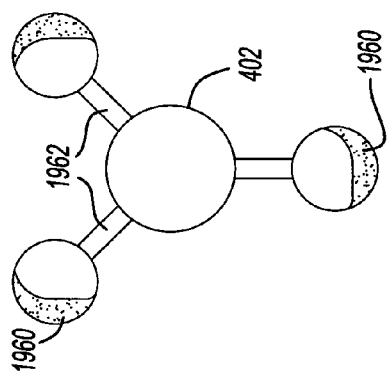
Figure 155:
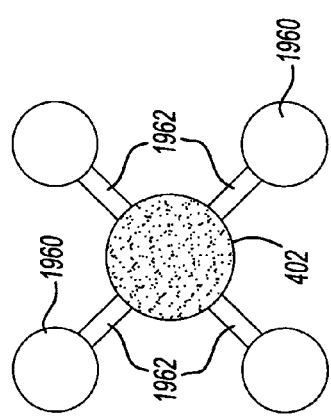
Figure 158:
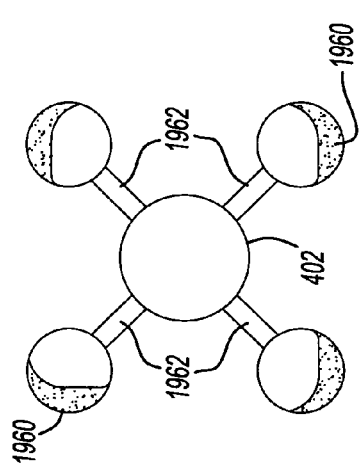
Figure 161:
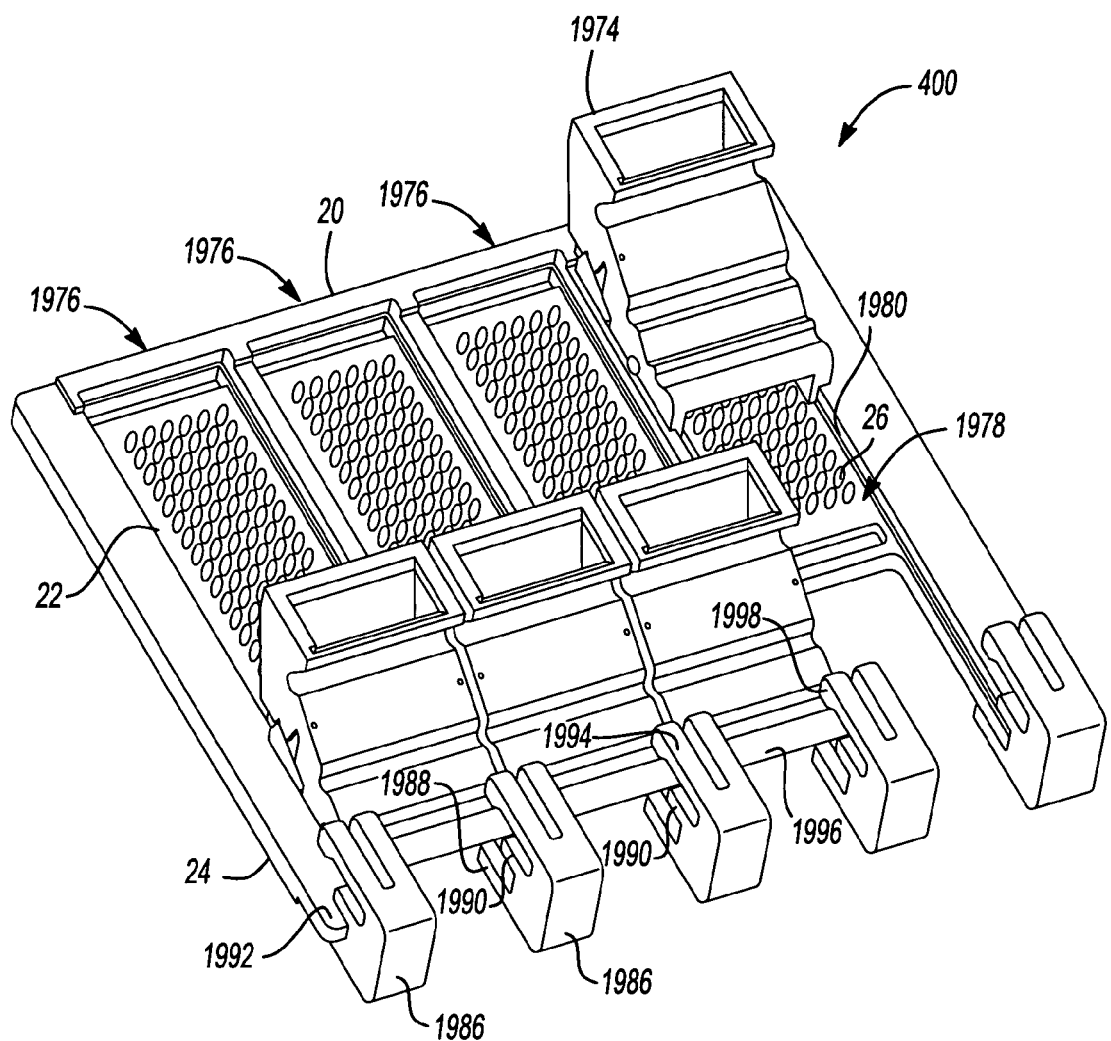
Figure 162:
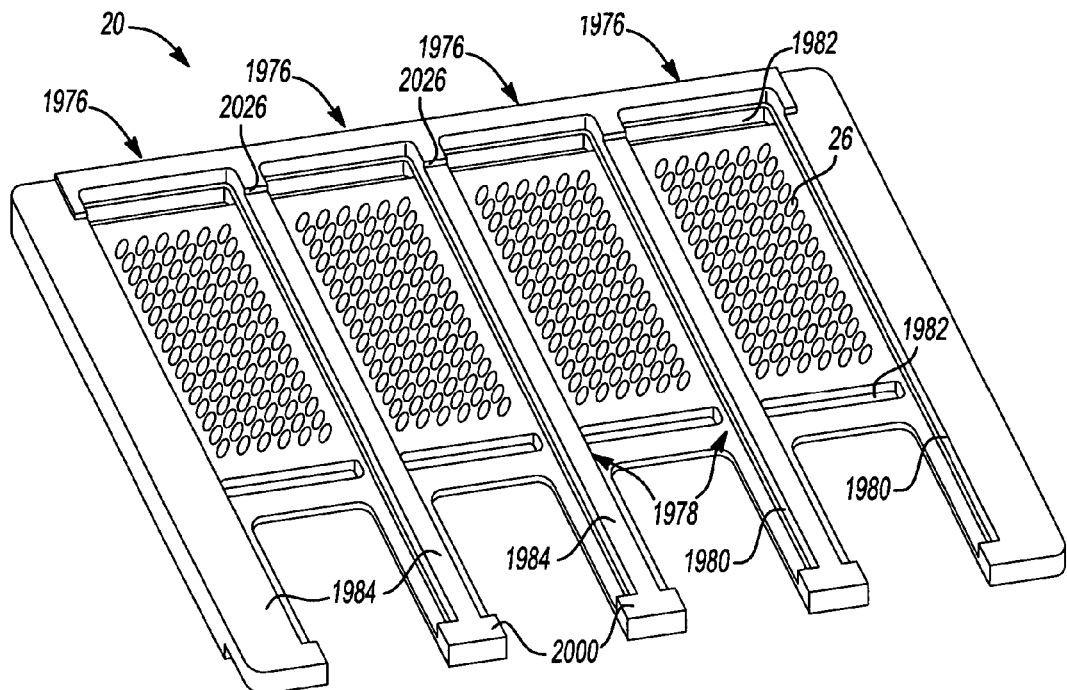
Figure 163:
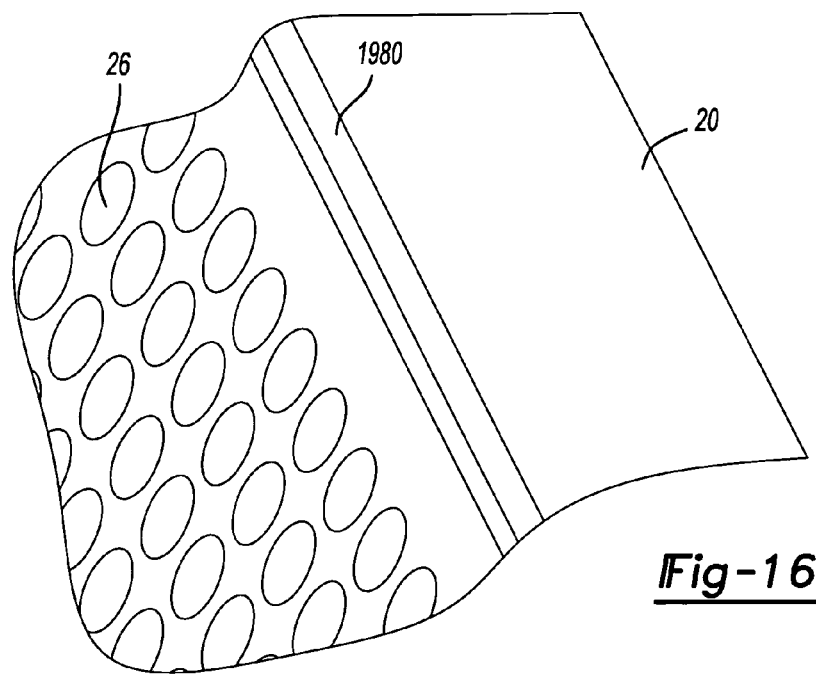
Figure 164:
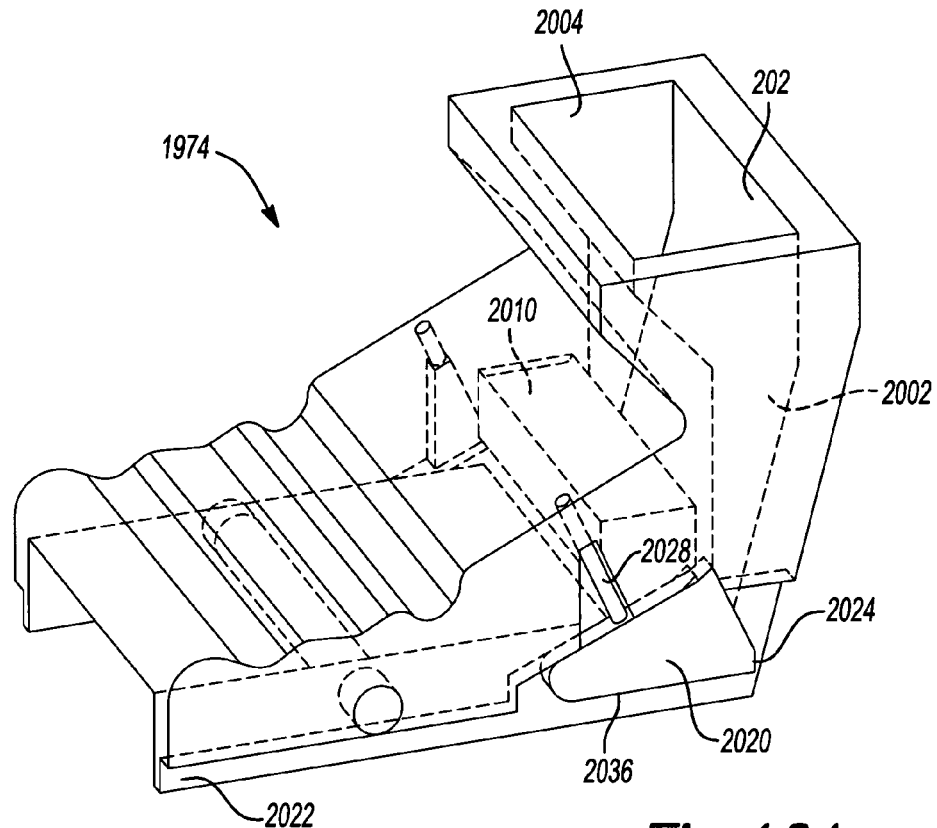
Figure 165:
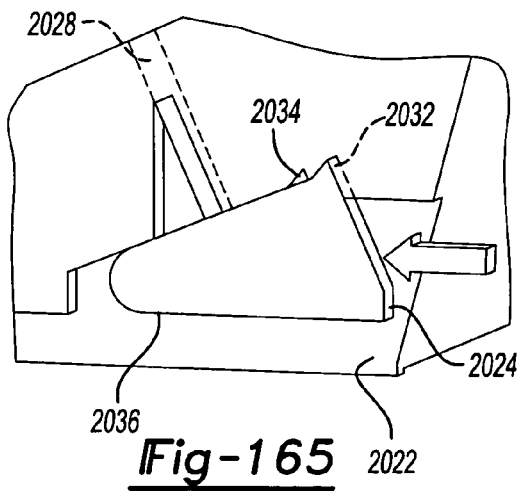
Figure 166:
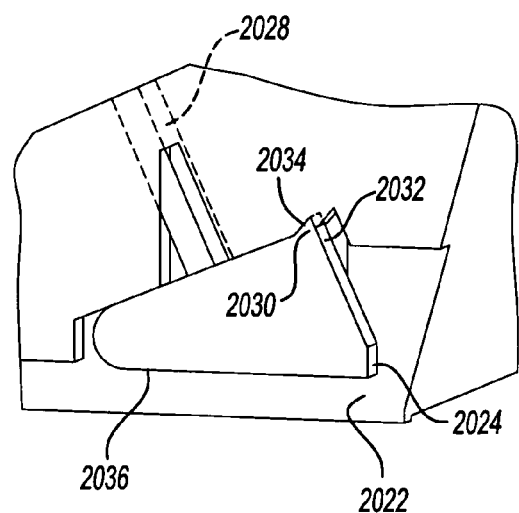
Figure 167:
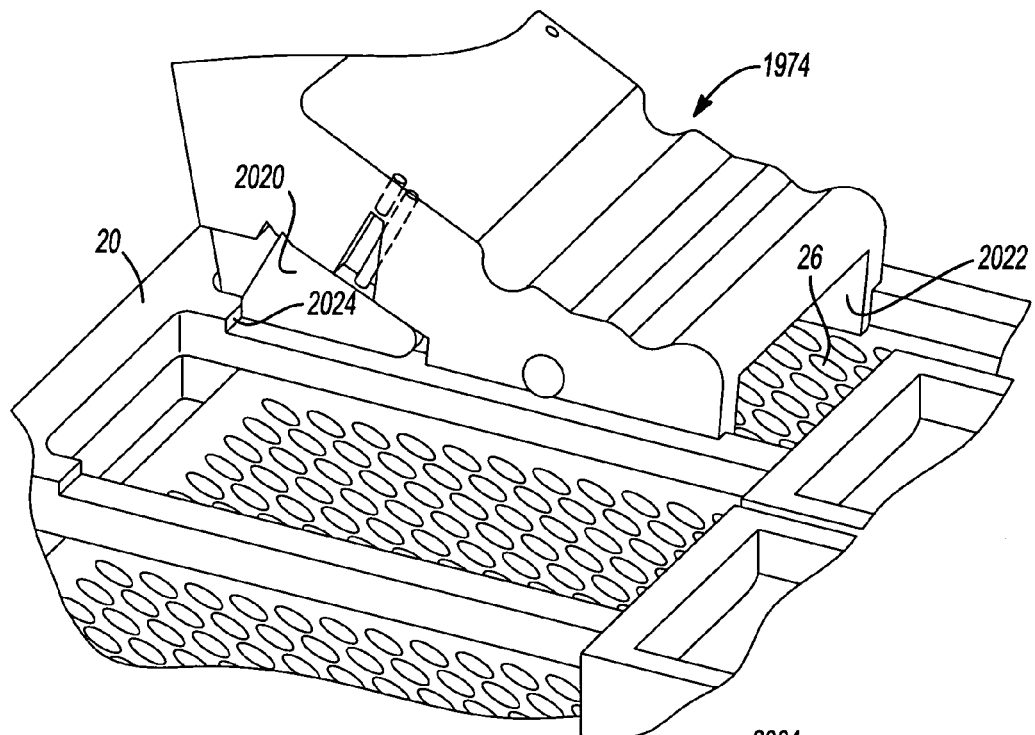
Figure 168:
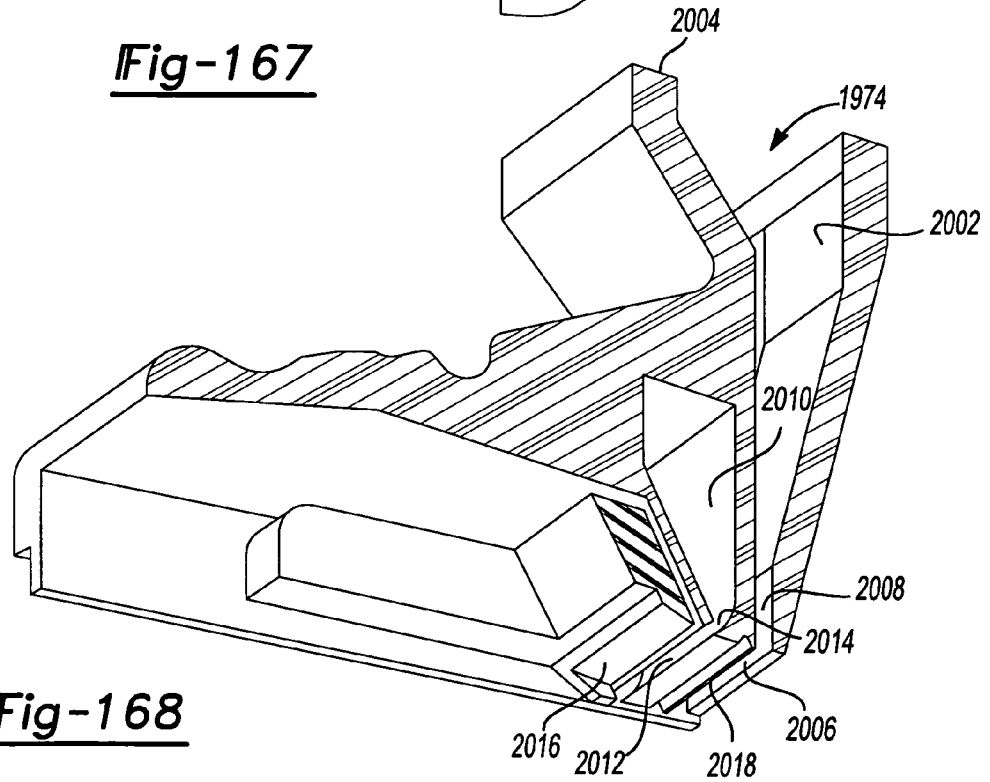
Figure 169:
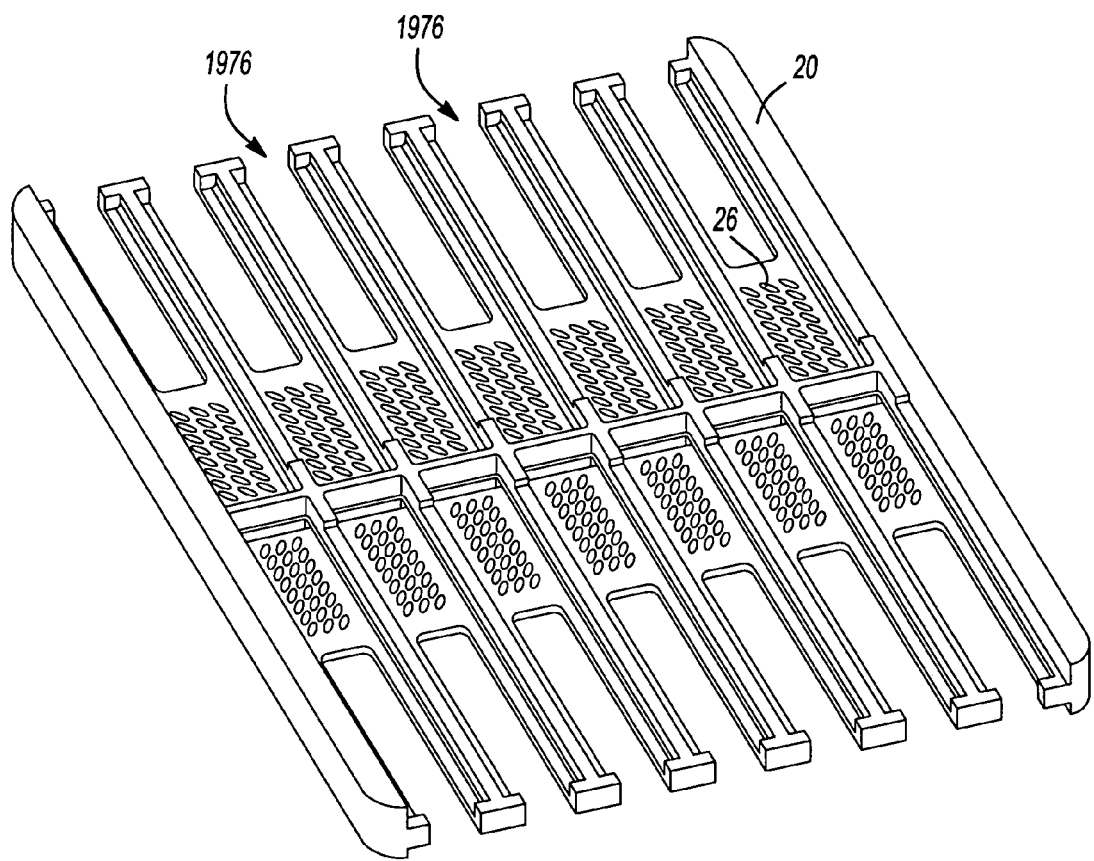

FIGS. 25(a)-(f) are top schematic views of a filling apparatus according to some embodiments;

FIG. 26 is a cross-sectional view illustrating a well of a microplate according to some embodiments;

FIG. 27 is a cross-sectional view illustrating a well of an inverted microplate according to some embodiments;

FIG. 28 is a top perspective view illustrating a multipiece microplate in accordance with some embodiments;

FIG. 29 is an exploded perspective view illustrating the multipiece microplate of FIG. 28 in accordance with some embodiments;

FIG. 30 is a top view illustrating the multipiece microplate in accordance with some embodiments;

FIG. 31 is a cross-sectional view of the multipiece microplate of FIG. 30 taken along Line 31-31;

FIG. 32 is an enlarged cross-sectional view of cap portion and main body portion of the multipiece microplate of FIG. 31;

FIG. 33 is an exploded top perspective view illustrating a filling apparatus comprising an intermediate layer according to some embodiments;

FIG. 34 is a cross-sectional view illustrating the filling apparatus comprising the intermediate layer according to some embodiments;

FIG. 35 is an exploded bottom perspective view illustrating the filling apparatus comprising the intermediate layer according to some embodiments;

FIG. 36 is a cross-sectional view illustrating the filling apparatus comprising the intermediate layer and nodules according to some embodiments;

FIG. 37 is a top schematic view of the filling apparatus comprising the intermediate layer and nodules according to some embodiments;

FIG. 38 is a cross-sectional view illustrating the filling apparatus comprising the intermediate layer, nodules, and sealing feature according to some embodiments;

FIG. 39 is a bottom perspective view of the intermediate layer of the filling apparatus according to some embodiments;

FIG. 40 is an exploded top perspective view illustrating a clamp system for a filling apparatus according to some embodiments;

FIG. 41 is an exploded top perspective view illustrating a filling apparatus comprising a vent layer according to some embodiments;

FIG. 42 is an exploded bottom perspective view illustrating the filling apparatus comprising the vent layer according to some embodiments;

FIG. 43 is a cross-sectional view illustrating the filling apparatus comprising the vent layer and a vent manifold according to some embodiments;

FIG. 44 is a top schematic view of the filling apparatus comprising the vent layer and circular vent apertures according to some embodiments;

FIG. 45 is a top schematic view of the filling apparatus comprising the vent layer and oblong vent apertures according to some embodiments;

FIG. 46 is a cross-sectional view illustrating the filling apparatus comprising the vent layer and pressure bores according to some embodiments;

FIG. 47 is a perspective view illustrating a filling apparatus comprising one or more assay input ports positioned on an end of an input layer according to some embodiments;

FIG. 48 is a perspective view illustrating a filling apparatus comprising one or more assay input ports positioned on a side of an input layer according to some embodiments;

FIG. 49 is a perspective view illustrating a filling apparatus comprising one or more assay input ports positioned on opposing sides of an input layer according to some embodiments;

FIG. 50 is a perspective view with portions illustrated in cross-section illustrating an assay input port according to some embodiments;

FIG. 51 is a cross-sectional view illustrating the filling apparatus of FIG. 50 according to some embodiments;

FIGS. 52-58 and 60 are cross-sectional views illustrating the progressive filling of a microplate according to some embodiments;

FIG. 59 is a top schematic view of the filling apparatus comprising reduced material areas for, at least in part, use in staking according to some embodiments;

FIGS. 61-66 are cross-sectional views illustrating the progressive filling of a microplate using a filling apparatus employing fluid overfill reservoirs according to some embodiments;

FIG. 67 is a cross-sectional view illustrating a filling apparatus employing fluid overfill reservoirs disposed in an output layer according to some embodiments;

FIGS. 68(a)-(g) are top schematic views illustrating various possible positions of the staging capillaries relative to corresponding microfluidic channels according to some embodiments;

FIGS. 69(a)-(g) are cross-sectional views illustrating various possible positions and configurations microfluidic channels and staging capillaries according to some embodiments;

FIG. 70 is an exploded perspective view illustrating a filling apparatus comprising a floating insert and cover according to some embodiments;

FIG. 71 is a cross-sectional view illustrating the filling apparatus comprising the floating insert according to some embodiments;

FIG. 72 is an exploded perspective view illustrating a filling apparatus comprising a floating insert according to some embodiments;

FIG. 73 is a cross-sectional view illustrating a floating insert according to some embodiments;

FIG. 74 is a cross-sectional view illustrating a floating insert comprising post members according to some embodiments;

FIG. 75 is a cross-sectional view illustrating a floating insert comprising tapered members according to some embodiments;

FIG. 76 is a cross-sectional view illustrating a floating insert comprising tapered members and a flanged base portion according to some embodiments;

FIG. 77 is a cross-sectional view illustrating the floating insert comprising tapered members and the flanged base portion inserted into a corresponding depression according to some embodiments;

FIG. 78 is a cross-sectional view illustrating the floating insert comprising tapered members and the flanged base portion inserted into the corresponding depression and assay flow therebetween according to some embodiments;

FIG. 79 is a cross-sectional view illustrating the floating insert comprising tapered members and the flanged base portion being forced down onto the corresponding depression according to some embodiments;

FIGS. 80-82 are cross-sectional views illustrating the progressive filling and release of assay from the filling apparatus illustrated in FIG. 72 according to some embodiments;

FIGS. 83 and 84 are cross-sectional views illustrating the filling and release of assay from a filling apparatus comprising weight members according to some embodiments;

FIG. 85 is a perspective view illustrating a filling apparatus comprising an output layer and reservoir pockets according to some embodiments;

FIG. 86 is a cross-sectional view illustrating the filling apparatus comprising the output layer according to some embodiments;

FIGS. 87-89 are cross-sectional views illustrating the progressive filling of a plurality of staging capillaries according to some embodiments;

FIG. 90 is a perspective view illustrating the filling apparatus comprising the surface wire assembly, reservoir pockets, and absorbent members further comprising a sloping overflow channel portion according to some embodiments;

FIGS. 91-92 are perspective views illustrating the filling apparatus comprising the surface wire assembly, the reservoir trough, and absorbent member further comprising a sloping portion according to some embodiments;

FIG. 93 is a perspective view illustrating a filling apparatus comprising a surface wire assembly, reservoir pockets, and absorbent members according to some embodiments;

FIG. 94 is a perspective view illustrating a funnel member comprising an assay chamber according to some embodiments;

FIG. 95 is a perspective view illustrating a funnel member comprising multiple discrete assay chambers according to some embodiments;

FIG. 96 is a perspective view illustrating a funnel member comprising multiple discrete assay chambers according to some embodiments;

FIG. 97 is a cross-sectional view illustrating a funnel member comprising a tip portion according to some embodiments;

FIG. 98 is a cross-sectional view illustrating a funnel member comprising a tip portion and a wiper member according to some embodiments;

FIG. 99 is a cross-sectional view illustrating a funnel member comprising a tip portion and a planar cavity according to some embodiments;

FIG. 100 is a cross-sectional view illustrating a funnel member comprising a tip portion and a wiper member spaced apart from the tip portion according to some embodiments;

FIG. 101 is a bottom perspective view illustrating a funnel member comprising multiple offset discrete assay chambers according to some embodiments;

FIG. 102 is a top plan view illustrating a funnel member comprising multiple offset discrete assay chambers and one or more apertures according to some embodiments;

FIG. 103 is a cross-sectional view illustrating a funnel member comprising multiple offset discrete assay chambers and one or more apertures according to some embodiments;

FIG. 104 is a top perspective view illustrating a multipiece funnel member comprising multiple offset discrete assay chambers and an internal siphon passage according to some embodiments;

FIG. 105 is a cross-sectional view illustrating the multipiece funnel member comprising multiple offset discrete assay chambers and the internal siphon passage according to some embodiments;

FIG. 106 is an exploded top perspective view illustrating a multipiece funnel member comprising portions separated generally vertically according to some embodiments;

FIG. 107 is an exploded bottom perspective view illustrating a multipiece funnel member comprising portions separated generally horizontally according to some embodiments;

FIG. 108 is an exploded top perspective view illustrating a filling apparatus comprising an upwardly-shaped member according to some embodiments;

FIG. 109 is a top perspective view illustrating the filling apparatus comprising the upwardly-shaped member according to some embodiments;

FIGS. 110-113 are cross-sectional views illustrating the progressive filling of an output layer using in part a capillary plane according to some embodiments;

FIGS. 114-119 are cross-sectional views illustrating the progressive filling of an output layer using in part a capillary plane and wall restraints according to some embodiments;

FIG. 120 is a top schematic view of a filling apparatus comprising microfluidic channels arranged in a cross-pattern according to some embodiments;

FIG. 121 is a top perspective view of the filling apparatus comprising microfluidic channels arranged in the cross-pattern according to some embodiments;

FIG. 122 is a top perspective view of a filling apparatus comprising microfluidic channels arranged in an S-shaped pattern according to some embodiments;

FIG. 123 is a top schematic view of the filling apparatus comprising microfluidic channels arranged in the S-shaped pattern according to some embodiments;

FIG. 124 is a top perspective view of a filling apparatus comprising microfluidic channels arranged in an S-shaped pattern having wall restraints according to some embodiments;

FIG. 125 is a top schematic view of the filling apparatus comprising microfluidic channels arranged in the S-shaped pattern having wall restraints according to some embodiments;

FIG. 126 is a top perspective view of a filling apparatus comprising microfluidic channels arranged in an S-shaped pattern having wall restraints extending from a side of a capillary plane according to some embodiments;

FIG. 127 is a top schematic view of the filling apparatus comprising the open vent network according to some embodiments;

FIG. 128 is a top perspective view of a filling apparatus comprising microfluidic channels arranged in a diagonal pattern according to some embodiments;

FIG. 129 is a top schematic view of the filling apparatus comprising microfluidic channels arranged in the diagonal pattern according to some embodiments;

FIG. 130 is an enlarged, top perspective view of the filling apparatus comprising microfluidic channels arranged in the diagonal pattern according to some embodiments;

FIG. 131 is an enlarged, top perspective view of a filling apparatus comprising microfluidic channels arranged in an H-shaped pattern according to some embodiments;

FIG. 132 is a top schematic view of the filling apparatus comprising microfluidic channels arranged in the H-shaped pattern according to some embodiments;

FIG. 133 is an enlarged, top perspective view of a filling apparatus comprising microfluidic channels arranged in one or more S-shaped patterns according to some embodiments;

FIG. 134 is a top schematic view of the filling apparatus comprising microfluidic channels arranged in one or more S-shaped patterns according to some embodiments;

FIG. 135 is an enlarged, top perspective view of the filling apparatus comprising microfluidic channels arranged in one or more S-shaped patterns according to some embodiments;

FIG. 136 is a top perspective view of a centrifuge during initial acceleration;

FIG. 137 is a top perspective view of the centrifuge during steady state operation;

FIG. 138 is an exploded top perspective view illustrating a filling apparatus comprising an open vent network according to some embodiments;

FIG. 139 is a top perspective view illustrating the filling apparatus comprising the open vent network according to some embodiments;

FIG. 140 is a top perspective view of the filling apparatus comprising the open vent network during an initial filling step according to some embodiments;

FIGS. 141-143 are top schematic views illustrating the progressive filling of the filling apparatus comprising the open vent network according to some embodiments;

FIG. 144 is a top schematic view illustrating a filling apparatus comprising delay-filled capillaries according to some embodiments;

FIGS. 145-148 are cross-sectional views illustrating the progressive filling of the filling apparatus comprising delay-filled capillaries according to some embodiments;

FIG. 149 is a top perspective view illustrating a filling apparatus comprising delay-filled channels according to some embodiments;

FIG. 150 is a top perspective view illustrating a filling apparatus comprising an overflow moat according to some embodiments;

FIGS. 151-152 are cross-sectional views illustrating the progressive filling of the filling apparatus comprising the overflow moat according to some embodiments;

FIG. 153 is a cross-sectional view illustrating a filling apparatus comprising burst pockets according to some embodiments;

FIG. 154 is an exploded top perspective view illustrating the filling apparatus comprising burst pockets according to some embodiments;

FIGS. 155-157 are top schematic views illustrating the burst pockets prior to centrifugation according to some embodiments;

FIGS. 158-160 are top schematic views illustrating the burst pockets after centrifugation according to some embodiments;

FIG. 161 is a top perspective view illustrating a filling apparatus comprising a sweep loader system according to some embodiments;

FIG. 162 is a top perspective view illustrating a microplate for use with the filling apparatus comprising the sweep loader system according to some embodiments;

FIG. 163 is an enlarged top perspective view illustrating the microplate according to some embodiments;

FIG. 164 is a top perspective view illustrating the sweep loader according to some embodiments;

FIG. 165 is a side perspective view illustrating a wedge elevator of the sweep loader in a lowered position according to some embodiments;

FIG. 166 is a side perspective view illustrating the wedge elevator of the sweep loader in a raised position according to some embodiments;

FIG. 167 is a top perspective view illustrating the sweep loader in a raised position according to some embodiments;

FIG. 168 is a bottom perspective view, with portions in cross-section, illustrating the sweep loader in the raised position according to some embodiments; and FIG. 169 is a top perspective view illustrating a microplate for use with the filling apparatus comprising the sweep loader system according to some embodiments.

Figure 170:
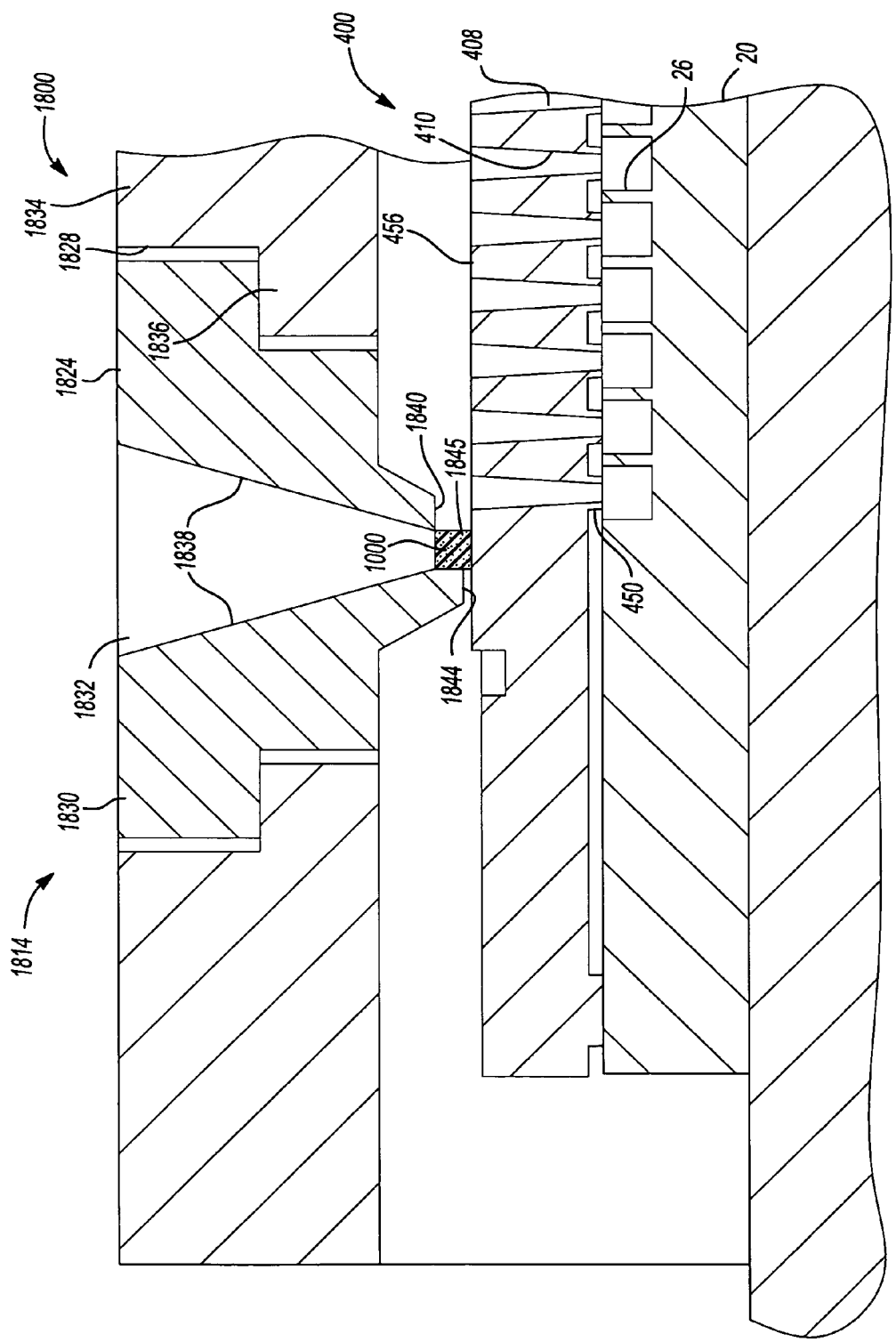
Figure 171:
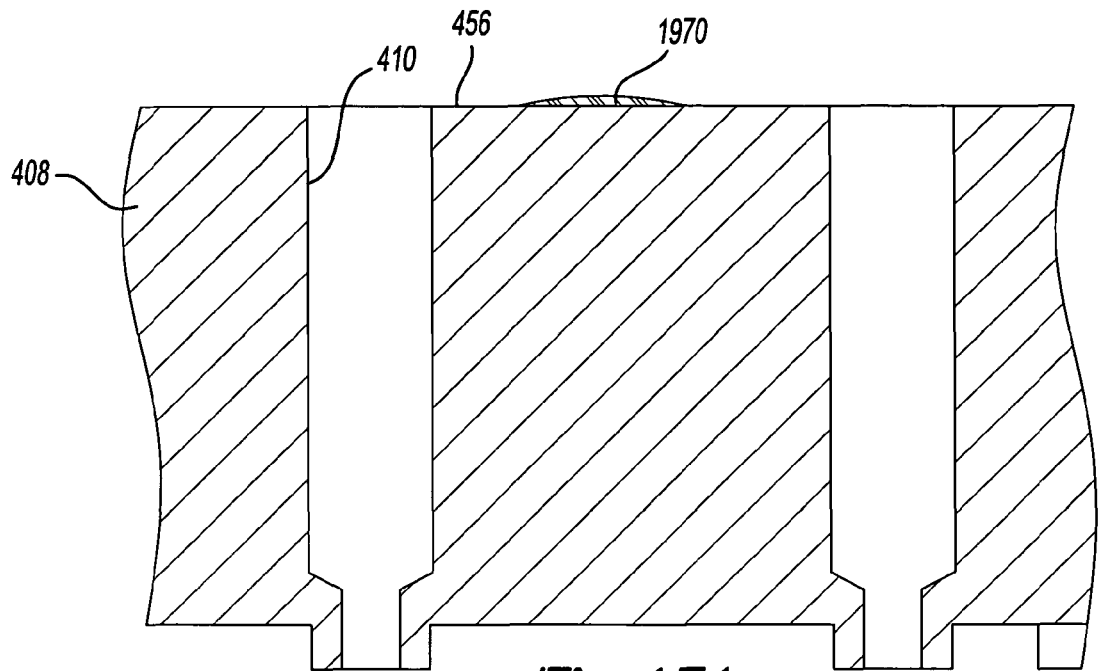
Figure 172:
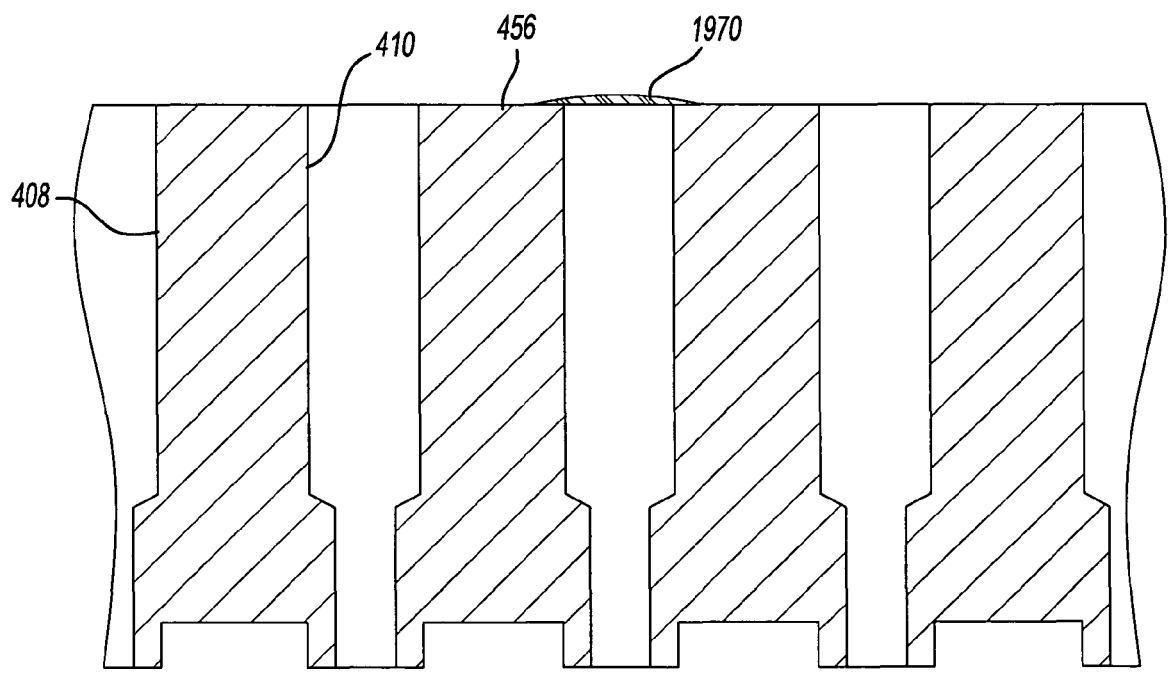

FIG. 170 is a cross-sectional view illustrating a filling apparatus comprising a porous material member according to some embodiments;

FIG. 171 is a cross-sectional view illustrating a filling apparatus comprising a hydrophobic feature disposed between staging capillaries according to some embodiments;

FIG. 172 is a cross-sectional view illustrating a filling apparatus comprising the hydrophobic feature aligned with staging capillaries according to some embodiments;

DESCRIPTION OF SOME EMBODIMENTS

The following description of some embodiments is merely exemplary in nature and is in no way intended to limit the present teachings, applications, or uses. Although the present teachings will be discussed in some embodiments as relating to polynucleotide amplification, such as PCR, such discussion should not be regarded as limiting the present teaching to only such applications.

The section headings and sub-headings used herein are for general organizational purposes only and are not to be construed as limiting the subject matter described in any way.

High-Density Sequence Detection System

In some embodiments, a high density sequence detection system comprises one or more components useful in an analytical method or chemical reaction, such as the analysis of biological and other materials containing polynucleotides. Such systems are, in some embodiments, useful in the analysis of assays, as further described below. High density sequence detection systems, in some embodiments, comprise an excitation system and a detection system which can be useful for analytical methods involving the generation and/or detection of electromagnetic radiation (e.g., visible, ultraviolet or infrared light) generated during analytical procedures. In some embodiments, such procedures include those comprising the use of fluorescent or other materials that absorb and/or emit light or other radiation under conditions that allow quantitative and/or qualitative analysis of a material (e.g., assays among those described herein). In some embodiments useful for polynucleotide amplification and/or detection, a high density sequence detection system can further comprise a thermocycler. In some embodiments, a high density sequence system can further comprise microplate and components for, e.g., filling and handling the microplate, such as a pressure clamp system. It will be understood that, although high density sequence detection systems are described herein with respect to specific microplates, assays and other embodiments, such systems and components thereof are useful with a variety of analytical platforms, equipment, and procedures.

Figure 1:
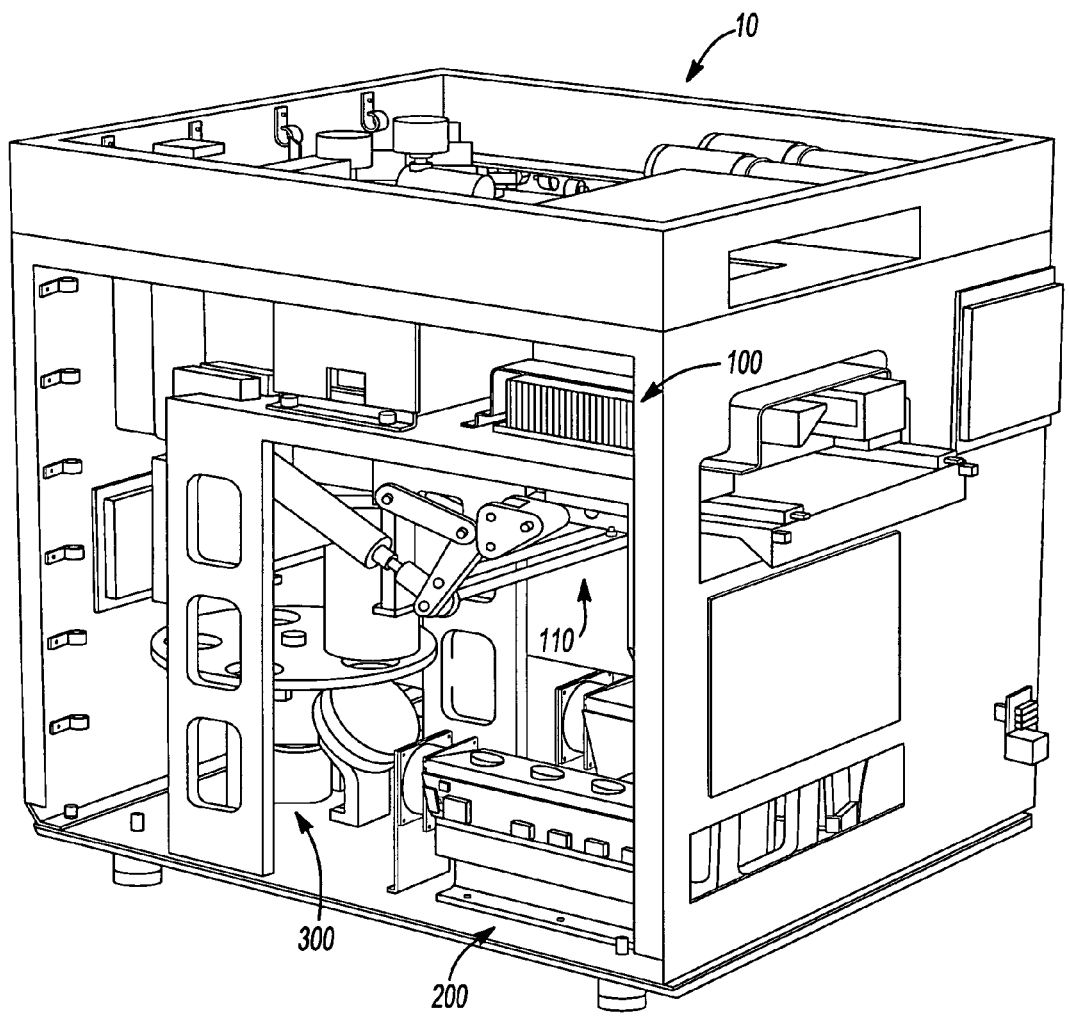
FIG. 1 is a perspective view illustrating a high-density sequence detection system according to some embodiments of the present teachings.

Referring to FIG. 1, a high-density sequence detection system 10 is illustrated in accordance with some embodiments of the present teachings. In some embodiments, high-density sequence detection system 10 comprises a microplate 20 containing an assay 1000 (see FIGS. 26 and 27), a thermocycler system 100, a pressure clamp system 110, an excitation system 200, and a detection system 300 disposed in a housing 1008.

In some embodiments, assay 1000 can comprise any material that is useful in, the subject of, a precursor to, or a product of, an analytical method or chemical reaction. In some embodiments for amplification and/or detection of polynucleotides, assay 1000 comprises one or more reagents (such as PCR master mix, as described further herein); an analyte (such as a biological sample comprising DNA, a DNA fragment, cDNA, RNA, or any other nucleic acid sequence), one or more primers, one or more primer sets, one or more detection probes; components thereof; and combinations thereof. In some embodiments, assay 1000 comprises a homogenous solution of a DNA sample, at least one primer set, at least one detection probe, a polymerase, and a buffer, as used in a homogenous assay (described further herein). In some embodiments, assay 1000 can comprise an aqueous solution of at least one analyte, at least one primer set, at least one detection probe, and a polymerase. In some embodiments, assay 1000 can be an aqueous homogenous solution. In some embodiments, assay 1000 can comprise at least one of a plurality of different detection probes and/or primer sets to perform multiplex PCR, which can be useful, for example, when analyzing a whole genome (e.g., 20,000 to 30,000 genes, or more) or other large numbers of genes or sets of genes.

Microplate

In some embodiments, a microplate comprises a substrate useful in the performance of an analytical method or chemical reaction. In some embodiments, the microplate is substantially planar, having substantially planar upper and lower surfaces, wherein the dimensions of the planar surfaces in the x- and y-dimensions are substantially greater than the thickness of the substrate in the z-direction. In some embodiments, a microplate can comprise one or more material retention regions or reaction chambers, configured to hold or support a material (e.g., an assay, as discussed below, or other solid or liquid) at one or more locations on or in the microplate. In some embodiments, such material retention regions can be wells, through-holes, reaction spots or pads, and the like. In some embodiments, such as shown in FIGS. 2-19, material retention regions comprise wells 26. In some embodiments, wells 26 can comprise a feature on or in the surface of the microplate wherein assay 1000 is contained at least in part by physical separation from adjacent features. Such well features can include, in some embodiments, depressions, indentations, ridges, and combinations thereof, in regular or irregular shapes. In some embodiments a microplate is single-use, wherein it is filled or otherwise used with a single assay for a single experiment or set of experiments, and is thereafter discarded. In some embodiments, a microplate is multiple-use, wherein it can be operable for use in a plurality of experiments or sets of experiments.

Referring now to FIGS. 2-19, in some embodiments, microplate 20 comprises a substantially planar construction having a first surface 22 and an opposing second surface 24 (see FIGS. 12-19). First surface 22 comprises a plurality of wells 26 disposed therein or thereon. The overall positioning of the plurality of wells 26 can be referred to as a well array. Each of the plurality of wells 26 is sized to receive assay 1000 (FIGS. 26 and 27). As illustrated in FIGS. 26 and 27, assay 1000 is disposed in at least one of the plurality of wells 26 and sealing cover 80 (FIG. 26) is disposed thereon (as will be discussed herein). In some embodiments, one or more of the plurality of wells 26 may not be completely filled with assay 1000, thereby defining a headspace 1006 (FIG. 26), which can define an air gap or other gas gap.

In some embodiments, the material retention regions of microplate 20 can comprise a plurality of reaction spots on the surface of the microplate. In such embodiments, a reaction spot can be an area on the microplate which localizes, at least in part by non-physical means, assay 1000. In such embodiments, assay 1000 can be localized in sufficient quantity, and isolation from adjacent areas on the microplate, so as to facilitate an analytical or chemical reaction (e.g., amplification of one or more target DNA) in the material retention region. Such localization can be accomplished by physical and chemical modalities, including, for example, physical containment of reagents in one dimension and chemical containment in one or more other dimensions.

Microplate Footprint

With reference to FIGS. 2-19, microplate 20 generally comprises a main body or substrate 28. In some embodiments, main body 28 is substantially planar. In some embodiments, microplate 20 comprises an optional skirt or flange portion 30 disposed about a periphery of main body 28 (see FIG. 2). Skirt portion 30 can form a lip around main body 28 and can vary in height. Skirt portion 30 can facilitate alignment of microplate 20 on thermocycler block 102. Additionally, skirt portion 30 can provide additional rigidity to microplate 20 such that during handling, filling, testing, and the like, microplate 20 remains rigid, thereby ensuring assay 1000, or any other components, disposed in each of the plurality of wells 26 does not contaminate adjacent wells. However, in some embodiments, microplate 20 can employ a skirtless design (see FIGS. 3-5) depending upon user preference.

In some embodiments, microplate 20 can be from about 50 to about 200 mm in width, and from about 50 to about 200 mm in length. In some embodiments, microplate 20 can be from about 50 to about 100 mm in width, and from about 100 to about 150 mm in length. In some embodiments, microplate 20 can be about 72 mm wide and about 120 mm long.

In order to facilitate use with existing equipment, robotic implements, and instrumentation, the footprint dimensions of main body 28 and/or skirt portion 30 of microplate 20, in some embodiments, can conform to standards specified by the Society of Biomolecular Screening (SBS) and the American National Standards Institute (ANSI), published January 2004 (ANSI/SBS 3-2004). In some embodiments, the footprint dimensions of main body 28 and/or skirt portion 30 of microplate 20 are about 127.76 mm (5.0299 inches) in length and about 85.48 mm (3.3654 inches) in width. In some embodiments, the outside corners of microplate 20 comprise a corner radius of about 3.18 mm (0.1252 inches). In some embodiments, microplate 20 comprises a thickness of about 0.5 mm to about 3.0 mm. In some embodiments, microplate 20 comprises a thickness of about 1.25 mm. In some embodiments, microplate 20 comprises a thickness of about 2.25 mm. One skilled in the art will recognize that microplate 20 and skirt portion 30 can be formed in dimensions other than those specified herein.

Plurality of Material Retention Regions

The density of material retention regions (i.e., number of material retention regions per unit surface area of microplate) and the size and volume of material retention regions can vary depending on the desired application and such factors as, for example, the species of the organism for which the methods of the present teachings may be employed. In some embodiments, the density of material retention regions can be from about 10 to about 1000 regions/cm$^2$, or from about 50 to about 100 regions/cm$^2$, for example about 79 regions/cm$^2$. In some embodiments, the density of material retention regions can be from about 150 to about 170 regions/cm$^2$. In some embodiments, the density of material retention regions can be from about 480 to about 500 regions/cm$^2$.

In some embodiments, the pitch of material retention regions on microplate 20 can be from about 50 to about 10000 µm, or from about 50 to about 1500 µm, or from about 450 to 550 µm. In some embodiments, the pitch of material retention regions on microplate 20 can be from about 50 to about 1000 µm, or from about 400 to 500 µm. In some embodiments, the pitch can be from about 1000 to 1200 µm. In some embodiments, the distance between the material retention regions (the thickness of the wall between chambers) can be from about 50 to about 200 µm, or from about 100 to about 200 µm, for example, about 150 µm.

In some embodiments, the total number of material retention regions on the microplate can be from about 5000 to about 100,000, or from about 5000 to about 50,000, or from about 5000 to about 10,000. In some embodiments, the microplate can comprise from about 10,000 to about 15,000 material retention regions. In some embodiments, the microplate can comprise from about 25,000 to about 35,000 material retention regions.

In order to increase throughput of genotyping, gene expression, and other assays, in some embodiments, microplate 20 comprises an increased quantity of the plurality of wells 26 beyond that employed in prior conventional microplates. In some embodiments, microplate 20 comprises 6,144 wells.

According to the present teachings, microplate 20 can comprise, but is not limited to, any of the array configurations of wells described in Table 1.

TABLE 1

| Total Number of Wells | Rows × Columns | Approximate Well Area |
|---|---|---|
| 96 | 8 × 12 | 9 × 9 mm |
| 384 | 16 × 24 | 4.5 × 4.5 mm |
| 1536 | 32 × 48 | 2.25 × 2.25 mm |
| 3456 | 48 × 72 | 1.5 × 1.5 mm |
| 6144 | 64 × 96 | 1.125 × 1.125 mm |
| 13824 | 96 × 144 | 0.75 × .075 mm |
| 24576 | 128 × 192 | 0.5625 × 0.5625 mm |
| 55296 | 192 × 288 | 0.375 × 0.375 mm |
| 768 | 24 × 32 | 3 × 3 mm |
| 1024 | 32 × 32 | 2.25 × 3 mm |
| 1600 | 40 × 40 | 1.8 × 2.7 mm |
| 1280 | 32 × 40 | 2.25 × 2.7 mm |
| 1792 | 32 × 56 | 2.25 × 1.714 mm |
| 2240 | 40 × 56 | 1.8 × 1.714 mm |
| 864 | 24 × 36 | 3 × 3 mm |
| 4704 | 56 × 84 | 1.257 × 1.257 mm |
| 7776 | 72 × 108 | 1 × 1 mm |
| 9600 | 80 × 120 | 0.9 × .09 mm |
| 11616 | 88 × 132 | 0.818 × 0.818 mm |
| 16224 | 104 × 156 | 0.692 × 0.692 mm |
| 18816 | 112 × 168 | 0.643 × 0.643 mm |
| 21600 | 120 × 180 | 0.6 × 0.6 mm |
| 27744 | 136 × 204 | 0.529 × 0.529 mm |
| 31104 | 144 × 216 | 0.5 × 0.5 mm |
| 34656 | 152 × 228 | 0.474 × 0.474 mm |
| 38400 | 160 × 240 | 0.45 × 0.45 mm |
| 42336 | 168 × 252 | 0.429 × 0.429 mm |
| 46464 | 176 × 264 | 0.409 × 0.409 mm |
| 50784 | 184 × 256 | 0.391 × 0.391 mm |

Material Retention Region Size and Shape

Figure 4:
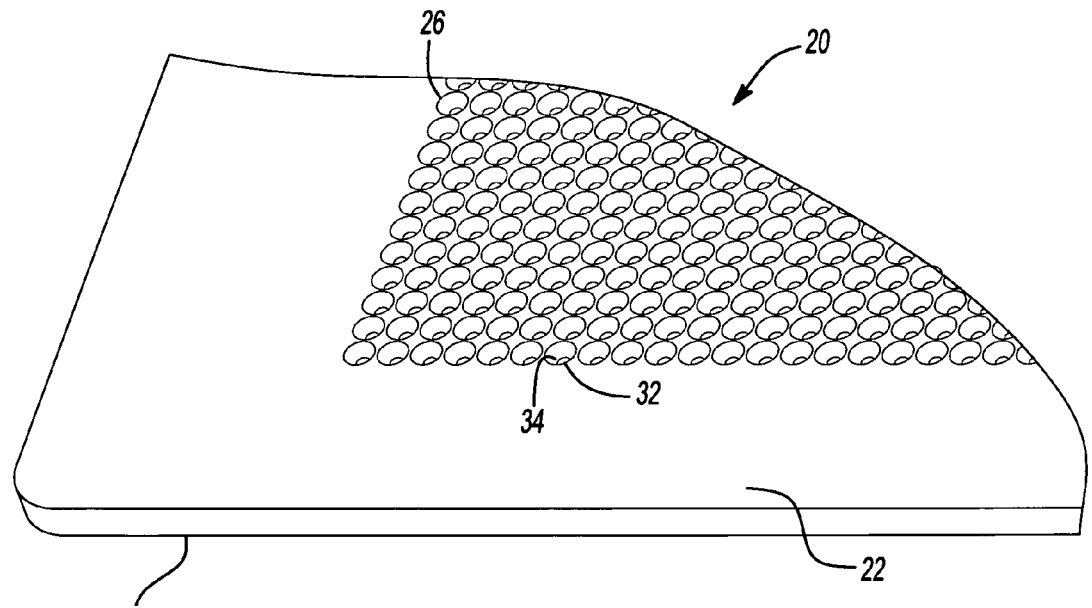
FIG. 4 is an enlarged perspective view illustrating a microplate in accordance with some embodiments comprising a plurality of wells comprising a circular rim portion.
Figure 5:
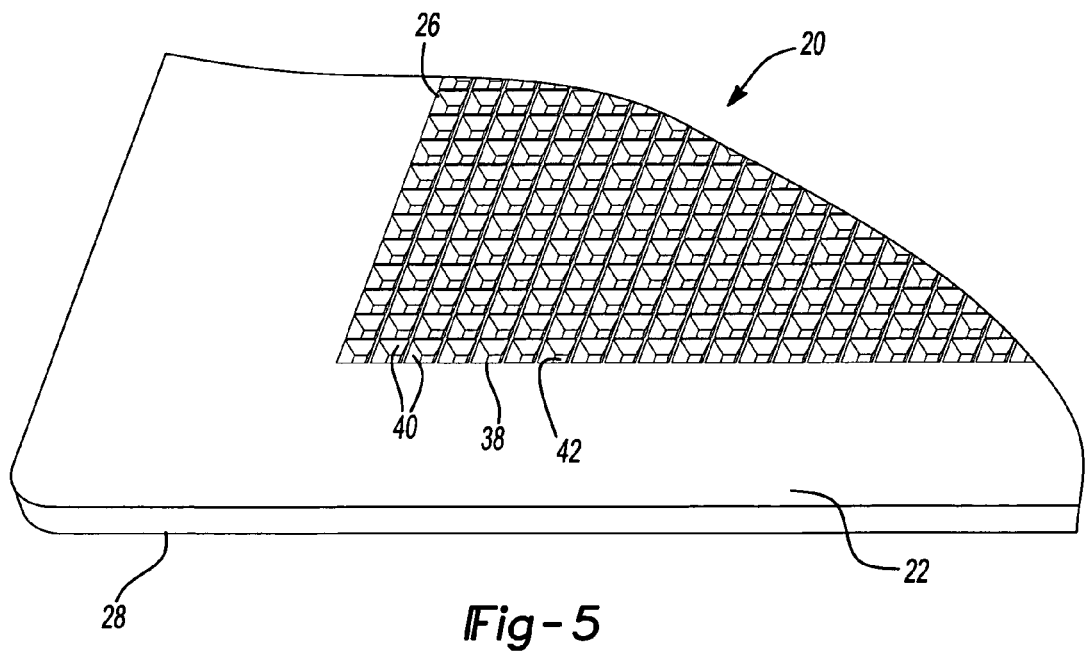
FIG. 5 is an enlarged perspective view illustrating a microplate in accordance with some embodiments comprising a plurality of wells comprising a square-shaped rim portion.

According to some embodiments, as illustrated in FIGS. 4 and 5, each of the plurality of material retention regions (e.g., wells 26) can be substantially equivalent in size. The plurality of wells 26 can have any cross-sectional shape. In some embodiments, as illustrated in FIGS. 4, 26, and 27, each of the plurality of wells 26 comprises a generally circular rim portion 32 (FIG. 4) with a downwardly-extending, generally-continuous sidewall 34 that terminate at a bottom wall 36 interconnected to sidewall 34 with a radius. A draft angle of sidewall 34 can be used in some embodiments. In some embodiments, the draft angle provides benefits including increased ease of manufacturing and minimizing shadowing (as discussed herein). The particular draft angle is determined, at least in part, by the manufacturing method and the size of each of the plurality of wells 26. In some embodiments, circular rim portion 32 can be about 1.0 mm in diameter, the depth of each of the plurality of wells 26 can be about 0.9 mm, the draft angle of sidewall 34 can be about 1° to 5° or greater and each of the plurality of wells 26 can have a center-to-center distance of about 1.125 mm. In some embodiments, the volume of each of the plurality of wells 26 can be about 500 nanoliters.

According to some embodiments, as illustrated in FIG. 5, each of the plurality of wells 26 comprises a generally square-shaped rim portion 38 with downwardly-extending sidewalls 40 that terminate at a bottom wall 42. A draft angle of sidewalls 40 can be used. Again, the particular draft angle is determined, at least in part, by the manufacturing method and the size of each of the plurality of wells 26. In some embodiments of wells 26 of FIG. 5, generally square-shaped rim portion 38 can have a side dimension of about 1.0 mm in length, a depth of about 0.9 mm, a draft angle of about 1° to 5° or greater, and a center-to-center distance of about 1.125 mm, generally indicated at A (see FIG. 27). In some embodiments, the volume of each of the plurality of wells 26 of FIG. 5 can be about 500 nanoliters. In some embodiments, the spacing between adjacent wells 26, as measured at the top of a wall dividing the wells, is less than about 0.5 m. In some embodiments, this spacing between adjacent wells 26 is about 0.25 mm.

In some embodiments, and in some configurations, the plurality of wells 26 comprising a generally circular rim portion 32 can provide advantages over the plurality of wells 26 comprising a generally square-shaped rim portion 38. In some embodiments, during heating, it has been found that assay 1000 can migrate through capillary action upward along edges of sidewalls 40. This can draw assay 1000 from the center of each of the plurality of wells 26, thereby causing variation in the depth of assay 1000. Variations in the depth of assay 1000 can influence the emission output of assay 1000 during analysis. Additionally, during manufacture of microplate 20, in some cases cylindrically shaped mold pins used to form the plurality of wells 26 comprising generally circular rim portion 32 can permit unencumbered flow of molten polymer thereabout. This unencumbered flow of molten polymer results in less deleterious polymer molecule orientation. In some embodiments, generally circular rim portion 32 provides more surface area along microplate 20 for improved sealing with sealing cover 80, as is discussed herein.

In some embodiments, the area of each material retention region can be from about 0.01 to about 0.05 mm$^2$. In some embodiments, the width of each material retention region can be from about 200 to about 2,000 microns, or from about 800 to about 3000 microns. In some embodiments, the depth of each material retention region can be about 1100 microns, or about 850 microns. In some embodiments, the surface area of each material retention region can be from about 0.01 to about 0.05 mm$^2$, or from about 0.02 to about 0.04 mm$^2$. In some embodiments, the aspect ratio (ratio of depth:width) of each material retention region can be from about 1 to about 4, or about 2.

In some embodiments, the volume of the material retention regions can be less than about 50 μl, or less than about 10 μl. In some embodiments, the volume can be from about 0.05 to about 500 nanoliters, from about 0.1 to about 200 nanoliters, from about 20 to about 150 nanoliters, from about 80 to about 120 nanoliters, from about 50 to about 100 nanoliters, from about 1 to about 5 nanoliters, or less than about 2 nanoliters.

Through-Hole Material Retention Regions

Figure 10:
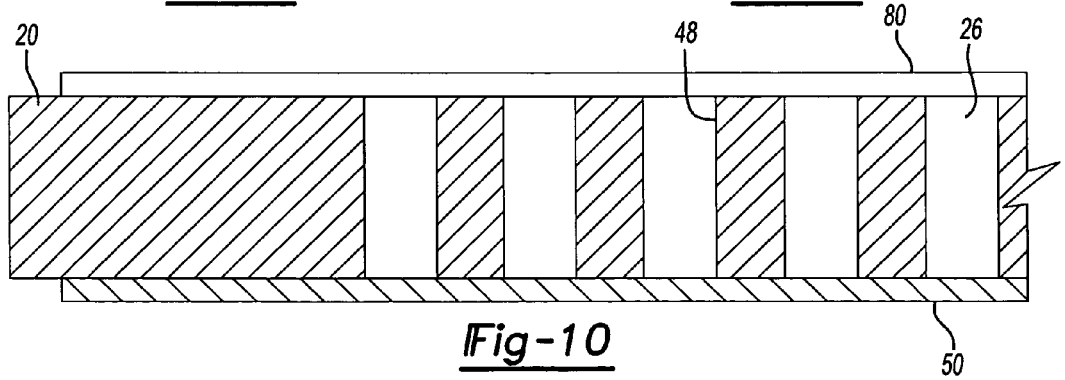
FIG. 10 is a cross-sectional view illustrating a microplate employing a plurality of apertures, a backing sheet, and a sealing cover according to some embodiments.
Figure 11:
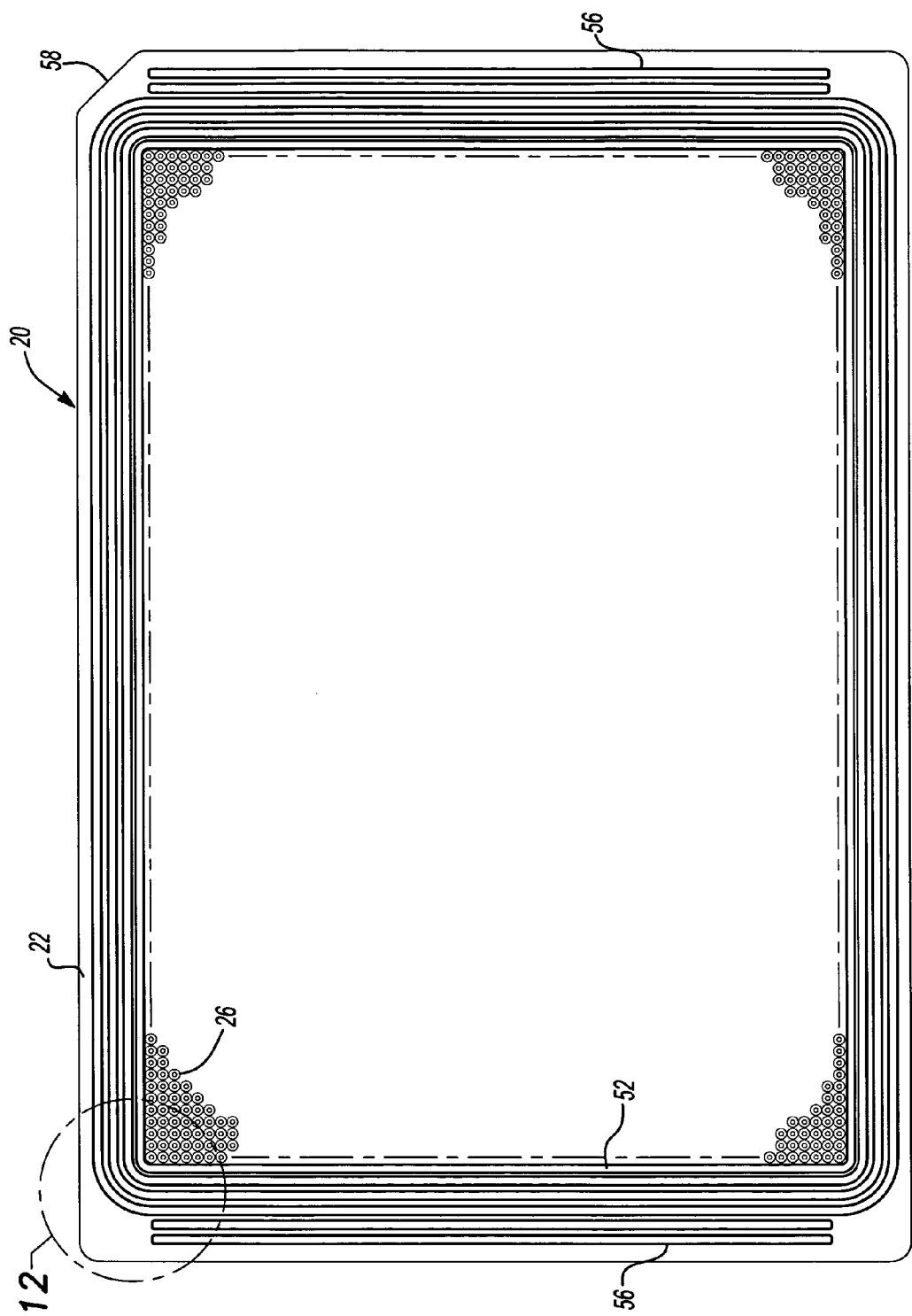
FIG. 11 is a top view illustrating a microplate in accordance with some embodiments comprising one or more grooves.

As illustrated in FIG. 10, in some embodiments, each of the material retention regions of microplate 20 can comprise a plurality of apertures 48 being sealed at least on one end by sealing cover 80. In some embodiments, each of the plurality of apertures 48 can be sealed on an opposing end with a backing sheet 50, which can have a clear or opaque adhesive. In some embodiments, backing sheet 50 can comprise a heat conducting material such as, for example, a metal foil or a metal coated plastic. In some embodiments, backing sheet 50 can be placed against thermocycler block 102 to aid in thermal conductivity and distribution. In some embodiments, backing sheet 50 can comprise a plurality of reaction spots (as discussed herein), coated on discrete areas of the surface of backing sheet 50, such that in some circumstances the plurality of reaction spots can be aligned with the plurality of apertures 48.

In some embodiments, a layer of mineral oil can be placed at the top of each of the plurality of apertures 48 before, or as an alternative to, placement of sealing cover 80 on microplate 20. In several of such embodiments, the mineral oil can fill a portion of each of the plurality of apertures 48 and provide an optical interface and can control evaporation of assay 1000.

Pressure Relief Bores

Figures 6, 7:
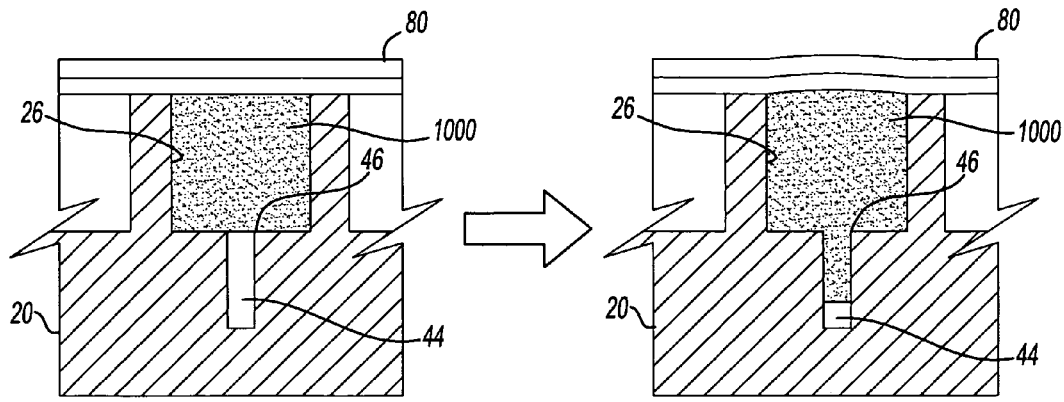
FIG. 6 is a cross-sectional view illustrating a well comprising a pressure relief bore according to some embodiments.
FIG. 7 is a cross-sectional view illustrating the well of FIG. 6 wherein the pressure relief bore is partially filled.

Referring now to FIGS. 6-9, in some embodiments, each of the plurality of wells 26 of microplate 20 can comprise a pressure relief bore 44. In some embodiments, pressure relief bore 44 is sized such that it does not initially fill with assay 1000 due to surface tension. However, when assay 1000 is heated during thermocycling, assay 1000 expands, thereby increasing an internal fluid pressure in each of the plurality of wells 26. This increased internal fluid pressure is sufficient to permit assay 1000 to flow into pressure relief bore 44 as illustrated in FIG. 7, thereby minimizing the pressure exerted on sealing cover 80. In some embodiments, each of the plurality of wells 26 can have one or a plurality of pressure relief bores 44.

Figures 8, 9:
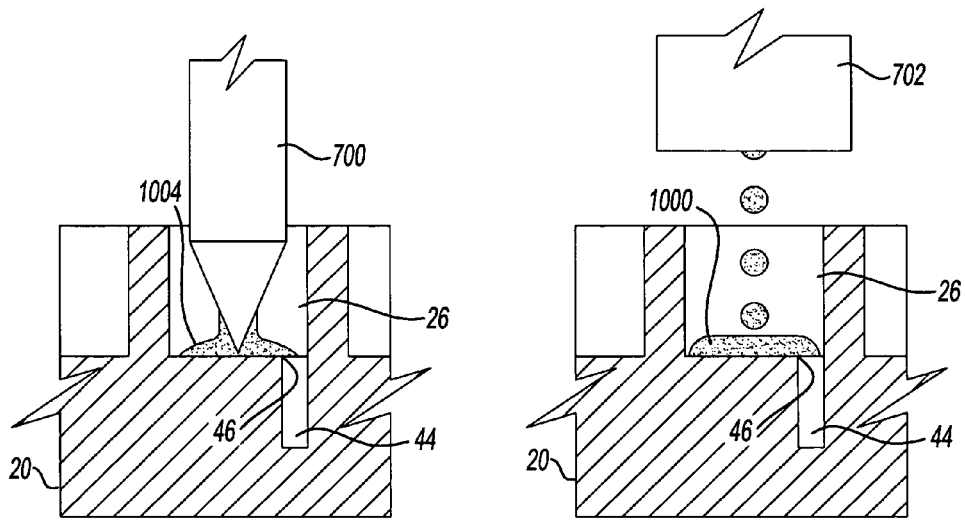
FIG. 8 is a cross-sectional view illustrating a well comprising an offset pressure relief bore according to some embodiments, being filled by a spotting device.
FIG. 9 is a cross-sectional view illustrating the well of FIG. 8 being filled by a micro-piezo dispenser.

In some embodiments, as illustrated in FIGS. 8 and 9, pressure relief bore 44 can be offset within each of the plurality of wells 26 so that each of the plurality of wells 26 can be filled with assay 1000 or other material 1004 via a spotting device 700 (FIG. 8) or a micro-piezo dispenser 702 (FIG. 9). In some embodiments, a top edge 46 of pressure relief bore 44 can be generally square and have minimal or no radius. This arrangement can reduce the likelihood that assay 1000 or other material 1004 will enter pressure relief bore 44 prior to thermocycling.

Grooves

Referring to FIGS. 11-15, in some embodiments, microplate 20 can comprise grooves 52 and grooves 54 disposed about a periphery of the plurality of wells 26. In some embodiments, grooves 52 can have depth and width dimensions generally similar to the depth and width dimensions of the plurality of wells 26 (FIGS. 12 and 13). In some embodiments, grooves 54 can have depth and width dimensions less than the depth and width dimensions of the plurality of wells 26 (FIGS. 14 and 15). In some embodiments, as illustrated in FIG. 12, additional grooves 56 can be disposed at opposing sides of microplate 20. In some embodiments, grooves 52, 54, and 56 can improve thermal uniformity among the plurality of wells 26 in microplate 20. In some embodiments, grooves 52, 54, and 56 can improve the sealing interface formed by sealing cover 80 and microplate 20. Grooves 52, 54, and 56 can also assist in simplifying the injection molding process of microplate 20. In some embodiments, a liquid solution similar to assay 1000 can be disposed in grooves 52, 54, and 56 to, in part, improve thermal uniformity during thermocycling.

Alignment Features

In some embodiments, as illustrated in FIGS. 2, 3, 11, and 14, microplate 20 comprises an alignment feature 58, such as a corner chamfer, a pin, a slot, a cut corner, an indentation, a graphic, or other unique feature that is capable of interfacing with a corresponding feature formed in a fixture, reagent dispensing equipment, and/or thermocycler. In some embodiments, alignment feature 58 comprises a nub or protrusion 60 as illustrated in FIG. 14. Additionally, in some embodiments, alignment features 58 are placed such that they do not interfere with sealing cover 80 or at least one of the plurality of wells 26. However, locating alignment features 58 near at least one of the plurality of wells 26 can provide improved alignment with dispensing equipment and/or thermocycler block 102.

Thermally Isolated Portion

In some embodiments, as illustrated in FIGS. 16-19, microplate 20 comprises a thermally isolated portion 62. Thermally isolated portion 62 can be disposed along at least one edge of main body 28. Thermally isolated portion 62 can be generally free of wells 26 and can be sized to receive a marking indicia 64 (discussed in detail herein) thereon. Thermally isolated portion 62 can further be sized to facilitate the handling of microplate 20 by providing an area that can be easily gripped by a user or mechanical device without disrupting the plurality of wells 26.

Still referring to FIGS. 16-19, in some embodiments, microplate 20 comprises a first groove 66 formed along first surface 22 and a second groove 68 formed along an opposing second surface 24 of microplate 20. First groove 66 and second groove 68 can be aligned with respect to each other to extend generally across microplate 20 from a first side 70 to a second side 72. First groove 66 and second groove 68 can be further aligned upon first surface 22 and second surface 24 to define a reduced cross-section 74 between thermally isolated portion 62 and the plurality of wells 26. This reduced cross-section 74 can provide a thermal isolation barrier to reduce any heat sink effect introduced by thermally isolated portion 62, which might otherwise reduce the temperature cycle of some of the plurality of wells 26.

Marking Indicia

Figure 2:
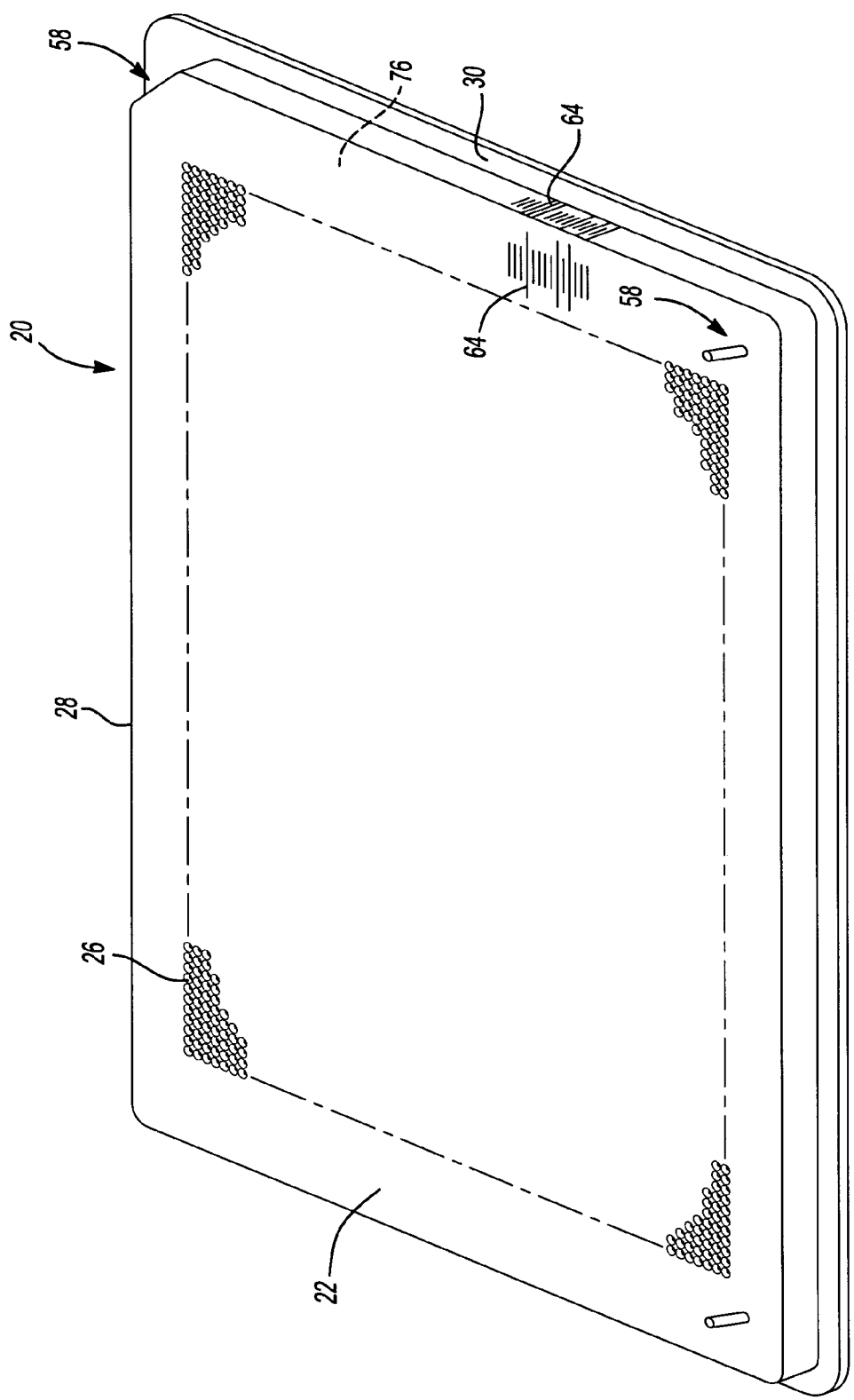
FIG. 2 is a top perspective view illustrating a microplate in accordance with some embodiments.
Figure 3:
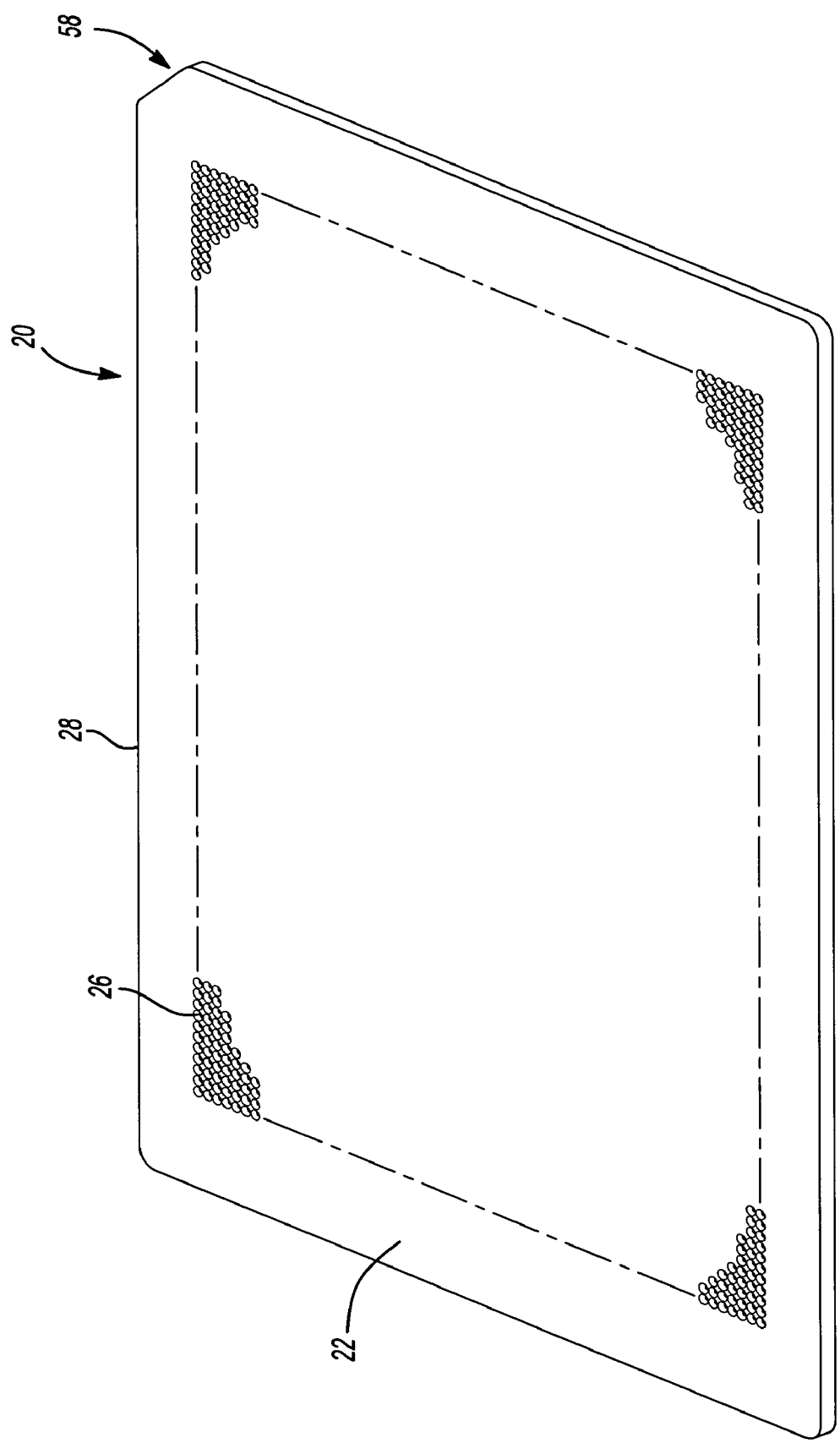
FIG. 3 is a top perspective view illustrating a microplate in accordance with some embodiments.
Figures 16, 17:
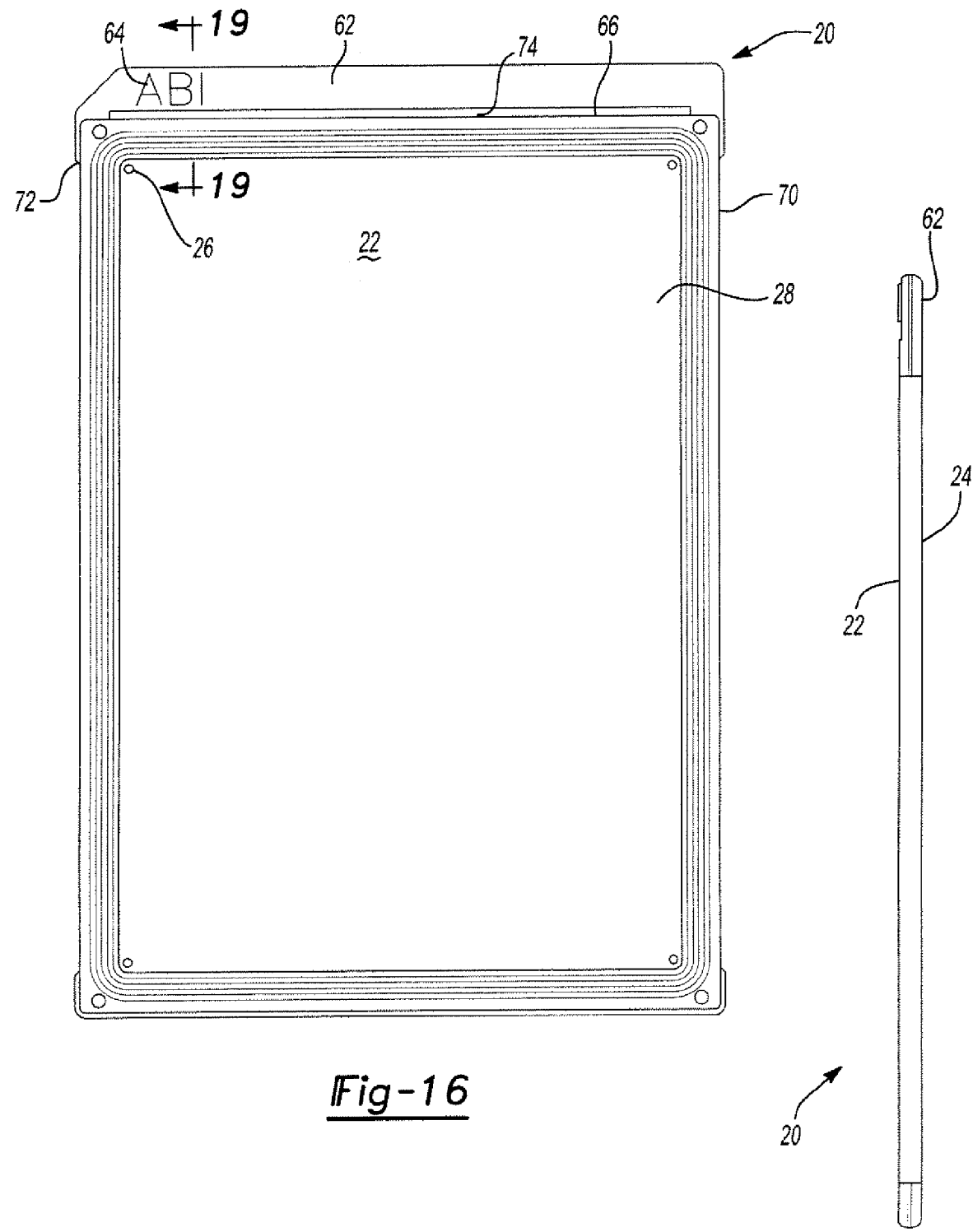
FIG. 16 is a top view illustrating a microplate in accordance with some embodiments comprising at least one thermally isolated portion.
FIG. 17 is a side view illustrating the microplate of FIG. 16.
Figure 18:
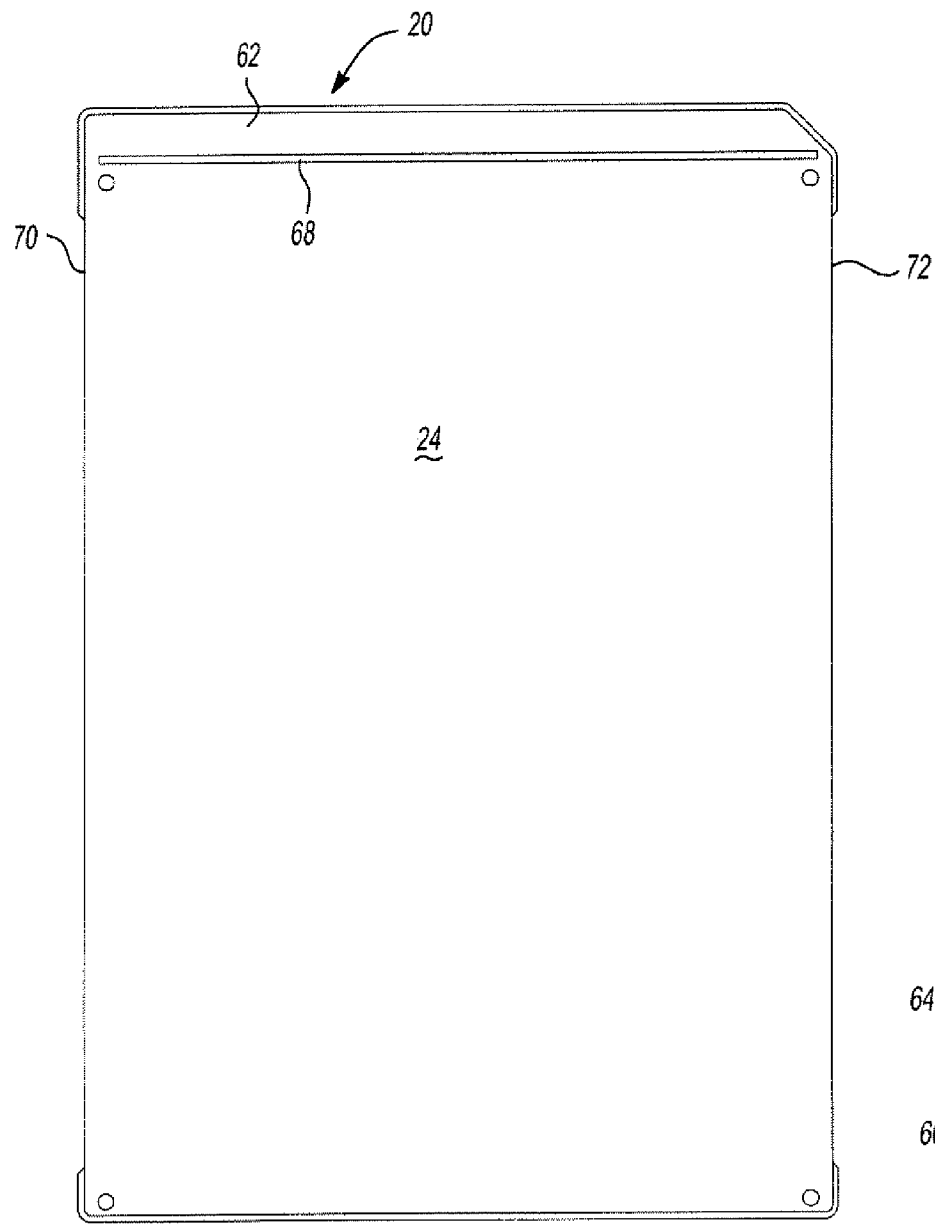
FIG. 18 is a bottom view illustrating the microplate of FIG. 16.
Figure 19:
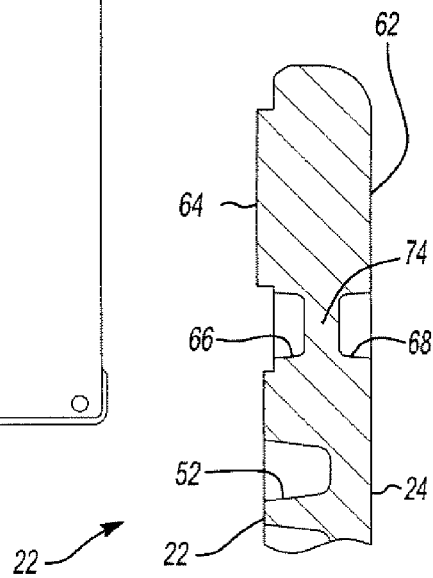
FIG. 19 is an enlarged cross-sectional view illustrating the microplate of FIG. 16 taken along Line 19-19.

In some embodiments, as illustrated in FIGS. 2, 16 and 17, microplate 20 comprises marking indicia 64, such as graphics, printing, lithograph, pictorial representations, symbols, bar codes, handwritings or any other type of writing, drawings, etchings, indentations, embossments or raised marks, machine readable codes (i.e. bar codes, etc.), text, logos, colors, and the like. In some embodiments, marking indicia 64 is permanent.

In some embodiments, marking indicia 64 can be printed upon microplate 20 using any known printing system, such as inkjet printing, pad printing, hot stamping, and the like. In some embodiments, such as those using a light-colored microplate 20, a dark ink can be used to create marking indicia 64 or vice versa.

In some embodiments, microplate 20 can be made of polypropylene and have a surface treatment applied thereto to facilitate applying marking indicia 64. In some embodiments, such surface treatment comprises flame treatment, corona treatment, treating with a surface primer, or acid washing. However, in some embodiments, a UV-curable ink can be used for printing on polypropylene microplates.

Still further, in some embodiments, marking indicia 64 can be printed upon microplate 20 using a $CO_2$ laser marking system. Laser marking systems evaporate material from a surface of microplate 20. Because $CO_2$ laser etching can produce reduced color changes of marking indicia 64 relative to the remaining portions of microplate 20, in some embodiments, a YAG laser system can be used to provide improved contrast and reduced material deformation.

In some embodiments, a laser activated pigment can be added to the material used to form microplate 20 to obtain improved contrast between marking indicia 64 and main body 28. In some embodiments, an antimony-doped tin oxide pigment can be used, which is easily dispersed in polymers and has marking speeds as high as 190 inches per second. Antimony-doped tin oxide pigments can absorb laser light and can convert laser energy to thermal energy in embodiments where indicia are created using a YAG laser.

In some embodiments, marking indicia 64 can identify microplates 20 to facilitate identification during processing. Furthermore, in some embodiments, marking indicia 64 can facilitate data collection so that microplates 20 can be positively identified to properly correlate acquired data with the corresponding assay. Such marking indicia 64 can be employed as part of Good Laboratory Practices (GLP) and Good Manufacturing Practices (GMP), and can further, in some circumstances, reduce labor associated with manually applying adhesive labels, manually tracking microplates, and correlating data associated with a particular microplate.

In some embodiments, marking indicia 64 can assist in alignment by placing a symbol or other machine-readable graphic on microplate 20. An optical sensor or optical eye can detect marking indicia 64 and can determine a location of microplate 20. In some embodiments, such location of microplate 20 can then be adjusted to achieve a predetermined position using, for example, a drive system of high-density sequence detection system 10, sealing cover applicator 1100, or other corresponding systems.

In some embodiments, the type (physical properties, characteristics, etc.) of marking indicia employed on a microplate can be selected so as to reduce thermal and/or chemical interference during thermocycling relative to what might otherwise occur with other types of marking indicia (e.g., common prior indicia designs, such as adhesive labels). For example, adhesive labels can, in some circumstances, interfere (e.g., chemically interact) with one or more reagents (e.g., dyes) being used.

Referring to FIG. 2, in some embodiments, a radio frequency identification (RFID) tag 76 can be used to electronically identify microplate 20. RFID tag 76 can be attached or molded within microplate 20. An RFID reader (not illustrated) can be integrated into high-density sequence detection system 10 to automatically read a unique identification and/or data handling parameters of microplate 20. Further, RFID tag 76 does not require line-of-sight for readability. It should be appreciated that RFID tag 76 can be variously configured and used according to various techniques, such as those described in commonly-assigned U.S. patent application Ser. No. 11/086,069, entitled "SAMPLE CARRIER DEVICE INCORPORATING RADIO FREQUENCY IDENTIFICATION, AND METHOD" filed herewith.

Multi-Piece Construction

In some embodiments, such as illustrated in FIGS. 28-32, microplate 20 can comprise a multi-piece construction. In some embodiments, microplate 20 can comprise main body 28 and a separate cap portion 95 that can be connected with main body 28. In some embodiments, cap portion 95 can be sized and/or shaped to mate with main body 28 such that the combination thereof results in a footprint that conforms to the above-described SBS and/or ANSI standards. Alternatively, main body 28 and/or cap portion 95 can comprise non-standard dimensions, as desired.

Cap portion 95 can be coupled with main body 28 in a variety of ways. In some embodiments, cap portion 95 comprises a cavity 96 (FIG. 32), such as a mortis, sized and/or shaped to receive a support member 97, such as a tenon, extending from main body 28 to couple cap portion 95 with main body 28. In some embodiments, cavity 96 of cap portion 95 and support member 97 of main body 28 can comprise an interference fit or other locking feature, such as a hook member, to at least temporarily join main body 28 and cap portion 95 during assembly. In some embodiments, support member 97 of main body 28 can comprise a cap alignment feature 98 that can interface with a corresponding feature 99 on cap portion 95 to properly align cap portion 95 relative to main body 28. In some embodiments, cap portion 95 can comprise alignment feature 58 for use in later alignment of microplate 20 as described herein. In some embodiments, alignment feature 58 can be disposed on main body 28 to reduce tolerance buildup caused by the interface of cap portion 95 and main body 28.

In some embodiments, cap portion 95 can be formed directly on main body 28, such as through over-molding. In such embodiments, main body 28 can be placed within a mold cavity that generally closely conforms to main body 28 and defines a cap portion cavity generally surrounding support member 97 of main body 28. Over-molding material can then be introduced about support member 97 within cap portion cavity to form cap portion 95 thereon.

In some embodiments, cap portion 95 comprises marking indicia 64 on any surface(s) thereon (e.g. top surface, bottom surface, side surface). In some embodiments, cap portion 95 can comprise an enlarged print area thereon relative to embodiments employing first groove 66 (FIG. 16-19). In some embodiments, cap portion 95 can be made of a material different from main body 28. In some embodiments, cap portion 95 can be made of a material that is particularly conducive to a desired form of printing or marking, such as through laser marking. In some embodiments, a laser-activated pigment can be added to the material used to form cap portion 95 to obtain improved contrast between marking indicia 64 and cap portion 95. In some embodiments, an antimony-doped tin oxide pigment can be used. In some embodiments, cap portion 95 can be color-coded to aid in identifying a particular microplate relative to others.

In some embodiments, cap portion 95 can serve to provide a thermal isolation barrier through the interface of cavity member 96 and support member 97 to reduce any heat sink effect of cap portion 95 relative to main body 28 to maintain a generally consistent temperature cycle of the plurality of wells 26. Cap portion 95 can be made, for example, of a non-thermally conductive material, such as one or more of those set forth herein, to, at least in part, help to thermally isolate cap portion 95 from main body 28.

In some embodiments, cap portion 95 can serve to conceal any injection molding gates coupled to support member 97 during molding. During manufacturing, as such gates are removed from any product, aesthetic variations can result. Any such aesthetic variations in main body 28 can be concealed in some embodiments using cap portion 95. In some case, injection-molding gates can lead to a localized increase in fluorescence. In some embodiments, such localized increase in fluorescence can be reduced using cap portion 95.

Microplate Material

In some embodiments, microplate 20 can comprise, at least in part, a thermally conductive material. In some embodiments, a microplate, in accordance with the present teachings, can be molded, at least in part, of a thermally conductive material to define a cross-plane thermal conductivity of at least about 0.30 W/mK or, in some embodiments, at least about 0.58 W/mK. Such thermally conductive materials can provide a variety of benefits, such as, in some cases, improved heat distribution throughout microplate 20, so as to afford reliable and consistent heating and/or cooling of assay 1000. In some embodiments, this thermally conductive material comprises a plastic formulated for increased thermal conductivity. Such thermally conductive materials can comprise, for example and without limitation, at least one of polypropylene, polystyrene, polyethylene, polyethyleneterephthalate, styrene, acrylonitrile, cyclic polyolefin, syndiotactic polystyrene, polycarbonate, liquid crystal polymer, conductive fillers or plastic materials; and mixtures or combinations thereof. In some embodiments, such thermally conductive materials include those known to those skilled in the art with a melting point greater than about 130° C. For example, microplate 20 can be made of commercially available materials such as RTP199X104849, COOLPOLY E1201, or, in some embodiments, a mixture of about 80% RTP199X104849 and 20% polypropylene.

In some embodiments, microplate 20 can comprise at least one carbon filler, such as carbon, graphite, impervious graphite, and mixtures or combinations thereof. In some cases, graphite has an advantage of being readily and cheaply available in a variety of shapes and sizes. One skilled in the art will recognize that impervious graphite can be non-porous and solvent-resistant. Progressively refined grades of graphite or impervious graphite can provide, in some cases, a more consistent thermal conductivity.

In some embodiments, one or more thermally conductive ceramic fillers can be used, at least in part, to form microplate 20. In some embodiments, the thermally conductive ceramic fillers can comprise boron nitrate, boron nitride, boron carbide, silicon nitride, aluminum nitride, and mixtures or combinations thereof.

In some embodiments, microplate 20 can comprise an inert thermally conductive coating. In some embodiments, such coatings can include metals or metal oxides, such as copper, nickel, steel, silver, platinum, gold, copper, iron, titanium, alumina, magnesium oxide, zinc oxide, titanium oxide, and mixtures thereof.

In some embodiments, microplate 20 comprises a mixture of a thermally conductive material and other materials, such as non-thermally conductive materials or insulators. In some embodiments, the non-thermally conductive material comprises glass, ceramic, silicon, standard plastic, or a plastic compound, such as a resin or polymer, and mixtures thereof to define a cross-plane thermal conductivity of below about 0.30 W/mK. In some embodiments, the thermally conductive material can be mixed with liquid crystal polymers (LCP), such as wholly aromatic polyesters, aromatic-aliphatic polyesters, wholly aromatic poly(ester-amides), aromatic-aliphatic poly(ester-amides), aromatic polyazomethines, aromatic polyester-carbonates, and mixtures thereof. In some embodiments, the composition of microplate 20 can comprise from about 30% to about 60%, or from about 38% to about 48% by weight, of the thermally conductive material.

The thermally conductive material and/or non-thermally conductive material can be in the form of, for example, powder particles, granular powder, whiskers, flakes, fibers, nanotubes, plates, rice, strands, hexagonal or spherical-like shapes, or any combination thereof. In some embodiments, the microplate comprises thermally conductive additives having different shapes to contribute to an overall thermal conductivity that is higher than any one of the individual additives alone.

In some embodiments, the thermally conductive material comprises a powder. In some embodiments, the particle size used herein can be between 0.10 micron and 300 microns. When mixed homogeneously with a resin in some embodiments, powders provide uniform (i.e. isotropic) thermal conductivity in all directions throughout the composition of the microplate.

As discussed above, in some embodiments, the thermally conductive material can be in the form of flakes. In some such embodiments, the flakes can be irregularly shaped particles produced by, for example, rough grinding to a desired mesh size or the size of mesh through which the flakes can pass. In some embodiments, the flake size can be between 1 micron and 200 microns. Homogenous compositions containing flakes can, in some cases, provide uniform thermal conductivity in all directions.

In some embodiments, the thermally conductive material can be in the form of fibers, also known as rods. Fibers can be described, among other ways, by their lengths and diameters. In some embodiments, the length of the fibers can be, for example, between 2 mm and 15 mm. The diameter of the fibers can be, for example, between 1 mm and 5 mm. Formulations that include fibers in the composition can, in some cases, have the benefit of reinforcing the resin for improved material strength.

In some embodiments, microplate 20 can comprise a material comprising additives to promote other desirable properties. In some embodiments, these additives can comprise flame-retardants, antioxidants, plasticizers, dispersing aids, marking additives, and mold-releasing agents. In some embodiments, such additives are biologically and/or chemically inert.

In some embodiments, microplate 20 comprises, at least in part, an electrically conductive material, which can improve reagent dispensing alignment. In this regard, electrically conductive material can reduce static build-up on microplate 20 so that the reagent droplets will not go astray during dispensing. In some embodiments, a voltage can be applied to microplate 20 to pull the reagent droplets into a predetermined position, particularly with a co-molded part where the bottom section can be electrically conductive and the sides of the plurality of wells 26 may not be electrically conductive. In some embodiments, a voltage field applied to the electrically conductive material under the well or wells of interest can pull assay 1000 into the appropriate wells.

In some embodiments, microplate 20 can be made, at least in part, of non-electrically conductive materials. In some embodiments, non-electrically conductive materials can at least in part comprise one or more of crystalline silica (3.0 W/mK), aluminum oxide (42 W/mK), diamond (2000 W/mK), aluminum nitride (150-220 W/mK), crystalline boron nitride (1300 W/mK), and silicon carbide (85 W/mK).

Microplate Surface Treatments

In some embodiments, the surface of the microplate 20 comprises an enhanced surface which can comprise a physical or chemical modality on or in the surface of the microplate so as to enhance support of, or filling of, assay 1000 in a material retention region (e.g., a well or a reaction spot). Such modifications can include chemical treatment of the surface, or coating the surface. In some embodiments, such chemical treatment can comprise chemical treatment or modification of the surface of the microplate so as to form relatively hydrophilic and hydrophobic areas. In some embodiments, a surface tension array can be formed comprising a pattern of hydrophilic sites forming material retention regions on an otherwise hydrophobic surface, such that the hydrophilic sites can be spatially segregated by hydrophobic areas. Reagents delivered to the surface tension array can be retained by surface tension difference between the hydrophilic sites and the hydrophobic areas.

In some embodiments, hydrophobic areas can be formed on the surface of microplate 20 by coating microplate 20 with a photoresist substance and using a photomask to define a pattern of material retention regions on microplate 20. After exposure of the photomasked pattern, at least a portion of the surface of microplate 20 can be reacted with a suitable reagent to form a stable hydrophobic surface. Such reagents can comprise, for example, one or more members of alkyl groups, such as, for example, fluoroalkylsilane or long chain alkylsilane (e.g. octadecylsilane). The remaining photoresist substance can then be removed and the solid support reacted with a suitable reagent, such as aminoalkyl silane or hydroxyalkyl silane, to form hydrophilic sites. In some embodiments, microplate 20 can be first reacted with a suitable derivatizing reagent to form a hydrophobic surface. Such reagents can comprise, for example, vapor or liquid treatment of fluoroalkylsiloxane or alkylsilane. The hydrophobic surface can then be coated with a photoresist substance, photopatterned, and developed.

In some embodiments, the exposed hydrophobic surface can be reacted with suitable derivatizing reagents to form hydrophilic sites. For example, in some embodiments, the exposed hydrophobic surface can be removed by wet or dry etch such as, for example, oxygen plasma and then derivatized by aminoalkylsilane or hydroxylalkylsilane treatment. The photoresist coat can then be removed to expose the underlying hydrophobic areas.

The exposed surface can be reacted with suitable derivatizing reagents to form hydrophobic areas. In some embodiments, the hydrophobic areas can be formed by fluoroalkylsiloxane or alkylsilane treatment. The photoresist coat can be removed to expose the underlying hydrophilic sites. In some embodiments, fluoroalkylsilane or alkylsilane can be employed to form a hydrophobic surface. In some embodiments, aminoalkyl silane or hydroxyalkyl silane can be used to form hydrophilic sites. In some embodiments, derivatizing reagents can comprise hydroxyalkyl siloxanes, such as allyl trichlorochlorosilane, and 7-oct-l-enyl trichlorochlorosilane; diol(bis-hydroxyalkyl)siloxanes; glycidyl trimethoxysilanes; aminoalkyl siloxanes, such as 3-aminopropyl trimethoxysilane; Dimeric secondary aminoalkyl siloxanes, such as bis(3-trimethoxysilylpropyl)amine; and combinations thereof.

In some embodiments, the surface of microplate 20 can be first reacted with a suitable derivatizing reagent to form hydrophilic sites. Suitable reagents can comprise, for example, vapor or liquid treatment of aminoalkylsilane or hydroxylalkylsilane. The derivatized surface can then be coated with a photoresist substance, photopatterned, and developed. In some embodiments, hydrophilic sites can be formed on the surface of microplate 20 by forming the surface, or chemically treating it, with compounds comprising free amino, hydroxyl, carboxyl, thiol, amido, halo, or sulfate groups. In some embodiments, the free amino, hydroxyl, carboxyl, thiol, amido, halo, or sulfate group of the hydrophilic sites can be covalently coupled with a linker moiety (e.g., polylysine, hexethylene glycol, and polyethylene glycol).

In some embodiments, hydrophilic sites and hydrophobic areas can be made without the use of photoresist. In some embodiments, a substrate can be first reacted with a reagent to form hydrophilic sites. At least some the hydrophilic sites can be protected with a suitable protecting agent. The remaining, unprotected, hydrophilic sites can be reacted with a reagent to form hydrophobic areas. The protected hydrophilic sites can then be unprotected. In some embodiments, a glass surface can be reacted with a reagent to generate free hydroxyl or amino sites. These hydrophilic sites can be reacted with a protected nucleoside coupling reagent or a linker to protect selected hydroxyl or amino sites. In some embodiments, nucleotide coupling reagents can comprise, for example, a DMT-protected nucleoside phosphoramidite, and DMT-protected H-phosphonate. The unprotected hydroxyl or amino sites can be reacted with a reagent, for example, perfluoroalkanoyl halide, to form hydrophobic areas. The protected hydrophilic sites can then be unprotected.

In some embodiments, the chemical modality can comprise chemical treatment or modification of the surface of microplate 20 so as to anchor one or more components of assay 1000 to the surface. In some embodiments, one or more components of assay 1000 can be anchored to the surface so as to form a patterned immobilization reagent array of material retention regions. In some embodiments, the immobilization reagent array can comprise a hydrogel affixed to microplate 20. In some embodiments, hydrogels can comprise cellulose gels, such as agarose and derivatized agarose; xanthan gels; synthetic hydrophilic polymers, such as cross-linked polyethylene glycol, polydimethyl acrylamide, polyacrylamide, polyacrylic acid (e.g., cross-linked with dysfunctional monomers or radiation cross-linking), and micellar networks; and mixtures thereof. In some embodiments, derivatized agarose can comprise agarose which has been chemically modified to alter its chemical or physical properties. In some embodiments, derivatized agarose can comprise low melting agarose, monoclonal anti-biotin agarose, streptavidin derivatized agarose, or any combination thereof.

In some embodiments, an anchor can be an attachment of a reagent to the surface, directly or indirectly, so that one or more reagents is available for reaction during a chemical or amplification method, but is not removed or otherwise displaced from the surface prior to reaction during routine handling of the substrate and sample preparation prior to use. In some embodiments, assay 1000 can be anchored by covalent or non-covalent bonding directly to the surface of the substrate. In some embodiments, assay 1000 can be bonded, anchored, or tethered to a second moiety (immobilization moiety) which, in turn, can be anchored to the surface of microplate 20. In some embodiments, assay 1000 can be anchored to the surface through a chemically releasable or cleavable site, for example by bonding to an immobilization moiety with a releasable site. Assay 1000 can be released from microplate 20 upon reacting with cleaving reagents prior to, during, or after manufacturing of microplate 20. Such release methods can include a variety of enzymatic, or non-enzymatic means, such as chemical, thermal, or photolytic treatment.

In some embodiments, assay 1000 can comprise a primer, which is releasable from the surface of microplate 20. In some embodiments, a primer can be initially hybridized to a polynucleotide immobilization moiety, and subsequently released by strand separation from the array-immobilized polynucleotides during manufacturing of microplate 20. In some embodiments, a primer can be covalently immobilized on microplate 20 via a cleavable site and released before, during, or after manufacturing of microplate 20. For example, an immobilization moiety can contain a cleavable site and a primer. The primer can be released via selective cleavage of the cleavable sites before, during, or after assembly. In some embodiments, the immobilization moiety can be a polynucleotide which contains one or more cleavable sites and one or more primer polynucleotides. A cleavable site can be introduced in an immobilized moiety during in situ synthesis. Alternatively, the immobilized moieties containing releasable sites can be prepared before they are covalently or non-covalently immobilized on the solid support. In some embodiments, chemical moieties for immobilization attachment to solid support can comprise carbamate, ester, amide, thiolester, (N)-functionalized thiourea, functionalized maleimide, amino, disulfide, amide, hydrazone, streptavidin, avidin/biotin, and gold-sulfide groups.

In some embodiments, microplate 20 can be coated with one or more thin conformal isotropic coatings operable to improve the surface characteristics of the microplate, the material retention regions, or both, for conducting a chemical or amplification reaction. In some embodiments, such treatments improve wettability of the surface, low moisture transmissivity of the surface, and high service temperature characteristics of the substrate.

Microplate Molding

In some embodiments, microplate 20 can be molded by first extruding a melt blend comprising a mixture of a polymer and one or more thermally conductive materials and/or additives. In some embodiments, the polymer and thermally conductive additives can be fed into a twin-screw extruder using a gravimetric feeder to create a well-dispersed melt blend. In some embodiments, the extruded melt blend can be transferred through a water bath to cool the melt blend before being pelletized and dried. The pelletized melt blend can then be heated above its melting point by an injection molding machine and then injected into a mold cavity. The mold cavity can generally conform to a desired shape of microplate 20. In some embodiments, the injection-molding machine can cool the injected melt blend to create microplate 20. Finally, microplate 20 can be removed from the injection-molding machine.

In some embodiments, two or more material types of pellets can be mixed together and the combination then placed in the injection molding machine to be melt blended during the injection molding process. In some embodiments, microplate 20 can be molded by first receiving pellet material from a resin supplier; drying the pellet material in a resin dryer; transferring the dried pellet material with a vacuum system into a hopper of a mold press; molding microplate 20; trimming any resultant gates or flash; and packaging microplate 20. In some embodiments, the mold cavity can be centrally gated along the second surface 24 of microplate 20. In some embodiments, the mold cavity can be gated along a perimeter of main body 28 and/or skirt portion 30 of microplate 20.

Microplate Filling

In some embodiments, one or more devices or fluid interconnect systems can be used to facilitate the placement of one or more components of assay 1000 within at least some of the plurality of wells 26 of microplate 20.

In some embodiments, microplate 20 can additionally comprise a filling feature, which is operable to facilitate filling of reagents and/or samples into the material retention regions of microplate. In some embodiments, filling devices can include, for example, physical and chemical modalities that direct, channel, route, or otherwise effect flow of reagents or samples on the surface of microplate 20, on the surface of sealing cover 80, or combinations thereof. In some embodiments, the filling device effects flow of reagents into material retention regions. In some embodiments, microplate 20 can comprise raised or depressed regions (e.g., barriers and trenches) to aid in the distribution and flow of liquids on the surface of the microplate. In some embodiments, the filling system comprises capillary channels. The dimensions of these features are variable, depending on factors, such as avoidance of air bubbles during use, handling convenience, and manufacturing feasibility.

In some embodiments, a filling apparatus 400 can be used to fill at least some of the plurality of wells 26 of microplate 20 with one or more components of assay 1000. It should be understood that filling apparatus 400 can comprise any one of a number of configurations.

Figure 20:
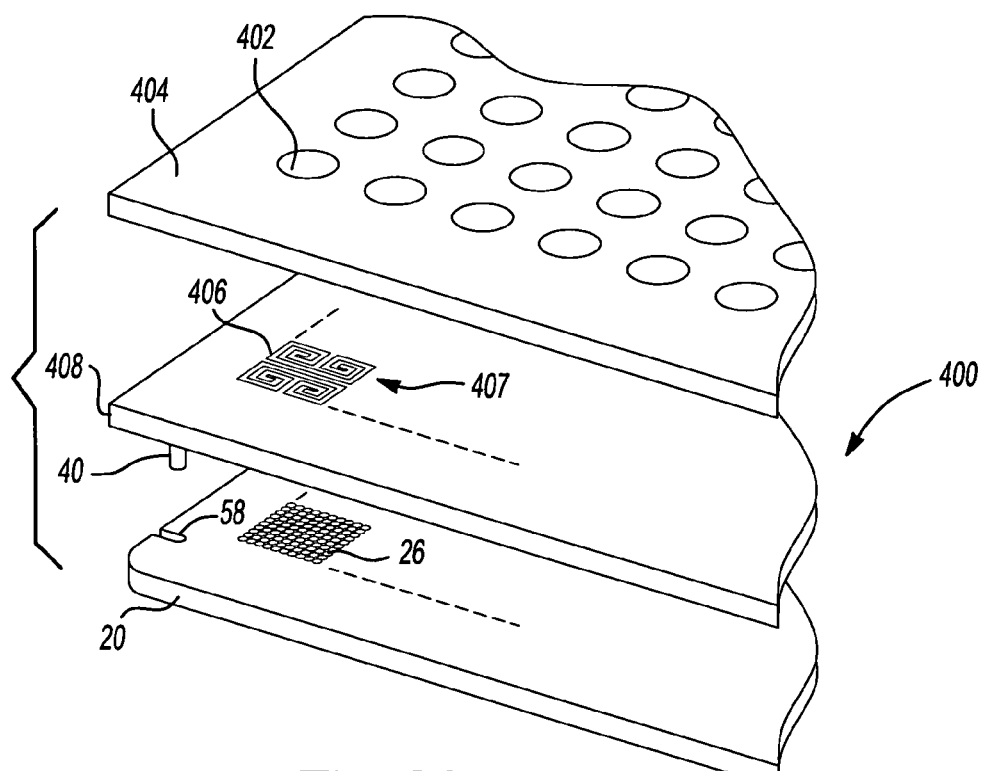
FIG. 20 is an exploded perspective view illustrating a filling apparatus according to some embodiments.
Figure 21:
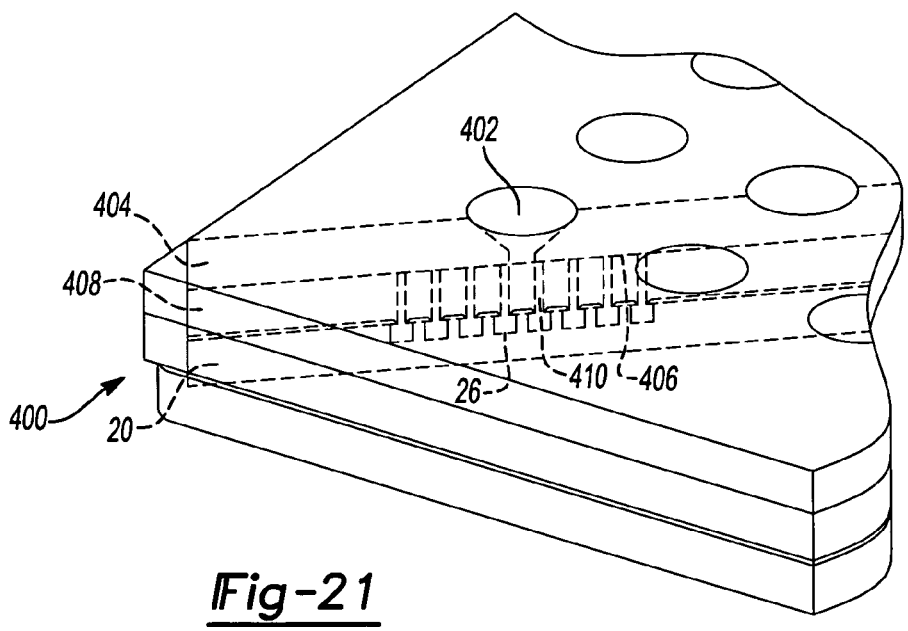
FIG. 21 is a cross-sectional perspective view of the filling apparatus of FIG. 20.
Figure 22A:
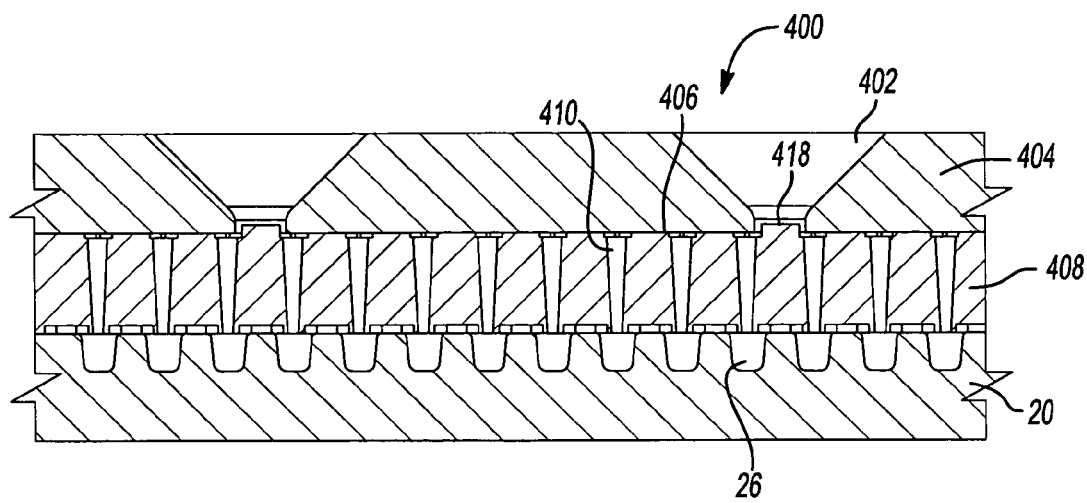
FIG. 22(a) is a cross-sectional perspective view of a filling apparatus according to some embodiments.

In some embodiments, referring to FIGS. 20-22(*b*), filling apparatus 400 comprises one or more assay input ports 402, such as about 96 input ports, disposed in an input layer 404. In some embodiments, assay input ports 402 of input layer 404 can be in fluid communication with a plurality of microfluidic channels 406 disposed in input layer 404, an output layer 408, or any other layer of filling apparatus 400. In some embodiments, the plurality of microfluidic channels 406 can be formed in an underside of input layer 404 and a seal member can be placed over the underside of input layer 404. In some embodiments, the seal member can comprise a perforation (e.g. hole) positioned over a desired location in microplate 20 to permit a discrete fluid communication passage to extend therethrough. In some embodiments, the plurality of microfluidic channels 406 can be arranged as a grouping 407 (FIG. 20). In some embodiments, assay input ports 402 can be positioned at a predetermined pitch (e.g. 9 mm) such that each assay input port 402 can be aligned with a center of each grouping 407. In some embodiments, the plurality of microfluidic channels 406 can be in fluid communication with a plurality of staging capillaries 410 formed in output layer 408 (FIGS. 21-22(*b*)).

In some embodiments, input layer 404 and output layer 408 can be bonded or otherwise joined together to form a single unit. This bond can be made with, among other things, a double-stick tape, a laser weld, an ultrasonic weld, or an adhesive. However, it should be appreciated that the bonding or otherwise joining of input layer 404 and output layer 408 is not required.

During filling, assay 1000 can be put into at least one assay input port 402 and can be fluidly channeled toward at least one of the plurality of microfluidic channels 406, first passing a surface tension relief post 418 in some embodiments. In some embodiments, surface tension relief post 418 can serve, at least in part, to evenly spread assay 1000 throughout the plurality of microfluidic channels 406 and/or engage a meniscus of assay 1000 to encourage fluid flow. Assay 1000 can be fluidly channeled through the plurality of microfluidic channels 406 and can collect in the plurality of staging capillaries 410 (FIG. 22(*b*)). Assay 1000 can then be held in the plurality of staging capillaries 410 by capillary or surface tension forces.

In some embodiments, as illustrated in FIGS. 21 and 22(*a*)-(*b*), microplate 20 can be attached to filling apparatus 400 so that each of the plurality of staging capillaries 410 is generally aligned with each of the plurality of wells 26. In some embodiments, filling apparatus 400 comprises alignment features 411 (FIG. 20) operably sized to engage corresponding alignment feature 58 on microplate 20 to, at least in part, facilitate proper alignment of each of the plurality of staging capillaries 410 with a corresponding (respective) one of the plurality of wells 26. In some embodiments, the combined unit of filling apparatus 400 and microplate 20 can then be placed in a centrifuge. The centrifugal force of the centrifuge can, at least in part, urge assay 1000 from the plurality of staging capillaries 410 into each of the plurality of wells 26 of microplate 20. Filling apparatus 400 can then be removed from microplate 20. In some embodiments, microplate 20 can then receive additional reagents and/or be sealed with sealing cover 80, or other sealing feature such as a layer of mineral oil, and then placed into high-density sequence detection system 10.

In some embodiments, capillary or surface tension forces encourage flow of assay 1000 through staging capillaries 410. In this regard, staging capillaries 410 can be of capillary size, for example, staging capillaries 410 can be formed with an exit diameter less than about 500 micron, and in some embodiments less than about 250 microns. In some embodiments, staging capillaries 410 can be formed, for example, with a draft angle of about 1-5° and can define any thickness sufficient to achieve a predetermined volume. To further encourage the desired capillary action in staging capillaries 410, staging capillaries 410 can be provided with an interior surface that is hydrophilic, i.e., wettable. For example, the interior surface of staging capillaries 410 can be formed of a hydrophilic material and/or treated to exhibit hydrophilic characteristics. In some embodiments, the interior surface comprises native, bound, or covalently attached charged groups. For example, one suitable surface, according to some embodiments, is a glass surface having an absorbed layer of a polycationic polymer, such as poly-l-lysine.

Ramps

In some embodiments, as illustrated in FIGS. 22(*b*) and 23(*a*)-(*b*), each of the plurality of staging capillaries 410 can comprise a ramp feature 414 disposed at an entrance thereof to achieve a predetermined capillary action. It should be appreciated that ramp feature 414 can be formed on one or more edges of the entrance to each of the plurality of staging capillaries 410. In some embodiments, ramp feature 414 can comprise a countersink lip or chamfered rim formed about the entire entrance. In some embodiments that do not employ the plurality of microfluidic channels 406, ramp feature 414 can be used to reduce an angle between staging capillary 410 and an upper surface 456 (to be described herein) of output layer 408 to aid in capillary flow and/or exposure time to a fluid bead moving thereby.

Nozzles Bottom Features

Figure 22B:
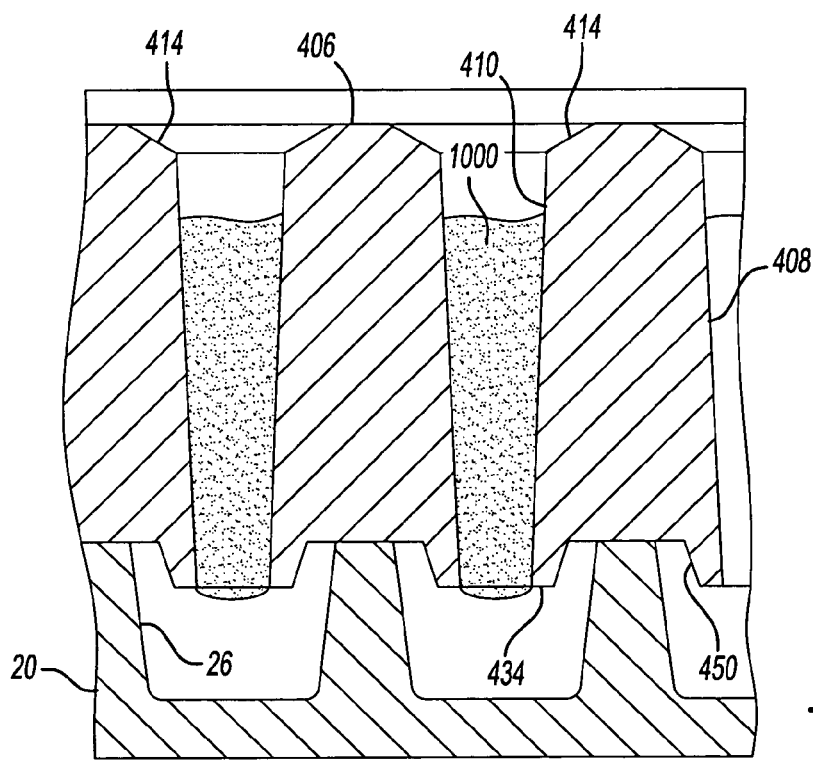
FIG. 22(b) is a cross-sectional view of a portion of a filling apparatus comprising a plurality of staging capillaries, microfluidic channels, and ramp features according to some embodiments.
Figure 24:
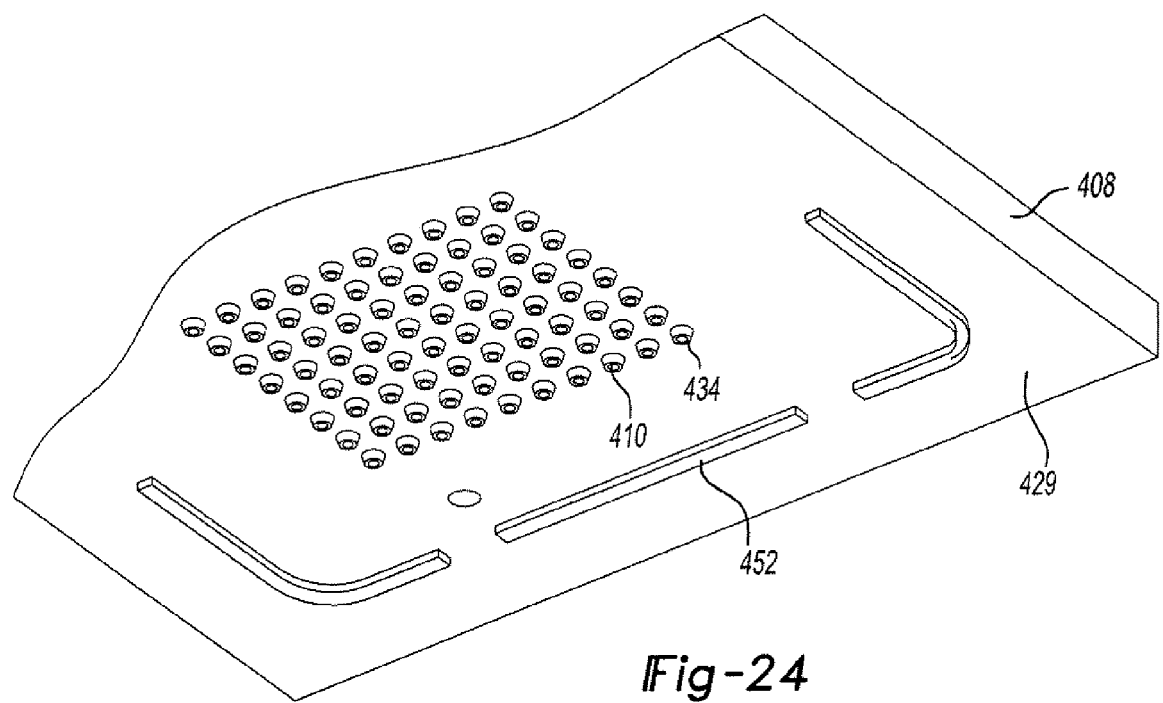
FIG. 24 is a bottom perspective view of an output layer of a filling apparatus comprising spacer features according to some embodiments.

In some embodiments, with reference to FIGS. 22(b) and 24, output layer 408 can comprise a protrusion 450 formed on an outlet 434 of staging capillary 410. In some embodiments, protrusion 450 can be shaped to cooperate with a corresponding shape of each of the plurality of wells 26. In some embodiments, protrusion 450 can be conically shaped to be received within circular rim portion 32 of each of the plurality of wells 26. In some embodiments, protrusion 450 can be square-shaped to be received within square-shaped rim portion 38 of each of the plurality of wells 26. Protrusion 450, in some embodiments, can define a sufficiently sharp surface such that the capillary force within staging capillary 410 can retain assay 1000 and protrusion 450 can inhibit movement of assay 1000 to adjacent wells 26. In some embodiments, protrusion 450 of output layer 408 can be positioned above microplate 20, flush with first surface 22 of microplate 20 (FIG. 22(a)), or disposed within well 26 of microplate 20 (FIG. 22(b)). In some embodiments, protrusion 450 can define a nozzle feature that comprises a diameter that is less than the diameter of the plurality of wells 26 to aid, at least in part, in capillary retention of assay 1000 within staging capillary 410.

Protrusion 450 can be provided with an exterior surface that is hydrophobic, i.e., one that causes aqueous medium deposited on the surface to bead. For example, protrusion 450 can be formed of a hydrophobic material and/or treated to exhibit hydrophobic characteristics. This can be useful, for example, to prevent spreading of a drop, formed at tip portion 1840. A variety of known hydrophobic polymers, such as polystyrene, polypropylene, and/or polyethylene, can be utilized to obtain desired hydrophobic properties. In addition, or as an alternative, a variety of lubricants or other conventional hydrophobic films can be applied to tip portion 1840.

Bottom Feature—Spacer

In some embodiments, as illustrated in FIG. 24, one or more spacer members 452 can be formed along bottom surface 429 of output layer 408 to, at least in part, achieve a desired spacing between output layer 408 and microplate 20. In some embodiments, spacer member 452 can be formed as an elongated member (FIG. 24), a post (FIG. 35), one or more spaced-apart members, or the like.

Fluidic Patterns

Figure 23A:
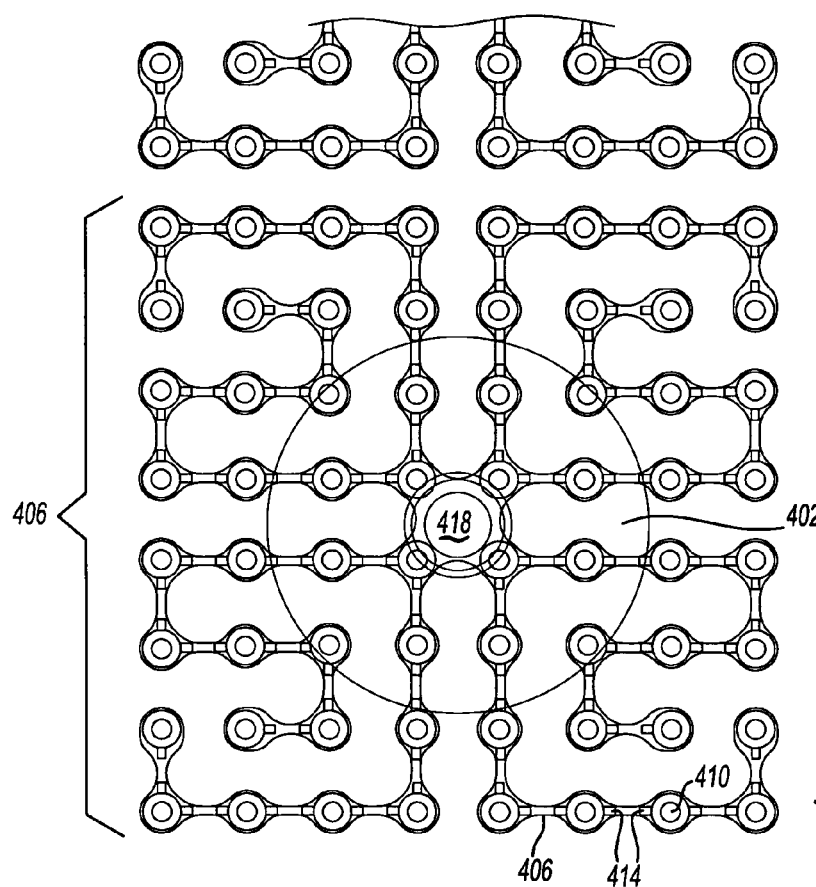
FIG. 23(a) is a top schematic view of a filling apparatus according to some embodiments.
Figure 23B:
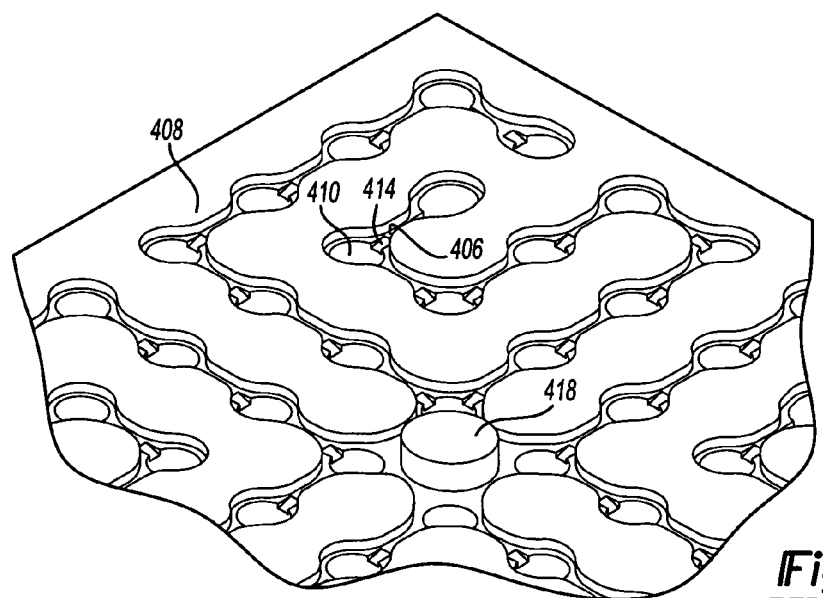
FIG. 23(b) is a top perspective view of a portion of a filling apparatus comprising a plurality of staging capillaries, microfluidic channels, and ramp features according to some embodiments.
Figure 25A:
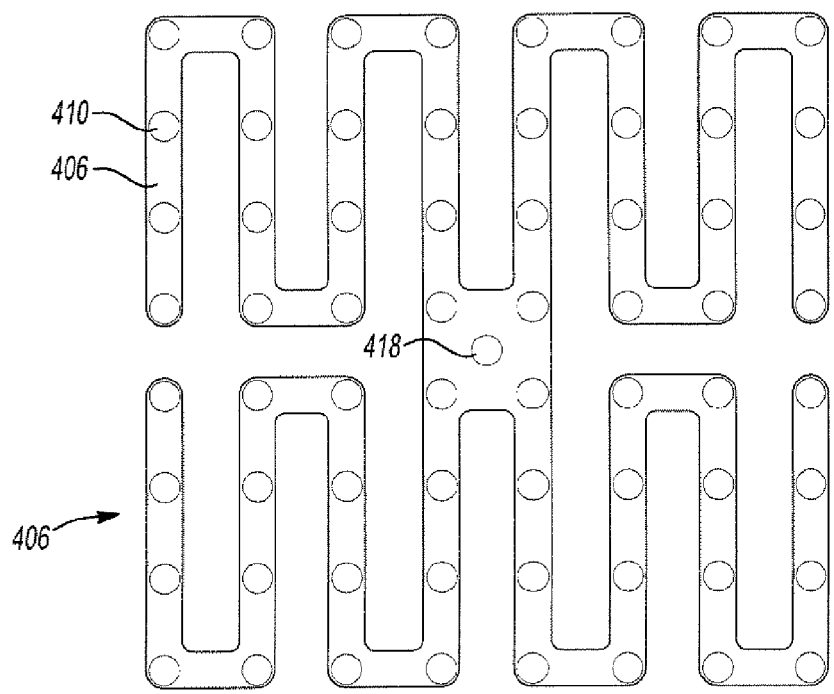
Figure 25B:
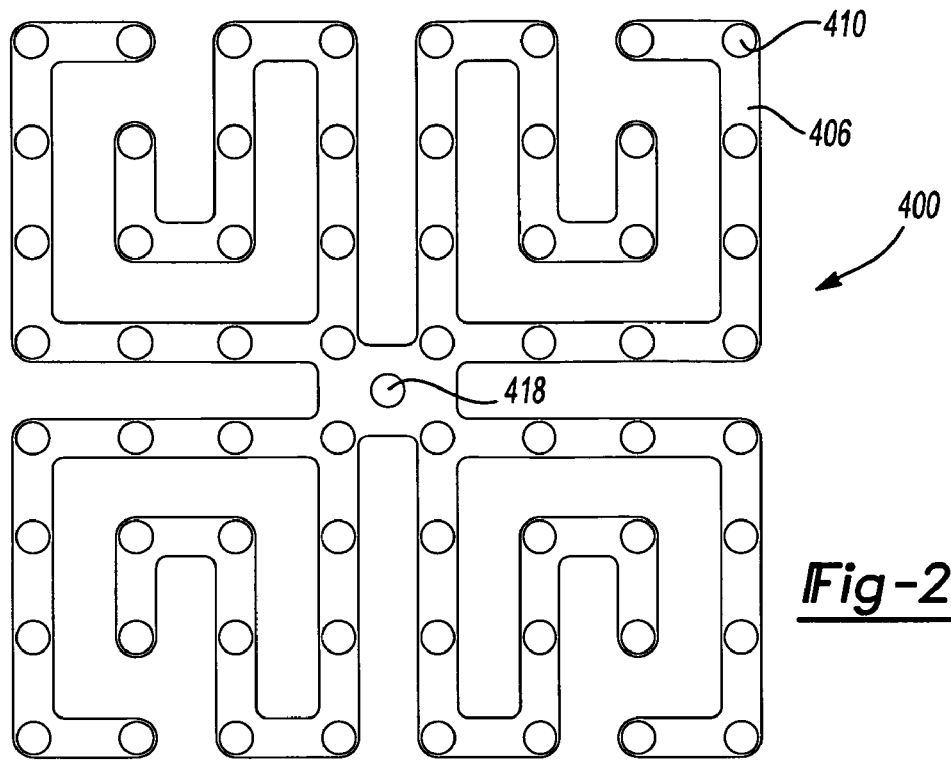
Figure 25C:
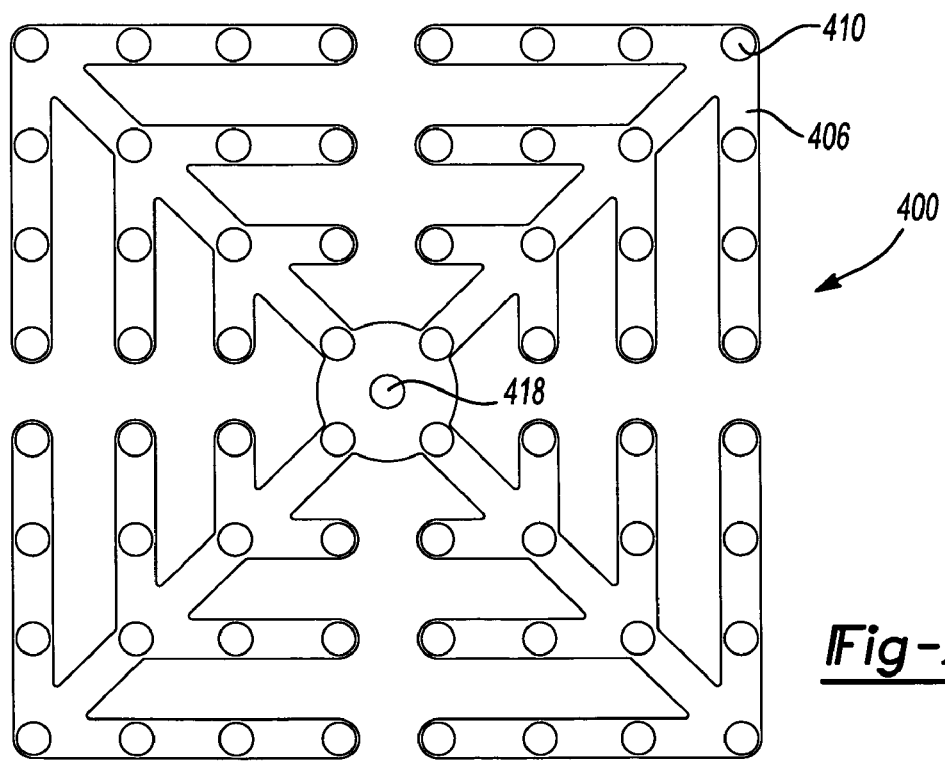
Figure 25D:
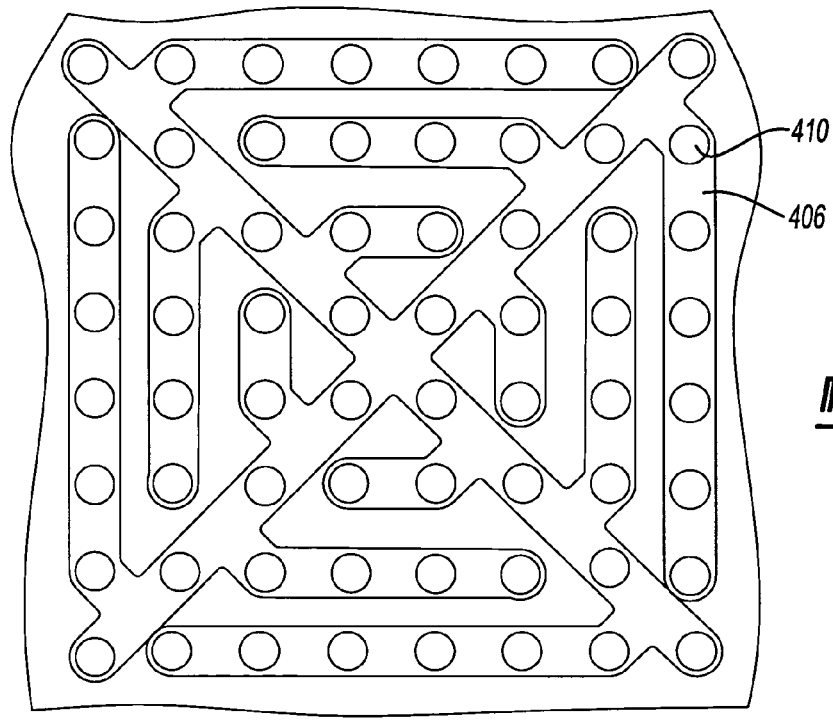
Figure 25E:
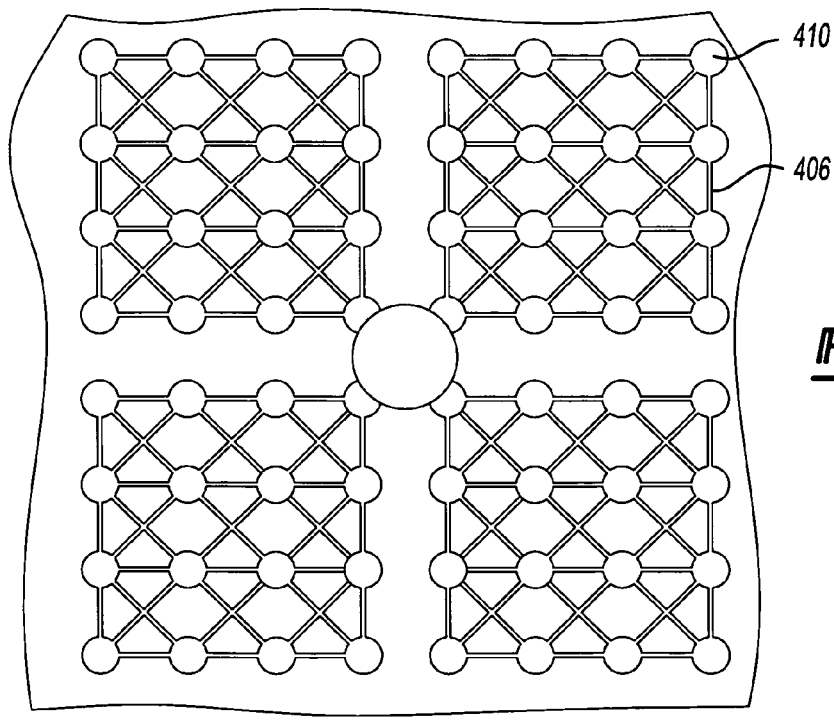
Figure 25F:
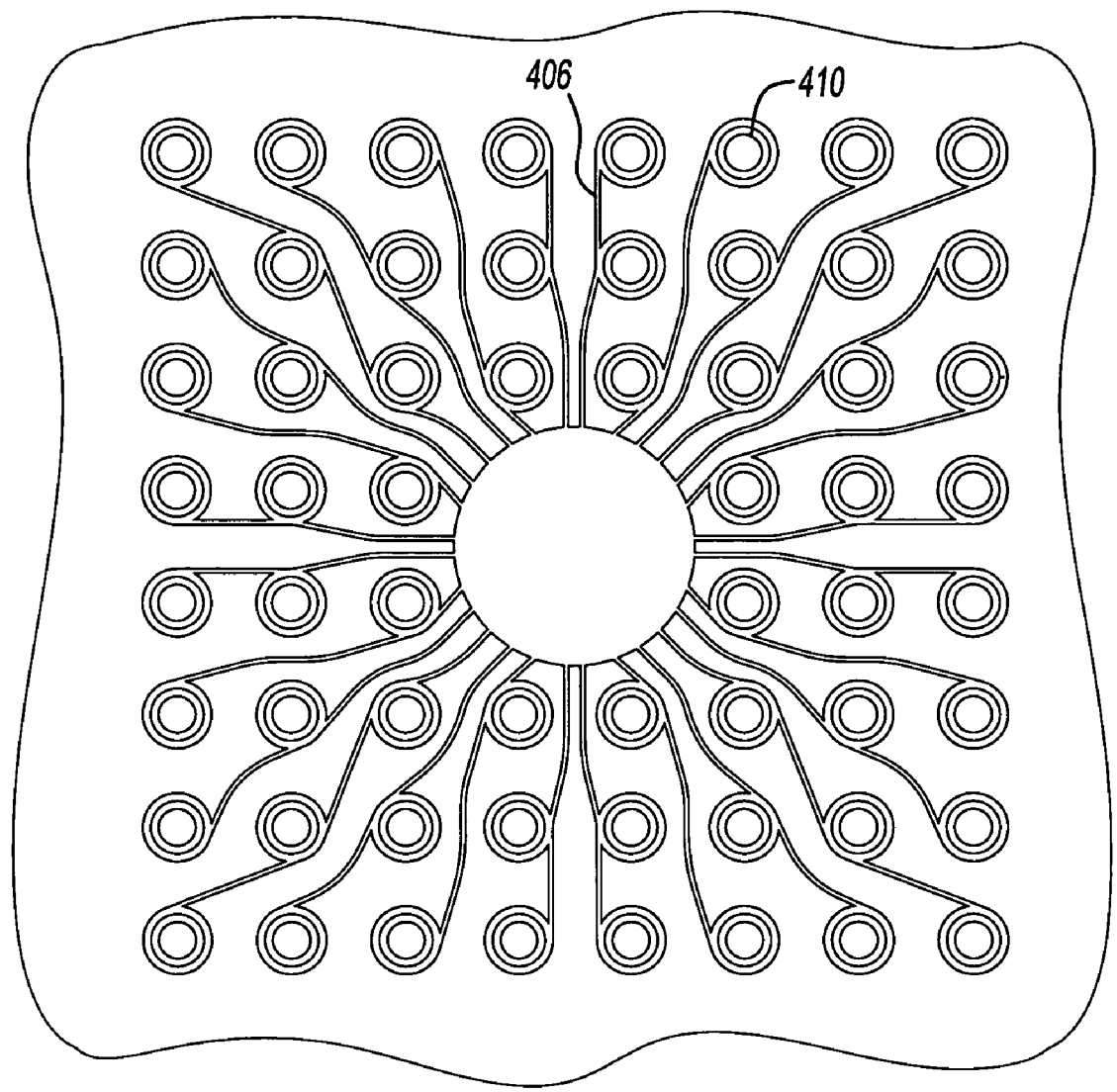

In some embodiments, as illustrated in FIGS. 23(a)-(b) and 25(a)(f), the plurality of microfluidic channels 406 can have any one of a plurality of configurations for carrying assay 1000 to each of the plurality of staging capillaries 410. In some embodiments, each of the plurality of staging capillaries 410 can be in fluid communication with only one of the plurality of microfluidic channels 406 (FIGS. 23(a)-(b), 25(a)-(d), and 25(f)) in a series-type configuration. In some embodiments, each of the plurality of staging capillaries 410 can be in fluid communication with two or more of the plurality of microfluidic channels 406 (FIG. 25(e)) in a multi-path or parallel-type configuration. In such parallel-type configurations, fluid can flow along the path of least resistance to fill each of the plurality of staging capillaries 410 in the least amount of time. In any configuration, the time required to fill each of the plurality of staging capillaries 410 can be reduced by reducing the length of each microfluidic channel 406. In some embodiments, a hybrid of the series-type and the parallel-type configurations can be used. In some embodiments, as illustrated in FIG. 25(f), each of the plurality of microfluidic channels 406 can be in fluid communication with only one edge of each of the plurality of staging capillaries 410 to provide pass-by and filling action simultaneously.

In some embodiments, each of the plurality of microfluidic channels 406 can exert, at least in part, a capillary force to draw fluid (e.g. assay 1000) therein to aid in reducing the time required to fill. The capillary force of each of the plurality of microfluidic channels 406 can be varied, at least in part, by varying at least the dimensional properties of the plurality of microfluidic channels 406 according to capillary principles.

Pressure Nodules

In some embodiments, as illustrated in FIGS. 33-40, filling apparatus 400 comprises input layer 404, output layer 408, and an intermediate layer 494, or any combination thereof for filling one or more components of assay 1000 into at least some of the plurality of wells 26 in microplate 20.

In some embodiments, intermediate layer 494 can be positioned and aligned between input layer 404 and output layer 408. In some embodiments, input layer 404 comprises assay input ports 402 extending therethrough. As illustrated in FIGS. 34 and 35, in some embodiments, each assay input port 402 can extend through input layer 404 and terminate at an extended outlet 496. In some embodiments, extended outlet 496 can be sized to extend from input layer 404 such that an end 498 of extended outlet 496 is spaced a predetermined distance from output layer 408 (FIG. 34). Extended outlet 496 can extend through a corresponding aperture 500 (FIG. 33) formed through intermediate layer 494.

In some embodiments, as illustrated in FIG. 34, extended outlet 496 can be aligned with surface tension relief post 418 extending upward from output layer 408. In some embodiments, an internal diameter of extended outlet 496 can be larger than an outer diameter of surface tension relief post 418 to permit surface tension relief post 418 to be at least partially received within extended outlet 496. Surface tension relief post 418, in some embodiments, can be sufficiently sized to facilitate even spreading of assay 1000 throughout the plurality of microfluidic channels 406 and/or engage a meniscus of assay 1000 within assay input port 402 to encourage flow. In some embodiments, extended outlet 496 and surface tension relief post 418 can cooperate to facilitate alignments of input layer 404, output layer 408, and intermediate layer 494.

In some embodiments, intermediate member 494 comprises microfluidic channels 406 extending there along (e.g., etched or otherwise formed in one major side thereof) in fluid communication with the plurality of staging capillaries 410 in output layer 408. For example, microfluidic channels 406, extending along a lower surface of intermediate layer 494, can communicate with upper-end openings of staging capillaries 410. It should be appreciated that the particular route configuration of microfluidic channels 406 can be any one of a number of configurations selected by one skilled in the art or one of those described herein. In some embodiments, intermediate member 494 can be compliant, or resiliently deformable, to permit flexing of intermediate member 494 in response to an external force. In some embodiments, intermediate member 494 can be made of polymeric materials, such as but not limited to rubber or silicone (PDMS).

As illustrated in FIGS. 35-38, in some embodiments, input layer 404 comprises one or more nodules 502 extending from a bottom surface 504. In some embodiments, nodules 502 can be patterned along bottom surface 504 such that each nodule 502 can engage a top surface 506 of compliant intermediate layer 494. During centrifugation, centripetal force exerted on input layer 404 can cause nodules 502 to engage compliant intermediate layer 494 to at least partially collapse or depress a segment of intermediate layer 494 against output layer 408 to minimize fluid communication between adjacent staging capillaries 410. In some embodiments, as illustrated in FIGS. 36 and 37, nodules 502 can be patterned such that each nodule 502 is positioned adjacent each of the plurality of staging capillaries 410. For example, nodules 502 can be disposed so that each nodule aligns, or corresponds, with a respective one of staging capillaries 410. In some embodiments, nodules 502 can be patterned over portions of microfluidic channels 406 to close microfluidic channel 406 during centrifugation. In some embodiments, as illustrated in FIG. 38, nodules 502 can be patterned over each of the plurality of staging capillaries 410 to seal each of the plurality of staging capillaries 410 during centrifugation. For example, upon being depressed by nodules 502 during centrifugation, segments of intermediate layer 494 can seal the upper end openings of respective, corresponding staging capillaries 410.

In some embodiments, as illustrated in FIGS. 38 and 39, a sealing feature 508 can extend from intermediate layer 494 that can be sized to fit into the corresponding staging capillary 410 by nodule 502 acting upon intermediate layer 494. These, and substantially equivalent, embodiments can be used to define a shut-off valve during centrifugation or anytime a force is applied to input layer 404 and/or intermediate layer 494.

It should be appreciated that the physical size and/or compliancy of one of more of input layer 404, intermediate layer 494, nodules 502, and sealing features 508 can be tailored to achieve a predetermined sealing engagement upon application of a predetermined amount of force. Additionally, it should be appreciated that nodules 502 and/or sealing feature 508 can be of any shape conducive to applying a force and sealing an opening, respectively, such as, but not limited to, triangular, square, or conical.

In some embodiments, to load each of the plurality of staging capillaries 410, a predetermined amount of assay 1000 can be placed at each assay input port 402. Capillary force, at least in part, can draw at least a portion of assay 1000 from assay input port 402 into microfluidic channels 406 and further fill at least some of the plurality of staging capillaries 410. In some embodiments, once at least some of the plurality of staging capillaries 410 are filled, output layer 408 and microplate 20 can be placed into a swing-arm centrifuge. In some embodiments, the centripetal force of the swing-arm centrifuge can be sufficient to overcome the surface tension of assay 1000 in each the plurality of staging capillaries 410, thereby forcing a metered volume of assay 1000 into each of the plurality of wells 26 of microplate 20. In some embodiments, the centripetal force of the centrifuge can be sufficient to exert a clamping force on at least one of input layer 404 and intermediate layer 494 to fluidly seal adjacent staging capillaries 410, either at the entrance thereof or therebetween, to prevent residual assay 1000 left in assay input port 402 or assay 1000 from an undesired one of the plurality of wells 26 of microplate 20 from overfilling a particular staging capillary. In some embodiments, an external force (e.g. mechanical, pneumatic, hydraulic, electro-mechanical, and the like) can be applied to exert a clamping force on at least one of input layer 404 and intermediate layer 494 to fluidly seal adjacent staging capillaries 410, either at the entrance thereof or therebetween.

In some embodiments, as illustrated in FIG. 40, at least some of input layer 404, intermediate layer 494, and output layer 408 can be used in conjunction with a clamp system 511. In some embodiments, clamp system 511 comprises a base structure 513 and one or more locking features 515 extending therefrom. In some embodiments, base structure 513 comprises at least one alignment feature 517 operably sized to engage a corresponding alignment feature 58 on microplate 20 to, at least in part, facilitate proper alignment of each of the plurality of staging capillaries 410 relative to each of the plurality of wells 26. In some embodiments, alignment feature 517 can further engage a corresponding alignment feature 519 formed in at least one of input layer 404, intermediate layer 494, and output layer 408. In some embodiments, at least some of microplate 20, input layer 404, intermediate layer 494, and output layer 408 can be coupled with base structure 513 such that locking feature 515 engages input layer 404 to exert a preload on intermediate layer 494 to prevent fluid flow and/or leakage of assay 1000 prior to achieving sufficient centrifugal speed in the centrifuge. In some embodiments, a top plate 521 can be used in conjunction with base structure 513 to ensure equal pressure application across input layer 404 by locking feature 515.

Venting

In some embodiments, as illustrated in FIGS. 41-46, filling apparatus 400 comprises input layer 404, output layer 408, and a vent layer 523, or any combination thereof for loading assay 1000 into at least some of the plurality of wells 26 in microplate 20. In some embodiments, output layer 408 comprises microfluidic channels 406 formed in a side thereof and extending there along in fluid communication with the plurality of staging capillaries 410 in output layer 408.

In some embodiments, input layer 404 comprises assay input ports 402 extending therethrough. As illustrated in FIGS. 42-43, in some embodiments, each assay input port 402 can extend through input layer 404 and terminate at extended outlet 496. In some embodiments, extended outlet 496 can be sized to extend from input layer 404 such that an end 498 of extended outlet 496 is generally flush to a top surface 525 of vent layer 523 and aligned to a flow aperture 527 extending through vent layer 523.

In some embodiments, input layer 404 comprises one or more vent features 529 (FIGS. 43-46). In some embodiments, vent feature 529 can be sized to have a capillary force associated therewith that is lower than a capillary force within microfluidic channels 406 and/or each of the plurality of staging capillaries 410 to reduce the likelihood of assay 1000 flow through or into vent feature 529. In some embodiments, vent feature 529 comprises a vent hole 531 extending through input layer 404 (FIGS. 41-45) and in communication with atmosphere. In some embodiments, vent hole 531 can be coupled to a chamber or manifold 533 (FIGS. 42 and 43) that can couple two or more vent apertures 535 formed in vent layer 523 to atmosphere.

In some embodiments, vent feature 529 comprises a pressure bore 537 (FIG. 44) associated with one or more of the plurality of staging capillaries 410. In some embodiments, pressure bore 537 can be formed in input layer 404. For example, pressure bore 537 can extend from a lower surface of input layer 404 toward, but stopping short of, an opposing surface. In some embodiments, plural pressure bores 537 are disposed in an array corresponding to an array defined by staging capillaries 410. Pressure bores 537, in some embodiments, can be sized to act as an air capacitor trapping a portion of air therein that can contract or expand during filling of assay 1000 into filling apparatus 400 and/or centrifuging assay 1000 into each of the plurality of wells 26, respectively.

Vent feature 529, in some embodiments, can at least partially relieve vacuum created when assay 1000 is centrifuged from each of the plurality of staging capillaries 410 into each of the corresponding plurality of wells 26 of microplate 20 and permit improved loading. In some embodiments, vent feature 529 can at least partially interrupt fluid flow between adjacent staging capillaries 410 by introducing an air gap therebetween. In some embodiments, such an air gap can provide consistent metering of assay 1000 loaded into each of the plurality of wells 26.

In some embodiments, vent layer 523 can be positioned and aligned between input layer 404 and output layer 408. In some embodiments, as illustrated in FIG. 43, flow aperture 527 of vent layer 523 can be aligned with surface tension relief post 418 extending upward from output layer 408. In some embodiments, an internal diameter of flow aperture 527 can be larger than the outer diameter of surface tension relief post 418 to permit surface tension relief post 418 to be at least partially received within flow aperture 527. Surface tension relief post 418, in some embodiments, can be sufficiently sized to facilitate even spreading of assay 1000 throughout the plurality of microfluidic channels 406 in output layer 408 and/or engage a meniscus of assay 1000 within assay input port 402 and/or flow aperture 527 to encourage flow. In some embodiments, extended outlet 496, flow aperture 527, and surface tension relief post 418 can cooperate to facilitate alignments of input layer 404, output layer 408, and vent layer 523.

As illustrated in FIGS. 43-45, in some embodiments, vent layer 523 can be aligned with input layer 404 and output layer 408 such that vent apertures 535 are positioned above or between each of the plurality of staging capillaries 410. In some embodiments, vent apertures 535 can be a circular bore (FIG. 44) or any other shape, such as oblong (FIG. 45), to accommodate for potential misalignment between input layer 404 and vent layer 523 and/or potential misalignment between vent layer 523 and output layer 408.

In some embodiments, vent layer 523 can be made of any material conducive to joining with input layer 404 and/or output layer 408. In some embodiments, vent layer 523 can comprise PDMS, which can aid in joining vent layer 523 to input layer 404 due to the intrinsic tackiness properties of PDMS. In some embodiments, vent layer 523 can be made using a double stick adhesive tape. In such embodiments, the double stick adhesive tape can be first applied to input layer 404 and then laser cut to accurately place vent apertures 535 to simplify assembly of input layer 404 and vent layer 523.

In some embodiments, to load each of the plurality of staging capillaries 410, a predetermined amount of assay 1000 can be placed at each assay input port 402. Such placement can be effected, for example, using an automated pipette system (e.g., a Biomek) or hand-operated single- or multi-channel pipette device (e.g., a Pipetman). Capillary force, at least in part, can draw at least a portion of assay 1000 from assay input port 402 into microfluidic channels 406 and further fill at least some of the plurality of staging capillaries 410. In some embodiments, outlet 434 of each of the plurality of staging capillaries 410 permits venting of air within each of the plurality of staging capillaries 410 during filling. In some embodiments, once at least some of the plurality of staging capillaries 410 are filled, input layer 404, vent layer 523, output layer 408, and microplate 20 can be placed into a swing-arm centrifuge. In some embodiments, the venting features 529 can reduce vacuum effects on assay 1000 during centrifugation to more easily meter a volume of assay 1000 into each of the plurality of wells 26 of microplate 20.

Capillary Plane

In some embodiments, as illustrated in FIGS. 108-119, filling apparatus 400 comprises input layer 404 and output layer 408 for loading assay 1000 (see FIG. 110) into at least some of the plurality of wells 26 in microplate 20. Input layer 404 comprises, in some embodiments, one or more assay input ports 402 each in fluid communication with at least a portion of the plurality of microfluidic channels 406 disposed in output layer 408. Assay input ports 402 can be configured to receive assay 1000 from any one of a number of sources, such as a pipette (see FIG. 110).

As illustrated in FIGS. 108-109, assay input ports 402 can comprise a geometry having a generally X-shaped depression; a central, upwardly-shaped member 1900; and radially extending arm channels 1902 terminating at through-holes 1904. In this regard, assay 1000 can be split to the four through-holes 1904 by virtue of fluid flow for quick and even filling.

Central, upwardly-shaped member 1900 can define any cross-sectional shape that is conducive to a particular application. In some embodiments, as illustrated in FIGS. 110-119, central, upwardly-shaped member 1900 can comprise a centrally-raised portion 1906 having downwardly-sloping sides 1908. Downwardly-sloping sides 1908 can be a continuous surface sweeping about centrally-raised portion 1906 or can be distinct surfaces descending from centrally-raised portion 1904, thereby providing flow direction control. In some embodiments, central, upwardly-shaped member 1900 can comprise a generally smooth contoured shape conducive to distributing assay 1000 with minimum splash back. Furthermore, central, upwardly-shaped member 1900 can serve to minimize penetration of pipette tip (see FIG. 110) within the structure of the plurality of microfluidic channels 406 disposed in output layer 408 by physically preventing its insertion. Additionally, central, upwardly-shaped member 1900 can serve to minimize the force of fluid flow of assay 1000, thereby minimizing the chance of overcoming the surface tension and/or capillary force of assay 1000 contained in the plurality of staging capillaries 410.

In some embodiments, output layer 408 comprises a microfluidic structure 1910 in fluid communication with the plurality of staging capillaries 410 for quickly distributing assay 1000 to the plurality of staging capillaries 410. In some embodiments, microfluidic structure 1910 comprises the plurality of microfluidic channels 406, arranged in a desired pattern or routing structure upon output layer 408, and a capillary plane 1912. More particularly, the plurality of microfluidic channels 406 can be arranged such that they fluidly interconnect two or more adjacent staging capillaries 410. Each of the plurality of microfluidic channels 406 can have a width and depth that is selected to achieve a desired capillary force. In some embodiments, the plurality of microfluidic channels 406 can be arranged as a grouping 407 (FIG. 108). In some embodiments, assay input ports 402 can be positioned at a predetermined pitch (e.g. 9 mm) such that a central axis of each assay input port 402 can be aligned with a center or other predetermined location of each grouping 407. Additionally, as discussed herein, at least some of the plurality of microfluidic channels 406 can comprise ramp features, surface treatments, and/or other features to achieve desired filling characteristics. These characteristics may vary depending on the size of staging capillaries 410, the type of assay 1000, the necessary fill times, and the like.

As illustrated in FIGS. 120-112 and 128-135, the plurality of microfluidic channels 406 can be arranged in any one of a number of orientations. For example, in some embodiments, the plurality of microfluidic channels 406 can be arranged in a cross-pattern (see FIGS. 120-121) to provide multiple fluid paths for assay 1000 to flow. In this cross-pattern, each of the plurality of staging capillaries 410 can receive assay 1000 by two or more microfluidic channels 406 to reduce fill time. While, in some embodiments, the plurality of microfluidic channels 406 can be arranged in an S-shape pattern as illustrated in FIG. 122. In this regard, each of the plurality of microfluidic channels 406 and the plurality of staging capillaries 410 are filled in series one after another. Referring to FIGS. 122-126, it should be noted that the illustrated S-shape pattern provides geometric restraint of assay 1000 during centrifuge. That is, in some embodiments as illustrated in FIG. 122, there are no more than two staging capillaries 410 coupled together via microfluidic channels 406 in the X-direction. Therefore, during the initial centrifuging of assay 1000 into each of the plurality of wells 26 of microplate 20, assay 1000 is inhibited from movement to downstream staging capillaries 410 in the X-direction. If the S-shaped pattern was shifted by 90 degrees, during centrifuge assay 1000 could be initially forced to one end of grouping 407 and could overfill associated wells 26 of microplate 20.

Additionally, in some embodiments as illustrated FIGS. 128-130, the plurality of microfluidic channels 406 can be arranged in a diagonal pattern relative the X-direction and the Y-direction. This arrangement provides microfluidic channels that do not reside in either the X-direction or Y-direction but rather at an angle thereto. In some embodiments, the plurality of microfluidic channels 406 can be generally disposed at an angle of about 15 degrees to about 90 degrees relative to the X-direction (i.e. the direction of the applied centripetal force during early centrifugation).

In some embodiments, as illustrated in FIGS. 131-132, the plurality of microfluidic channels 406 can be arranged in an H-shaped pattern. In this arrangement, adjacent staging capillaries 410 are fluidly coupled in series via microfluidic channels 406 along a fluidic row 1924 in the Y-direction (see FIG. 132). In some embodiments, each fluidic row 1924 can be interconnected to an adjacent fluidic row 1924 via a fluidic connector 1926 in the X-direction. In this arrangement, assay 1000 can freely flow along fluidic rows 1924 (Y-direction) to fill the plurality of staging capillaries 410 and further flow to adjacent fluidic rows 1924 along fluidic connectors 1926 (X-direction). However, during centrifugation, angular acceleration, which will be substantially applied in the X-direction, will not cause a substantial amount of assay 1000 to flow to downstream staging capillaries 410. To further minimize this flow, fluidic connectors 1926 can be arranged such that they are offset relative to each other in the Y-direction as illustrated in FIG. 132. This minimizes the length of any fluidic channel extending in the X-direction.

In some embodiments, as illustrated in FIGS. 133-135, the plurality of microfluidic channels 406 can comprise two or more S-shaped fluidic patterns 1928 interconnected by a plurality of fluidic connectors 1926 disposed in a Y-direction (see FIG. 134). Specifically, in some embodiments, S-shaped fluidic patterns 1928 can comprise a plurality of first fluidic portions 1930 extending in a Y-direction fluidly connecting two or more staging capillaries 410. A plurality of second fluidic portion 1932 extending in an X-direction can be fluidly coupled between the plurality of fluidic portions 1930 in an alternating pattern to define S-shaped fluidic patterns 1928. Fluidic connectors 1926 can fluidly couple adjacent second fluidic portions 1932 in a Y-direction. This arrangement generally minimizes the number of staging capillaries 410 connected in the Y-direction to provide additional resistance to undesirable flow of assay 1000.

In some embodiments, output layer 408 can comprise one or more surface tension relief post 418 can be disposed in through-holes 1904 to, at least in part, evenly spread assay 1000 throughout the plurality of microfluidic channels 406 and/or engage a meniscus of assay 1000 to encourage fluid flow. Surface tension relief post 418 can, according to some embodiments, be hydrophilic in order to further encourage fluid flow into through-holes 1904 and, thus, microfluidic channels 406. In some embodiments, an internal diameter of through-holes 1904 can be larger than an outer diameter of surface tension relief post 418 to permit surface tension relief post 418 to be at least partially received within through-holes 1904. In some embodiments, through-holes 1904 and surface tension relief posts 418 can cooperate to facilitate alignment of input layer 404 and output layer 408.

In some embodiments, input layer 404 and output layer 408 can be physically coupled together, using, for example, adhesive and/or chemical bonding, laser welding, and/or ultrasonic welding, as illustrated in FIG. 109, to form a unitary member. In doing so, bottom surface 504 of input layer 404 (see FIG. 110) can span a topside of output layer 408. In some embodiments, bottom surface 504 of input layer 404 can engage or otherwise sealingly contact a first surface 1914 of output layer 408 to define an interface generally resistant to fluid flow. As input layer 404 and output layer 408 are brought together, a second surface 1916 of output layer 408 is spaced apart from bottom surface 504 of input layer 404 to form a volume. In other words, in some embodiments, second surface 1916 is lower than first surface 1914. Accordingly, this formed volume, bound by bottom surface 504, second surface 1916, and the interface between first surface 504 and bottom surface 504 forms capillary plane 1912. In some embodiments, as illustrated in FIGS. 120-122, capillary plane 1912 can receive assay 1000 therein and form a single, generally continuous, fluid sheet across grouping 407. In this regard, during filling, assay 1000 would first generally spread across capillary plane 1912 and then be rapidly and efficiently drawn into the plurality of microfluidic channels 406 and staging capillaries 410. In some embodiments, all corners within capillary plane 1912 are rounded to reduce localized surface tension to minimize retention of assay 1000 in corners of capillary plane 1912 and further concentrate the flow of assay 1000 over the plurality of microfluidic channels 406 and the plurality of staging capillaries 410.

In some embodiments, as illustrated in FIGS. 123-126, output layer 408 can comprise one or more wall restraints 1918 disposed between at least some of the plurality of microfluidic channels 406 and the plurality of staging capillaries 410. In some embodiments, wall restraints 1918 extend upward and engage bottom surface 504 to define an interface generally resistant to fluid flow. Wall restraints 1918 can be positioned in any position that aids fluid flow and/or controls distribution of assay 1000. However, it should be understood that capillary plane 1912 remains substantially continuous. In some embodiments, wall restraints 1918 can be centrally located with fluid flow openings 1920 on opposing ends thereof (FIGS. 123-124). In some embodiments, wall restraints 1918 can extend to one side of capillary plane 1912 to define an S-shaped capillary plane 1912 (FIGS. 125-126). In some embodiments, wall restraints 1918 induce a stronger capillary force in capillary plane 1912 and further reduce the overall volume of capillary plane 1912 leading to reduced waste of assay 1000. In some embodiments, wall restraints 1918 can be used to oppose any fluid forces acting in the X-direction (see FIG. 122) during centrifugation.

The strength of the capillary force generated by capillary plane 1912 is geometrically determined by the distance between second surface 1916 of output layer 408 and bottom surface 504 of input layer 404. The Laplace pressure generated can be controlled according to the following relationship:

$$\Delta P_{la} = \frac{2(h+w)(\gamma_{sa} - \gamma_{sl})}{wh}$$

wherein
γsa=Surface tension at the Solid-Air boundary
γsl=Surface tension at the Solid-Liquid boundary
w=Width of the capillary plane
h=Height of the capillary plane In some embodiments, the combination of capillary plane 1912 and the plurality of microfluidic channels 406 serves to affectively draw assay 1000 into the plurality of staging capillaries 410 at a rate faster than without capillary plane 1912. In some embodiments, the capillary force generated increases from capillary plane 1912 to the plurality of microfluidic channels 406 to the plurality of staging capillaries 410, thereby serving to evenly draw and load assay 1000 into the plurality of staging capillaries 410.

In some embodiments, capillary plane 1912 further provides a uniform pressure above each of the plurality of staging capillaries 410 during centrifuge. In some embodiments, this uniform pressure is equivalent to atmospheric pressure. That is, once capillary plane 1912 is evacuated of assay 1000 during the filling process, the open expanse of capillary plane 1912 can serve as a vent system venting the area above each of the plurality of staging capillaries 410 to atmosphere or other applied pressure (or vacuum). In some embodiments, this arrangement serves to eliminate or, at least, minimize the formation of internal micro-vacuums in what would be otherwise a closed and connected fluidic network. These internal vacuums can induce purging of assay 1000 from both adjacent staging capillaries 410 and/or entire fluid networks thereby leading to undesirable overfilling/under filling and reduced accuracy. By including a vent and providing a thin volume of atmospheric pressure above the plurality of staging capillaries 410 the internal vacuums can be quickly dissipated. In some embodiments, the plurality of microfluidic channels 406 can serve a dual functionality, in that they can provide a complete circuit of fluid connection between the plurality of staging capillaries 410 and further assist in equilibrating the volume of assay 1000 from capillary plane 1912 over grouping 407 for improved filling accuracy and precision.

During filling of embodiments having an unobstructed capillary plane 1912 (see FIGS. 120-122), assay 1000 is first injected into assay input ports 402 of input layer 404 (FIG. 110). Capillary forces and/or gravitational pressures urge assay 1000 into and evenly across capillary plane 1912 (FIGS. 126-111). The stronger capillary force of the plurality of microfluidic channels 406 draws assay 1000 therein and further urges assay 1000 toward the plurality of staging capillaries 410. The stronger capillary force of the plurality of staging capillaries 410 draws assay 1000 therein from the plurality of microfluidic channels 406 (FIG. 113).

Figure 114:
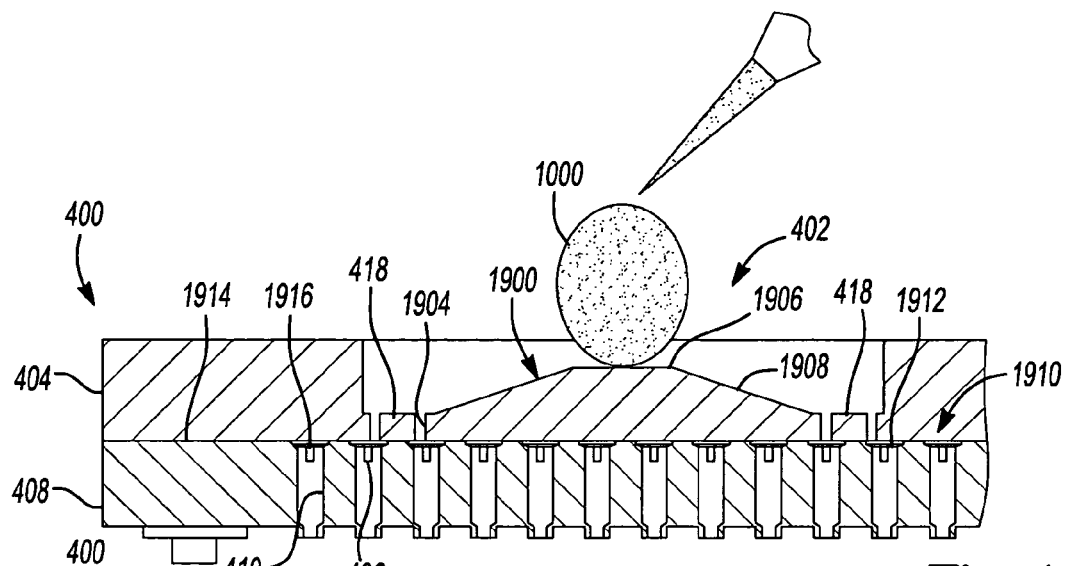
Figure 115:
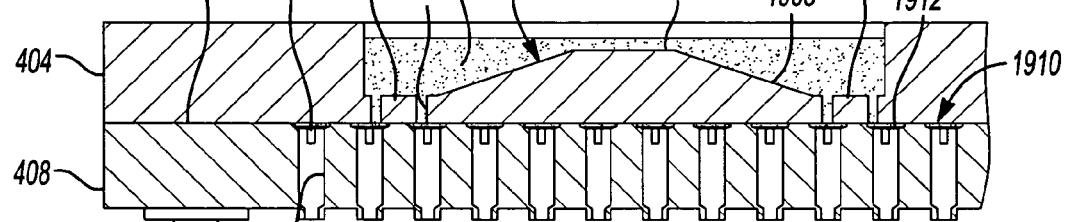
Figure 116:
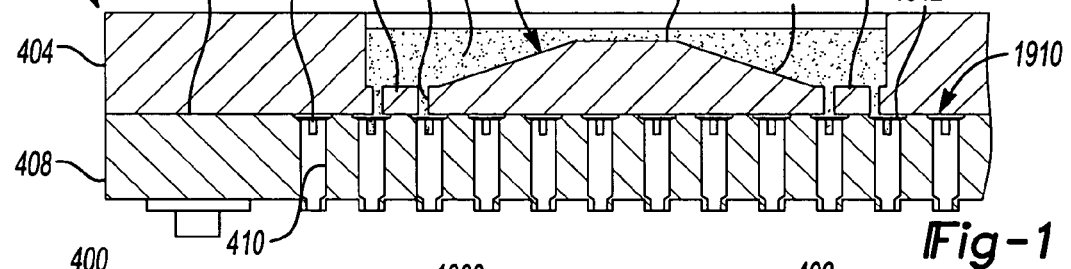
Figure 117:
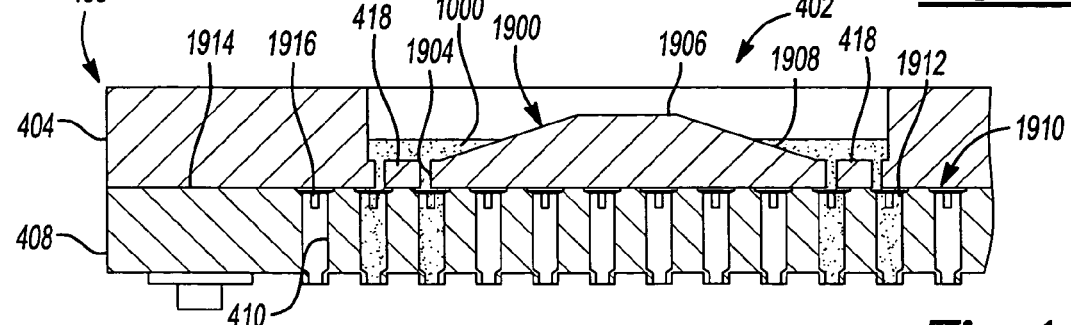
Figure 118:
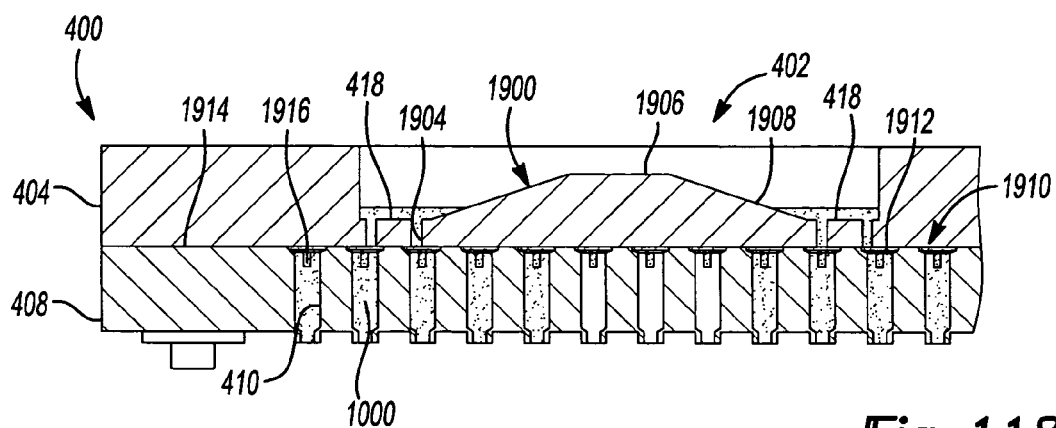
Figure 119:
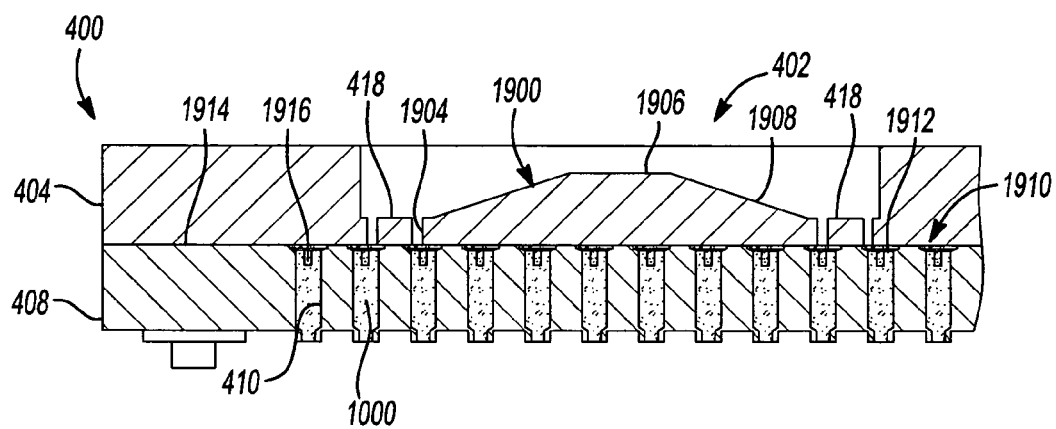

During filling of embodiments having restraint walls 1918 disposed in capillary plane 1912 (see FIGS. 123-126), assay 1000 is injected into assay input ports 402 of input layer 404 (FIG. 114). Capillary forces and/or gravitational pressures urge assay 1000 into a portion of capillary plane 1912 bound by restraint walls 1918 (FIGS. 115-116). Assay 1000 then flows through and/or around restraint walls 1918 to fill capillary plane 1912. Simultaneously, the stronger capillary force of the plurality of microfluidic channels 406 draws assay 1000 therein and further urges assay 1000 toward the plurality of staging capillaries 410. The stronger capillary force of the plurality of staging capillaries 410 draws assay 1000 therein from the plurality of microfluidic channels 406 (FIG. 117-119).

As illustrated in FIGS. 136-137, once the plurality of staging capillaries 410 have been filled with assay 1000, filling apparatus 400 and microplate 20 are centrifuged in a swing-arm style centrifuge, which serves to overcome the surface tension and/or capillary force of assay 1000 within the plurality of staging capillaries 410, to urge assay 1000 from the plurality of staging capillaries 410 to the plurality of wells 26 of microplate 20. Initially, as illustrated in FIG. 136, filling apparatus 400 and microplate 20 are subjected to a centripetal acceleration and angular acceleration. However, at steady-state, filing apparatus 40 and microplate 20 are generally subjected to a centripetal force (see FIG. 137).

Open Channel Microfluidic Network

In some embodiments, the plurality of microfluidic channels 406 can be arranged to neutralize, minimize, suppress, or otherwise manipulate the fluid forces exerted during early stages of centrifugation in a swing-arm system centrifuge. In other words, in some embodiments, fluid flow forces can be managed through the use of various features, geometries, and spatial orientation of the plurality of microfluidic channels 406 to improve precision and accuracy of the dispensed volumes of assay 1000.

In some embodiments, as illustrated in FIGS. 138-139, filling apparatus 400 comprises input layer 404 and output layer 408 for loading assay 1000 (see FIG. 140) into at least some of the plurality of wells 26 in microplate 20. Input layer 404 comprises, in some embodiments, one or more assay input ports 402 each in fluid communication with at least a portion of the plurality of microfluidic channels 406 disposed in output layer 408. In some embodiments, each of the plurality of microfluidic channels 406 comprises a pair of sidewalls, a bottom, and an opened top. Therefore, flow control of the plurality of microfluidic channels 406 can be controlled by the sizing of the sidewalls and bottom (also known as the aspect ratio).

Assay input ports 402 can be configured to receive assay 1000 from any one of a number of sources, such as a pipette (see FIG. 140). As illustrated in FIGS. 138-139, assay input ports 402 can comprise generally sloped sides extending to a through-hole in fluid communication with the plurality of microfluidic channels 406. In some embodiments, input layer 404 can comprise a plurality of open slots 1922 formed there through. The plurality of open slots 1922 can be positioned above at least some of the plurality of microfluidic channels 406 to provide generally uniform, zero-air-resistance to the plurality of staging capillaries 410. The plurality of open slots 1922 can be arranged to maximize the number of the plurality of microfluidic channels 406 and the plurality of staging capillaries 410 exposed directly to atmosphere.

In some embodiments, output layer 408 comprises a microfluidic structure 1910 in fluid communication with the plurality of staging capillaries 410 for quickly distributing assay 1000 to the plurality of staging capillaries 410. In some embodiments, microfluidic structure 1910 comprises the plurality of microfluidic channels 406, arranged in a desired pattern or routing structure upon output layer 408, and a capillary plane 1912. More particularly, the plurality of microfluidic channels 406 can be arranged such that they fluidly interconnect two or more adjacent staging capillaries 410. Each of the plurality of microfluidic channels 406 can have a width and depth that is selected to achieve a desired capillary force. In some embodiments, the plurality of microfluidic channels 406 can be arranged as a grouping 407 (FIG. 138). In some embodiments, assay input ports 402 can be positioned at a predetermined pitch (e.g. 9 mm) such that a central axis of each assay input port 402 can be aligned with a center or other predetermined portion of each grouping 407. Additionally, as discussed herein, at least some of the plurality of microfluidic channels 406 can comprise ramp features, surface treatments, and/or other features to achieve desired filling characteristics. These characteristics may vary depending on the size of staging capillaries 410, the type of assay 1000, the necessary fill times, and the like. As illustrated in FIG. 127, in some embodiments, the plurality of open slots 1922 formed in input layer 404 can be sized such that, other than the coverage of assay input ports 402, the plurality of microfluidic channels 406 and the plurality of staging capillaries 410 are exposed directly to atmosphere without the need for venting shafts, tubes, conduits, or channels. In some embodiments, the plurality of open slots 1922 can substantially surround assay input ports 402. Accordingly, the present of internal vacuums created during centrifuge can be reduced by either the plurality of open slots 1922 or high aspect ratios of the plurality of microfluidic channels 406, or a combination thereof.

During filling of embodiments employing the plurality of open slots 1922 (see FIGS. 140-143), assay 1000 is first injected into assay input ports 402 of input layer 404 (FIGS. 140-141). Capillary forces and/or gravitational pressures urge assay 1000 into the plurality of microfluidic channels 406 and along the particular fluidic path (see FIGS. 142-143). The stronger capillary force of the plurality of staging capillaries 410 draws assay 1000 therein from the plurality of microfluidic channels 406. As illustrated in FIGS. 136-137, once the plurality of staging capillaries 410 have been filled with assay 1000, filling apparatus 400 and microplate 20 are centrifuged in a swing-arm style centrifuge, which serves to overcome the surface tension and/or capillary force of assay 1000 within the plurality of staging capillaries 410, to urge assay 1000 from the plurality of staging capillaries 410 to the plurality of wells 26 of microplate 20.

Assay Ports on Sides

In some embodiments, as illustrated in FIGS. 47-58, filling apparatus 400 can comprise assay input ports 402 positioned within and/or upon output layer 408. In some embodiments, as illustrated in FIG. 47, assay input ports 402 can be positioned at an end 420 of output layer 408. For example, such assay input ports can be positioned along a short dimension of a major surface (e.g., a top surface) of the output layer, adjacent and parallel to an end thereof. In some embodiments, as illustrated in FIG. 48, assay input ports 402 can be positioned at a side 422 of output layer 408. For example, such assay input ports can be positioned along a long dimension of a major surface (e.g., a top surface) of the output layer, adjacent and parallel to a side thereof. Still further, in some embodiments, as illustrated in FIG. 49, assay input ports 402 can be positioned at opposing ends 420 or opposing sides 422 (not illustrated) of output layer 408. In some embodiments, assay input ports 402 can be positioned at opposing ends 420 or opposing sides 422 (not illustrated) of output layer 408 with a fluid interrupt 409 (e.g. wall or barrier) to fluidly isolate those assay input ports 402 on one end or side from the remaining assay input ports 402 on the other end or side.

As illustrated in FIG. 50, in some embodiments, assay input ports 402 can each comprise a fluid well 424 bound by a plurality of upstanding walls 426. In some embodiments, fluid well 424 of each assay input port 402 can be in fluid communication with one or more corresponding microfluidic channels 406 through a throat 430 formed in fluid well 424. For example, such a throat can be formed in a lower region of the fluid well, so as to fluidly communicate the fluid well with the microfluidic channels. Throat 430 can comprise a diameter of, for example, 2 mm or less, 1 mm or less, 0.5 mm or less, or 0.25 mm or less. In some embodiments, such as illustrated in FIG. 50, throat 430 comprises a reservoir in fluid communication with one or more microfluidic channel 406. In some embodiments, surface tension relief post 418 can be disposed in throat 430 to, at least in part, evenly spread assay 1000 throughout the plurality of microfluidic channels 406 and/or engage a meniscus of assay 1000 to encourage fluid flow. Surface tension relief post can, according to some embodiments, comprise a hydrophilic sites in order to further encourage fluid flow into the throat and, thus, the microchannels.

In some embodiments, as illustrated in at least FIGS. 51-58, microfluidic channels 406 can be in fluid communication with the plurality of staging capillaries 410 extending from microfluidic channel 406, through output layer 408, to a bottom surface 429. In some embodiments, bottom surface 429 can be spaced apart from first surface 22 of microplate 20 (FIG. 51) or can be in contact with first surface 22 of microplate 20. In some embodiments, each of the plurality of staging capillaries 410 can be generally aligned with a corresponding one of the plurality of wells 26 of microplate 20. In some embodiments, a protective covering (not shown) can be disposed over microfluidic channels 406 to provide, at least in part, protection from contamination, reduced evaporation, and the like. It should be understood that such protective covering can be used with any of the various configurations set forth herein.

Figure 52:
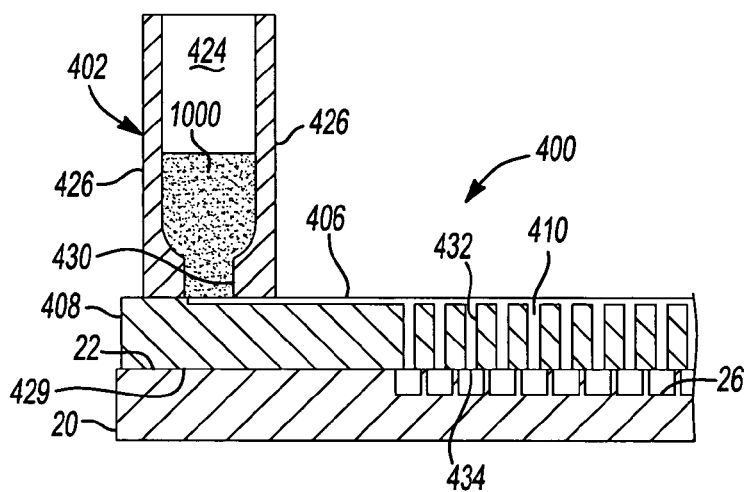
Figure 53:
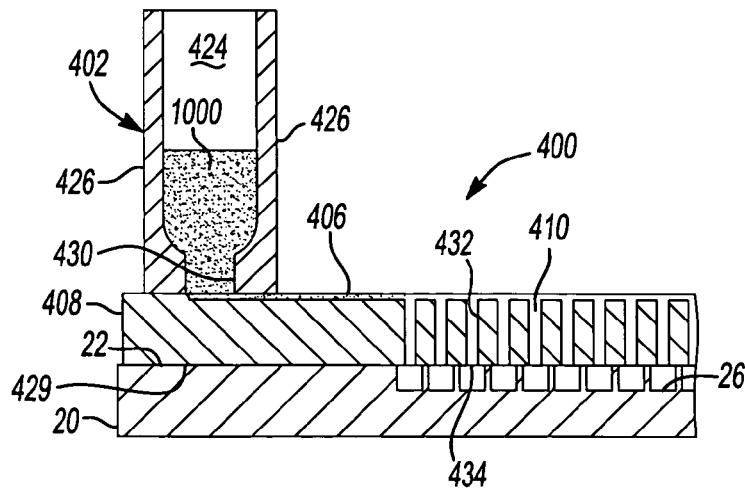
Figure 54:
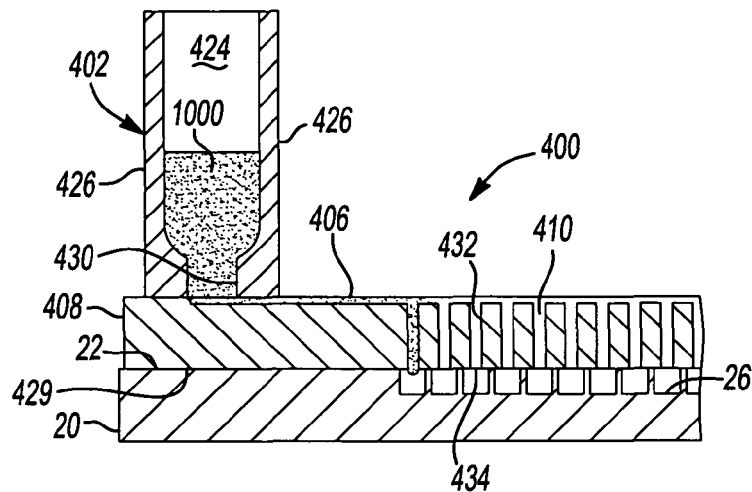
Figure 55:
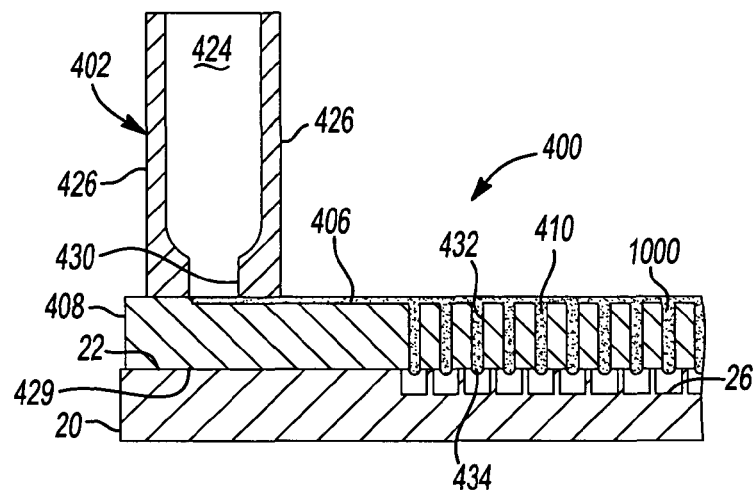

Referring to FIGS. 52-58, to perform a filling operation, each assay input port 402 can be at least partially filled with assay 1000 or different assays or fluids (FIG. 52). At least in part through hydraulic pressure and/or capillary force, assay 1000 can flow from fluid well 424 of each assay input port 402 through throat 430 into the one or more microfluidic channels 406 (FIG. 53). As assay 1000 flows across an end-opening or mouth 432 of each of the plurality of staging capillaries 410, capillary action, at least in part, draws a metered amount of assay 1000 therein (FIG. 54). Assay 1000 can continue to flow down the one or more microfluidic channels 406 until each of the plurality of staging capillaries 410 can be at least partially filled with assay 1000 (FIG. 55). In some embodiments, assay 1000 in each of the plurality of staging capillaries 410 can be held therein by capillary or surface tension forces to aid in the equal metering of assay 1000 to be loaded in each of the plurality of wells 26. In some embodiments, outlet 434 of each of the plurality of staging capillaries 410 permits venting of air within each of the plurality of staging capillaries 410 during filling.

Figure 56:
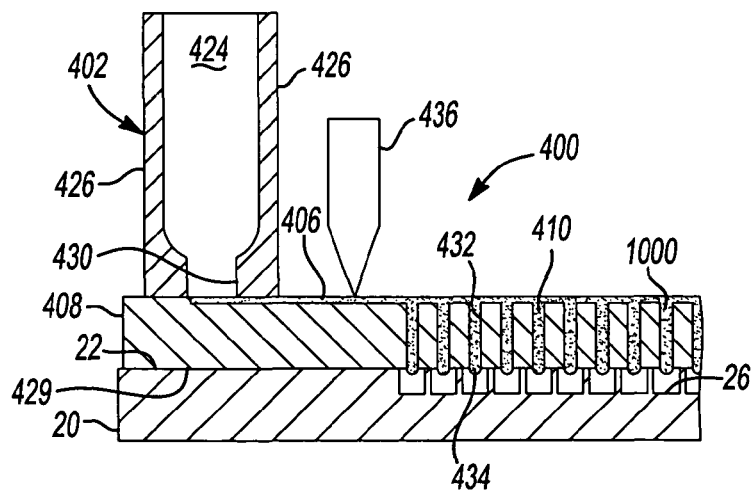
Figure 57:
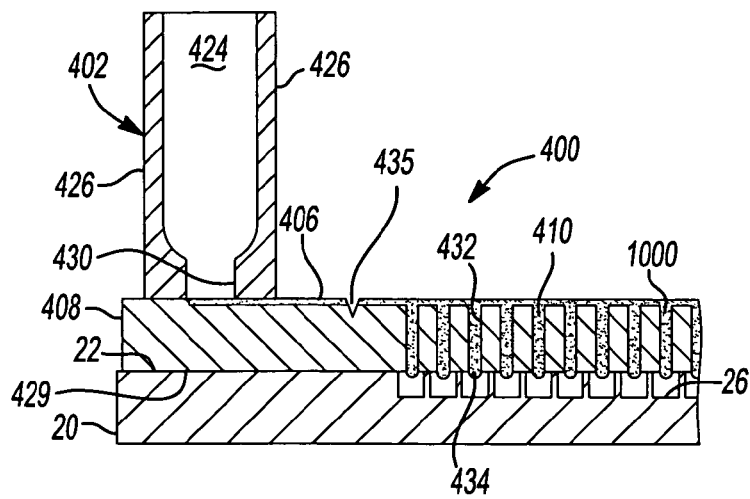

As illustrated in FIGS. 56 and 57, in some embodiments, filling apparatus 400 can be stake cut, generally indicated at 435, via device 436 along a portion of one or more microfluidic channels 406. In some embodiments, stake-cutting serves to, at least in part, aid in metering of assay 1000 in each well 26 by isolating the plurality of staging capillaries 410 from any excess assay 1000 left in each assay input port 402. This arrangement can minimize additional assay 1000 left within each assay input port 402 from overfilling each of the plurality of wells 26 during later centrifugation. In some embodiments, stake cutting can be completed through mechanical and/or thermal deformation (e.g. heat staking) of output layer 408. It should be appreciated that a Zbig valve can be used to achieve fluid isolation between the plurality of staging capillaries 410 and assay input port 402, such as those described in commonly-assigned U.S. patent application Ser. No. 10/336,274, filed Jan. 3, 2003 and PCT Application No. WO 2004/011147 A1.

Figure 58:
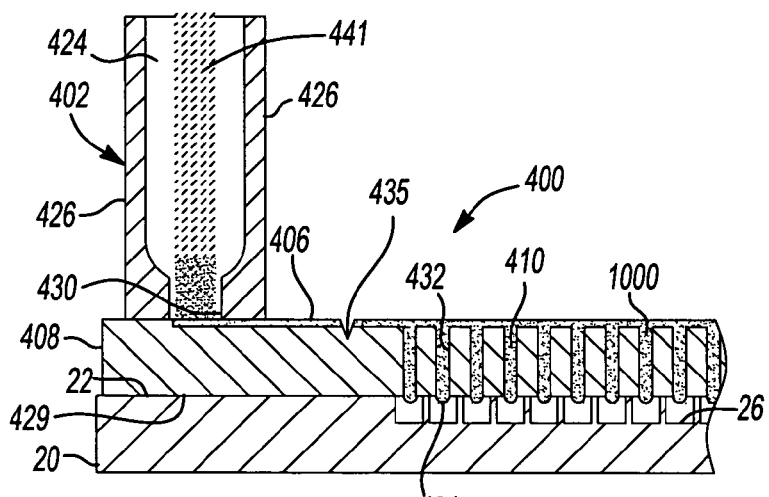

As illustrated in FIG. 59, in some embodiments, filling apparatus 400 can comprise reduced material areas 438 disposed in output layer 408. In some embodiments, reduced-material areas 438 comprise one or more cutout portions 440 (e.g. voids, slots, holes, grooves) formed in output layer 408 on opposing sides of microfluidic channels 406. The use of reduced material areas 438 can provide, among other things, reduced thermal capacity in the localized areas, which can increase the rate of heat staking and/or stake cutting. In some embodiments, the elongated shape of cutout portion 440 can accommodate any misalignment of the staking tool relative to output layer 408. In some embodiments, following staking, excess assay 1000 in assay input ports 402 and/or the upstream portion of microfluidic channels 406 relative to stake cut 435 can be removed, if desired. In some embodiments, this can be accomplished by employing a wicking member 441, as illustrated in FIG. 58.

Figure 60:
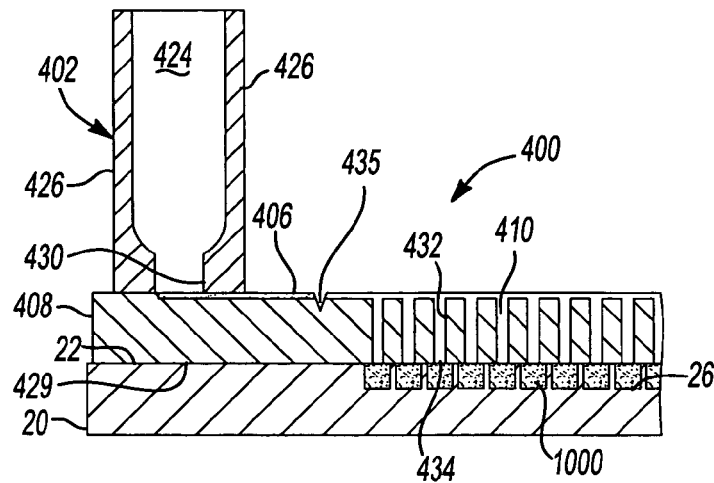

In some embodiments, once at least some of the plurality of staging capillaries 410 are filled, output layer 408 and microplate 20 can be placed into a swing-arm centrifuge. In some embodiments, the centripetal force of the swing-arm centrifuge can be sufficient to overcome the surface tension of assay 1000 in each the plurality of staging capillaries 410, thereby forcing a metered volume of assay 1000 into each of the plurality of wells 26 of microplate 20 (FIG. 60).

Referring again to FIGS. 47-49, filling apparatus 400 can be configured in any one of a number of configurations as desired. As described above, as illustrated in FIG. 47, assay input ports 402 can be positioned at end 420 of output layer 408. When this configuration is used with a microplate comprising 6,144 wells, filling apparatus 400 can comprise, for example, eight assay input ports 402 that can each be in fluid communication with eight respective microfluidic channels 406. Each of the eight microfluidic channels 406 can be in fluid communication with ninety-six respective staging capillaries 410. In some embodiments, as illustrated in FIG. 48, assay input ports 402 can be positioned at side 422 of output layer 408. When this configuration is used with a microplate comprising 6,144 wells, filling apparatus 400 can comprise, for example, eight assay input ports 402 that can each be in fluid communication with twelve respective microfluidic channels 406. Each of the twelve microfluidic channels 406 can be in fluid communication with sixty-four respective staging capillaries 410. This configuration can provide shorter channel lengths, which, in some circumstances, can have more rapid capillary filling times relative to the configuration of FIG. 47.

In some embodiments, as illustrated in FIG. 49, assay input ports 402 can be positioned at opposing ends 420 or opposing sides 422 (configuration not illustrated) of output layer 408. When the configuration illustrated in FIG. 49 is used with a microplate comprising 6,144 wells, filling apparatus 400 can comprise, for example, sixteen assay input ports 402 that can each be in fluid communication with twelve respective microfluidic channels 406. Each of the twelve microfluidic channels 406 can be in fluid communication with thirty-two respective staging capillaries 410. Likewise, when sixteen assay input ports 402 are positioned along opposing sides 422, sixteen assay input ports 402 can each be in fluid communication with eight respective microfluidic channels 406. Each of the eight microfluidic channels 406 can be in fluid communication with forty-eight respective staging capillaries 410. These configurations can provide shorter channel lengths, which, in some circumstances, can have more rapid capillary filling times relative to the configurations of FIGS. 47 and 48.

In some embodiments, the plurality of microfluidic channels 406 can be oriented such that, during centrifugation, they are perpendicular to an axis of revolution of the centrifuge. In some embodiments, this orientation can limit the flow of assay 1000 along the plurality of microfluidic channels 406 during centrifugation.

Overfill Solutions

In some embodiments, metering a predetermined amount of assay 1000 into each of the plurality of staging capillaries 410 and finally into each of the plurality of wells 26 can be achieved using a plurality of overfill reservoirs disposed in output layer 408. Referring to FIGS. 61-66, in some embodiments, filling apparatus 400 comprises fluid well 424 in fluid communication with one or more corresponding microfluidic channels 406 in fluid communication with the plurality of staging capillaries 410. In some embodiments, at least one microfluidic channel 406 comprises one or more fluid overfill reservoir 442 in fluid communication therewith. In some embodiments, the one or more fluid overfill reservoir 442 can be a bore opened at one end (e.g., a bore extending into output layer 408 from a surface thereof; with the bore having an open upper-end and a closed bottom end.)

Figure 61:
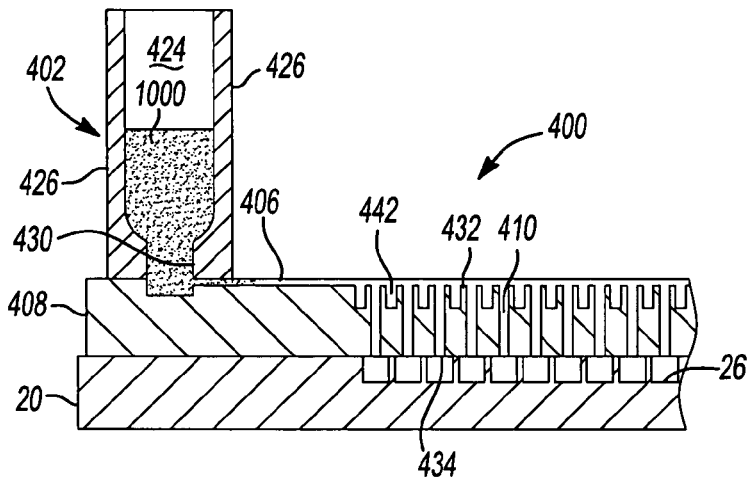
Figure 62:
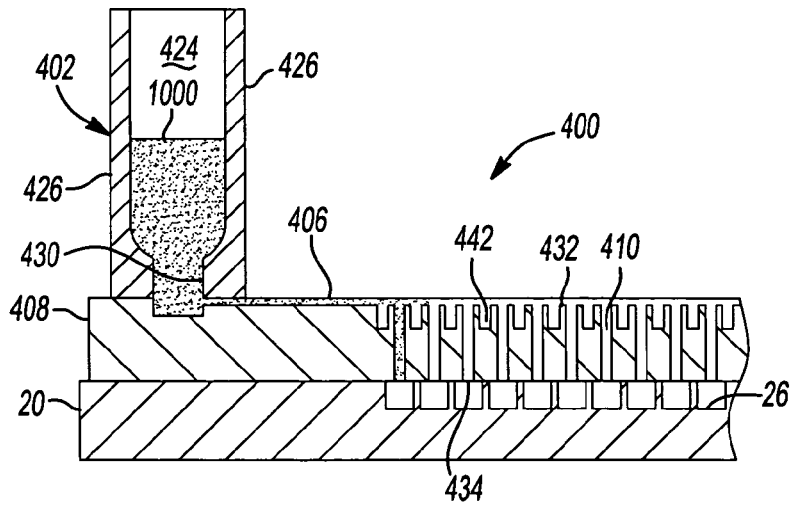
Figure 63:
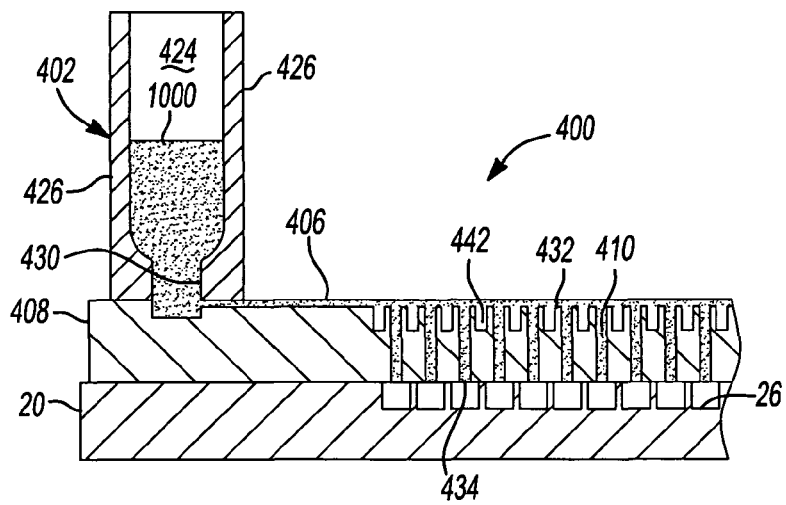

As illustrated in FIGS. 61-66, to perform a filling operation, each assay input port 402 can be at least partially filled with assay 1000 or other desired fluid (FIG. 61). At least in part through hydraulic pressure and/or capillary force, assay 1000 can flow from fluid well 424 of each assay input port 402 into the one or more microfluidic channels 406 (FIG. 61). As assay 1000 flows across an upper-end opening or mouth 432 of each of the plurality of staging capillaries 410, capillary action, at least in part, draws a metered amount of assay 1000 therein (FIG. 62). Assay 1000 can continue to flow down the one or more microfluidic channels 406 until each of the plurality of staging capillaries 410 can be at least partially filled with assay 1000 (FIG. 63). In some embodiments, fluid overfill reservoir 442 can generally inhibit assay 1000 from flowing into fluid overfill reservoir 442, at least in part because of the single opening therein generally preventing air within fluid overfill reservoir 442 from exiting. In some embodiments, fluid overfill reservoir can have a diameter equal to that of staging capillaries 410 and a depth of about 0.05 inch, or less.

In some embodiments, assay 1000 in each of the plurality of staging capillaries 410 can be held therein by capillary or surface tension forces to aid in the equal metering of assay 1000 to be loaded in each of the plurality of wells 26. In some embodiments, a lower-end opening or open-air outlet 434 of each of the plurality of staging capillaries 410 permit venting of air within each of the plurality of staging capillaries 410 during filling.

Figure 64:
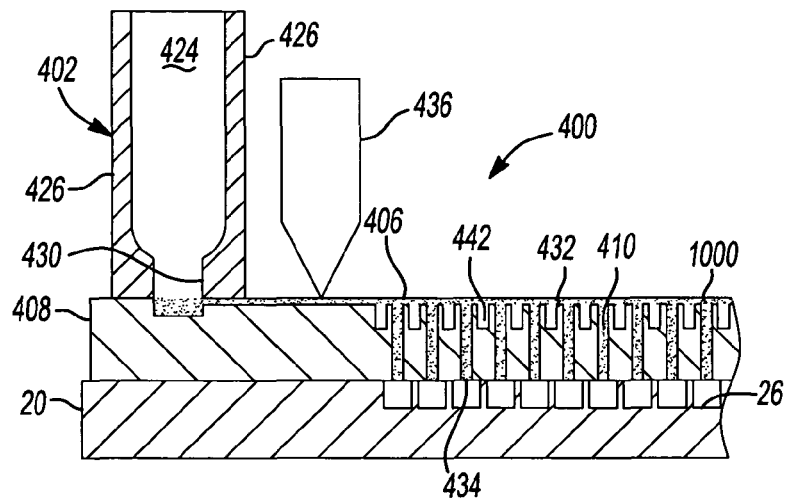
Figure 65:
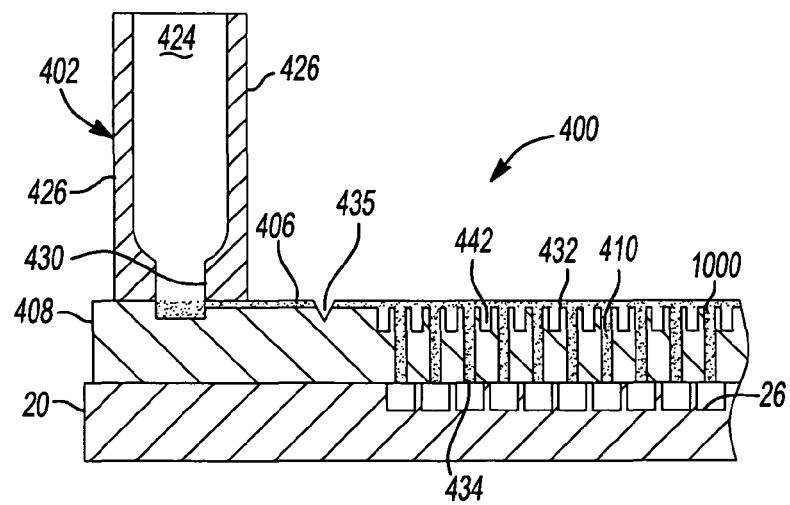

As illustrated in FIGS. 64 and 65 and described above, in some embodiments, filling apparatus 400 can be stake cut, generally indicated at 435, via device 436 along a portion of one or more microfluidic channels 406. It should be appreciated that stake-cutting or staking can be carried out, as previously described.

Figure 66:
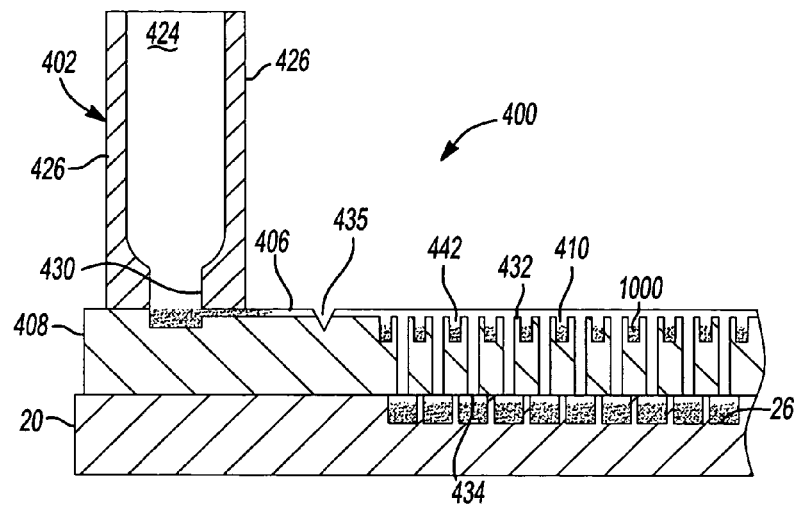

In some embodiments, once at least some of the plurality of staging capillaries 410 are filled, at least output layer 408 and microplate 20 can be placed into a swing-arm centrifuge. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20 (FIG. 66). In some embodiments, the centripetal force of the centrifuge can be sufficient to force overfill fluid (e.g. assay 1000 still remaining in microfluidic channels 406) into overfill reservoir 442, thereby displacing the air within overfill reservoir 442, rather than into the plurality of staging capillaries 410. In some embodiments, this air can serve to isolate one staging capillary 410 from an adjacent staging capillary 410. In some embodiments, overfill reservoir 442 can act as a reservoir for excess assay 1000. As illustrated in FIG. 67, in some embodiments, overfill reservoir 442 can be disposed within output layer 408 and generally aligned with and positioned below at least one assay input port 402 in output layer 408.

Microfluidic Channel Shapes

Figure 68:
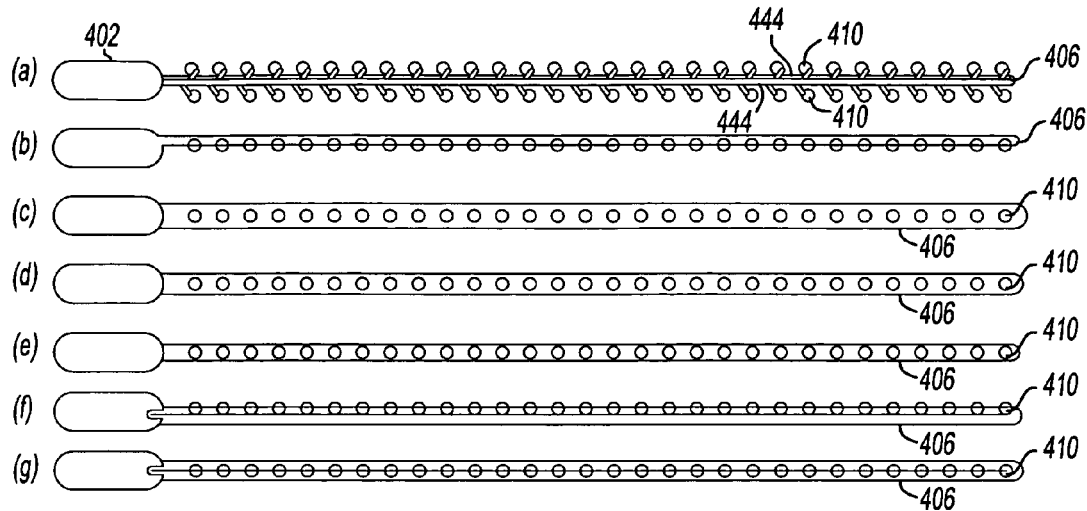
Figure 69:
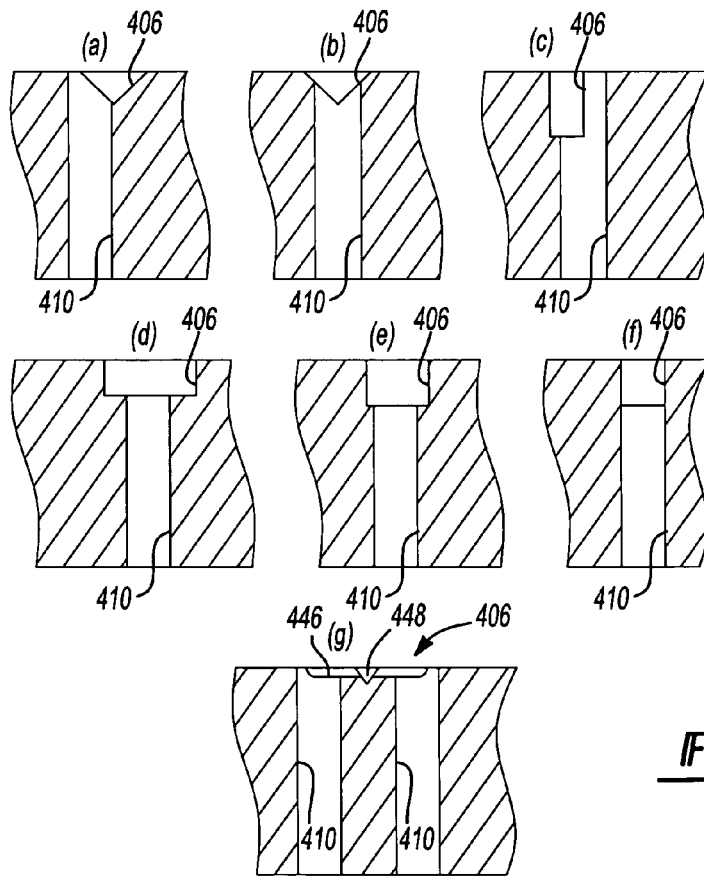

As illustrated in FIGS. 68(a)-(g) and 69(a)-(g), in some embodiments, microfluidic channels 406 can have any one or a combination of various configurations. In some embodiments, as illustrated in FIG. 68(a), each microfluidic channel 406 can be in fluid communication with a pair of rows of the plurality of staging capillaries 410 via feeder channels 444. In some embodiments, as illustrated in FIGS. 68(b), 69(a), and 69(c), microfluidic channel 406 can be in fluid communication with a row of staging capillaries 410 that can be offset to one side of microfluidic channel 406. In some embodiments, as illustrated in FIGS. 68(c)-(e) and 69(d)-(f), a cross dimension, e.g., width, of microfluidic channel 406 can vary relative to a diameter of each of the plurality of staging capillaries 410 ranging from larger than the diameter of each staging capillaries 410 to about equal to the diameter of each staging capillaries 410 to less than the diameter of each staging capillary (FIGS. 25(e)-(f)). In some embodiments, as illustrated in FIGS. 68(f), 68(g), 69(a), and 69(b), microfluidic channel 406 can have a generally triangular cross-section that can be either aligned with or offset from staging capillaries 410. In some embodiments, as illustrated in FIG. 69(g), microfluidic channel 406 can have a single channel portion 446 fluidly coupled to two or more rows of staging capillaries 410. In some embodiments, single channel portion 446 comprises a centrally disposed feature 448 to, in part, aid in fluid splitting between adjacent rows of staging capillaries 410.

In some embodiments, capillary or surface tension forces encourage flow of assay 1000 through microfluidic channels 406. In this regard, microfluidic channels 406 can be of capillary size, for example, microfluidic channels 406 can be formed with a width of less than about 500 micron, and in some embodiments less than about 125 microns, less than about 100 microns, or less than about 50 microns. In some embodiments, microfluidic channels 406 can be formed, for example, with a depth of less than about 500 micron, and in some embodiments less than about 125 microns, less than about 100 microns, or less than about 20 microns. To further encourage the desired capillary action in microfluidic channels 406, microfluidic channels 406 can be provided with an interior surface that is hydrophilic, i.e., wettable. For example, the interior surface of microfluidic channels 406 can be formed of a hydrophilic material and/or treated to exhibit hydrophilic characteristics. In some embodiments, the interior surface comprises native, bound, or covalently attached charged groups. For example, one suitable surface, according to some embodiments, is a glass surface having an absorbed layer of a polycationic polymer, such as poly-l-lysine.

Capillary Overflow Control

In some embodiments, filling apparatus 400 can comprise an overflow retention system 1950 to receive and/or contain overflow of assay 1000 during filling of the plurality of staging capillaries 410. In some embodiments, overflow retention system 1950 can improve the filling accuracy of each of the plurality of staging capillaries 410. In other words, prior art systems employing simply pipetting of sample into a plate can yield varying volumes of sample due to the infrequent calibration of pipettes. Accordingly, in some embodiments, it can be beneficial to include overflow retention system 1950 to at least in part improve filling accuracy of assay 1000 in the plurality of staging capillaries 410, minimize waste of assay 1000, and enable use of pipettes for initial loading.

In some embodiments, as illustrated in FIGS. 144-148, overflow retention system 1950 can comprise one or more delay-filled capillaries 1952 positioned downstream from one or more staging capillaries 410. In this regard, the plurality of staging capillaries 410 upstream from delay-filled capillary 1952 are first filled with assay 1000 via the plurality of microfluidic channels 406. That is, staging capillary 410a will first fill, then staging capillary 410b to staging capillary 410n, until finally excess assay 1000 can be taken up by delay-filled capillary 1952 through capillary action. During centrifugation, assay 1000 disposed in delay-filled capillaries 1952 remains separate from that in or above the plurality of staging capillaries 410, thereby preventing or at least minimizing overfilling of well 26 of microplate 20. In some embodiments, delay-filled capillaries 1952 can be smaller than the plurality of staging capillaries 410 to create a relatively higher capillary force on assay 1000. In doing so, the higher capillary force in delay-filled capillaries 1952 can ensure that assay 1000 remains therein during centrifugation.

Figure 145:
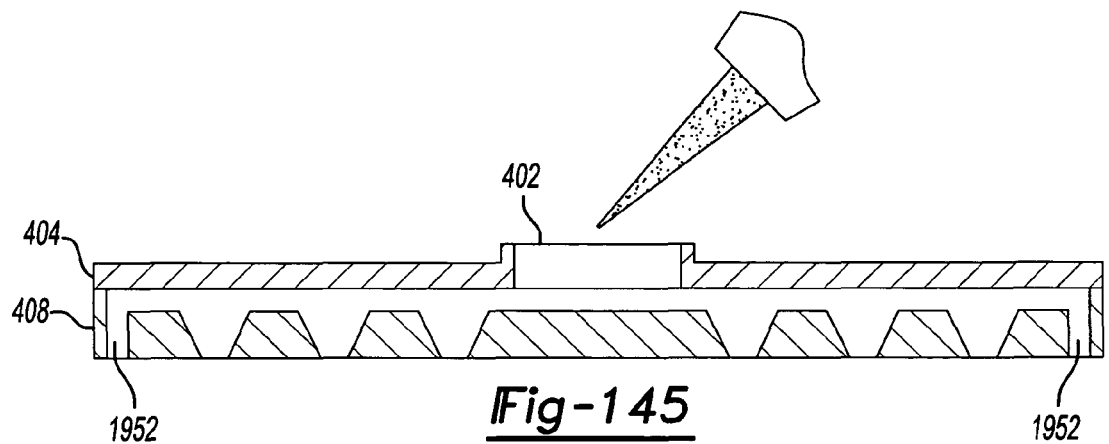
Figure 146:
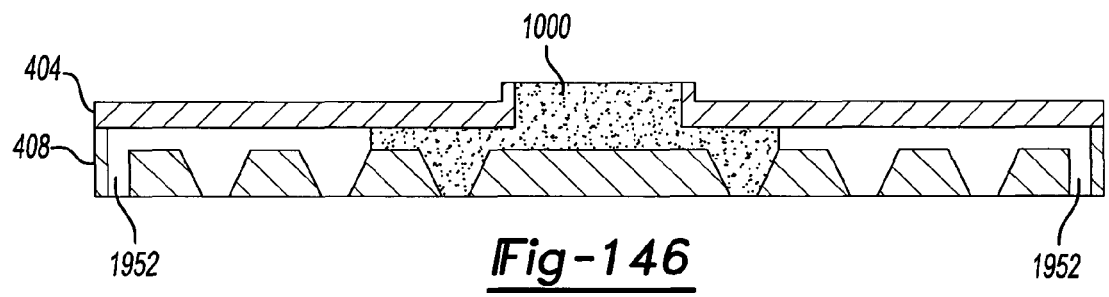
Figure 147:
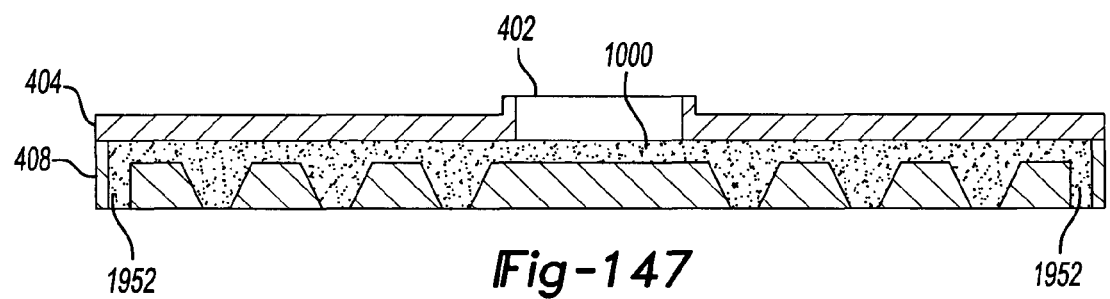
Figure 148:
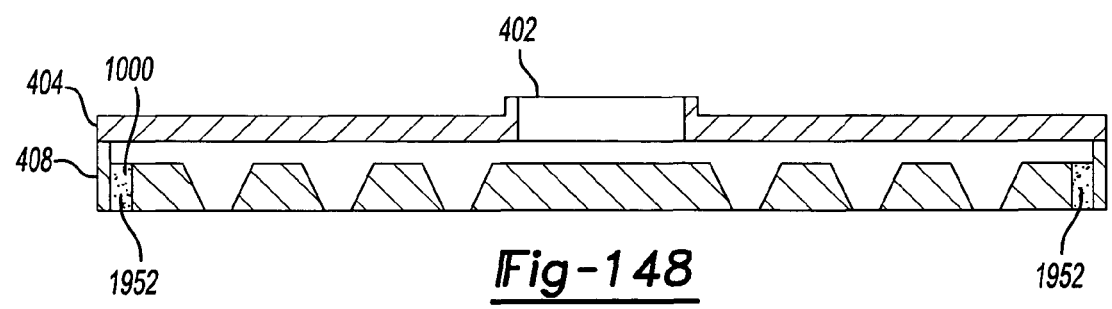

During filling of embodiments employing delay-filled capillaries 1952 (see FIGS. 145-148), assay 1000 is first injected into assay input ports 402 of input layer 404 (FIG. 145). Capillary forces and/or gravitational pressures urge assay 1000 into the plurality of microfluidic channels 406 and along the particular fluidic path (see FIGS. 146-147). The stronger capillary force of the plurality of staging capillaries 410 can draw assay 1000 therein from the plurality of microfluidic channels 406. Finally, excess assay 1000 reaches delay-filled capillaries 1952 and is drawn therein through capillary action. As illustrated in FIG. 148, once the plurality of staging capillaries 410 have been filled with assay 1000 and the excess drawn in to delay-filled capillaries 1952, filling apparatus 400 and microplate 20 are centrifuged in a swing-arm style centrifuge, which serves to overcome the surface tension and/or capillary force of assay 1000 within the plurality of staging capillaries 410, to urge assay 1000 from the plurality of staging capillaries 410 to the plurality of wells 26 of microplate 20. The excess assay 1000 remains in delay-filled capillaries 1952 (FIG. 148).

In some embodiments, as illustrated in FIG. 149, overflow retention system 1950 can comprise one or more delay-filled channels 1953 positioned throughout the network of staging capillaries 410, in addition to or in place of delay-filled capillaries 1952 positioned at the end of a series of staging capillaries 410. In other words, as illustrated in FIG. 149, delay-filled channels 1953 can be positioned at strategic points or randomly throughout output layer 408. In some embodiments, delay-filled channels 1953 can be open channels, separate from said plurality of microfluidic channels 406 and/or capillary plane 1912, extending between adjacent staging capillaries 410 or microfluidic channels 406 (FIG. 149). To delay filling thereof until after the plurality of staging capillaries 410 are filled, delay-filled channels 1953 can be sized to have a capillary force less than the plurality of staging capillaries 410 and greater than capillary plane 1912. In this regard, the plurality of staging capillaries 410 fill before delay-filled capillary 1952 are first filled with assay 1000 due to their great capillary force. Delay-filled channels 1953 then fill with the remaining assay 1000 from capillary plane 1912. During centrifugation, assay 1000 disposed in delay-filled channels 1953 remain fluidly separate from that in or above the plurality of staging capillaries 410, thereby preventing or at least minimizing overfilling of well 26 of microplate 20.

In some embodiments, as illustrated in FIGS. 150-152, overflow retention system 1950 can comprise an overflow moat 1954 to receive excess assay 1000 therein during centrifugation. In some embodiments, overflow moat 1954 can be a depression or countersunk feature having a bottom 1956 and side retaining walls 1958 in fluid communication with capillary plane 1912. Overflow moat 1954 can be positioned below and generally aligned with assay input port 402. During centrifugation, excess assay 1000 is urged and retained within overflow moat 1954 to prevent overflow of assay 1000 into the plurality of staging capillaries 410. It should be understood that overflow moat 1954 can be sized such that overflow moat 1954 does not encourage flow from capillary plane 1912 during filling, however does encourage flow and retention of excess assay 1000 during centrifugation. This arrangement serves to, at least in part, urge assay 1000 to the plurality of staging capillaries 410 during filling. Once again, after centrifugation, only excess assay 1000 will remain in overflow moat 1954 while the volumes of the plurality of staging capillaries 410 are dispensed.

In some embodiments, as illustrated in FIGS. 153-160, overflow retention system 1950 can comprise one or more burst pockets 1960 disposed in input layer 404. More particularly, as illustrated in FIG. 153, in some embodiments input layer 404 can comprise burst pockets 1960 formed on an underside thereof. Burst pockets 1960 can be in fluid communication with assay input port 402 such that during centrifugation (particularly early centrifugation), excess assay 1000 can be driven into burst pockets 1960 and retained therein to prevent or at least minimize overflow of assay 1000 into the plurality of staging capillaries 410 and later into wells 26. As illustrated in FIGS. 154-160, burst pockets 1960 can have any shape conducive to receiving assay 1000 during centrifugation. In some embodiments, one or a pair of burst pockets 1960 can be in fluid communication with assay input port 402 through a communication line 1962 (FIGS. 157 and 160). Additionally, in some embodiments, additional burst pockets 1960 can be used at each assay input port 402, such as three (FIG. 156), four (FIG. 158), or more. Burst pockets 1960 can be sized to contain a typical amount of overflow assay 1000 therein. Likewise, communication lines 1962 can be sized to prevent substantial flow of assay 1000 therethrough during filing of the plurality of staging capillaries 410 yet permit flow of assay 1000 therethrough during centrifugation. Additionally, in some embodiments, burst pockets 1960 can be disposed along a plane separate or otherwise offset (in a direction orthogonal to the plane of the plurality of staging capillaries 410) from the plurality of microfluidic channels 406 and/or capillary plane 1912 to further prevent or inhibit inadvertent flow of assay 1000 into burst pockets 1960 prior to centrifugation. In this way, excess assay 1000 can remain in assay input port 402 after filling of the plurality of staging capillaries 410 and will then be driven or urge into communication lines 1962 and burst pockets 1960 under forces exerted during initial centrifugation (see FIGS. 158-160).

Floating Inserts

In some embodiments, as illustrated in FIGS. 70-84, filling apparatus 400 comprises output layer 408, a floating insert 460, a cover 464, port member 467, or any combination thereof for loading assay 1000 into at least some of the plurality of wells 26 in microplate 20.

In some embodiments, output layer 408 comprises one or more recessed regions or depressions 454 formed in an upper surface 456 of output layer 408. Each depression 454 can be, in some embodiments, sized and/or shaped to receive floating insert 460 therein. In some embodiments comprising two or more depressions 454, at least one wall 458 can be used to separate each depression 454 to define grouping 407 of staging capillaries 410 of any desired quantity and orientation.

In some embodiments, as illustrated in FIG. 71, floating insert 460 and depression 454 can together define a capillary gap 468 between a bottom surface 470 of floating insert 460 and a top surface 472 of depression 454. In some embodiments, capillary gap 468 can result from surface variations in bottom surface 470 of floating insert 460 and/or top surface 472 of depression 454 and/or spacing gaps formed therebetween. It should be appreciated that capillary gap 468 can be quite small; therefore, the drawings of the present application may exaggerate this feature for ease of printing and understanding. In some embodiments, capillary gap 468 exhibits a capillary force sufficient to draw assay 1000 there along and to mouth 432 of each staging capillary 410. In some embodiments, bottom surface 470 of floating insert 460 and/or top surface 472 of depression 454 can be treated and/or coated to enhance the hydrophilic properties of capillary gap 468. In some embodiments, capillary gap 468 can be in fluid communication with an aperture 462 extend through floating insert 460. Aperture 462 can be centrally located relative to floating insert 460 or can be located to one side and/or corner thereof. In some embodiments, aperture 462 comprises an assay receiving well 463 (FIG. 72-84). In such embodiments, port member 467 is optional.

As illustrated in FIG. 71, in some embodiments, to reduce capillary force between a sidewall 474 of floating insert 460 and wall 458 of depression 454, the thickness of floating insert 460 and the depth of depression 454 can be minimized to shorten the length of any resulting capillary channel and, thus, reduce the overall capillary force in this region. In some embodiments, as illustrated in FIGS. 72-84, floating insert 460 comprises a flanged base portion 490 to reduce the potential capillary surface between sidewall 474 of floating insert 460 and wall 458 of depression 454. In some embodiments, a hydrophic surface can be employed between floating insert 460 and wall 458 of depression 454 to reduce capillary force therebetween. In some embodiments, this hydrophic surface can result from native material characteristics, treatments, coatings, and the like.

In some embodiments, as illustrated in FIGS. 74-79, floating insert 460 can be shaped to, at least in part, achieve any particular capillary and/or flow characteristics. In some embodiments, as illustrated in FIGS. 74-76, floating insert 460 can comprise a plurality of flow features 478 to, at least in part, extend the capillary surface to facilitate capillary flow. In some embodiments, for example, each of the plurality of flow features 478 comprises a post member 480 (FIG. 74) extending orthogonally from bottom surface 470 of floating insert 460. In some embodiments, post member 480 comprises a radiused root portion 482 to facilitate capillary flow, if desired. In some embodiments, post member 480 can be offset within the corresponding staging capillary 410 and can, if desired, contact a sidewall of staging capillary 410. In some embodiments, each of the plurality of flow features 478 comprises a tapered member 484 (FIGS. 75-79) extending from bottom surface 470 of floating insert 460. In some embodiments, each of the plurality of staging capillaries 410 comprises a corresponding mating entrance feature 486 (FIGS. 75, 77, and 78) to closely conform to each flow feature 478 to define a transition capillary gap 488. Tapered member 484 can be conically shaped (FIGS. 75-76) to closely conform to the complementarily-shaped mating entrance feature 486 in staging capillary 410. It should be appreciated that in some embodiments, the plurality of flow features 478 can further serve to individually plug or seal each corresponding capillary 410 during centrifugation (FIG. 79).

In some embodiments, floating insert 460 can comprise any material conducive to encourage capillary action along capillary gap 468, such as but not limited to plastic, glass, elastomer, and the like. In some embodiments, floating insert 460 can be made of at least two materials, such that an upper portion can be made of a first material and a lower portion can be made of a second material. In some embodiments, the second material can provide a desired compliancy, hydrophilicity, or any other desire property for improved fluid flow and/or sealing of staging capillaries 410. In some embodiments, the tapered members can include a seal-facilitating film, coating, or gasket thereon.

In some embodiments, as seen in FIG. 71, cover 464 can be used, at least in part, to retain floating insert 460 within each depression 454, if desired. In some embodiments, cover 464 comprises an aperture 466 generally aligned with an aperture 462 of floating insert 460. In some embodiments, cover 464 comprises a pressure sensitive adhesive to, at least in part, retain floating insert 460 within depression 454.

As illustrated in FIGS. 70 and 71, in some embodiments, port member 467 comprises assay input port 402. In some embodiments, port member 467 can comprise a material comprising sufficient weight such that during centrifugation, the centripetal force of port member 467 exerted upon floating insert 460 and output layer 408 can aid in closing off cross-communication of fluid between adjacent staging capillaries 410, as the upper-end openings of staging capillaries 410 can be covered and sealed by the lower surface of floating insert 460. In some embodiments, port member 467 can be sized such that its footprint (e.g. the surface area of a bottom surface 476 of port member 467) can be smaller than the opening of depression 454 to aid in the exertion of centripetal force on floating insert 460 during centrifuge.

In some embodiments, as illustrated in FIG. 80-82, to load each of the plurality of staging capillaries 410, a predetermined amount of assay 1000 can be placed at each assay input port 402 when used with port member 467 or receiving well 463. Capillary gap 468 can be sized to provide sufficient capillary force to draw at least a portion of assay 1000 from assay input port 402 or receiving well 463 into capillary gap 468. The capillary force of capillary gap 468 can be, at least in part, due to the non-rigid connection between floating insert 460 and output layer 408. As illustrated in FIG. 81, as assay 1000 is drawn into and spreads about capillary gap 468, each of the plurality of staging capillaries 410 in fluid communication with capillary gap 468 can begin to fill, at least in part, by capillary force as described herein.

In some embodiments, once at least some of the plurality of staging capillaries 410 are filled, at least output layer 408 and microplate 20 can be placed into a centrifuge. For example, the pieces can be clamped or otherwise held together, and then placed in a bucket centrifuge as a unit. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20. In some embodiments, the centripetal force of the centrifuge can also cause floating insert 460 to be forced and, thus, pressed against top surface 472 of depression 454. In some embodiments, where port member 467 is installed (FIGS. 70 and 71) or any additional weight member 492 (FIGS. 83 and 84), this additional weight can further apply a force upon floating insert 460 to force floating insert 460 against top surface 472 of depression 454. This force on floating insert 460 against top surface 472 of depression 454 can help to fluidly isolate each staging capillaries 410 from adjacent staging capillaries 410 for improved metering.

It should be appreciated that any component of filling apparatus 400, such as input layer 404, output layer 408, floating insert 460, cover 464, port member 467, intermediate layer 494, vent layer 523, etc., can comprise a plate, tile, disk, chip, block, wafer, laminate, and any combinations thereof, and the like.

Sweep Loader

In some embodiments, as illustrated in FIGS. 161-168, filing apparatus 400 can comprise a sweep loader 1974 that can sweep across microplate 20 to fill the plurality of wells 26 contained therein with assay 1000. That is, as illustrated in FIGS. 161-163 and 169, microplate 20 can comprise a substantially planar construction having first surface 22 and opposing second surface 24 (see FIGS. 12-19, 171, and 169). First surface 22 comprises the plurality of wells 26 disposed therein or thereon. Each of the plurality of wells 26 is sized to receive assay 1000. In some embodiments, microplate 20 can be partitioned into discrete and/or distinct well groupings 1976. Each of the distinct well groupings 1976 can be serviced by a separate and distinct sweep loader 1974 such that each distinct well grouping 1976 can contain a wholly different assay 1000 and/or other materials that can be processed simultaneously without concern for cross-contamination and the like. Additionally, such distinct well groupings 1976 can enable a number of smaller samples to be tested in a reduced number of runs to permit economies of scale and, thus, reduced costs. In some embodiments, such as that illustrated in FIG. 161, microplate 20 can be divided into four well groupings 1976, wherein each well grouping 1976 contains ninety-six wells 26. Each of wells 26 can be spaced about 1.25 mm apart center-to-center. Each well 26 can contain about 300 nanoliters of assay 1000. However, it should be understood that other sizes and spacing of wells 26 are possible. In some embodiments, microplate 20 can be molded out of plastic or die cast out of aluminum or other metal. In fact, in some embodiments, microplate 20 can be metal or heat resistant plastic since no plastic seal needs to be welded thereto.

In some embodiments, each of the plurality of wells 26 of microplate 20 can be shaped as long and shallow volumes, as illustrated in FIG. 163. To achieve such shape, one can sweep a narrow ellipse in a circle so that the axis of the sweep is above surface 22 of microplate 20. The long axis of each well 26 can be tilted slightly so that the plurality of wells 26 can be closely packed with the spacing roughly equal in each direction. This shape of wells 26 can be used in conjunction with sweep loader 1974 such that as sweep loader 1974 sweeps over the surface of well grouping 1976, assay 1000 is introduced into each well 26 and excess assay 1000 is wiped away in a single pass. This shape of wells 26 further minimize air bubbles from being trapped as assay 1000 enters the plurality of wells 26. As will be discussed herein, sweep loader 1974 can further deposit a layer of oil or similar sealing material over microplate 20 following loadings. To further facilitate filling, each of the plurality of wells 26 can be hydrophilic, either through inherent material properties, through coatings, and the like. Likewise, in some embodiments, the top surface of microplate 20 can be hydrophobic, either through inherent material properties, through coatings, and the like, to direct assay 1000 toward each of the plurality of wells 26 or otherwise direct assay 1000 to a predetermine location or direction.

Still referring to FIGS. 161-163, 167, and 169, microplate 20 can comprise a track system 1978 for receiving and/or guiding sweep loader 1974. Track system 1978 can comprise upright walls 1980 disposed on opposing sides of well grouping 1976 that engage correspondingly sized flange members extending downward from sweep loader 1974, as will be described herein. Accordingly, in some embodiments, a top surface of well grouping 1976 can be lower than a periphery of microplate 20 to further define such separate and distinct well groupings 1976. In some embodiments, microplate 20 can comprise one or more assay overflow reservoirs 1982 disposed at an end(s) of well grouping 1976 to receive excess assay 1000 during filling of wells 26. Still further, in some embodiments, microplate 20 can comprise an area for staging sweep loaders 1974 in a position apart from the plurality of wells 26. To support sweep loaders 1974 in this staging position (see FIG. 161), microplate 20 can comprise a pair of support arms 1984 for each sweep loader 1974. The pair of support arms 1984 can extend in a U-shape from microplate 20, such that track system 1978 extends to an end thereof to provide seamless sliding movement of sweep loader 1974 from the staging position to a position over the plurality of wells 26 and then returned to the staging position without interruption (see FIGS. 161 and 162). To prevent overrun and/or to retain sweep loaders 1974 in the staging position, in some embodiments staging clips 1986 (FIG. 161) can be used. Staging clips 1986 can be generally W-shaped in profile such that a first leg 1988 and center leg 1990 can capture and retain an end 1992 of support arm 1984 of microplate 20. Furthermore, a second leg 1994 and center leg 1990 can capture and retain an upturned retaining feature 1996 formed on sweep loader 1974. In some embodiments, second leg 1994 can comprise a downwardly-turned feature 1998 sized to cooperate with upturned retaining feature 1996 of sweep loader 1974. It should be understood that any retaining mechanism could be use, although some benefits of the present system may not be realized. Still further, in some embodiments, microplate 20 can comprise a physical stop member 2000 to aid in capturing sweep loader 1974 in the staging position. It should also be understood that microplates 20 having more than four well groupings 1976 can be used, such as for example a microplate 20 having fourteen well groupings 1976 as illustrated in FIG. 169.

As illustrated in FIGS. 164-168, in some embodiments, sweep loader 1974 comprises several features that aid in the deposition and filling of the plurality of wells 26 of microplate 20 with assay 1000. To this end, sweep loader 1974 can comprise an assay chamber 2002 adapted for receiving assay 1000 therein having an input opening 2004 and an output slot 2006. In some embodiments, output slot 2006 is sized to retain assay 1000 within assay chamber 2002 until such time that output slot 2006 is spaced sufficiently close enough to the top surface of well grouping 1976 to create a capillary force to draw assay 1000 therefrom. In some embodiments, assay chamber 2002 can further comprise a necked area 2008 to maintain proper fluid pressures therein. In some embodiments, sweep loader 1974 comprises an oil chamber 2010. Oil chamber 2010 can be prefilled prior to distribution to an end user, if desired. In some embodiments, oil chamber 2010 is prefilled and a foil layer is disposed over an output slot 2012 of oil chamber 2010. In some embodiments, output slot 2012 of oil chamber 2010 can comprise a sloped section 2014 to aid in directing oil over the plurality of wells 26 during filling. In order to ensure the proper thickness of oil deposited over the plurality of wells 26, an oil scraper 2016 can be used. In some embodiments, oil scraper 2016 is positioned along an underside of sweep loader 1974 and is spaced a predetermined distance from the surface of well grouping 1976.

During filling, assay 1000 is loaded into assay chamber 2002 using any known technique and/or apparatus, such as a pipette. Sweep loader 1974 can be them moved, either manually or via mechanical or robotic means, from the staging position to a position over the plurality of wells 26 of microplate 20 at a controlled rate such that flanges 2022 extending from a bottom thereof engage and guide sweep loader 1974 along track system 1978. During this initial movement from the staging position, the foil layer can be removed or otherwise ripped to reveal the oil contained in oil chamber 2010. Once sweep loader 1974 is positioned over well grouping 1976, a gap is formed between output slot 2006 of assay chamber 2002 and the upper surface of well grouping 1976 creating a capillary force urging a fluid bead of assay 1000 out of assay chamber 2002, onto well grouping 1976, and finally into each of the plurality of wells 26 under increases capillary force. Continued movement of sweep loader 1974 draws this fluid bead across well grouping 1976 filling all of the plurality of wells 26, while an assay scraper 2018 (FIG. 168) can be employed behind this fluid bead to control deposition of assay 1000 in some embodiments. Similarly during this time, a gap is formed between output slot 2012 of oil chamber 2010 and the upper surface of well grouping 1976 creating a capillary force urging an oil bead out of oil chamber 2010 and onto well grouping 1976 in the form of a protective oil seal over the plurality of wells 26. The thickness of this protective oil seal can be controlled by the specific dimensions of oil scraper 2016. As sweep loader 1974 approaches the opposing end of well grouping 1976, excess assay 1000 and/or oil can be received and contained overflow reservoir 1982.

In some embodiments, once sweep loader 1974 contacts the opposing side of microplate 20, wedge elevators 2020 raise sweep loader 1974 to break the assay fluid bead and the oil fluid bead to resist further flow thereof. More particularly, as illustrated in FIGS. 164-167, in some embodiments sweep loader 1974 comprise one or more wedge elevators 2020 disposed adjacent to flanges 2020. Wedge elevators 2020 can be generally wedge shaped having a contact end 2024. Contact end 2024 is sized and positioned to contact a fence 2026 formed at a far end of microplate 20 (FIG. 162). Wedge elevator 2020 can be retained via any known method, such as spring wires 2028 and the like. During operation, wedge elevators 2020 can contact fence 2026 after sweeping across the plurality of wells 26 causing wedge elevators 2020 to move from a lowered position (FIG. 165) to a raised position (FIGS. 166 and 167). More particularly, a cam point 2030 of wedge elevator 2020 moves from a first notch 2032 formed in the sidewall of sweep loader 1974 to a second notch 2034 formed in the sidewall. First notch 2032 can be higher on the sidewall of sweep loader 1974 relative to second notch 2034 causing sweep loader 1974 to be spaced closer to the plurality of wells 26. A lower rail edge 2036 of wedge elevators 2020 contacts a top surface 2038 of track system 1978 to support sweep loader 1974 upon track system 1978 during sliding movement. Once raised by virtue of contact between wedge elevators 2020 and fence 2026, sweep loader 1974 can be slid back to the staging position and snapped into place via staging clips 1986.

Surface Wipe

As illustrated, for example, in FIGS. 85-92, in some embodiments, filling apparatus 400 does not include the plurality of microfluidic channels 406. In some embodiments, for example, filling apparatus 400 comprises output layer 408 and a surface wipe assembly 1800 for loading assay 1000 into at least some of the plurality of wells 26 in microplate 20. In some embodiments, surface wipe assembly 1800 comprises one or more of a base support 1810, a drive assembly 1812, a funnel assembly 1814, or any combination thereof.

In some embodiments, such as illustrated in FIG. 85, base support 1810 can be a generally planar support member operable to support microplate 20 and output layer 408 thereon. In some embodiments, base support 1810 comprises an alignment feature 1818 that can engage corresponding alignment feature 58 (refer to previous figures) of microplate 20 and/or alignment feature 519 of output layer 408 to maintain microplate 20 and output layer 408 in a predetermined alignment relative to each other and/or funnel assembly 1814.

In some embodiments, drive assembly 1812 comprises a drive motor 1816; a guide member 1820, coupled to or formed in base support 1810; a tracking member 1822, coupled to or formed in funnel assembly 1814; and control system 1010. In some embodiments, guide member 1820 and tracking member 1822 are sized and/or shaped to slidingly engage with each other to provide guiding support for funnel assembly 1814 as it moves relative to base support 1810. In some embodiments, drive motor 1816 can be operably coupled to tracking member 1822 or base support 1810 to move tracking member 1822 relative to guide member 1820 via known drive transmission interfaces, such as mechanical drives, pneumatic drives, hydraulic drives, electromechanical drives, and the like. In some embodiments, drive motor 1816 can be controlled in response to control signals from control system 1010 or a separate control system. In some embodiments, drive motor 1816 can be operably controlled in response to a switch device controlled by a user.

In some embodiments, funnel assembly 1814 comprises a spanning portion 1824 generally extending above output layer 408. In some embodiments, spanning portion 1824 can be supported on opposing ends by tracking member 1822 of drive assembly 1812 and a foot member 1826. Tracking member 1822 and foot member 1826 can each be coupled to spanning portion 1824 via conventional fasteners in some embodiments. Foot member 1826 can be generally arcuately shaped so as to reduce the contact area between foot member 1826 and base support 1810. In some embodiments, foot member 1826 can be made of a reduced friction material, such as Delrin®.

In some embodiments, spanning portion 1824 of funnel assembly 1814 comprises a slot 1828 formed vertically therethrough that can be sized and/or shaped to receive a funnel member 1830 therein. As illustrated in FIGS. 85-92, funnel member 1830 can comprise one or more assay chambers 1832 for receiving one or more different assays therein. It should be appreciated that drive assembly 1812 and funnel assembly 1814 can be configured to track in a direction perpendicular to that illustrated in the accompanying figures to provide an increased number of assay chambers 1832 and reduced track distances. In some embodiments, such as illustrated in FIG. 86, funnel member 1830 can comprise a flange portion 1834 extending about a top portion thereof. Flange portion 1834 of funnel member 1830 can be sized and/or shaped to rest upon a corresponding flange portion 1836 of slot 1828 of spanning portion 1824 to support funnel member 1830. However, it should be appreciated that funnel member 1830 can comprise any outer profile complementary to slot 1828.

Assay chambers 1832, in some embodiments, can be shaped to provide a predetermined assay capacity for filling all of a predetermined number and/or grouping of the plurality of staging capillaries 410 in output layer 408. In some embodiments, assay chamber 1832 comprises converging sidewalls 1838 that terminate at a tip portion 1840.

In some embodiments, such as illustrated in FIG. 87-89, to load each of the plurality of staging capillaries 410, a predetermined amount of assay 1000 can be placed in each assay chamber 1832. In some embodiments, each assay chamber 1832 comprises a different assay. Assay 1000 is drawn down along sidewalls 1838 to tip portion 1840 to form a fluid bead 1842 extending from tip portion 1840 that can be in contact with upper surface 456 of output layer 408. In some embodiments, drive assembly 1812 can be actuated to advance funnel assembly 1814 across output layer 408 at a predetermined rate, as illustrated in FIG. 88. However, it should be appreciated that funnel assembly 1814 can be advanced manually across output layer 408. As funnel assembly 1814 is advanced across output layer 408, in some embodiments, fluid bead 1842 can contact the upper-end opening or entrance of each of the plurality of staging capillaries 410 and begin to fill, at least in part, by capillary force as described herein.

As illustrated in at least FIGS. 86-89, 91, and 98, in some embodiments, fluid bead 1842 can be bound by a lip or wiper member 1844 extending downwardly from tip portion 1840 of funnel member 1830. In some embodiments, wiper member 1844 can, at least in part, wipe and/or remove excess assay 1000 on upper surface 456 of output layer 408 as funnel member 1830 moves thereabout. In some embodiments, a sponge or other porous material member 1845 can be disposed, positioned, or otherwise fixed to tip portion 1840 of funnel member 1830 (FIG. 91). Porous material member 1845 can, at least in part, serve to control and/or meter assay 1000 into the plurality of staging capillaries 410. In other words, porous material member 1845 can serve as a physical barrier to inhibit free flow of assay 1000. The size and shape of the plurality of air pockets within porous material member 1845 can be selected to inhibit such free flow of assay 1000. However, during dispensing and/or filling, porous material member 1845 can be compressed or otherwise deformed to displace the air within the plurality of air pockets to permit flow of assay 1000 therethrough. The degree of assay flow prevention or ease of liquid passage can be controlled by at least the following parameters of porous material member 1845: pore size, durometer, and any surface treatments to vary the surface chemistries (i.e., make it more or less hydrophobic or hydrophilic).

In some embodiments, such as illustrated in FIGS. 85 and 89, as funnel assembly 1814 continues past the last of the plurality of staging capillaries 410, some assay 1000 can be forced off upper surface 456 of output layer 408 at an edge 1846 into at least one overflow channel 1848. In some embodiments, once at least some of the plurality of staging capillaries 410 are filled, at least output layer 408 and microplate 20 can be placed into a centrifuge. In some embodiments, the centripetal force of the centrifuge can be sufficient to overcome the capillary force and/or surface tension of assay 1000 in each the plurality of staging capillaries 410, thereby forcing a metered volume of assay 1000 into each of the plurality of wells 26 of microplate 20.

In some embodiments, such as illustrated in FIG. 85, the excess assay 1000 in overflow channel 1848 can be contained using one or more reservoir pockets 1850. In some embodiments, reservoir pocket 1850 can be in fluid communication with at least one overflow channel 1848. In some embodiments, reservoir pocket 1850 can be deeper than overflow channel 1848 to encourage flow of assay 1000 to reservoir pocket 1850. During centrifugation, centripetal force can further encourage assay 1000 to flow to reservoir pocket 1850, thereby reducing the likelihood of any contamination or cross-feed between adjacent staging capillaries 410. In some embodiments, an extended wall member 1852 can be positioned about reservoir pocket 1850 to further contain assay 1000.

In some embodiments, such as illustrated in FIGS. 90 and 91, the excess assay 1000 in overflow channel 1848 can be contained using a reservoir trough 1854. In some embodiments, an absorbent member 1856 can be disposed in reservoir trough 1854 to absorb excess assay 1000 therein. In some embodiments, absorbent member 1856 can be a hydrophilic fiber membrane. As illustrated in FIG. 91, reservoir trough 1854 can be sloped toward absorbent member 1856 to facilitate absorption of excess assay 1000. In some embodiments, absorbent member 1856 can be removable to permit removal and relocating of the excess assay 1000 prior to centrifugation.

In some embodiments, such as illustrated in FIGS. 92 and 93, funnel member 1830 can comprise two or more discrete assay chambers 1832 for delivering one or more different assays. In such embodiments, for example, output layer 408 can comprise one or more central overflow channels 1858 extending along upper surface 456 of output layer 408 to receive at least some overflow assay 1000. In some embodiments, central overflow channels 1858 are each disposed between each separate grouping of staging capillaries 410 served by each discrete assay chamber 1832. In some embodiments, as illustrated in FIG. 92, central overflow channel 1858 can be sloped down to at least one of overflow channel 1848 (FIG. 85), reservoir pocket 1850 (FIG. 85), reservoir trough 1854 (FIG. 90), or absorbent member 1856 (FIG. 92). As illustrated in FIG. 93, in some embodiments, absorbent member 1856 can be sized and/or shaped to fit with an enlarged reservoir pocket 1850.

In some embodiments, as illustrated in FIGS. 171-172, output layer 408 can comprise one or more central hydrophobic lines or features 1970 extending along upper surface 456 of output layer 408. In some embodiments, hydrophobic lines 1970 are each disposed between each separate grouping of staging capillaries 410 served by each discrete assay chamber 1832. In embodiments providing sufficient spacing between adjacent groupings and/or staging capillaries 410, hydrophobic lines 1970 can be disposed between staging capillaries 410 (see FIG. 171). However, in embodiments providing less spacing between adjacent groupings and/or staging capillaries 410, hydrophobic lines 1970 can be disposed along a line of staging capillaries 410 (see FIG. 172) such that the upper opening of each staging capillary 410 along such line is open to permit filling of assay 1000, but the space between staging capillaries 410 in that line is covered with such hydrophobic line 1970. The use of hydrophobic lines 1970 can provide reduced manufacturing complexity, compared to injection molding small walls or channels, and consequently reduced manufacturing cost. Additionally, application of hydrophobic lines 1970 can be completed in an operation separate from initial manufacturing, thereby permitting economies of scale for output layers having differing shapes of staging capillary groups. In some embodiments, hydrophobic lines 1970 can be formed on output layer 408 through pad printing, silk screening, plasma coating, and the like. In some embodiments, hydrophobic lines 1970 can be made of PDMS, silicone, Teflon, paralene, any other hydrophobic material, or combinations thereof.

Funnel Member

As illustrated in FIGS. 94-107, in some embodiments, funnel member 1830 of funnel assembly 1814 can be any one of a number of configurations sufficient to maintain fluid bead 1842 in contact with upper surface 456 of output layer 408. In some embodiments, a predetermined shape of fluid bead 1842 and/or a predetermined flowrate of assay 1000 through tip portion 1840 can be achieved through the particular configuration of funnel member 1830.

As illustrated in FIG. 94-96, in some embodiments, funnel member 1830 comprises one or more assay chambers 1832 in fluid communication with tip portion 1840. As described above, in embodiments comprising two or more assay chambers 1832 (FIG. 95), multiple assays can be used such that a different assay can be disposed in each assay chamber 1832. It should be understood that any number of assay chambers 1832 can be used (e.g., 2, 4, 6, 8, 10, 12, 16, 20, 32, 64, or more).

In some embodiments, tip portion 1840 can be configured to define a capillary force and/or surface tension sufficient to prevent assay 1000 from exiting assay chamber 1832 prior to fluid bead 1842 engaging upper surface 456 and to permit assay 1000 to be pulled into each of the plurality of staging capillaries 410 during filling of the staging capillaries. As illustrated in FIG. 97, tip portion 1840 comprises a restricted orifice 1860 that is sized to increase surface tension to retain assay 1000 with assay chamber 1832. In some embodiments, tip portion 1840 can be spaced apart from an underside surface 1862 to, at least in part, inhibit assay 1000 from collecting between funnel member 1830 and output layer 408. In some embodiments, as illustrated in FIG. 98, restricted orifice 1860 can be used with wiper member 1844 to increase surface tension to retain assay 1000 and to wipe and/or remove excess assay 1000 on upper surface 456 of output layer 408. In some embodiments, such as illustrated in FIG. 99, tip portion 1840 can comprise a planar cavity 1864 disposed in fluid communication with restricted orifice 1860. In some embodiments, planar cavity 1864 can encourage the formation of wider and/or shallower fluid bead 1842 relative to similar configurations not employing planar cavity 1864. In some configurations, the wider and/or shallower fluid bead 1842 can, at least in part, prolong the time fluid bead 1842 is in contact with each of the plurality of staging capillaries 410.

As illustrated in FIG. 100, in some embodiments, funnel member 1830 can comprise wiper 1844 spaced apart from tip portion 1840 to wipe and/or remove excess assay 1000 on upper surface 456 of output layer 408. In some embodiments, wiper 1844 can extend a distance from underside surface 1862 of funnel member 1830 equal to about a distance from underside surface 1862 to a distal end of tip portion 1840. As illustrated in FIGS. 101-103, each tip portion 1840 associated with each assay chamber 1832 can be offset relative to adjacent tip portions 1840. In some embodiments, this offset relationship between adjacent tip portions 1840 can permit the plurality of staging capillaries 410 to be closely spaced with reduced likelihood for crosstalk between adjacent fluid beads 1842.

Still referring to FIGS. 101-103, in some embodiments, restricted orifice 1860 comprises an elongated slot 1866 (FIG. 101) generally extending from one edge of tip portion 1840 to the opposing edge to define an elongated fluid bead 1842. However, in some embodiments, restricted orifice 1860 comprises one or more apertures 1868. In some embodiments, the reduced cross-sectional area of apertures 1868 relative to that of elongated slot 1866 can serve to withstand a fluid head pressure exerted by assay 1000 in assay chamber 1832 that would otherwise overcome the surface tension of fluid bead 1842 exiting elongated slot 1866 and possibly lead to premature discharge of assay 1000. In some embodiments, the restricted orifice 1860 can be collinear as well as offset as illustrated in (FIG. 101).

In some embodiments, such as illustrated in FIGS. 104-106, funnel member 1830 can comprise an internal siphon passage 1870 to, at least in part, control the flowrate of assay 1000 from restricted orifice 1860. In some embodiments, funnel member 1830 comprises a main chamber 1872 fluidly coupled to a delivery chamber 1874 via siphon passage 1870. In some embodiments, siphon passage 1870 can be positioned along a bottom of main chamber 1872. Siphon passage 1870 can comprise an upturned section 1876 that can require assay 1000 in main chamber 1872 to flow, at least in part, against the force of gravity. In some embodiments, main chamber 1872 and delivery chamber 1874 can be fluidly coupled at the top thereof by a top chamber 1878. When main chamber 1872 is filled at least partially above top chamber 1878, the excess assay 1000 can flow across top chamber 1878 into delivery chamber 1874. During filling, as the level of assay 1000 drops below the bottom surface of top chamber 1878 and assay 1000 flows from restricted orifice 1860, assay 1000 within delivery chamber 1874 can be replaced through the siphoning action of siphon passage 1870 at the bottom of main chamber 1872. This arrangement can reduce the fluid head pressure exerted at restricted orifice 1860. Accordingly, the fluid head pressure exerted at restricted orifice 1860 can be generally to about the fluid head pressure of assay 1000 contained in delivery chamber 1874.

In some embodiments, as illustrated in FIGS. 106 and 107, funnel member 1830 can be formed with a two- or more-piece construction. As illustrated in FIG. 106, funnel member 1830 can comprise a first section 1880 and a second section 1882. First section 1880 can comprise one or more desired features. For example, as illustrated in FIG. 106, upturned section 1876 of FIG. 105 can be formed in first section 1880. First section 1880 and second section 1882 can then be joined or otherwise mated along a generally vertical joining line 1884 (FIG. 105) to form funnel member 1830. In some embodiments, first section 1880 and second section 1882 can be joined or otherwise mated along a generally horizontal joining line 1886 (FIG. 107). In some embodiments, first section 1880 and second section 1882 can be made from different materials to achieve a predetermined performance. In some embodiments, second section 1882 can be made of an elastomer to provide enhance flexibility to accommodate for variations in output layer 408 and enhanced wiping performance of wiper member 1844.

Surface Treatment

In some embodiments, portions of filling apparatus 400 that are intended to contact assay 1000, such as assay input ports 402, microfluidic channels 406, the plurality of staging capillaries 410, and the like, can be hydrophilic. Likewise, in some embodiments, surfaces not intended to contact assay 1000 can be hydrophobic.

In some embodiments, filling apparatus 400 comprises a treatment to increase surface energy thereof to improve flow and/or capillary action of any surface of filling apparatus 400 exposed to assay 1000, such as assay input ports 402, microfluidic channels 406, staging capillaries 410, microfluidic channels 406, depression 454, upper surface 456, etc. In some embodiments, surface energy can be improved, for example, when using a polymer material in the manufacture of filling apparatus 400, through surface modification of the polymer material via Michael addition of acrylamide or PEO-acrylate onto laminated surface; surface grafting of acrylamide or PEO-acrylate via atom transfer radical polymerization (ARTP); surface grafting of acrylamide via Ce(IV) mediated free radical polymerization; surface initiated living radical polymerization on chloromethylated surface; coating of negatively charged polyelectrolytes; plasma CVD of acrylic acid, acrylamide, and other hydrophilic monomers; or surface adsorption of an ionic or non-ionic surfactant. In some embodiments, surfactants, such as those set forth in Tables 2 and 3, can be used.

TABLE 2

Surfactants for Coating

| No. | Name | MW | Hydrophile Lipophile Balance (HLB) |
|---|---|---|---|
| 1 | Tetronic 901 | 4700 | 3 |
| 2 | Tetronic 1107 | 1500 | 24 |
| 3 | Tetronic 1301 | 6800 | 2 |
| 4 | Poly(styrene-b-ethylene oxide) | Mn: 3600–67000 | |
| 5 | Poly(stryrene-b-sodium acrylate) | Mn: 1800–42500 | |
| 6 | Triton X-100 | | 13.5 |
| 7 | Triton X-100 reduced | | |
| 8 | Tween 20 | 1228 | 16.7 |
| 9 | Tween 85 | 1839 | 11 |
| 10 | Span 83 | 1109.56 | 3.7 |
| 11 | Span 80 | 428.62 | 4.3 |
| 12 | Span 40 | 402.58 | 6.7 |

Tetronic:

$$\left[ H \!-\!\!\left(OCH_2CH_2\right)_{\!m}\!\!\left(O\!-\!CH(CH_3)\!-\!CH_2\right)_{\!n}\right]_2 \!\!N\!-\!CH_2CH_2\!-\!N\!\!\left[\!\left(CH_2\!-\!CH(CH_3)\!-\!O\right)_{\!n}\!\!\left(CH_2CH_2O\right)_{\!m}\!H\right]_2$$

Triton X-100:

$$HO\!-\!\!\left(CH_2CH_2O\right)_{\!10}\!\!-\!C_6H_4\!-\!C_8H_{17}$$

Triton X-100 reduced:

$$HO\!-\!\!\left(CH_2CH_2O\right)_{\!10}\!\!-\!C_6H_{10}\!-\!C_8H_{17}$$

Span 80:

$$\begin{array}{l} CH_2\!-\!\!\!\!\!\!\!\!\!\!\!\!\!\!\!\!\!\!\!\!\!\!\!\!\!\!\!\! \\ H\!-\!COH \\ HO\!-\!CH \\ H\!-\!C \\ CHOH \\ CH_2\!-\!O\!-\!R \end{array}$$
(R = —COC$_{17}$H$_{33}$ oleate)

Spam 83:

$$\begin{array}{l} CH_2\!-\!\!\!\!\!\!\!\!\!\!\!\!\!\!\!\!\!\!\!\!\!\!\!\!\!\!\!\! \\ H\!-\!COR \\ RO\!-\!CH \\ H\!-\!C \\ CHOH \\ CH_2\!-\!O\!-\!R \end{array}$$
(R = —COC$_{17}$H$_{33}$ oleate)

TABLE 2-continued

Surfactants for Coating

| No. | Name | MW | Hydrophile Lipophile Balance (HLB) |
|---|---|---|---|

Spam 20:

```
        CH2─
        │
  H ── COH
        │     O
 HO ── CH
        │
   H ── C
        │
        CHOH
        │
        CH2 ── O ── R
```

(R = ──COC$_{17}$H$_{33}$ laurate)

Tween:
Poly(oxyethylene)sorbitan monolauate

TABLE 3

Surfactants for Wetting Polypropylene

Acids:

| | |
|---|---|
| Dodecyl sulfate, Na salt | CH$_2$(CH$_2$)$_{11}$OSO$_3^-$ Na$^+$ |
| Octadecyl sulfate, Na salt | CH$_3$(CH$_2$)$_{17}$OSO$_3^-$ Na$^+$ |

Quaternary ammonium compounds:

| | |
|---|---|
| Cetyltrimethylammonium bromide | CH$_3$(CH$_2$)$_{15}$N$^+$(CH$_3$)$_3$ Br$^-$ |
| Octadecyltrimethylammonium bromide | CH$_3$(CH$_2$)$_{17}$N$^+$(CH$_3$)$_3$Br$^-$ |

Ethers:

| | |
|---|---|
| Brij-52 | CH$_3$(CH$_2$)$_{15}$(OCH$_2$CH$_2$)$_2$OH |
| Brij 56 | CH$_3$(CH$_2$)$_{15}$(OCH$_2$CH$_2$)$_{10}$OH |
| Brij 58 | CH$_3$(CH$_2$)$_{15}$(OCH$_2$CH$_2$)$_{20}$OH |
| Brij 72 | CH$_3$(CH$_2$)$_{17}$(OCH$_2$CH$_2$)$_2$OH |
| Brij 76 | CH$_3$(CH$_2$)$_{17}$(OCH$_2$CH$_2$)$_{10}$OH |
| Brij 78 | CH$_3$(CH$_2$)$_{17}$(OCH$_2$CH$_2$)$_{20}$OH |

Esters:

| | |
|---|---|
| Poly(ethylene glycol) monolaurate | CH$_3$(CH$_2$)$_{10}$CO(OCH$_2$CH$_2$)$_{4.5}$OH |
| Poly(ethyleneglycol) distearate | CH$_3$(CH$_2$)$_{16}$─CO─(OCH$_2$)$_9$─O─CO─(CH$_2$)$_{16}$CH$_3$ |
| Poly(ethyleneglycol)dioleate | CH$_3$(CH$_2$)$_7$CH=CH(CH$_2$)$_7$─CO─(OCH$_2$)$_9$─O─CO─(CH$_2$)$_7$CH=CH(CH$_2$)$_7$CH$_3$ |

In some embodiments, filling apparatus 400 can comprise polyolefins; poly(cyclic olefins); polyethylene terephthalate; poly(alkyl(meth)acrylates); polystyrene; poly(dimethyl siloxane); polycarbonate; structural polymers, for example, poly(ether sulfone), poly(ether ketone), poly(ether ether ketone), and liquid crystalline polymers; polyacetal; polyamides; polyimides; poly(phenylene sulfide); polysulfones; poly(vinyl chloride); poly(vinyl fluoride); poly(vinylidene fluoride); copolymers thereof; and mixtures thereof.

In some embodiments, a co-agent can be employed to enhance the hydrophilicity and/or improve the shelf life of filling apparatus 400. Co-agents can be, for example, a water-soluble or slightly water-soluble homopolymer or copolymers prepared by monomers comprising, for example, (meth) acrylamide; N-methyl(methyl)acrylamide, N,N-dimethyl (methyl)acrylamide, N-ethyl(meth)acrylamide, N-n-propyl (meth)acrylamide, N-iso-propyl(meth)acrylamide, N-ethyl-N-methyl(meth)acrylamide, N,N-diethyl(meth)acrylamide, N-hydroxymethyl(meth)acrylamide, N-(3-hydroxypropyl) (meth)acrylamide, N-vinylformamide, N-vinylacetamide, N-methyl-N-vinylacetamide, vinyl acetate that can be hydrolyzed to give vinylalcohol after polymerization, 2-hydroxyethyl (meth)acrylate, 3-hydroxypropyl(meth)acrylate, N-vinypyrrolidone, poly(ethylene oxide) (meth)acrylate, N-(meth)acryloxysuccinimide, N-(meth)acryloylmorpholine, N-2,2,2-trifluoroethyl (meth)acrylamide, N-acetyl (meth)acrylamide, N-amido(meth)acrylamide, N-acetamido (meth)acrylamide, N-tris(hydroxymethyl)methyl(meth) acrylamide, N-(methyl)acryloyltris(hydroxymethyl)methylamine, (methyl)acryloylurea, vinyloxazolidone, vinylmethyloxazolidone, and combinations thereof. In some embodiments, the co-agent can be poly(acrylic acid-co-N,N-dimethylacrylamide) or poly(N,N-dimethyl acrylamide-co-styrene sulfonic acid).

What is claimed is:

1. A filling system for receiving a sample comprising:
   an output layer having a plurality of capillaries, each of said plurality of capillaries having an inlet and an outlet, said output layer having at least one hydrophobic feature disposed thereon separating a first grouping of said plurality of capillaries from a second grouping of said plurality of capillaries; and
   a surface wipe assembly comprising:
      a base supporting said output layer; and
      a funnel assembly engaging said base and moveable relative to said base, said funnel assembly having a funnel member sized to receive said sample, said funnel member having an outlet for delivering a fluid bead of said sample along a top surface of said output layer and in fluid communication with each of said plurality of capillaries such that a portion of said fluid bead is drawn within at least some of the plurality of capillaries in response to capillary force, said funnel assembly and said output layer being moveable relative to each other between a first position and a second position to draw said fluid bead across said top surface.

2. The filling system according to claim 1 wherein said at least one hydrophobic feature is a line extending substantially from one end of said output layer to an opposing end.

3. The filling system according to claim 1 wherein said hydrophobic feature is disposed between adjacent rows of said plurality of capillaries.

4. The filling system according to claim 1 wherein said hydrophobic feature is disposed along a row of said plurality of capillaries.

5. The filling system according to claim 1 wherein said at least one hydrophobic feature is formed on said output layer through at least one of pad printing, silk screening, and plasma coating.

6. The filling system according to claim 1 wherein said at least one hydrophobic feature is made of at least one of PDMS, silicone, Teflon, and paralene.

7. The filling system according to claim 1, further comprising:
- a drive assembly operably coupled to one of said output layer and said funnel assembly to provide said relative movement of said funnel assembly and said output layer between said first position and said second position.

8. The filling system according to claim 7 wherein said drive assembly comprises:
- a drive motor operably coupled to one of said output layer and said funnel assembly; and
- a control system operably coupled to said drive motor, said control system selectively actuating said drive motor in response to a control input.

9. The filling system according to claim 8 wherein said drive assembly further comprises:
- said base support for supporting said output layer;
- a guide member extending from said base support; and
- a tracking member extending from said funnel assembly, said tracking member engagable with said guide member to guide said funnel assembly relative to said output layer.

10. The filling system according to claim 9 wherein said funnel assembly comprises:
- a spanning portion having a slot formed therethrough;
- a funnel member disposed in said slot.

11. The filling system according to claim 1 wherein said output layer comprises:
- an overflow channel formed therein, said overflow channel being in fluid communication with at least a portion of said top surface of said output layer.

12. The filling system according to claim 1 wherein said funnel assembly comprises:
- a funnel member having a first sample chamber and a second sample chamber, said first sample chamber being in fluid communication with said first grouping of said plurality of capillaries and said second sample chamber being in fluid communication with said second grouping of said plurality of capillaries.

13. The filling system according to claim 1 wherein each of said plurality of capillaries is sized to provide sufficient force to draw a predetermined volume of said sample therein and permit release of said sample from each of said plurality of capillaries in response to an applied centripetal force.

14. A filling system for receiving a sample comprising:
- an output layer having a plurality of capillaries, each of said plurality of capillaries having an inlet and an outlet, said output layer having at least one hydrophobic feature separating a first grouping of said plurality of capillaries from a second grouping of said plurality of capillaries; and
- a surface wipe assembly comprising:
  - a base supporting said output layer; and
  - a funnel assembly engaging said base and moveable relative to said base, said funnel assembly having a first sample chamber and a second sample chamber, said first sample chamber being in fluid communication with said first grouping of said plurality of capillaries and said second sample chamber being in fluid communication with said second grouping of said plurality of capillaries, said first grouping being separate from said second grouping, said first sample chamber and said second sample chamber delivering separate fluid beads of said sample along said top surface of said output layer and in fluid communication with said first grouping and said second grouping respectively to draw at least a portion of said fluid bead in to at least some of the plurality of capillaries in response to capillary force.

15. The filling system according to claim 14 wherein said at least one hydrophobic feature is a line extending substantially from one end of said output layer to an opposing end.

16. The filling system according to claim 14 wherein said hydrophobic feature is disposed between adjacent rows of said plurality of capillaries.

17. The filling system according to claim 14 wherein said hydrophobic feature is disposed along a row of said plurality of capillaries.

18. The filling system according to claim 14 wherein said at least one hydrophobic feature is formed on said output layer through at least one of pad printing, silk screening, and plasma coating.

19. The filling system according to claim 14 wherein said at least one hydrophobic feature is made of at least one of PDMS, silicone, Teflon, and paralene.

20. The filling system according to claim 14, further comprising:
- a drive assembly operably coupled to one of said output layer and said funnel assembly to provide relative movement of said funnel assembly and said output layer between a first position and a second position.

21. The filling system according to claim 15 wherein said drive assembly comprises:
- a drive motor operably coupled to one of said output layer and said funnel assembly; and
- a control system operably coupled to said drive motor, said control system selectively actuating said drive motor in response to a control input.

22. The filling system according to claim 21 wherein said drive assembly further comprises:
- said base support for supporting said output layer;
- a guide member extending from said base support; and
- a tracking member extending from said funnel assembly, said tracking member engagable with said guide member to guide said funnel assembly relative to said output layer.

23. The filling system according to claim 22 wherein said funnel assembly comprises:
- a spanning portion having a slot formed therethrough;
- a funnel member disposed in said slot.

24. The filling system according to claim 20 wherein said output layer comprises:
- an overflow channel formed therein, said overflow channel being in fluid communication with at least a portion of said top surface of said output layer.

25. The filling system according to claim 24 wherein said funnel assembly comprises:
a funnel member having a first sample chamber and a second sample chamber, said first sample chamber being in fluid communication with said first grouping of said plurality of capillaries and said second sample chamber being in fluid communication with said second grouping of said plurality of capillaries.

26. The filling system according to claim 20 wherein each of said plurality of capillaries is sized to provide sufficient force to draw a predetermined volume of said sample therein and permit release of said sample from each of said plurality of capillaries in response to an applied centripetal force.

27. A method of distributing a sample comprising:
providing the device of claim 1; and
drawing a first fluid bead of a first sample across said output layer such that at least a portion of said first fluid bead is drawn within said first grouping of said plurality of capillaries.

28. The method according to claim 27 further comprising:
drawing a second fluid bead of a second sample across said output layer such that at least a portion of said second fluid bead is drawn within a second of said plurality of capillaries.

* * * * *